United States Patent
Gomtsyan et al.

(10) Patent No.: US 8,802,711 B2
(45) Date of Patent: Aug. 12, 2014

(54) TRPV1 ANTAGONISTS

(75) Inventors: Arthur Gomtsyan, Vernon Hills, IL (US); Jerome F. Daanen, Racine, WI (US); Gregory A. Gfesser, Lindenhurst, IL (US); Michael E. Kort, Lake Bluff, IL (US); Chih-Hung Lee, Vernon Hills, IL (US); Heath A. McDonald, Wonder Lake, IL (US); Pamela S. Puttfarcken, Libertyville, IL (US); Eric A. Voight, Pleasant Prairie, WI (US); Philip R. Kym, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 177 days.

(21) Appl. No.: 13/426,732

(22) Filed: Mar. 22, 2012

(65) Prior Publication Data

US 2012/0245163 A1    Sep. 27, 2012

Related U.S. Application Data

(60) Provisional application No. 61/467,533, filed on Mar. 25, 2011.

(51) Int. Cl.
| C07D 265/36 | (2006.01) |
| C07D 215/38 | (2006.01) |
| C07D 217/02 | (2006.01) |
| C07D 231/56 | (2006.01) |
| A61K 31/17  | (2006.01) |
| A61K 31/538 | (2006.01) |
| A61K 31/192 | (2006.01) |
| A61K 31/472 | (2006.01) |

(52) U.S. Cl.
USPC .................................. 514/405; 548/362.1

(58) Field of Classification Search
USPC .................................. 548/362.1; 514/405
See application file for complete search history.

(56) References Cited

U.S. PATENT DOCUMENTS

| 6,353,011 | B1 | 3/2002 | Pershadsingh et al. |
| 6,993,311 | B2 | 1/2006 | Li et al. |
| 7,015,233 | B2 | 3/2006 | Gomtsyan et al. |
| 7,375,126 | B2 | 5/2008 | Gomtsyan et al. |
| 7,504,520 | B2 | 3/2009 | Gomtsyan et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,622,493 | B2 | 11/2009 | Brown et al. |
| 7,875,627 | B2 | 1/2011 | Turner et al. |
| 7,910,751 | B2 | 3/2011 | Uchida et al. |
| 7,998,982 | B2 | 8/2011 | Vasudevan et al. |
| 8,026,256 | B2 | 9/2011 | Gomtsyan et al. |
| 8,084,616 | B2 | 12/2011 | Gomtsyan et al. |
| 8,604,053 | B2 * | 12/2013 | Gomtsyan et al. ............ 514/310 |
| 2003/0109700 | A1 | 6/2003 | Ksander |
| 2006/0128689 | A1 | 6/2006 | Gomtsyan et al. |
| 2007/0099954 | A1 | 5/2007 | Gomtsyan et al. |
| 2008/0153871 | A1 | 6/2008 | Bayburt et al. |
| 2008/0287676 | A1 | 11/2008 | Gomtsyan et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2010/0016285 | A1 | 1/2010 | Uchida et al. |
| 2013/0158067 | A1 | 6/2013 | Woller et al. |
| 2013/0172334 | A1 | 7/2013 | Dart et al. |
| 2013/0345255 | A1 | 12/2013 | Gomtsyan et al. |

FOREIGN PATENT DOCUMENTS

| EP | 2128157 A1 | 7/2008 |
| JP | 2011201777 | 10/2011 |
| WO | 9507271 A1 | 3/1995 |
| WO | 9710223 A1 | 3/1997 |
| WO | 03097586 A1 | 11/2003 |
| WO | 2004046133 A1 | 6/2004 |

(Continued)

OTHER PUBLICATIONS

Ainai, T et al., "A New Reagent System for Installation of an Aryl Group onto the Monoacetate of 4-Cyclopentene-1,3-diol," *Tetrahedron Lett.*, 44(20): 3983-3986 (2003).
Apostolidis, A. et al., "Capsaicin Receptor TRPV1 in Urothelium of Neurogenic Human Bladders and Effect of Intravesical Resiniferatoxin," Urology, 65(2): 400-405 (2005).
Barone, F. C. et al., "Brain Cooling During Transient Focal Ischemia Provides Complete Neuroprotection," Neurosci. Biobehay. Rev., 21(1): 31-44 (1997).
Bennett, G. J., "A Peripheral Mononeuropathy in Rat that Produces Disorders of Pain Sensation Like Those Seen in Man," Pain, 33(1): 87-107 (1988).

(Continued)

*Primary Examiner* — Kahsay Habte

(57) ABSTRACT

Disclosed herein are compounds of formula (I) or pharmaceutically acceptable salts, solvates, or combinations thereof,

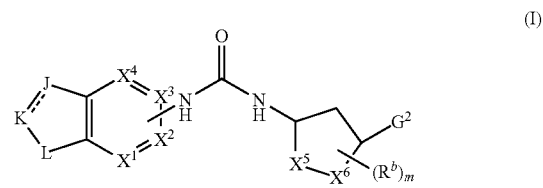

(I)

wherein $X^1$, $X^2$, $X^3$, $X^4$, J, K, L, $X^5$, $X^6$, $R^b$, $G^2$, and m are defined in the specification. Compositions comprising such compounds and methods for treating conditions and disorders using such compounds and compositions are also disclosed.

25 Claims, No Drawings

(56) References Cited

FOREIGN PATENT DOCUMENTS

| | | | |
|---|---|---|---|
| WO | 2005016915 | A1 | 2/2005 |
| WO | 2005040100 | A1 | 5/2005 |
| WO | 2005099353 | A2 | 10/2005 |
| WO | 2006008754 | A1 | 1/2006 |
| WO | 2006065484 | A2 | 6/2006 |
| WO | 2007010383 | A1 | 1/2007 |
| WO | 2007042906 | A1 | 4/2007 |
| WO | 2007121299 | A2 | 10/2007 |
| WO | 2008040360 | A2 | 4/2008 |
| WO | 2008040361 | A2 | 4/2008 |
| WO | 2008059339 | A2 | 5/2008 |
| WO | 2008075196 | A1 | 6/2008 |
| WO | 2008079683 | A2 | 7/2008 |
| WO | 2008091021 | A1 | 7/2008 |
| WO | 2008110863 | A1 | 9/2008 |
| WO | 2010010935 | A1 | 1/2010 |
| WO | 2010045401 | A1 | 4/2010 |
| WO | 2010045402 | A1 | 4/2010 |
| WO | 2010063634 | A1 | 6/2010 |

OTHER PUBLICATIONS

Bernard, S. A. et al., "Treatment of Comatose Survivors of Out-of-Hospital Cardiac Arrest With Induced Hypothermia," N. Engl. J. Med., 346(8): 557-563 (2002).
Beylot, M. et al., "In vivo Studies of Intrahepatic Metabolic Pathways," Diabetes & Metabolism (Paris), 23: 251-257 (1997).
Blagojevic, N. et al., "Role of Heavy Water in Boron Neutron Capture Therapy," Dosimetry & Treatment Planning for Neutron Capture Therapy, Editors R. Zamenhof, G. Solares and O. Harling, Advanced Medical Publishing, Madison, WI. pp. 125-134 (1994).
Blake, M. I. et al., "Studies With Deuterated Drugs," J. Pharm. Sci. 64(3): 367-391 (1975).
Brickner, S. J. et al., "Synthesis and Antibacterial Activity of U-100592 and U-100766, Two Oxazolidinone Antibacterial Agents for the Potential Treatment of Multidrug-Resistant Gram-Positive Bacterial Infections," J Med Chem, 39(3): 673-679 (1996).
Caterina, M. J. et al., "The Vanilloid Receptor: A Molecular Gateway to the Pain Pathway," Annu. Rev. Neurosci., 24: 487-517 (2001).
Caterina, M. J. et al., "Impaired Nociception and Pain Sensation in Mice Lacking the Capsaicin Receptor," Science, 288(5464): 306-313 (2000).
Caterina, M. J. et al., "The Capsaicin Receptor: A Heat-Activated Ion Channel in the Pain Pathway," Nature, 389(6653): 816-824 (1997).
Chaplan, S.R. et al., "Quantitative Assessment of Tactile Allodynia in the Rat Paw," J. Neurosci. Methods, 53(1): 55-63 (1994).
Coimbra, C. et al., "Moderate Hypothermia Mitigates Neuronal Damage in the Rat Brain When Initiated Several Hours Following Transient Cerebral Ischemia," Acta Neuropathol. 87(4): 325-331 (1994).
Colbourne, F. et al., "Prolonged but Delayed Postischemic Hypothermia: A Long-term Outcome Study in the Rat Middle Cerebral Artery Occlusion Model," J. Cereb. Blood Flow Metab., 20(1-2): 1702-1708 (2000).
Cross, L. C. et al., "IUPAC 1974 Recommendations for Section E, Fundamental Stereochemistry," Pure Appl. Chem., 45: 13-30 (1976).
Czajka, D. M. et al., "Effect of Deuterium Oxide on the Reproductive Potential of Mice," Ann. N.Y. Acad. Sci., 84: 770-779 (1960).
Czajka, D. M. et al., "Physiological Effects of Deuterium on Dogs," Am. J. Physiol., 201(2): 357-362 (1961).
Davis, J. et al., "Vanilloid Receptor-1 is Essential for Inflammatory Thermal Hyperalgesia," Nature, 405: 183-187 (2000).
Dixon, W.J., "Efficient Analysis of Experimental Observations," Annu. Rev. Pharmacol. Toxicol., 20: 441-462 (1980).
Fernihough, J. et al. "Regulation of Calcitonin Gene-Related Peptide and TRPV1 in a Rat Model of Osteoarthritis," Neurosci. Left., 388(2): 75-80 (2005).
Foster, Allan B. "Deuterium Isotope Effects in the Metabolism of Drugs and Xenobiotics: Implications of Drug Design," Advances in Drug Research, vol. 14, pp. 2-36 (Bernard Testa, Editor), Academic press, London, 1985.
Garami, A. et al., "Contributions of Different Modes of TRPV1 Activation to TRPV1 Antagonist-Induced Hyperthermia" J. Neurosci., 30(4): 1435-1440 (2010).
Garrett, C. E. et al., "The Enantioselective Reduction of 2'-Fluoroacetophenone Utilizing a Simplified CBS-Reduction Procedure," Tetrahedron Asymmetry, 13(13): 1347-1349 (2002).
Gavva, N. R. et al., "Pharmacological Blockade of the Vanilloid Receptor TRPV1 Elicits Marked Hyperthermia in Humans" Pain, 136(1-2): 202-210 (2008).
Gavva, N. R. et al., "Repeated Administration of Vanilloid Receptor TRPV1 Antagonists Attenuates Hyperthermia Elicited by TRPV1 Blockade" J. Pharmacol. Exp. Ther., 323(1): 128-137 (2007).
Gavva, N. R. et al., "The Vanilloid Receptor TRPV1 is Tonically Activated in vivo and Involved in Body Temperature Regulation" J. Neurosci., 27(13): 3366-3374 (2007).
Geppetti, P. et al., "The Transient Receptor Potential Vanilloid 1: Role in Airway Inflammation and Disease," Eur. J. Pharmacol., 533(1-3): 207-214 (2006).
Gilchrist, H. D. et al., "Enhanced Withdrawal Responses to Heat and Mechanical Stimuli Following Intraplantar Injection of Capsaicin in Rats," Pain, 67(1): 179-188 (1996).
Greene, T. et al., Editor, Protective Groups in Organic Synthesis (3rd ed.), John Wiley & Sons, NY (1999), (20 pages, Table of Contents).
Grennan, D. M. et al., "Rheumatoid Arthritis," Textbook of Pain, $3^{rd}$ Ed., Patrick Wall et al. Editors, Churchill Livingstone, pp. 397-407 (1994).
Hayes, P. et al. "Cloning and functional expression of a human orthologue of rat vanilloid receptor-1," Pain, 88(2): 205-215 (2000).
Higuchi T. et al., "Pro-drugs as Novel Delivery Systems," vol. 14 of the A.C.S. Symposium Series; American Chemical Society, Washington, DC, 1975. (13 pages, Table of Contents).
Holzer, M. et al., "Mild Therapeutic Hypothermia to Improve the Neurologic Outcome After Cardiac Arrest," N. Engl. J. Med., 346(8): 549-556 (2002).
Honore, P. et al., "A-425619 [1-isoquinolin-5-yl-3-(4-trifluoromethyl-benzyl)-urea], A Novel Transient Receptor Potential Type V1 Receptor Antagonist, Relieves Pathophysiological Pain Associated With Inflammation and Tissue Injury in Rats," J. Pharmacol. Exp. Ther., 314(1): 410-421 (2005).
Houge, J. H. et al., "Pathophysiology and First-Line Treatment of Osteoarthritis," Ann. Pharmacother., 36(4): 679-686 (2002).
Iida, T. et al., "Attenuated Fever Response in Mice Lacking TRPV1" Neurosci. Left., 378(1): 28-33 (2005).
International Search Report and Written Opinion issued in Application No. PCT/US2012/030096 on Jul. 4, 2012 (8 pages).
IUPAC 1993 Recommendations (IUPAC, Commission on Nomenclature of Organic Chemistry. *A Guide to IUPAC Nomenclature of Organic Compounds (Recommendations 1993)*, 1993, Blackwell Scientific publications).
Kikushima K. et al., "Palladium-Catalyzed Asymmetric Conjugate Addition of Arylboronic Acids to Five-, Six-, and Seven-Membered β-Substituted Cyclic Enones: Enantioselective Construction of All-Carbon Quaternary Stereocenters," *J. Am. Chem. Soc., 133(18)*: 6902-6905 (2011).
Jia, Y. et al., "Anandamide Induces Cough in Conscious Guinea-Pigs Through VR1 Receptors," Br. J. Pharmacol., 137(6): 831-836 (2002).
Joshi et al., "Comparison of Antinociceptive Actions of Standard Analgesics in Attenuating Capsaicin and Nerve-Injury-Induced Mechanical Hypersensitivity," Neuroscience 143(2): 587-596 (2006).
Kato, S. et al., "Synthesis of Deuterated Mosapride Citrate," J. Labeled Comp. Radiopharmaceut., 36(10): 927-932 (1995).
Kawai, N. et al., "Effects of delayed intraischemic and postischemic hypothermia on a focal model of transient cerebral ischemia in rats," Stroke, 31: 1982-89; discussion 1989 (2000).
Kim S. H. et al., "An Experimental Model for Peripheral Neuropathy Produced by Segmental Spinal Nerve Ligation in the Rat," Pain 50(2): 355-363 (1992).
Kort, M. E. et al., "2 TRPV1 Antagonists: Clinical Setbacks and Prospects for Future Development," Progress in Medicinal Chemistry, vol. 51, pp. 57-70, G. Lawton and D.R. Witty Editors, Elsevier B.V., (2012).

(56) References Cited

OTHER PUBLICATIONS

Kushner, D. J. et al., "Pharmacological Uses and Perspectives of Heavy Water and Deuterated Compounds," Can. J. Physiol. Pharmacol., 77(2): 79-88 (1999).
Lehto, S. G. et al., "Antihyperalgesic effects of (R,E)-N-(2-hydroxy-2,3-dihydro-1H-inden-4-yl)-3-(2-(piperidin-1-yl)-4-(trifluoromethyl)phenyl)-acrylamide (AMG8562), A Novel Transient Receptor Potential Vanilloid Type 1 Modulator That Does Not Cause Hyperthermia in Rats" J. Pharmacol. Exp. Ther., 326(1): 218-229 (2008).
Levine, J. et al., "Inflammatory Pain," Textbook of Pain, 3$^{rd}$ Ed., Patrick Wall et al. Editors, Churchill Livingstone, pp. 45-56 (1994).
Lizondo, J et al., "Linezolid—Oxazolidinone Antibacterial" Drugs Future, 21(11): 1116-1123 (1996).
Lukin, et al. "Practical Method for Asymmetric Addition of Arylboronic Acids to α,β-Unsaturated Carbonyl Compounds Utilizing an in Situ Prepared Rhodium Catalyst," *J Org. Chem.*, 74: 929-931 (2009).
Lukin, K. et al., "Development of a Large Scale Asymmetric Synthesis of Vanilloid Receptor (TRPV1) Antagonist ABT-102," *Org. Process Res. Dev.*, 11(3): 578-584 (2007).
Maier, C. M. et al., "Delayed Induction and Long-Term Effects of Mild Hypothermia in a Focal Model of Transient Cerebral Ischemia: Neurological Outcome and Infarct Size," J. Neurosurg., 94(1): 90-96 (2001).
Maier, C. M. et al., "Optimal Depth and Duration of Mild Hypothermia in a Focal Model of Transient Cerebral Ischemia: Effects on Neurologic Outcome, Infarct Size, Apoptosis, and Inflammation," Stroke, 29: 2171-2180 (1998).
Mallesham, B et al., "Highly Efficient Cui-Catalyzed Coupling of Aryl Bromides With Oxazolidinones Using Buchwald's Protocol: A Short Route to Linezolid and Toloxatone," Org Left, 5(7): 963-965 (2003).
Marsch, R. et al., "Reduced Anxiety, Conditioned Fear, and Hippocampal Long-Term Potentiation in Transient Receptor Potential Vanilloid Type 1 Receptor-Deficient Mice," J. Neurosci., 27(4): 832-839 (2007).
McCarthy, C. et al., "Osteoarthritis," Textbook of Pain, 3$^{rd}$ Ed., Patrick Wall et al. Editors, Churchill Livingstone, pp. 387-395 (1994).
Meyer, R. A. et al., "Peripheral Neural Mechanisms of Nociception," Textbook of Pain, 3$^{rd}$ Ed., Patrick Wall et al. Editors, Churchill Livingstone, pp. 13-44 (1994).
Millan, Mark J. "The Induction of Pain: An Integrative Review," Prog. Neurobiol., 57: 1-164 (1999). (Uploaded in 2 parts due to size).
Murata, Y. et al., "Peripheral and Central Distribution of TRPV1, Substance P and CGRP of Rat Corneal Neurons," Brain Res., 1085(1): 87-94 (2006).
Nolano, M. et al., "Topical Capsaicin in Humans: Parallel Loss of Epidermal Nerve Fibers and Pain Sensation," Pain, 81(1-2): 135-145 (1999).
Onesti, S. T. et al., "Transient Hypothermia Reduces Focal Ischemic Brain Injury in the Rat," Neurosurgery, 29(3): 369-373 (1991).
Ooboshi, H. et al., "Hypothermia Inhibits Ischemia-Induced Efflux of Amino Acids and Neuronal Damage in the Hippocampus of Aged Rats," Brain Res., 884(1): 23-30 (2000).
Prescott, David M., Editor, Methods in Cell Biology, vol. XIV, Academic Press, New York, N.Y., (1976), (12 pages, Table of Contents).

Reilly, R. M. et al., "Pharmacology of Modality-Specific Transient Receptor Potential Vanilloid-1 Antagonists That Do Not Alter Body Temperature," Journal of Pharmacology and Experimental Therapeutics, 342(2): 416-428 (2012).
Roche, Edward B., Editor, Bioreversible Carriers in Drug Design, American Pharmaceutical Association and Pergamon Press (1987), (4 pages, Table of Contents).
Sappington, R. M. et al., "TRPV1: Contribution to Retinal Ganglion Cell Apoptosis and Increased Intracellular Ca2+ With Exposure to Hydrostatic Pressure," Invest. Ophthalmol. Vis. Sci., 50(2): 717-728 (2009).
Steiner, A. A. et al., "Nontherrnal Activation of Transient Receptor Potential Vanilloid-1 Channels in Abdominal Viscera Tonically Inhibits Autonomic Cold-Defense Effectors" J. Neurosci., 27(28): 7459-7468 (2007).
Suri, A. et al., "The Emerging Role of TRPV1 in Diabetes and Obesity," Trends Pharmacol. Sci., 29(1): 29-36 (2008).
Swanson, D. M. et al., "Identification and Biological Evaluation of 4-(3-trifluoromethylpyridin-2-yl)piperazine-l-carboxylic acid (5-trifluoromethylpyridin-2-yl)amide, a High Affinity TRPV1 (VR1) Vanilloid Receptor Antagonist" J. Med. Chem., 48(6): 1857-1872 (2005).
Szallasi, A. et al., "The Vanilloid Receptor TRPV1: 10 Years From Channel Cloning to Antagonist Proof-Of-Concept" Nature Rev., 6: 357-373 (2007).
Tamayo, N. et al., "Design and Synthesis of Peripherally Restricted Transient Receptor Potential Vanilloid 1 (TRPV1) Antagonists" J. Med. Chem., 51(9): 2744-2757 (2008).
Thomson J. F., "Physiological Effects of D20 in Mammals," Ann. NY Acad. Sci., 84: 736-744 (1960).
Tzavara, E. et al., "Endocannabinoids Activate Transient Receptor Potential Vanilloid 1 Receptors to Reduce Hyperdopaminergia-Related Hyperactivity: Therapeutic Implications," Biol. Psych., 59: 508-515 (2006).
Voight, E. A. et al., "Transient receptor potential vanilloid-1 antagonists: a survey of recent patent literature," Expert Opinion Ther. Patents, 20(9): 1107-1122 (2010).
Watanabe N. et al, "Immunohistochemical Localization of Vanilloid Receptor Subtype 1 (TRPV1) in the Guinea Pig Respiratory System," Pulmonary Pharmacol. Ther., 18(3): 187-197 (2005).
Woolf, C. J. et al., "Neuronal Plasticity: Increasing the Gain in Pain," Science, 288(5472): 1765-1768 (2000).
Woolf, C. J. et al., "Implications of Recent Advances in the Understanding of Pain Pathophysiology for the Assessment of Pain in Patients," Pain Supp., 82(6): S141-S147 (1999).
Woolf, C. J. et al. "Neuropathic Pain: Aetiology, Symptoms, Mechanisms, and Management," Lancet, 353(9168): 1959-1964 (1999).
Yamashita, K. et al., "Mild Hypothermia Ameliorates Ubiquitin Synthesis and Prevents Delayed Neuronal Death in the Gerbil Hippocampus," Stroke, 22(12): 1574-1581 (1991).
Zhang, Y. et al., "The Effect of Intraischemic Mild Hypothermia on Focal Cerebral Ischemia/Reperfusion Injury," Acta Anaesthesiol. Sin., 39(2): 65-69 (2001).
Zhang, F. et al., "Transient Receptor Potential Vanilloid 1 Activation Induces Inflammatory Cytokine Release in Corneal Epithelium Through MAPK Signaling," J. Cell. Physiol., 213(3): 730-739 (2007).

* cited by examiner

TRPV1 ANTAGONISTS

RELATED APPLICATION INFORMATION

This application claims the benefit of U.S. Patent Application No. 61/467,533, filed on Mar. 25, 2011, the contents of which are herein incorporated by reference.

TECHNICAL FIELD

Described herein are ureas which are useful for treating pain, cough, bladder overactivity, urinary incontinence, or conditions and disorders modulated by the TRPV1 channel. Pharmaceutical compositions comprising said compounds and methods for treating pain, cough, bladder overactivity, urinary incontinence, or conditions and disorders modulated by the TRPV1 channel are also included.

BACKGROUND OF THE INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist, can reduce inflammation-induced hyperalgesia in animal models. TRPV1 receptors are also localized on sensory afferents, which innervate the bladder. Capsaicin or resiniferatoxin have been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

In the course of characterizing analgesic properties of structurally distinct TRPV1 antagonists, multiple investigators have observed core body temperature elevating ("hyperthermic") attributes of these compounds in rodent behavioral models of pain (Swanson, D. M. et al. *J. Med. Chem.* 2005, 48, 1857; Gavva, N. R. et al. *J. Pharmacol. Exp. Ther.* 2007, 323, 128; Steiner, A. A. et al. *J. Neurosci.* 2007, 27, 7459; Tamayo, N. et al. *J. Med. Chem.* 2008, 51, 2744; Gavva, N. R. et al. *J. Neurosci.* 2007, 27, 3366). Often modest (0.5° C.), the associated temperature elevation can be considerably more robust (1-2° C.), and also has been reported preclinically in dogs and monkeys (Gavva, N. R. et al. *J. Pharmacol. Exp. Ther.* 2007, 323, 128; Gavva, N. R. et al. *J. Neurosci.* 2007, 27, 3366) and in human subjects in the course of clinical trials (Gavva, N. R. et al. *Pain* 2008, 136, 202). These effects have the potential to be self-limiting; they are generally transient and attenuate with repeat dosing (Gavva, N. R. et al. *J. Pharmacol. Exp. Ther.* 2007, 323, 128). The temperature effects are considered to be mechanism based (Iida, T. et al. *Neurosci. Lett.* 2005, 378, 28) since TRPV1 null mice show no deficits in thermoregulation, even when dosed with antagonists that elevate temperature in wild-type mice (Steiner, A. A. et al. *J. Neurosci.* 2007, 27, 7459; Garami, A. et al. *J. Neurosci.* 2010, 30, 1435).

Accordingly, there is a need to understand and separate the nociceptive and thermoregulatory functions of TRPV1. We describe herein a series of novel TRPV1 antagonists.

SUMMARY OF THE INVENTION

One aspect is directed towards compounds of formula (I) or pharmaceutical salts, solvates, prodrugs, or combinations thereof,

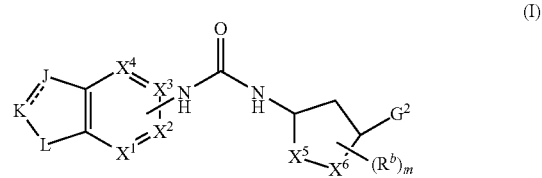

(I)

wherein
one of $X^1$, $X^2$, $X^3$, and $X^4$ is C, and the others are $C(R^a)$ or N, with the proviso that no more than two of $X^1$, $X^2$, $X^3$, and $X^4$ are N; wherein each $R^a$ is the same or different, and is independently hydrogen, —CN, $NO_2$, alkyl, halogen, haloalkyl, $OR^x$, or $N(R^x)_2$;

J is $C(R^{1J}R^{2J})$, $CR^{3J}$, N, $NR^{4J}$, S, S(O), $S(O)_2$, or O;

K is $C(R^{1k}R^{2k})$, C(O), $CR^{3k}$, N, $NR^{4k}$, S, S(O), $S(O)_2$, or O;

L is $C(R^{1L}R^{2L})C(R^{1L}R^{2L})$, $C(R^{1L}R^{2L})$, $NR^{3L}$, $C(R^{4L}R^{5L})$—O, $C(R^{4L}R^{5L})$—$NR^{6L}$, $C(R^{4L}R^{5L})$—S, C(O)$NR^{6L}$, N=$CR^{7L}$, $C(R^{4L}R^{5L})$—S(O), or $C(R^{4L}R^{5L})$—$S(O)_2$;

wherein $C(R^{4L}R^{5L})$—O, $C(R^{4L}R^{5L})$—$NR^{6L}$, $C(R^{4L}R^{5L})$—S, $C(O)NR^{6L}$, N=$CR^{7L}$, $C(R^{4L}R^{5L})$—S(O), and $C(R^{4L}R^{5L})$—$S(O)_2$ are attached to K through the left ends of the groups;

===== is a single bond or a double bond;

$R^{1J}$, $R^{4J}$, $R^{1k}$, $R^{1L}$, $R^{3L}$, $R^{4L}$, $R^{5L}$, and $R^{6L}$, at each occurrence, are each independently hydrogen, alkyl, or haloalkyl;

$R^{4k}$ is hydrogen, alkyl, haloalkyl, or hydroxyalkyl;

$R^{2J}$, $R^{3J}$, $R^{3k}$, $R^{2L}$, and $R^{7L}$ at each occurrence, are each independently hydrogen, halogen, haloalkyl, $OR^x$, or $N(R^x)_2$;

$R^{2k}$ is hydrogen, alkyl, halogen, haloalkyl, $OR^x$, or $N(R^x)(R^{1xa})$ wherein $R^{1xa}$ is hydrogen, alkyl, haloalkyl, hydroxyalkyl, or alkoxyalkyl; or $R^x$ and $R^{1xa}$, together with the nitrogen atom form a ring that is morpholinyl or homomorpholinyl;

$X^5$-$X^6$ is $CR^{3a}R^{3b}$, $C(R^3R^4)C(R^5R^6)$, $CR^7$=$CR^8$, or $C(R^9R^{10})C(R^{11}R^{12})C(R^{13}R^{14})$;

$R^4$, $R^6$, $R^7$, $R^8$, $R^{10}$, $R^{12}$, and $R^{14}$, are the same or different, and are each independently hydrogen, alkyl, or haloalkyl;

$R^{3a}$ and $R^{3b}$ are each independently hydrogen, alkyl, halogen, or haloalkyl;

$R^3$, $R^5$, $R^9$, $R^{11}$, and $R^{13}$, are the same or different, and are each independently hydrogen, —CN, alkyl, halogen, haloalkyl, $OR^x$, or $N(R^x)_2$;

$R^3$ and $R^5$, together with the carbon atoms to which they are attached, optionally form a $C_3$-$C_6$ cycloalkyl that is optionally substituted with 1, 2, 3, or 4 substituents independently selected from the group consisting of alkyl, halogen, and haloalkyl;

m is 0, 1, 2, 3, or 4;

each $R^b$ is an optional substituent and at each occurrence, is independently —CN, alkyl, halogen, haloalkyl, $OR^x$, or $N(R^x)_2$;

each $R^x$ is independently hydrogen, alkyl, or haloalkyl;

ring $G^2$ is aryl, heteroaryl, cycloalkyl, cycloalkenyl, or heterocycle, each of which is independently unsubstituted or substituted with 1, 2, 3, 4, or 5 substituents independently selected from the group consisting of alkyl, alkenyl, alkynyl, halogen, oxo, haloalkyl, CN, $NO_2$, —$OR^f$, —$OC(O)R^e$, —$OC(O)N(R^f)(R^g)$, —$SR^f$, —$S(O)_2R^e$, —$S(O)_2N(R^f)(R^g)$, —$C(O)R^f$, —$C(O)OR^f$, —$C(O)N(R^f)(R^g)$, —$N(R^f)(R^g)$, —$N(R^g)C(O)R^e$, —$N(R^g)S(O)_2R^e$, —$N(R^g)C(O)O(R^e)$, —$N(R^g)C(O)N(R^f)(R^g)$, $G^a$, —($C_1$-$C_6$ alkylenyl)-$OR^f$, —($C_1$-$C_6$ alkylenyl)-$OC(O)R^e$, —($C_1$-$C_6$ alkylenyl)-$OC(O)N(R^f)(R^g)$, —($C_1$-$C_6$ alkylenyl)-$S(O)_2R^e$, —($C_1$-$C_6$ alkylenyl)-$S(O)_2N(R^f)(R^g)$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)(R^g)$, —($C_1$-$C_6$ alkylenyl)-$N(R^f)(R^g)$, —($C_1$-$C_6$ alkylenyl)-$N(R^g)C(O)R^e$, —($C_1$-$C_6$ alkylenyl)-$N(R^g)S(O)_2R^e$, —($C_1$-$C_6$ alkylenyl)-$N(R^g)C(O)O(R^e)$, —($C_1$-$C_6$ alkylenyl)-$N(R^g)C(O)N(R^f)(R^g)$, —($C_1$-$C_6$ alkylenyl)-CN, and —($C_1$-$C_6$ alkylenyl)-$G^a$;

$R^e$, at each occurrence, is independently alkyl, alkenyl, alkynyl, haloalkyl, hydroxyalkyl, alkoxyalkyl, haloalkoxyalkyl, $G^a$, or —($C_1$-$C_6$ alkylenyl)-$G^a$;

$R^f$, at each occurrence, is independently hydrogen, alkyl, alkenyl, alkynyl, haloalkyl, hydroxyalkyl, alkoxyalkyl, haloalkoxyalkyl, $G^a$, or —($C_1$-$C_6$ alkylenyl)-$G^a$;

$R^g$, at each occurrence, is independently hydrogen, alkyl, alkenyl, alkynyl, haloalkyl, benzyl, or monocyclic cycloalkyl;

$G^a$, at each occurrence, is independently aryl, heteroaryl, cycloalkyl, cycloalkenyl, or heterocycle, each of which is optionally substituted with 1, 2, 3, 4, or 5 substituents independently selected from the group consisting of alkyl, alkenyl, alkynyl, halogen, haloalkyl, —CN, oxo, —$OR^h$, —$OC(O)R^i$, —$OC(O)N(R^h)_2$, —$SR^h$, —$S(O)_2R^i$, —$S(O)_2N(R^h)_2$, —$C(O)R^h$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, —($C_1$-$C_6$ alkylenyl)-$OR^i$, —($C_1$-$C_6$ alkylenyl)-$OC(O)R^i$, —($C_1$-$C_6$ alkylenyl)-$OC(O)N(R^h)_2$, —($C_1$-$C_6$ alkylenyl)-$S(O)_2R^i$, —($C_1$-$C_6$ alkylenyl)-$S(O)_2N(R^h)_2$, —($C_1$-$C_6$ alkylenyl)-$C(O)R^h$, —($C_1$-$C_6$ alkylenyl)-$C(O)OR^h$, —($C_1$-$C_6$ alkylenyl)-$C(O)N(R^h)_2$, —($C_1$-$C_6$ alkylenyl)-$N(R^h)_2$, —($C_1$-$C_6$ alkylenyl)-$N(R^h)C(O)R^i$, —($C_1$-$C_6$ alkylenyl)-$N(R^h)S(O)_2R^i$, —($C_1$-$C_6$ alkylenyl)-$N(R^h)C(O)O(R^i)$, —($C_1$-$C_6$ alkylenyl)-$N(R^h)C(O)N(R^h)_2$, and —($C_1$-$C_6$ alkylenyl)-CN;

$R^h$, at each occurrence, is independently hydrogen, alkyl, or haloalkyl; and $R^i$, at each occurrence, is independently alkyl or haloalkyl;

with the proviso that when $X^4$ is C, $X^1$, $X^2$, and $X^3$ are $C(R^a)$ wherein $R^a$ is hydrogen, ===== is a single bond, J is $C(R^{1J}R^{2J})$ wherein $R^{1J}$ and $R^{2J}$ are hydrogen, K is $C(R^{1k}R^{2k})$ wherein $R^{1k}$ is hydrogen and $R^{2k}$ is OH, L is $C(R^{1L}R^{2L})C(R^{1L}R^{2L})$ wherein $R^{1L}$ and $R^{2L}$ are hydrogen, m is 0, and $X^5$-$X^6$ is $C(R^3R^4)C(R^5R^6)$ or $C(R^9R^{10})C(R^{11}R^{12})C(R^{13}R^{14})$ wherein $R^3$, $R^4$, $R^5$, $R^6$, $R^9$, $R^{10}$, $R^{11}$, $R^{12}$, $R^{13}$, and $R^{14}$ are hydrogen, then $G^2$ is other than aryl.

Another aspect is related to methods for treating ischemia such as acute cerebral ischemia, cerabrovascular ischemia; pain such as acute pain, chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, post herpetic neuralgia, post operative pain, post stroke pain, and menstrual pain; bladder disease such as incontinence, bladder overactivity, micturition disorder, renal colic and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; emesis such as cancer chemotherapy-induced emesis, or obesity, said method comprising the step of administering a therapeutically effective amount of a compound described herein, or a pharmaceutically acceptable salt, solvate, salt of a solvate, or solvate of a salt thereof, to a subject in need thereof, alone or in combination with an analgesic (e.g. acetaminophen, opioids such as, but not limited to, morphine), or a nonsteroidal anti-inflammatory drug (NSAID), or a combination thereof, and with or without a pharmaceutically acceptable carrier.

Further, included herein are uses of present compounds or pharmaceutically acceptable salts, solvates, salts of solvates, or solvates of salts thereof, for the manufacture of medicaments for the treatment of the diseases or conditions described above, with or without a pharmaceutically acceptable carrier, and alone, or in combination with an analgesic (e.g. acetaminophen, opioids), or with a nonsteroidal anti-inflammatory drug (NSAID), or a combination thereof.

Provided herein are compounds of formulat 1, or pharmaceutically acceptable salts or solvents thereof wherein said compounds exhibits less than about a 10% increase in response latency of noxious thermosensation in a tail immersion model relative to vehicle control, and even further a less than about a 25% increase in response latency of noxious thermosensation in a tail immersion model relative to vehicle control.

Further provided herein are compounds of formula 1, or pharmaceutically acceptable salts or solvates thereof wherein said compound blocks about 75% or less calcium flux caused by activation of human TRPV1 at about a pH of 5.0, and exhibits less than about a 10% increase in response latency of noxious thermosensation in a tail immersion model relative to vehicle control, and even further a less than about a 25% increase in response latency of noxious thermosensation in a tail immersion model relative to vehicle control.

These and other objectives are described in the following paragraphs. These objectives should not be deemed to narrow the scope of the invention.

DETAILED DESCRIPTION OF THE INVENTION

Disclosed herein are compounds of formula (I)

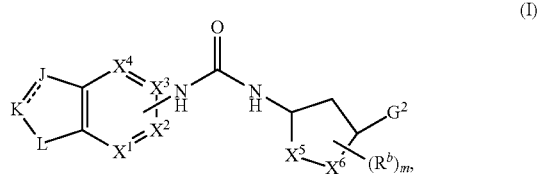

wherein $X^1$, $X^2$, $X^3$, $X^4$, $X^5$, $X^6$, J, K, L, $R^b$, $G^2$, and m are as defined above in the Summary and below in the Detailed Description. Compositions comprising such compounds and methods for treating conditions and disorders using such compounds and compositions are also disclosed.

For a variable that occurs more than one time in any substituent or in the compound of the invention or any other formula herein, its definition on each occurrence is independent of its definition at every other occurrence. Combinations of substituents are permissible only if such combinations result in stable compounds. Stable compounds are compounds which can be isolated from a reaction mixture.

A). DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. The term "$C_1$-$C_4$ alkoxy" as used herein, means a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylenyl group, as defined herein. Non-limiting examples of alkoxyalkyl include tert-butoxymethyl, 2-ethoxyethyl, 2-methoxyethyl, and methoxymethyl.

The term "alkyl" as used herein, means a saturated, straight or branched hydrocarbon chain containing from 1 to 10 carbon atoms. In some instances, the number of carbon atoms in an alkyl moiety is indicated by the prefix "$C_x$-$C_y$," wherein x is the minimum and y is the maximum number of carbon atoms in the substituent. Thus, for example, "$C_1$-$C_6$ alkyl" refers to an alkyl substituent containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 6 ($C_1$-$C_6$ alkylenyl) carbon atoms or of 1 to 4 carbon atoms ($C_1$-$C_4$ alkylenyl). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means a straight or branched chain hydrocarbon group containing from 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryls are attached to the parent molecular moiety through any carbon atom contained within the ring systems and can be unsubstituted or substituted.

The term "cycloalkyl" or "cycloalkane" as used herein, means a monocyclic and a bicyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The term "$C_3$-$C_6$ cycloalkyl" as used herein, means a monocyclic carbocyclic ring containing three, four, five, or six carbon atoms, zero heteroatom, and zero double bond. The bicyclic cycloalkyl is a monocyclic cycloalkyl fused to a monocyclic cycloalkyl ring. The monocyclic and the bicyclic cycloalkyl groups can contain one or two alkylene bridges of one, two, three, or four carbon atoms wherein each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane, tricyclo[3.3.1.0$^{3,7}$] nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl, and trifluoropropyl.

The term "haloalkoxy" as used herein, means an alkoxy group, as defined herein, in which one, two, three, four, five or six hydrogen atoms are replaced by halogen. The term "$C_1$-$C_4$ haloalkoxy" as used herein, means a $C_1$-$C_4$ alkoxy group, as defined herein, in which one, two, three, four, five, or six hydrogen atoms are replaced by halogen. Representative examples of haloalkoxy include, but are not limited to, 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkylenyl group, as defined herein.

The term "heterocycle" or "heterocyclic" as used herein, means a monocyclic heterocycle, a bicyclic heterocycle, and a spiro heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl (including 1,2,3,6-tetrahydropyridin-1-yl), tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a] pyrazin-2-yl, hexahydropyrano[3,4-b][1,4]oxazin-1(5H)-yl. The monocyclic heterocycle and the bicyclic heterocycle can contain one or two alkylene bridges or alkenylene bridge, or mixture thereof, each consisting of 1, 2, 3, or 4 carbon atoms and each linking two non adjacent atoms of the ring system. Examples of such bridged heterocycle include, but are not limited to, azabicyclo[2.2.1]heptyl (including 2-azabicyclo [2.2.1]hept-2-yl), 8-azabicyclo[3.2.1]oct-8-yl, octahydro-2, 5-epoxypentalene, hexahydro-2H-2,5-methanocyclopenta [b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H, 4H-spiro[1,3-benzodioxine-2,4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic, and the spiro heterocycles are connected to the parent molecular moiety through any carbon atom or any nitrogen atom contained within the ring systems. The nitrogen and sulfur heteroatoms in the heterocycle rings can optionally be oxidized and the nitrogen atoms can optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring can contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl (including 1,2,4-oxadiazolyl), oxazolyl (e.g. 1,3-oxazolyl), pyridinyl, pyridazinyl, pyrimidinyl, pyrazinyl, pyrazolyl, pyrrolyl, tetrazolyl, thiadiazolyl, thiazolyl (e.g. 1,3-thiazolyl), thienyl, triazolyl (1,2,4-triazolyl), and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, and sulfur.

The term "hydroxyl" or "hydroxy" means a —OH group.

The term "hydroxyalkyl" as used herein, means a —OH group appended to the parent molecular moiety through an alkylenyl group, as defined herein. Non-limiting examples of hydroxyalkyl include 2-hydroxyethyl and 2-methyl-3-hydroxypropyl.

The term "oxo" as used herein, means a =O group.

If a substituent is described as "substituted", a non-hydrogen radical is in the place of a hydrogen radical on any substitutable atom of the substituent. Thus, for example, a substituted heterocycle substituent is a heterocycle substituent in which at least one non-hydrogen radical is in the place of a hydrogen radical on the heterocycle substituent. It should be recognized that if there are more than one substitution on a substituent, each non-hydrogen radical can be identical or different (unless otherwise stated).

If a substituent is described as being "optionally substituted," the substituent can be either (1) not substituted or (2) substituted. If a substituent is described as being optionally substituted with up to a particular number of non-hydrogen radicals, that substituent can be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen can be optionally substituted with up to 2 non-hydrogen radicals, whereas a secondary amino nitrogen can be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the pharmaceutical agent being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

B) COMPOUNDS

TRPV1 antagonists of formula (I) are as described above.

Particular values of variable groups in compounds of formula (I) are as follows. Such values can be used where appropriate with any of the other values, definitions, claims or embodiments defined hereinbefore or hereinafter.

In compounds of formula (I), $X^1$, $X^2$, $X^3$, and $X^4$ have values as described in the Summary. In certain embodiments, $X^4$ is C and $X^1$, $X^2$, and $X^3$ are $C(R^a)$ or N; examples of such compounds include those of formula (I-i)

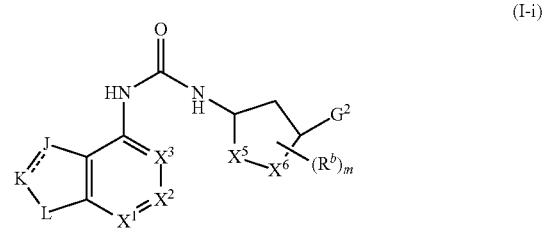

(I-i)

wherein $X^1$, $X^2$, $X^3$, $X^5$, $X^6$, J, K, L, $G^2$, $R^b$, and m of (I-i) are as described in the Summary and embodiments herein above and below. In certain embodiments of compounds of formula (I) and (I-i), $X^1$, $X^2$, and $X^3$ are $C(R^a)$. In yet other embodiments of compounds of formula (I) and (I-i), one of $X^1$, $X^2$, and $X^3$ is N and the others are $C(R^a)$.

In certain embodiments, $X^3$ is C and $X^1$, $X^2$, and $X^4$ are $C(R^a)$ or N; examples of such compounds include those of formula (I-ii)

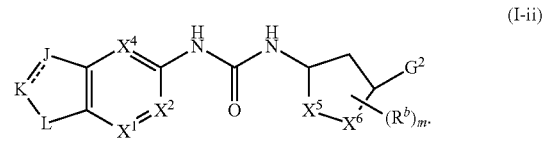

(I-ii)

wherein $X^1$, $X^2$, $X^4$, $X^5$, $X^6$, J, K, L, $G^2$, $R^b$, and m of (I-ii) are as described in the Summary and embodiments herein above and below. In certain embodiments of compounds of formula (I) and (I-ii), $X^1$, $X^2$, and $X^4$ are $C(R^a)$. In yet other embodiments of compounds of formula (I) and (I-ii), one of $X^1$, $X^2$, and $X^4$ is N and the others are $C(R^a)$.

In certain embodiments, $X^2$ is C and $X^1$, $X^3$, and $X^4$ are $C(R^a)$ or N; examples of such compounds include those of formula (I-iii)

(I-iii)

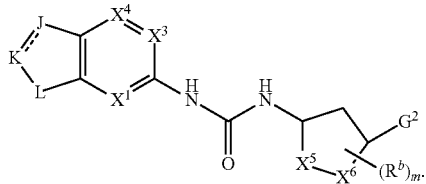

wherein $X^1, X^3, X^4, X^5, X^6, J, K, L, G^2, R^b$, and m of (I-iii) are as described in the Summary and embodiments herein above and below. In certain embodiments of compounds of formula (I) and (I-iii), $X^1, X^3$, and $X^4$ are $C(R^a)$. In yet other embodiments of compounds of formula (I) and (I-iii), one of $X^1, X^3$, and $X^4$ is N and the others are $C(R^a)$.

$R^a$ for compounds of formula (I), (I-i), (I-ii), and (I-iii) are as described in the Summary; for example, in certain embodiments, $R^a$ are the same or different, and are each independently hydrogen or halogen (e.g. F). In yet other embodiments, $R^a$ is hydrogen.

In compounds of formula (I), (I-i), (I-ii), and (I-iii), J, K, and L have values as described in the Summary and embodiments herein.

Provided herein are compounds of formula (I), (I-i), (I-ii), and (I-iii) wherein the ring

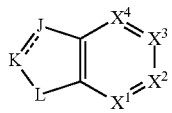

is one of the following structures:

(a)

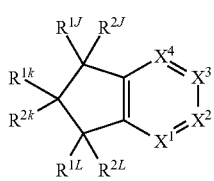

(b)

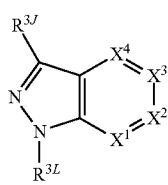

(c)

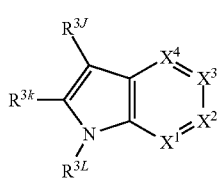

(d)

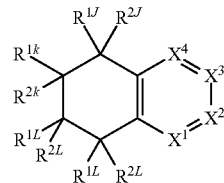

(e)

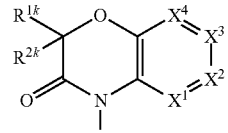

(f)

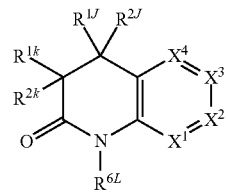

(g)

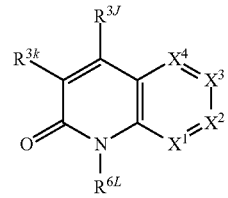

(h)

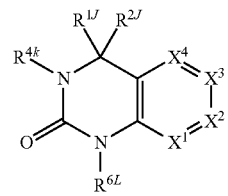

(i)

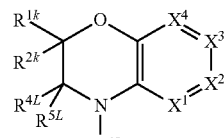

(j)

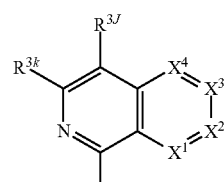

wherein $X^1, X^2, X^3, X^4, R^{1J}, R^{2J}, R^{3J}, R^{1k}, R^{2k}, R^{3k}, R^{1L}, R^{2L}, R^{3L}, R^{4L}, R^{5L}, R^{6L}$, and $R^{7L}$ are as disclosed in the Summary and embodiments herein.

In certain embodiments, J is $C(R^{1J}R^{2J})$ and ===== is a single bond; wherein $R^{1J}$ and $R^{2J}$ are the same or different, and are as described in the Summary, for example, $R^{1J}$ and $R^{2J}$ are the same or different, and are each independently hydrogen or alkyl (e.g. methyl, ethyl), or for example, $R^{1J}$ and $R^{2J}$ are hydrogen. In yet other embodiments, J is $NR^{4J}$ or O and ===== is a single bond; wherein $R^{4J}$ is as described in the Summary, for example, $R^{4J}$ is hydrogen. In yet other embodiments, J is O and ===== is a single bond. In yet other embodiments, J is $CR^{3J}$ and ===== is a double bond, wherein $R^{3J}$ is as described in the Summary, for example, $R^{3J}$ is hydrogen or alkyl (e.g. methyl), or for example, $R^{3J}$ is hydrogen.

In certain embodiments, L is $C(R^{1L}R^{2L})C(R^{1L}R^{2L})$, $C(R^{1L}R^{2L})$, $NR^{3L}$, $C(R^{4L}R^{5L})$—$NR^{6L}$, $C(O)NR^{6L}$, or $N=CR^{7L}$. In certain embodiments, L is $C(R^{1L}R^{2L})$, $NR^{3L}$, $C(O)NR^{6L}$, or $N=CR^{7L}$. In certain embodiments, L is $C(O)NR^{6L}$. In certain embodiments, L is $C(R^{1L}R^{2L})C(R^{1L}R^{2L})$ or $C(R^{1L}R^{2L})$. In certain embodiments, L is $NR^{3L}$. In certain embodiments, L is $C(R^{4L}R^{5L})$—$NR^{6L}$. In certain embodiments, L is $N=CR^{7L}$. $R^{1L}$, $R^{2L}$, $R^{3L}$, $R^{4L}$, $R^{5L}$, $R^{6L}$, and $R^{7L}$ are as described in the Summary, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

In certain embodiments, J is $CR^{3J}$, K is N or $CR^{3k}$, L is $NR^{3L}$, and ===== is a double bond. $R^{3J}$ and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

In certain embodiments, J is $CR^{3J}$, K is N, L is $NR^{3L}$, and ===== is a double bond. $R^{3J}$ and $R^{3L}$ are as described in the Summary, for example, $R^{3J}$ and $R^{3L}$ are the same or different, and are each independently hydrogen or alkyl (e.g. methyl), or for example, $R^{3J}$ and $R^{3L}$ are hydrogen.

In certain embodiments, ===== is a single bond, J is $C(R^{1J}R^{2J})$, L is $C(R^{1L}R^{2L})$, K is $C(R^{1k}R^{2k})$ wherein $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, and $R^{1k}$ are the same or different, and are each independently hydrogen or alkyl, and $R^{2k}$ is OH; or for exam $R^{1J}$, $R^{2J}$, $R^{1L}$, $R^{2L}$, and $R^{1k}$ are hydrogen, and $R^{2k}$ is OH.

In certain embodiments, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$ wherein $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

In certain embodiments, J is $C(R^{1J}R^{2J})$, K is $C(R^{1k}R^{2k})$, L is $C(O)NR^{6L}$, and ===== is a single bond. $R^{1J}$, $R^{2J}$, $R^{1k}$, $R^{2k}$, and $R^{6L}$ are as described in the Summary, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

In certain embodiments, J is $C(R^{1J}R^{2J})$, K is $NR^{4k}$, L is $C(O)NR^{6L}$, and ===== is a single bond. $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$, for example, is alkyl (e.g. methyl) or hydroxyalkyl (e.g. 2-hydroxyethyl), or $R^{4k}$, for example, is hydroxyalkyl (e.g. 2-hydroxyethyl).

In certain embodiments, J is $CR^{3J}$, K is $CR^{3k}$, L is $C(O)NR^{6L}$, and ===== is a double bond. $R^{3J}$, $R^{3k}$, and $R^{6L}$ are as described in the Summary, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

In certain embodiments, J is O, K is $C(R^{1k}R^{2k})$, L is $C(O)NR^{6L}$, and ===== is a single bond. $R^{1k}$, $R^{2k}$, and $R^{6L}$ are as described in the Summary, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alky (e.g. methyl).

In certain embodiments, ===== is a double bond, J is $CR^{3J}$, K is $CR^{3k}$, and L is $N=CR^{7L}$; wherein $R^{3J}$, $R^{3k}$, and $R^{7L}$ are as described in the Summary, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

In certain embodiments, J is O, K is $C(R^{1k}R^{2k})$, L is $C(R^{4L}R^{5L})$—$NR^{6L}$, and ===== is a single bond, wherein $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

In compounds of formula (I), (I-i), (I-ii), and (I-iii), $X^5$-$X^6$ is $CR^{3a}R^{3b}$, $C(R^3R^4)C(R^5R^6)$, $CR^7=CR^8$ or $C(R^9R^{10})C(R^{11}R^{12})C(R^{13}R^{14})$. In certain embodiments, $X^5$-$X^6$ is $CR^{3a}R^{3b}$, $C(R^3R^4)C(R^5R^6)$, or $C(R^9R^{10})C(R^{11}R^{12})C(R^{13}R^{14})$. In certain embodiments, $X^5$-$X^6$ is $C(R^3R^4)C(R^5R^6)$, or $C(R^9R^{10})C(R^{11}R^{12})C(R^{13}R^{14})$. In certain embodiments, $X^5$-$X^6$ is $CR^{3a}R^{3b}$. In certain embodiments, $X^5$-$X^6$ is $C(R^3R^4)C(R^5R^6)$. In certain embodiments, $X^5$-$X^6$ is $CR^7=CR^8$. In certain embodiments, $X^5$-$X^6$ is $C(R^9R^{10})C(R^{11}R^{12})C(R^{13}R^{14})$. $R^{3a}$, $R^{3b}$, $R^3$, $R^4$, $R^5$, $R^6$, $R^7$, $R^8$, $R^9$, $R^{10}$, $R^{11}$, $R^{12}$, $R^{13}$, and $R^{14}$ are as described in the Summary. For example, in certain embodiments, $R^{3a}$, $R^{3b}$, $R^3$, $R^4$, $R^5$, $R^6$, $R^7$, $R^8$, $R^9$, $R^{10}$, $R^{11}$, $R^{12}$, $R^{13}$, and $R^{14}$ are the same or different, and are each independently hydrogen or alkyl. In certain embodiments, $R^{3a}$, $R^{3b}$, $R^3$, $R^4$, $R^5$, $R^6$, $R^7$, $R^8$, $R^9$, $R^{10}$, $R^{11}$, $R^{12}$, $R^{13}$, and $R^{14}$ are hydrogen. In certain embodiments, $R^4$ and $R^6$ are each independently hydrogen or alkyl (e.g. methyl, ethyl), and $R^3$ and $R^5$ are each independently hydrogen or OH. In certain embodiments, $R^4$ and $R^6$ are hydrogen, and $R^3$ and $R^5$, together with the carbon atoms to which they are attached, form an optionally substituted cyclopropyl ring.

$R^b$ and m compounds of formula (I), (I-i), (I-ii), and (I-iii) are as described in the Summary. In certain embodiments, m is 0. In certain embodiments, m is 1. In certain embodiments, $R^b$, at each occurrence, are the same or different, and are each independently alkyl, halogen, haloalkyl, or $OR^x$ (e.g. OH). In certain embodiments, each $R^b$ is the same or different, and is alkyl (e.g. methyl) or $OR^x$ (e.g. OH).

In certain embodiments, m is 1, $R^b$ is methyl or OH. In the embodiment that m is 1, $R^b$, for example, is attached to the carbon atom that bears the $G^2$ moiety.

$G^2$ in formula (I), (I-i), (I-ii), and (I-iii) has values as described in the Summary and embodiments herein.

In certain embodiments, $G^2$ is optionally substituted aryl (e.g. optionally substituted phenyl), optionally substituted heteroaryl (e.g. optionally substituted monocyclic heteroaryl such as, but not limited to, pyridinyl, thiazolyl, oxazolyl, each of which is optionally substituted), or optionally substituted cycloalkyl (e.g. monocyclic cycloalkyl such as, but not limited to, optionally substituted cyclohexyl).

In certain embodiments, $G^2$ is optionally substituted aryl (e.g. optionally substituted phenyl).

In certain embodiments, $G^2$ is optionally substituted phenyl.

In certain embodiments, $G^2$ is unsubstituted phenyl.

In certain embodiments, $G^2$ is optionally substituted heteroaryl (e.g. optionally substituted monocyclic heteroaryl such as, but not limited to, pyridinyl, thiazolyl, oxazolyl, each of which is optionally substituted).

In certain embodiments, $G^2$ is optionally substituted cycloalkyl (e.g. monocyclic cycloalkyl such as, but not limited to, optionally substituted cyclohexyl).

The optional substituents of $G^2$ are as described in the Summary. For example, in certain embodiments, the optional substituents of $G^2$ are selected from the group consisting of alkyl (e.g. methyl, ethyl, tert-butyl), halogen (e.g. F), haloalkyl (e.g. trifluoromethyl), —$OR^f$, —$SR^f$, and —$N(R^f)(R^g)$. $R^f$ and $R^g$ are as defined in the Summary, for example, $R^f$ and $R^g$ are the same of different, and are each independently hydrogen, alkyl, or haloalkyl.

It is appreciated that compounds of formula (I), (I-i), (I-ii), and (I-iii) with combinations of the above embodiments, including particular, more particular, and preferred embodiments are contemplated.

Accordingly, one aspect is directed to a group of compounds of formula (I) and (I-i) wherein $X^1$, $X^2$, and $X^3$ are $C(R^a)$, J is $C(R^{1J}R^{2J})$ and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-i) wherein $X^1$, $X^2$, and $X^3$ are $C(R^a)$, ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-i) wherein $X^1$, $X^2$, and $X^3$ are $C(R^a)$, ===== is a double bond, and J is $CR^{3J}$, wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-i) wherein $X^1$, $X^2$, and $X^3$ are $C(R^a)$, and L is $C(R^{1L}R^{2L})C(R^{1L}R^{2L})$, $C(R^{1L}R^{2L})$, $NR^{3L}$, $C(R^{4L}R^{5L})NR^{6L}$, $C(O)NR^{6L}$, or N=$CR^{7L}$. In certain embodiments, L is $C(R^{1L}R^{2L})$, $NR^{3L}$, $C(O)NR^{6L}$, or N=$CR^{7L}$. In certain embodiments, L is $C(O)NR^{6L}$. In certain embodiments, L is $C(R^{1L}R^{2L})C(R^{1L}R^{2L})$ or $C(R^{1L}R^{2L})$. In certain embodiments, L is $NR^{3L}$. In certain embodiments, L is $C(R^{4L}R^{5L})$—$NR^{6L}$. In certain embodiments, L is N=$CR^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

Another aspect is directed to a group of compounds of formula (I) and (I-i) wherein $X^1$, $X^2$, and $X^3$ are $C(R^a)$, J is $CR^{3J}$, K is N or $CR^{3k}$, L is $NR^{3L}$, and ===== is a double bond. $R^a$, $R^{3k}$, $R^{3J}$, and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-i) wherein $X^1$, $X^2$, and $X^3$ are $C(R^a)$, J is $CR^{3J}$, K is N, L is $NR^{3L}$, and ===== is a double bond. $R^a$, $R^{3J}$, and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-i) wherein $X^1$, $X^2$, and $X^3$ are $C(R^a)$, ===== is a single bond, J is $C(R^{1J}R^{2J})$, L is $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-i) wherein $X^1$, $X^2$, and $X^3$ are $C(R^a)$, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-i) wherein $X^1$, $X^2$, and $X^3$ are $C(R^a)$, J is $C(R^{1J}R^{2J})$, K is $C(R^{1k}R^{2k})$, L is $C(O)NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

Another aspect is directed to a group of compounds of formula (I) and (I-i) wherein $X^1$, $X^2$, and $X^3$ are $C(R^a)$, J is $C(R^{1J}R^{2J})$, K is $NR^{4k}$, L is $C(O)NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$, for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-i) wherein $X^1$, $X^2$, and $X^3$ are $C(R^a)$, J is $CR^{3J}$, K is $CR^{3k}$, L is $C(O)NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-i) wherein $X^1$, $X^2$, and $X^3$ are $C(R^a)$, J is O, K is $C(R^{1k}R^{2k})$, L is $C(O)NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-i) wherein $X^1$, $X^2$, and $X^3$ are $C(R^a)$, ===== is a double bond, J is $CR^{3J}$, K is $CR^{3k}$, and L is N=$CR^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-i) wherein $X^1$, $X^2$, and $X^3$ are $C(R^a)$, J is O, K is $C(R^{1k}R^{2k})$, L is $C(R^{4L}R^{5L})$—$NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

Another aspect is directed to a group of compounds of formula (I) and (I-i) wherein one of $X^1$, $X^2$, and $X^3$ is N and the others are $C(R^a)$, J is $C(R^{1J}R^{2J})$, and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-i) wherein one of $X^1$, $X^2$, and $X^3$ is N and the others are $C(R^a)$, ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-i) wherein one of $X^1$, $X^2$, and $X^3$ is N and the others are $C(R^a)$, ===== is a double bond, and J is $CR^{3J}$ wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-i) wherein one of $X^1$, $X^2$, and $X^3$ is N and the others are $C(R^a)$, and L is $C(R^{1L}R^{2L})C(R^{1L}R^{2L})$, $C(R^{1L}R^{2L})$, $NR^{3L}$, $C(R^{4L}R^{5L})NR^{6L}$, $C(O)NR^{6L}$, or $N=CR^{7L}$. In certain embodiments, L is $C(R^{1L}R^{2L})$, $NR^{3L}$, $C(O)NR^{6L}$, or $N=CR^{7L}$. In certain embodiments, L is $C(O)NR^{6L}$. In certain embodiments, L is $C(R^{1L}R^{2L})C(R^{1L}R^{2L})$ or $C(R^{1L}R^{2L})$. In certain embodiments, L is $NR^{3L}$. In certain embodiments, L is $C(R^{4L}R^{5L})$—$NR^{6L}$. In certain embodiments, L is $N=CR^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl)l, or halogen (e.g. Cl).

Another aspect is directed to a group of compounds of formula (I) and (I-i) wherein one of $X^1$, $X^2$, and $X^3$ is N and the others are $C(R^a)$, J is $CR^{3J}$, K is N or $CR^{3k}$, L is $NR^{3L}$, and ===== $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-i) wherein one of $X^1$, $X^2$, and $X^3$ is N and the others are $C(R^a)$, J is $CR^{3J}$, K is N, L is $NR^{3L}$, and ===== is a double bond. $R^a$, $R^{3J}$, and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-i) wherein one of $X^1$, $X^2$, and $X^3$ is N and the others are $C(R^a)$, ===== is a single bond, J is $C(R^{1J}R^{2J})$, L is $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-i) wherein one of $X^1$, $X^2$, and $X^3$ is N and the others are $C(R^a)$, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-i) wherein one of $X^1$, $X^2$, and $X^3$ is N and the others are $C(R^a)$, J is $C(R^{1J}R^{2J})$, K is $C(R^{1k}R^{2k})$, L is $C(O)NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

Another aspect is directed to a group of compounds of formula (I) and (I-i) wherein one of $X^1$, $X^2$, and $X^3$ is N and the others are $C(R^a)$, J is $C(R^{1J}R^{2J})$, K is $NR^{4k}$, L is $C(O)NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$ for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-i) wherein one of $X^1$, $X^2$, and $X^3$ is N and the others are $C(R^a)$, J is $CR^{3J}$, K is $CR^{3k}$, L is $C(O)NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-i) wherein one of $X^1$, $X^2$, and $X^3$ is N and the others are $C(R^a)$, J is O, K is $C(R^{1k}R^{2k})$, L is $C(O)NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-i) wherein one of $X^1$, $X^2$, and $X^3$ is N and the others are $C(R^a)$, ===== is a double bond, J is $CR^{3J}$, K is $CR^{3k}$, and L is $N=CR^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-i) wherein one of $X^1$, $X^2$, and $X^3$ is N and the others are $C(R^a)$, J is O, K is $C(R^{1k}R^{2k})$, L is $C(R^{4L}R^{5L})$—$NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$, are the same or different, and are each independently hydrogen or alkyl (e.g. methyl).

Another aspect is directed to a group of compounds of formula (I) and (I-ii) wherein $X^1$, $X^2$, and $X^4$ are $C(R^a)$, J is $C(R^{1J}R^{2J})$ and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-ii) wherein $X^1$, $X^2$, and $X^4$ are $C(R^a)$, ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-ii) wherein $X^1$, $X^2$, and $X^4$ are $C(R^a)$, ===== is a double bond, and J is $CR^{3J}$, wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-ii) wherein $X^1$, $X^2$, and $X^4$ are $C(R^a)$, and L is $C(R^{1L}R^{2L})C(R^{1L}R^{2L})$, $C(R^{1L}R^{2L})$, $NR^{3L}$, $C(R^{4L}R^{5L})NR^{6L}$, $C(O)NR^{6L}$, or $N=CR^{7L}$. In certain embodiments, L is $C(R^{1L}R^{2L})$, $NR^{3L}$, $C(O)NR^{6L}$, or $N=CR^{7L}$. In certain embodiments, L is $C(O)NR^{6L}$. In certain embodiments, L is $C(R^{1L}R^{2L})C(R^{1L}R^{2L})$ or $C(R^{1L}R^{2L})$. In certain embodiments, L is $NR^{3L}$. In certain embodiments, L is $C(R^{4L}R^{5L})—NR^{6L}$. In certain embodiments, L is $N=CR^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

Another aspect is directed to a group of compounds of formula (I) and (I-ii) wherein $X^1$, $X^2$, and $X^4$ are $C(R^a)$, J is $CR^{3J}$, K is N or $CR^{3k}$, L is $NR^{3L}$, and ===== is a double bond. $R^a$, $R^k$, $R^{3J}$, and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-ii) wherein $X^1$, $X^2$, and $X^4$ are $C(R^a)$, J is $CR^{3J}$, K is N, L is $NR^{3L}$, and ===== is a double bond. $R^a$, $R^{3J}$, and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-ii) wherein $X^1$, $X^2$, and $X^4$ are $C(R^a)$, ===== is a single bond, J is $C(R^{1J}R^{2J})$, L is $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-ii) wherein $X^1$, $X^2$, and $X^4$ are $C(R^a)$, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-ii) wherein $X^1$, $X^2$, and $X^4$ are $C(R^a)$, J is $C(R^{1J}R^{2J})$, K is $C(R^{1k}R^{2k})$, L is $C(O)NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

Another aspect is directed to a group of compounds of formula (I) and (I-ii) wherein $X^1$, $X^2$, and $X^4$ are $C(R^a)$, J is $C(R^{1J}R^{2J})$, K is $NR^{4k}$, L is $C(O)NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$, for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-ii) wherein $X^1$, $X^2$, and $X^4$ are $C(R^a)$, J is $CR^{3J}$, K is $CR^{3k}$, L is $C(O)NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-ii) wherein $X^1$, $X^2$, and $X^4$ are $C(R^a)$, J is O, K is $C(R^{1k}R^{2k})$, L is $C(O)NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-ii) wherein $X^1$, $X^2$, and $X^4$ are $C(R^a)$, ===== is a double bond, J is $CR^{3J}$, K is $CR^{3k}$, and L is $N=CR^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-ii) wherein $X^1$, $X^2$, and $X^4$ are $C(R^a)$, J is O, K is $C(R^{1k}R^{2k})$, L is $C(R^{4L}R^{5L})—NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

Another aspect is directed to a group of compounds of formula (I) and (I-ii) wherein one of $X^1$, $X^2$, and $X^4$ is N and the others are $C(R^a)$, J is $C(R^{1J}R^{2J})$ and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-ii) wherein one of $X^1$, $X^2$, and $X^4$ is N and the others are $C(R^a)$, ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-ii) wherein one of $X^1$, $X^2$, and $X^4$ is N and the others are $C(R^a)$, ===== is a double bond, and J is $CR^{3J}$, wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-ii) wherein one of $X^1$, $X^2$, and $X^4$ is N and the others are $C(R^a)$, and L is $C(R^{1L}R^{2L})C(R^{1L}R^{2L})$, $C(R^{1L}R^{2L})$, $NR^{3L}$, $C(R^{4L}R^{5L})NR^{6L}$, $C(O)NR^{6L}$, or $N=CR^{7L}$. In certain embodiments, L is $C(O)NR^{6L}$. In certain embodiments, L is $C(R^{1L}R^{2L})C(R^{1L}R^{2L})$ or $C(R^{1L}R^{2L})$. In certain embodiments, L is $NR^{3L}$. In certain embodiments, L is $C(R^{4L}R^{5L})$—$NR^{6L}$. In certain embodiments, L is $N=CR^{7L}$. In certain embodiments, L is $C(R^{1L}R^{2L})$, $NR^{3L}$, $C(O)NR^{6L}$, or $N=CR^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

Another aspect is directed to a group of compounds of formula (I) and (I-ii) wherein one of $X^1$, $X^2$, and $X^4$ is N and the others are $C(R^a)$, J is $CR^{3J}$, K is N or $CR^{3k}$, L is $NR^{3L}$, and ===== is a double bond. $R^a$, $R^k$, $R^{3J}$, and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-ii) wherein one of $X^1$, $X^2$, and $X^4$ is N and the others are $C(R^a)$, J is $CR^{3J}$, K is N, L is $NR^{3L}$, and ===== is a double bond. $R^a$, $R^{3J}$, and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-ii) wherein one of $X^1$, $X^2$, and $X^4$ is N and the others are $C(R^a)$, ===== is a single bond, J is $C(R^{1J}R^{2J})$, L is $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-ii) wherein one of $X^1$, $X^2$, and $X^4$ is N and the others are $C(R^a)$, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$, wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-ii) wherein one of $X^1$, $X^2$, and $X^4$ is N and the others are $C(R^a)$, J is $C(R^{1J}R^{2J})$, K is $C(R^{1k}R^{2k})$, L is $C(O)NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

Another aspect is directed to a group of compounds of formula (I) and (I-ii) wherein one of $X^1$, $X^2$, and $X^4$ is N and the others are $C(R^a)$, J is $C(R^{1J}R^{2J})$, K is $NR^{4k}$, L is $C(O)NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$ for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-ii) wherein one of $X^1$, $X^2$, and $X^4$ is N and the others are $C(R^a)$, J is $CR^{3J}$, K is $CR^{3k}$, L is $C(O)NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-ii) wherein one of $X^1$, $X^2$, and $X^4$ is N and the others are $C(R^a)$, J is O, K is $C(R^{1k}R^{2k})$, L is $C(O)NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-ii) wherein one of $X^1$, $X^2$, and $X^4$ is N and the others are $C(R^a)$, ===== is a double bond, J is $CR^{3J}$, K is $CR^{3k}$, and L is $N=CR^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-ii) wherein one of $X^1$, $X^2$, and $X^4$ is N and the others are $C(R^a)$, J is O, K is $C(R^{1k}R^{2k})$, L is $C(R^{4L}R^{5L})$—$NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

Another aspect is directed to a group of compounds of formula (I) and (I-iii) wherein $X^1$, $X^3$, and $X^4$ are $C(R^a)$, J is $C(R^{1J}R^{2J})$ and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-iii) wherein $X^1$, $X^3$, and $X^4$ are $C(R^a)$, ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-iii) wherein $X^1$, $X^3$, and $X^4$ are $C(R^a)$, ===== is a double bond, and J is $CR^{3J}$, wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-iii) wherein $X^1$, $X^3$, and $X^4$ are C($R^a$), and L is C($R^{1L}R^{2L}$)C($R^{1L}R^{2L}$), C($R^{1L}R^{2L}$), $NR^{3L}$, C($R^{4L}R^{5L}$)$NR^{6L}$, C(O)$NR^{6L}$, or N=C$R^{7L}$. In certain embodiments, L is C($R^{1L}R^{2L}$), $NR^{3L}$, C(O)$NR^{6L}$, or N=C$R^{7L}$. In certain embodiments, L is C(O)$NR^{6L}$. In certain embodiments, L is C($R^{1L}R^{2L}$)C($R^{1L}R^{2L}$) or C($R^{1L}R^{2L}$). In certain embodiments, L is $NR^{3L}$. In certain embodiments, L is C($R^{4L}R^{5L}$)—$NR^{6L}$. In certain embodiments, L is N=C$R^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

Another aspect is directed to a group of compounds of formula (I) and (I-iii) wherein $X^1$, $X^3$, and $X^4$ are C($R^a$), J is C$R^{3J}$, K is N or C$R^{3k}$, L is $NR^{3L}$, and ===== is a double bond. $R^a$, $R^k$, $R^{3J}$, and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-iii) wherein $X^1$, $X^3$, and $X^4$ are C($R^a$), J is C$R^{3J}$, K is N, L is $NR^{3L}$, and ===== is a double bond. $R^a$, $R^{3J}$ and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-iii) wherein $X^1$, $X^3$, and $X^4$ are C($R^a$), ===== is a single bond, J is C($R^{1J}R^{2J}$), L is C($R^{1L}R^{2L}$), and K is C($R^{1k}R^{2k}$); wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-iii) wherein $X^1$, $X^3$, and $X^4$ are C($R^a$), ===== is a single bond, J is C($R^{1J}R^{2J}$), L is C($R^{1L}R^{2L}$)C($R^{1L}R^{2L}$) or C($R^{1L}R^{2L}$), and K is C($R^{1k}R^{2k}$); wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-iii) wherein $X^1$, $X^3$, and $X^4$ are C($R^a$), J is C($R^{1J}R^{2J}$), K is C($R^{1k}R^{2k}$), L is C(O)$NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or N($R^x$)($R^{1xa}$); or $R^{2k}$, for example, is hydrogen or N($R^x$)($R^{1xa}$).

Another aspect is directed to a group of compounds of formula (I) and (I-iii) wherein $X^1$, $X^3$, and $X^4$ are C($R^a$), J is C($R^{1J}R^{2J}$), K is $NR^{4k}$, L is C(O)$NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$, for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-iii) wherein $X^1$, $X^3$, and $X^4$ are C($R^a$), J is C$R^{3J}$, K is C$R^{3k}$, L is C(O)$NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-iii) wherein $X^1$, $X^3$, and $X^4$ are C($R^a$), J is O, K is C($R^{1k}R^{2k}$), L is C(O)$NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-iii) wherein $X^1$, $X^3$, and $X^4$ are C($R^a$), ===== is a double bond, J is C$R^{3J}$, K is C$R^{3k}$, and L is N=C$R^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or N($R^x$)$_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-iii) wherein $X^1$, $X^3$, and $X^4$ are C($R^a$), J is O, K is C($R^{1k}R^{2k}$), L is C($R^{4L}R^{5L}$)—$NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

Another aspect is directed to a group of compounds of formula (I) and (I-iii) wherein one of $X^1$, $X^3$, and $X^4$ is N and the others are C($R^a$), J is C($R^{1J}R^{2J}$) and ===== is a single bond; wherein $R^a$, $R^{1J}$, and $R^{2J}$ are the same or different, and are as described in the Summary and embodiments herein above, for example, $R^{1J}$ and $R^{2J}$ are the same or different, and are each independently hydrogen or alkyl (e.g. methyl, ethyl), or for example, $R^{1J}$ and $R^{2J}$ are hydrogen.

Another aspect is directed to a group of compounds of formula (I) and (I-iii) wherein one of $X^1$, $X^3$, and $X^4$ is N and the others are C($R^a$), ===== is a single bond, and J is $NR^{4J}$ or O; wherein $R^a$ and $R^{4J}$ are as described in the Summary and embodiments herein above, for example, $R^{4J}$ is hydrogen. In certain embodiments, J is O.

Another aspect is directed to a group of compounds of formula (I) and (I-iii) wherein one of $X^1$, $X^3$, and $X^4$ is N and the others are C($R^a$), ===== is a double bond, and J is C$R^{3J}$, wherein $R^a$ and $R^{3J}$ are as described in the Summary and embodiments herein above, for example, $R^{3J}$ is hydrogen or alkyl (e.g. methyl), or for example, $R^{3J}$ is hydrogen.

Another aspect is directed to a group of compounds of formula (I) and (I-iii) wherein one of $X^1$, $X^3$, and $X^4$ is N and the others are C($R^a$), and L is C($R^{1L}R^{2L}$)C($R^{1L}R^{2L}$), C($R^{1L}R^{2L}$), $NR^{3L}$, C($R^{4L}R^{5L}$)$NR^{6L}$, C(O)$NR^{6L}$, or N=C$R^{7L}$. In certain embodiments, L is C($R^{1L}R^{2L}$), $NR^{3L}$, C(O)$NR^{6L}$, or N=C$R^{7L}$. In certain embodiments, L is C(O)$NR^{6L}$. In certain embodiments, L is C($R^{1L}R^{2L}$)C($R^{1L}R^{2L}$) or C($R^{1L}R^{2L}$). In certain embodiments, L is $NR^{3L}$. In certain embodiments, L is $C(R^{4L}R^{5L})$—$NR^{6L}$. In certain embodiments, L is N=$CR^{7L}$. $R^a$, $R^{1L}$, $R^{2L}$, $R^{3L}$, $R^{4L}$, $R^{5L}$, $R^{6L}$, and $R^{7L}$ are as described in the Summary and embodiments herein above, for example, $R^{1L}$, $R^{2L}$, $R^{3L}$, $R^{4L}$, $R^{5L}$, and $R^{6L}$, are the same or different, and are each independently hydrogen or alkyl (e.g. methyl), or for example, $R^{1L}$, $R^{2L}$, $R^{3L}$, $R^{4L}$, $R^{5L}$, and $R^{6L}$ are hydrogen. $R^{7L}$, for example, is hydrogen, alkyl (e.g. methyl), or halogen (e.g. Cl).

Another aspect is directed to a group of compounds of formula (I) and (I-iii) wherein one of $X^1$, $X^3$, and $X^4$ is N and the others are $C(R^a)$, J is $CR^{3J}$, K is N or $CR^{3k}$, L is $NR^{3L}$, and ===== is a double bond. $R^a$, $R^k$, $R^{3J}$, and $R^{3L}$ are as described in the Summary, for example, $R^{3k}$, $R^{3J}$, and $R^{3L}$ are the same or different, and are each independently hydrogen or alkyl (e.g. methyl), or for example, $R^{3k}$, $R^{3J}$, and $R^{3L}$ are hydrogen.

Another aspect is directed to a group of compounds of formula (I) and (I-iii) wherein one of $X^1$, $X^3$, and $X^4$ is N and the others are $C(R^a)$, J is $CR^{3J}$, K is N, L is $NR^{3L}$, and ===== is a double bond. $R^a$, $R^{3J}$, and $R^{3L}$ are as described in the Summary and embodiments herein above, for example, $R^{3J}$ and $R^{3L}$ are the same or different, and are each independently hydrogen or alkyl (e.g. methyl), or for example, $R^{3J}$ and $R^{3L}$ are hydrogen.

Another aspect is directed to a group of compounds of formula (I) and (I-iii) wherein one of $X^1$, $X^3$, and $X^4$ is N and the others are $C(R^a)$, ===== is a single bond, J is $C(R^{1J}R^{2J})$, L is $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary and embodiments herein above, for example, $R^{1J}$, $R^{2J}$, $R^{1L}$, $R^{2L}$, and $R^{1k}$ are the same or different, and are each independently hydrogen or alkyl, and $R^{2k}$ is OH; or for example, $R^{1J}$, $R^{2J}$, $R^{1L}$, $R^{2L}$, and $R^{1k}$ are hydrogen, and $R^{2k}$ is OH.

Another aspect is directed to a group of compounds of formula (I) and (I-iii) wherein one of $X^1$, $X^3$, and $X^4$ is N and the others are $C(R^a)$, ===== is a single bond, J is $C(R^{1J}R^{2J})$, L is $C(R^{1L}R^{2L})C(R^{1L}R^{2L})$ or $C(R^{1L}R^{2L})$, and K is $C(R^{1k}R^{2k})$; wherein $R^a$, $R^{1J}$, $R^{2J}$, $R^{1L}$, $R^{2L}$, $R^{1k}$, and $R^{2k}$ are as described in the Summary, for example, $R^{1J}$, $R^{2J}$, $R^{1L}$, $R^{2L}$, $R^{1k}$, and $R^{2k}$, are the same or different, and are each independently hydrogen or alkyl (e.g. methyl); or for example, $R^{1J}$, $R^{2J}$, $R^{1L}$, $R^{2L}$, $R^{1k}$, and $R^{2k}$ are hydrogen.

Another aspect is directed to a group of compounds of formula (I) and (I-iii) wherein one of $X^1$, $X^3$, and $X^4$ is N and the others are $C(R^a)$, J is $C(R^{1J}R^{2J})$, K is $C(R^{1k}R^{2k})$, L is $C(O)NR^{6L}$, and ===== is a single bond. $R^a$, $R^{1J}$, $R^{2J}$, $R^{1k}$, $R^{2k}$, and $R^{6L}$ are as described in the Summary and embodiments herein above, for example, $R^{1J}$, $R^{2J}$, $R^{1k}$, and $R^{6L}$ are the same or different, and at each occurrence, are each independently hydrogen, alkyl, or haloalkyl, or for example, $R^{1J}$, $R^{2J}$, $R^{1k}$, and $R^{6L}$ are the same or different, and are each independently hydrogen or alkyl (e.g. methyl, ethyl). $R^{2k}$, for example, is hydrogen, alkyl (e.g. methyl), or $N(R^x)(R^{1xa})$; or $R^{2k}$, for example, is hydrogen or $N(R^x)(R^{1xa})$.

Another aspect is directed to a group of compounds of formula (I) and (I-iii) wherein one of $X^1$, $X^3$, and $X^4$ is N and the others are $C(R^a)$, J is $C(R^{1J}R^{2J})$, K is $NR^{4k}$, L is $C(O)NR^{6L}$, and ===== is a single bond. $R^a$, $R^{1J}$, $R^{2J}$, $R^{4k}$, and $R^{6L}$ are as described in the Summary, for example, $R^{1J}$, $R^{2J}$, and $R^{6L}$ are the same or different, and at each occurrence, are each independently hydrogen or alkyl (e.g. methyl, ethyl), or $R^{1J}$, $R^{2J}$, and $R^{6L}$ are hydrogen. $R^{4k}$ for example, is alkyl (e.g. methyl) or hydroxyalkyl (e.g. 2-hydroxyethyl), or $R^{4k}$, for example, is hydroxyalkyl (e.g. 2-hydroxyethyl).

Another aspect is directed to a group of compounds of formula (I) and (I-iii) wherein one of $X^1$, $X^3$, and $X^4$ is N and the others are $C(R^a)$, J is $CR^{3J}$, K is $CR^{3k}$, L is $C(O)NR^{6L}$, and ===== is a double bond. $R^a$, $R^{3J}$, $R^{3k}$, and $R^{6L}$ are as described in the Summary and embodiments herein above, for example, $R^{3J}$, $R^{3k}$, and $R^{6L}$ are the same or different, and at each occurrence, are each independently hydrogen, alkyl, or haloalkyl, or for example, $R^{3J}$, $R^{3k}$, and $R^{6L}$ are the same or different, and are each independently hydrogen or alkyl (e.g. methyl).

Another aspect is directed to a group of compounds of formula (I) and (I-iii) wherein one of $X^1$, $X^3$, and $X^4$ is N and the others are $C(R^a)$, J is O, K is $C(R^{1k}R^{2k})$, L is $C(O)NR^{6L}$, and ===== is a single bond. $R^a$, $R^{1k}$, $R^{2k}$, and $R^{6L}$ are as described in the Summary and embodiments herein above, for example, $R^{1k}$, $R^{2k}$, and $R^{6L}$ are the same or different, and are each independently hydrogen, alkyl, or haloalkyl, or for example, $R^{1k}$, $R^{2k}$, and $R^{6L}$ are the same or different, and are each independently hydrogen or alkyl (e.g. methyl).

Another aspect is directed to a group of compounds of formula (I) and (I-iii) wherein one of $X^1$, $X^3$, and $X^4$ is N and the others are $C(R^a)$, ===== is a double bond, J is $CR^{3J}$, K is $CR^{3k}$, and L is N=$CR^{7L}$; wherein $R^a$, $R^{3J}$, $R^{3k}$, and $R^{7L}$ are as described in the Summary and embodiments herein above, for example, $R^{3J}$ is hydrogen, $R^{3k}$ is hydrogen, alkyl (e.g. methyl, ethyl, 2-methylpropyl, isopropyl), or $N(R^x)_2$ wherein $R^x$ is as described in the Summary, and $R^{7L}$ is hydrogen, alkyl (e.g. methyl), or halogen (e.g. Cl).

Another aspect is directed to a group of compounds of formula (I) and (I-iii) wherein one of $X^1$, $X^3$, and $X^4$ is N and the others are $C(R^a)$, J is O, K is $C(R^{1k}R^{2k})$, L is $C(R^{4L}R^{5L})$—$NR^{6L}$, and ===== is a single bond, wherein $R^a$, $R^{1k}$, $R^{2k}$, $R^{4L}$, $R^{5L}$, and $R^{6L}$, are as described in the Summary, for example, $R^{1k}$, $R^{2k}$, $R^{4L}$, $R^{5L}$, and $R^{6L}$ are the same or different, and are each independently hydrogen or alkyl (e.g. methyl).

Within each group of compounds of formula (I), (I-i), (I-ii), and (I-iii) described above, $X^5$-$X^6$, and $G^2$ are as described in the Summary and embodiments herein above.

Thus, within each group of compounds of formula (I), (I-i), (I-ii), and (I-iii) described above, examples of a subgroup include those wherein $X^5$-$X^6$ is $C(R^{3a}R^{3b})$, $C(R^3R^4)C(R^5R^6)$ or $C(R^9R^{10})C(R^{11}R^{12})C(R^{13}R^{14})$.

Examples of another subgroup include those wherein $X^5$-$X^6$ is $C(R^3R^4)C(R^5R^6)$ or $C(R^9R^{10})C(R^{11}R^{12})C(R^{13}R^{14})$.

Examples of another subgroup include those wherein $X^5$-$X^6$ is $C(R^{3a}R^{3b})$.

Examples of another subgroup include those wherein $X^5$-$X^6$ is $C(R^3R^4)C(R^5R^6)$.

Examples of yet another subgroup include those wherein $X^5$-$X^6$ is $CR^7$=$CR^8$.

Examples of yet another subgroup include those wherein $X^5$-$X^6$ is $C(R^9R^{10})C(R^{11}R^{12})C(R^{13}R^{14})$.

Examples of still another subgroup include those wherein $X^5$-$X^6$ is $C(R^3R^4)C(R^5R^6)$ or $C(R^9R^{10})C(R^{11}R^{12})C(R^{13}R^{14})$, and $G^2$ is optionally substituted aryl (e.g. optionally substituted phenyl), optionally substituted heteroaryl (e.g. optionally substituted monocyclic heteroaryl such as, but not limited to, pyridinyl, thiazolyl, oxazolyl, each of which is optionally substituted), or optionally substituted cycloalkyl (e.g. optionally substituted monocyclic cycloalkyl).

Examples of another subgroup include those wherein $X^5$-$X^6$ is $C(R^3R^4)C(R^5R^6)$, and $G^2$ is optionally substituted aryl (e.g. optionally substituted phenyl), optionally substituted heteroaryl (e.g. optionally substituted monocyclic heteroaryl such as, but not limited to, pyridinyl, thiazolyl, oxazolyl, each of which is optionally substituted), or optionally substituted cycloalkyl (e.g. optionally substituted monocyclic cycloalkyl).

Examples of yet another subgroup include those wherein $X^5$-$X^6$ is $CR^7$=$CR^8$, and $G^2$ is optionally substituted aryl (e.g. optionally substituted phenyl), optionally substituted heteroaryl (e.g. optionally substituted monocyclic heteroaryl such as, but not limited to, pyridinyl, thiazolyl, oxazolyl, each of which is optionally substituted), or optionally substituted cycloalkyl (e.g. optionally substituted monocyclic cycloalkyl).

Examples of yet another subgroup include those wherein $X^5$-$X^6$ is $C(R^9R^{10})C(R^{11}R^{12})C(R^{13}R^{14})$, and $G^2$ is optionally substituted aryl (e.g. optionally substituted phenyl), optionally substituted heteroaryl (e.g. optionally substituted monocyclic heteroaryl such as, but not limited to, pyridinyl, thiazolyl, oxazolyl, each of which is optionally substituted), or optionally substituted cycloalkyl (e.g. optionally substituted monocyclic cycloalkyl).

Examples of still another subgroup include those wherein $X^5$-$X^6$ is $C(R^3R^4)C(R^5R^6)$ or $C(R^9R^{10})C(R^{11}R^{12})C(R^{13}R^{14})$, and $G^2$ is optionally substituted aryl (e.g. optionally substituted phenyl).

Examples of another subgroup include those wherein $X^5$-$X^6$ is $C(R^3R^4)C(R^5R^6)$, and $G^2$ is optionally substituted aryl (e.g. optionally substituted phenyl).

Examples of yet another subgroup include those wherein $X^5$-$X^6$ is $CR^7$=$CR^8$, and $G^2$ is optionally substituted aryl (e.g. optionally substituted phenyl).

Examples of yet another subgroup include those wherein $X^5$-$X^6$ is $C(R^9R^{10})C(R^{11}R^{12})C(R^{13}R^{14})$, and $G^2$ is optionally substituted aryl (e.g. optionally substituted phenyl).

Examples of still another subgroup include those wherein $X^5$-$X^6$ is $C(R^3R^4)C(R^5R^6)$ or $C(R^9R^{10})C(R^{11}R^{12})C(R^{13}R^{14})$, and $G^2$ is optionally substituted phenyl.

Examples of another subgroup include those wherein $X^5$-$X^6$ is $C(R^3R^4)C(R^5R^6)$, and $G^2$ is optionally substituted phenyl.

Examples of yet another subgroup include those wherein $X^5$-$X^6$ is $CR^7$=$CR^8$, and $G^2$ is optionally substituted phenyl.

Examples of yet another subgroup include those wherein $X^5$-$X^6$ is $C(R^9R^{10})C(R^{11}R^{12})C(R^{13}R^{14})$, and $G^2$ is optionally substituted phenyl.

Examples of still another subgroup include those wherein $X^5$-$X^6$ is $C(R^3R^4)C(R^5R^6)$ or $C(R^9R^{10})C(R^{11}R^{12})C(R^{13}R^{14})$, $G^2$ is optionally substituted heteroaryl (e.g. optionally substituted monocyclic heteroaryl such as, but not limited to, pyridinyl, thiazolyl, oxazolyl, each of which is optionally substituted).

Examples of another subgroup include those wherein $X^5$-$X^6$ is $C(R^3R^4)C(R^5R^6)$, and $G^2$ is optionally substituted heteroaryl (e.g. optionally substituted monocyclic heteroaryl such as, but not limited to, pyridinyl, thiazolyl, oxazolyl, each of which is optionally substituted).

Examples of yet another subgroup include those wherein $X^5$-$X^6$ is $CR^7$=$CR^8$, and $G^2$ is optionally substituted heteroaryl (e.g. optionally substituted monocyclic heteroaryl such as, but not limited to, pyridinyl, thiazolyl, oxazolyl, each of which is optionally substituted).

Examples of yet another subgroup include those wherein $X^5$-$X^6$ is $C(R^9R^{10})C(R^{11}R^{12})C(R^{13}R^{14})$, and $G^2$ is optionally substituted heteroaryl (e.g. optionally substituted monocyclic heteroaryl such as, but not limited to, pyridinyl, thiazolyl, oxazolyl, each of which is optionally substituted).

Examples of still another subgroup include those wherein $X^5$-$X^6$ is $C(R^3R^4)C(R^5R^6)$ or $C(R^9R^{10})C(R^{11}R^{12})C(R^{13}R^{14})$, and $G^2$ is optionally substituted cycloalkyl (e.g. optionally substituted monocyclic cycloalkyl).

Examples of another subgroup include those wherein $X^5$-$X^6$ is $C(R^3R^4)C(R^5R^6)$, and $G^2$ is optionally substituted cycloalkyl (e.g. optionally substituted monocyclic cycloalkyl).

Examples of yet another subgroup include those wherein $X^5$-$X^6$ is $CR^7$=$CR^8$, and $G^2$ is optionally substituted cycloalkyl (e.g. optionally substituted monocyclic cycloalkyl).

Examples of yet another subgroup include those wherein $X^5$-$X^6$ is $C(R^9R^{10})C(R^{11}R^{12})C(R^{13}R^{14})$, and $G^2$ is optionally substituted cycloalkyl (e.g. optionally substituted monocyclic cycloalkyl).

Within each group and subgroups of compounds of formula (I), (I-i), (I-ii), and (I-iii) described above, $R^{3a}$, $R^{3b}$, $R^3$, $R^4$, $R^5$, $R^6$, $R^7$, $R^8$, $R^9$, $R^{10}$, $R^{11}$, $R^{12}$, $R^{13}$, $R^{14}$, $R^b$, m, $R^a$, and the optional substituents of $G^2$ have meanings as described in the Summary and Detailed Description sections.

Exemplary compounds include, but are not limited to,

1-[(2R)-2-hydroxy-2,3-dihydro-1H-inden-4-yl]-3-[(1R,3S)-3-phenylcyclopentyl]urea;
1-[(2S)-2-hydroxy-2,3-dihydro-1H-inden-4-yl]-3-[(1R,3S)-3-phenylcyclopentyl]urea;
1-[(2R)-2-methyl-3-oxo-3,4-dihydro-2H-1,4-benzoxazin-8-yl]-3-[(1R,3S)-3-phenylcyclopentyl]urea;
1-(1-methyl-1H-indazol-4-yl)-3-[(1R,3S)-3-phenylcyclopentyl]urea;
1-(2-oxo-1,2,3,4-tetrahydroquinolin-7-yl)-3-[(1R,3S)-3-phenylcyclopentyl]urea;
1-(6-fluoro-3-methylisoquinolin-5-yl)-3-[(1R,3S)-3-phenylcyclopentyl]urea;
1-(1H-indazol-4-yl)-3-[(1R,3S)-3-phenylcyclopentyl]urea;
1-[(2R)-2-hydroxy-2,3-dihydro-1H-inden-4-yl]-3-[(1S,3S)-3-phenylcyclopentyl]urea;
1-[(2S)-2-hydroxy-2,3-dihydro-1H-inden-4-yl]-3-[(1S,3S)-3-phenylcyclopentyl]urea;
1-[(2R)-2-methyl-3-oxo-3,4-dihydro-2H-1,4-benzoxazin-8-yl]-3-[(1S,3S)-3-phenylcyclopentyl]urea;
1-(1-methyl-1H-indazol-4-yl)-3-[(1S,3S)-3-phenylcyclopentyl]urea;
1-(2-oxo-1,2,3,4-tetrahydroquinolin-7-yl)-3-[(1S,3S)-3-phenylcyclopentyl]urea;
1-(6-fluoro-3-methylisoquinolin-5-yl)-3-[(1S,3S)-3-phenylcyclopentyl]urea;
1-(1H-indazol-4-yl)-3-[(1S,3S)-3-phenylcyclopentyl]urea;
1-[(2R)-2-hydroxy-2,3-dihydro-1H-inden-4-yl]-3-[(1R,3R)-3-phenylcyclopentyl]urea;
1-[(2S)-2-hydroxy-2,3-dihydro-1H-inden-4-yl]-3-[(1R,3R)-3-phenylcyclopentyl]urea;
1-[(2R)-2-methyl-3-oxo-3,4-dihydro-2H-1,4-benzoxazin-8-yl]-3-[(1R,3R)-3-phenylcyclopentyl]urea;
1-(1-methyl-1H-indazol-4-yl)-3-[(1R,3R)-3-phenylcyclopentyl]urea;
1-(2-oxo-1,2,3,4-tetrahydroquinolin-7-yl)-3-[(1R,3R)-3-phenylcyclopentyl]urea;
1-(6-fluoro-3-methylisoquinolin-5-yl)-3-[(1R,3R)-3-phenylcyclopentyl]urea;
1-(1H-indazol-4-yl)-3-[(1R,3R)-3-phenylcyclopentyl]urea;
1-[(2R)-2-hydroxy-2,3-dihydro-1H-inden-4-yl]-3-[(1S,3R)-3-phenylcyclopentyl]urea;
1-[(2S)-2-hydroxy-2,3-dihydro-1H-inden-4-yl]-3-[(1S,3R)-3-phenylcyclopentyl]urea;
1-[(2R)-2-methyl-3-oxo-3,4-dihydro-2H-1,4-benzoxazin-8-yl]-3-[(1S,3R)-3-phenylcyclopentyl]urea;
1-(1-methyl-1H-indazol-4-yl)-3-[(1S,3R)-3-phenylcyclopentyl]urea;
1-(2-oxo-1,2,3,4-tetrahydroquinolin-7-yl)-3-[(1S,3R)-3-phenylcyclopentyl]urea;
1-(6-fluoro-3-methylisoquinolin-5-yl)-3-[(1S,3R)-3-phenylcyclopentyl]urea;
1-(1H-indazol-4-yl)-3-[(1S,3R)-3-phenylcyclopentyl]urea;

1-[3-(4-tert-butylphenyl)cyclohexyl]-3-(1H-indazol-4-yl)urea;
1-(1H-indazol-4-yl)-3-{3-[4-(trifluoromethyl)phenyl]cyclohexyl}urea;
1-(1H-indazol-4-yl)-3-{(1R,3R)-3-[4-(trifluoromethyl)phenyl]cyclohexyl}urea;
1-(1H-indazol-4-yl)-3-{(1S,3S)-3-[4-(trifluoromethyl)phenyl]cyclohexyl}urea;
1-(1H-indazol-4-yl)-3-{(1S,3R)-3-[4-(trifluoromethyl)phenyl]cyclohexyl}urea;
1-(1H-indazol-4-yl)-3-{(1R,3S)-3-[4-(trifluoromethyl)phenyl]cyclohexyl}urea;
1-(1H-indazol-4-yl)-3-[(1S,3S)-3-phenylcyclohexyl]urea;
1-(1H-indazol-4-yl)-3-[(1R,3S)-3-phenylcyclohexyl]urea;
1-[3-(4-tert-butylphenyl)cyclopentyl]-3-(1H-indazol-4-yl)urea;
1-(1H-indazol-4-yl)-3-[cis-3-(pyridin-2-yl)cyclopentyl]urea;
1-(1H-indazol-4-yl)-3-[trans-3-(pyridin-2-yl)cyclopentyl]urea;
1-(1H-indazol-4-yl)-3-[3-(4-methoxyphenyl)cyclopentyl]urea;
1-(1H-indazol-4-yl)-3-{(1S,3S)-3-[4-(trifluoromethyl)phenyl]cyclopentyl}urea;
1-(1H-indazol-4-yl)-3-{(1R,3S)-3-[4-(trifluoromethyl)phenyl]cyclopentyl}urea;
1-(1H-indazol-4-yl)-3-{(1S,3R)-3-[4-(trifluoromethyl)phenyl]cyclopentyl}urea;
1-(1H-indazol-4-yl)-3-{(1R,3R)-3-[4-(trifluoromethyl)phenyl]cyclopentyl}urea;
1-[(3S)-3-(4-fluorophenyl)cyclopentyl]-3-(1H-indazol-4-yl)urea;
1-(1H-indazol-4-yl)-3-{(3S)-3-[4-(methylsulfanyl)phenyl]cyclopentyl}urea;
1-{(3S)-3-[4-(dimethylamino)phenyl]cyclopentyl}-3-(1H-indazol-4-yl)urea;
1-(1H-indazol-4-yl)-3-[(1S,4R)-4-phenylcyclopent-2-en-1-yl]urea;
1-((1S,3R)-3-cyclohexylcyclopentyl)-3-(1H-indazol-4-yl)urea;
1-(1-methyl-2-oxo-1,2-dihydroquinolin-5-yl)-3-((1S,3R)-3-phenylcyclopentyl)urea;
1-(1-methyl-2-oxo-1,2-dihydroquinolin-5-yl)-3-((1R,3S)-3-phenylcyclopentyl)urea;
1-[(1S,2S,3R,4S)-2,3-dihydroxy-4-phenylcyclopentyl]-3-(1H-indazol-4-yl)urea;
1-[(1S,2R,3S,4S)-2,3-dihydroxy-4-phenylcyclopentyl]-3-(1H-indazol-4-yl)urea;
1-[(1R,2R,4S,5R)-6,6-difluoro-4-phenylbicyclo[3.1.0]hex-2-yl]-3-(1H-indazol-4-yl)urea;
1-(1H-indazol-4-yl)-3-[(1S,2R,4S,5S)-4-phenylbicyclo[3.1.0]hex-2-yl]urea;
1-(1H-indazol-4-yl)-3-(cis-3-phenylcyclobutyl)urea;
1-(1H-indazol-4-yl)-3-(trans-3-phenylcyclobutyl)urea;
1-[(trans)-3-hydroxy-3-phenylcyclopentyl]-3-(1H-indazol-4-yl)urea;
1-[(2R)-2-hydroxy-2,3-dihydro-1H-inden-4-yl]-3-(trans-3-phenylcyclobutyl)urea;
1-[(2R)-2-hydroxy-2,3-dihydro-1H-inden-4-yl]-3-(cis-3-phenylcyclobutyl)urea;
1-[(1R,3S)-3-(2-fluorophenyl)cyclopentyl]-3-(1H-indazol-4-yl)urea;
1-[(1S,3S)-3-(2-fluorophenyl)cyclopentyl]-3-(1H-indazol-4-yl)urea;
1-(1H-indazol-4-yl)-3-[(1R,4S)-4-phenylcyclopent-2-en-1-yl]urea;
1-[(1S,3S)-3-(3-fluorophenyl)cyclopentyl]-3-(1H-indazol-4-yl)urea;
1-[(1R,3S)-3-(3-fluorophenyl)cyclopentyl]-3-(1H-indazol-4-yl)urea;
1-[(1R,3R)-3-(2-fluorophenyl)cyclopentyl]-3-(1H-indazol-4-yl)urea;
1-[(1S,3R)-3-(2-fluorophenyl)cyclopentyl]-3-(1H-indazol-4-yl)urea;
1-[(1R,3R)-3-(3-fluorophenyl)cyclopentyl]-3-(1H-indazol-4-yl)urea;
1-[(1S,3R)-3-(3-fluorophenyl)cyclopentyl]-3-(1H-indazol-4-yl)urea;
1-(6-fluoro-3-methylisoquinolin-5-yl)-3-[(1R,3S)-3-(2-fluorophenyl)cyclopentyl]urea;
1-(6-fluoro-3-methylisoquinolin-5-yl)-3-[(1S,3S)-3-(2-fluorophenyl)cyclopentyl]urea;
1-(1H-indazol-4-yl)-3-[(1S,3R)-3-methyl-3-phenylcyclopentyl]urea;
1-(1H-indazol-4-yl)-3-[(1R,3R)-3-methyl-3-phenylcyclopentyl]urea;
1-(6-fluoro-3-methylisoquinolin-5-yl)-3-[(1S,3S)-3-(3-fluorophenyl)cyclopentyl]urea;
1-(6-fluoro-3-methylisoquinolin-5-yl)-3-[(1R,3R)-3-methyl-3-phenylcyclopentyl]urea;
1-(6-fluoro-3-methylisoquinolin-5-yl)-3-[(1R,3S)-3-(3-fluorophenyl)cyclopentyl]urea;
1-(1-methyl-2-oxo-1,2,3,4-tetrahydroquinolin-7-yl)-3-[(1R,3S)-3-phenylcyclopentyl]urea;
1-[(1R,3R)-3-(3-fluorophenyl)cyclopentyl]-3-(1-methyl-2-oxo-1,2-dihydroquinolin-5-yl)urea;
1-[(1S,3R)-3-(3-fluorophenyl)cyclopentyl]-3-(1-methyl-2-oxo-1,2-dihydroquinolin-5-yl)urea;
1-[(1S,3R)-3-(2-fluorophenyl)cyclopentyl]-3-(1-methyl-2-oxo-1,2-dihydroquinolin-5-yl)urea;
1-[(1R,3R)-3-(2-fluorophenyl)cyclopentyl]-3-(1-methyl-2-oxo-1,2-dihydroquinolin-5-yl)urea;
1-(6-fluoro-3-methylisoquinolin-5-yl)-3-[(1R,3R)-3-(2-fluorophenyl)cyclopentyl]urea;
1-(6-fluoro-3-methylisoquinolin-5-yl)-3-[(1S,3R)-3-(2-fluorophenyl)cyclopentyl]urea;
1-(6-fluoro-3-methylisoquinolin-5-yl)-3-[(1R,3R)-3-(3-fluorophenyl)cyclopentyl]urea;
1-(6-fluoro-3-methylisoquinolin-5-yl)-3-[(1S,3R)-3-(3-fluorophenyl)cyclopentyl]urea;
1-[(1R,3R)-3-(3-fluorophenyl)cyclopentyl]-3-[(2S)-2-hydroxy-2,3-dihydro-1H-inden-4-yl]urea;
1-[(1S,3R)-3-(3-fluorophenyl)cyclopentyl]-3-[(2S)-2-hydroxy-2,3-dihydro-1H-inden-4-yl]urea;
1-[(1R,3R)-3-(2-fluorophenyl)cyclopentyl]-3-[(2S)-2-hydroxy-2,3-dihydro-1H-inden-4-yl]urea;
1-[(1S,3R)-3-(2-fluorophenyl)cyclopentyl]-3-[(2S)-2-hydroxy-2,3-dihydro-1H-inden-4-yl]urea;
1-[(1R,3R)-3-(3-fluorophenyl)cyclopentyl]-3-[(2R)-2-hydroxy-2,3-dihydro-1H-inden-4-yl]urea;
1-[(1S,3R)-3-(3-fluorophenyl)cyclopentyl]-3-[(2R)-2-hydroxy-2,3-dihydro-1H-inden-4-yl]urea;
1-[(1R,3R)-3-(2-fluorophenyl)cyclopentyl]-3-[(2R)-2-hydroxy-2,3-dihydro-1H-inden-4-yl]urea;
1-[(1S,3R)-3-(2-fluorophenyl)cyclopentyl]-3-[(2R)-2-hydroxy-2,3-dihydro-1H-inden-4-yl]urea;
1-(1-methyl-2-oxo-1,2,3,4-tetrahydroquinolin-5-yl)-3-[(1R,3S)-3-phenylcyclopentyl]urea;
1-(1-methyl-2-oxo-1,2,3,4-tetrahydroquinolin-5-yl)-3-[(1S,3R)-3-phenylcyclopentyl]urea;
1-(1-methyl-2-oxo-1,2,3,4-tetrahydroquinolin-5-yl)-3-[(1S,3S)-3-phenylcyclopentyl]urea;

1-[(1R,3R)-3-(3-fluorophenyl)cyclopentyl]-3-(1-methyl-2-oxo-1,2,3,4-tetrahydroquinolin-5-yl)urea;
1-[(1S,3R)-3-(3-fluorophenyl)cyclopentyl]-3-(1-methyl-2-oxo-1,2,3,4-tetrahydroquinolin-5-yl)urea;
1-[(1R,3R)-3-(2-fluorophenyl)cyclopentyl]-3-(1-methyl-2-oxo-1,2,3,4-tetrahydroquinolin-5-yl)urea;
1-[(1S,3R)-3-(2-fluorophenyl)cyclopentyl]-3-(1-methyl-2-oxo-1,2,3,4-tetrahydroquinolin-5-yl)urea;
1-[(1R,3R)-3-(3-fluorophenyl)cyclopentyl]-3-(1-methyl-1H-indazol-4-yl)urea;
1-[(1S,3R)-3-(3-fluorophenyl)cyclopentyl]-3-(1-methyl-1H-indazol-4-yl)urea;
1-[(1R,3R)-3-(2-fluorophenyl)cyclopentyl]-3-(1-methyl-1H-indazol-4-yl)urea;
1-[(1S,3R)-3-(2-fluorophenyl)cyclopentyl]-3-(1-methyl-1H-indazol-4-yl)urea;
1-(1-methyl-2-oxo-1,2,3,4-tetrahydroquinolin-7-yl)-3-[(1S,3R)-3-phenylcyclopentyl]urea;
1-(1-methyl-2-oxo-1,2,3,4-tetrahydroquinolin-7-yl)-3-[(1S,3S)-3-phenylcyclopentyl]urea;
1-[(1R,3R)-3-(3-fluorophenyl)cyclopentyl]-3-(1-methyl-2-oxo-1,2,3,4-tetrahydroquinolin-7-yl)urea;
1-[(1S,3R)-3-(3-fluorophenyl)cyclopentyl]-3-(1-methyl-2-oxo-1,2,3,4-tetrahydroquinolin-7-yl)urea;
1-[(1R,3R)-3-(2-fluorophenyl)cyclopentyl]-3-(1-methyl-2-oxo-1,2,3,4-tetrahydroquinolin-7-yl)urea;
1-[(1S,3R)-3-(2-fluorophenyl)cyclopentyl]-3-(1-methyl-2-oxo-1,2,3,4-tetrahydroquinolin-7-yl)urea;
1-(2,3-dihydro-1H-inden-4-yl)-3-[(1R,3S)-3-phenylcyclopentyl]urea;
1-(2,3-dihydro-1H-inden-4-yl)-3-[(1S,3S)-3-phenylcyclopentyl]urea;
1-[3-(2-hydroxyethyl)-2-oxo-1,2,3,4-tetrahydroquinazolin-7-yl]-3-[(1S,3R)-3-phenylcyclopentyl]urea;
1-[3-(2-hydroxyethyl)-2-oxo-1,2,3,4-tetrahydroquinazolin-7-yl]-3-[(1S,3S)-3-phenylcyclopentyl]urea;
1-[(1R,3R)-3-(3-fluorophenyl)cyclopentyl]-3-[3-(2-hydroxyethyl)-2-oxo-1,2,3,4-tetrahydroquinazolin-7-yl]urea;
1-[(1S,3R)-3-(3-fluorophenyl)cyclopentyl]-3-[3-(2-hydroxyethyl)-2-oxo-1,2,3,4-tetrahydroquinazolin-7-yl]urea;
1-[(1S,3R)-3-(2-fluorophenyl)cyclopentyl]-3-[3-(2-hydroxyethyl)-2-oxo-1,2,3,4-tetrahydroquinazolin-7-yl]urea;
1-(1-methyl-2-oxo-1,2-dihydroquinolin-5-yl)-3-[(1S,3S)-3-phenylcyclopentyl]urea;
1-(1H-indazol-4-yl)-3-[(trans)-3-(4-methyl-1,3-thiazol-2-yl)cyclopentyl]urea;
1-(1H-indazol-4-yl)-3-[(1S,3R)-3-(4-methyl-1,3-thiazol-2-yl)cyclopentyl]urea;
1-(1H-indazol-4-yl)-3-[(1R,3S)-3-(4-methyl-1,3-thiazol-2-yl)cyclopentyl]urea;
1-(1H-indazol-4-yl)-3-[(1S,3R)-3-(4-methyl-1,3-oxazol-2-yl)cyclopentyl]urea;
1-(1H-indazol-4-yl)-3-[(1R,3S)-3-(4-methyl-1,3-oxazol-2-yl)cyclopentyl]urea;
1-(2,3-dihydro-1H-inden-4-yl)-3-[(1S,3R)-3-phenylcyclopentyl]urea;
1-(6-fluoro-3-methylisoquinolin-5-yl)-3-[(1S,3R)-3-(5-methyl-1,3-oxazol-2-yl)cyclopentyl]urea;
1-(1H-indazol-4-yl)-3-[(1S,3R)-3-(5-methyl-1,3-oxazol-2-yl)cyclopentyl]urea;
1-(6-fluoro-3-methylisoquinolin-5-yl)-3-[(1R,3S)-3-(5-methyl-1,3-oxazol-2-yl)cyclopentyl]urea;
1-(1H-indazol-4-yl)-3-[(1R,3S)-3-(5-methyl-1,3-oxazol-2-yl)cyclopentyl]urea;
1-(1H-indazol-4-yl)-3-{(1R*,3R*)-3-[4-(trifluoromethyl)-1,3-thiazol-2-yl]cyclopentyl}urea;
1-(1H-indazol-4-yl)-3-{(1R*,3S*)-3-[4-(trifluoromethyl)-1,3-thiazol-2-yl]cyclopentyl}urea;
1-(1H-indazol-4-yl)-3-{(1R)-3-[4-(trifluoromethyl)-1,3-thiazol-2-yl]cyclopentyl}urea;
1-(6-fluoro-3-methylisoquinolin-5-yl)-3-[(1R,3S)-3-(4-methyl-1,3-thiazol-2-yl)cyclopentyl]urea;
1-(6-fluoro-3-methylisoquinolin-5-yl)-3-[(1R,3R)-3-(4-methyl-1,3-thiazol-2-yl)cyclopentyl]urea;
1-(6-fluoro-3-methylisoquinolin-5-yl)-3-[(1S,3S)-3-(4-methyl-1,3-thiazol-2-yl)cyclopentyl]urea;
1-(6-fluoro-3-methylisoquinolin-5-yl)-3-[(1S,3R)-3-(4-methyl-1,3-thiazol-2-yl)cyclopentyl]urea;
1-(1-chloroisoquinolin-5-yl)-3-[(1R,3S)-3-phenylcyclopentyl]urea;
1-(1H-indol-4-yl)-3-[(1R,3S)-3-phenylcyclopentyl]urea;
1-[(1R,3S)-3-phenylcyclopentyl]-3-(5,6,7,8-tetrahydronaphthalen-1-yl)urea;
1-[6-fluoro-3-(2-methylpropyl)isoquinolin-5-yl]-3-[(1R,3S)-3-phenylcyclopentyl]urea;
1-(3-ethyl-6-fluoroisoquinolin-5-yl)-3-[(1R,3S)-3-phenylcyclopentyl]urea;
1-(3-amino-1-methylisoquinolin-5-yl)-3-[(1R,3S)-3-phenylcyclopentyl]urea;
1-[3-(morpholin-4-yl)-2-oxo-1,2,3,4-tetrahydroquinolin-7-yl]-3-[(1R,3S)-3-phenylcyclopentyl]urea;
1-[3-(1,4-oxazepan-4-yl)-2-oxo-1,2,3,4-tetrahydroquinolin-7-yl]-3-[(1R,3S)-3-phenylcyclopentyl]urea;
1-{3-[(2-methoxyethyl)(methyl)amino]-2-oxo-1,2,3,4-tetrahydroquinolin-7-yl}-3-[(1R,3S)-3-phenylcyclopentyl]urea;
1-(4-methyl-3,4-dihydro-2H-1,4-benzoxazin-6-yl)-3-[(1R,3S)-3-phenylcyclopentyl]urea; and
1-(3,4-dihydro-2H-1,4-benzoxazin-6-yl)-3-[(1R,3S)-3-phenylcyclopentyl]urea.

Compounds described herein can exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Chiral center, of which the relative but not the absolute configuration is known are labeled as R* or S* according to Rule 7.2.2 as defined in IUPAC 1993 Recommendations (IUPAC, Commission on Nomenclature of Organic Chemistry. *A Guide to IUPAC Nomenclature of Organic Compounds (Recommendations 1993)*, 1993, Blackwell Scientific publications). Thus, for example, 1-(1H-indazol-4-yl)-3-{(1R*,3S*)-3-[4-(trifluoromethyl)-1,3-thiazol-2-yl]cyclopentyl}urea means 1-(1H-indazol-4-yl)-3-{(1R,3S)-3-[4-(trifluoromethyl)-1,3-thiazol-2-yl]cyclopentyl}urea or 1-(1H-indazol-4-yl)-3-{(1S,3R)-3-[4-(trifluoromethyl)-1,3-thiazol-2-yl]cyclopentyl}urea.

It can be appreciated that two or more asymmetric centers can be present in the present compounds, hence several diastereomers and enantiomers of the exemplified structures can often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

For example, compounds of formula (I-i) may be isolated as any one of the stereisomers as shown below, or mixtures of two or more of the stereoisomers of various ratio:

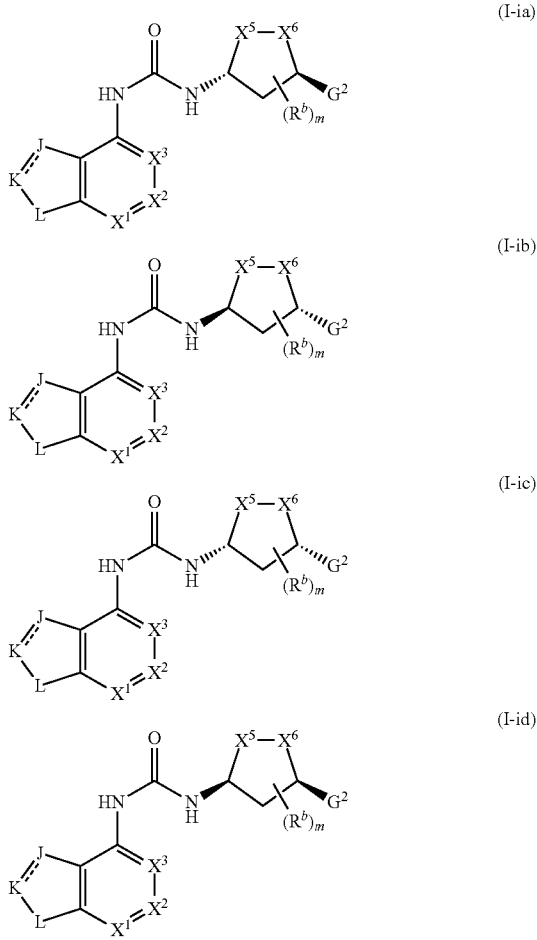

It is to be understood that the substituents and variables, and combinations thereof, in formula (I-ia)-(I-id) have the same values as those of formula (I-i) as discussed above.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed hererin can exhibit the phenomenon of tautomerism.

Thus, the formula drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formula drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of TRPV1 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to TRPV1 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions, potentially altering the pharmcokinetic profile or efficacy relative to the non-isotopic compound.

C) GENERAL SYNTHESIS

This invention is intended to encompass compounds described herein when prepared by synthetic processes or by metabolic processes. Preparation of the compounds by metabolic processes includes those occurring in the human or animal body (in vivo) or processes occurring in vitro.

The compounds can be prepared by a variety of processes well known for the preparation of compounds of this class. For example, compounds disclosed herein wherein the groups $X^1$, $X^2$, $X^3$, $X^4$, $X^5$, $X^6$, J, K, L, $R^{3k}$, $R^{3L}$, $R^3$, $R^4$, $R^5$, $R^6$, $R^7$, $R^8$, $R^9$, $R^{10}$, $R^{11}$, $R^{12}$, $R^{13}$, $R^{14}$, $R^{3L}$, $R^{3k}$, $R^a$, $R^b$, m, and $G^2$ have the meanings as set forth in the summary and detailed description sections unless otherwise noted, can be synthesized as shown in the accompanying Schemes 1-8.

As used in the descriptions of the schemes and the examples, certain abbreviations are intended to have the following meanings: AcO for acetate; BINAP for 2,2'-bis(diphenylphosphino)-1,1'-binaphthyl; n-BuLi for n-butyllithium; DBU for 1,8-diazabicyclo[5.4.0]undec-7-ene, DCE for dichloroethane; (iPr)$_2$NEt and DIPEA for diisopropylethyl amine; DMF for dimethylformamide; DMSO for dimethyl sulfoxide; DSC for N,N'-disuccinimidyl carbonate; DME for dimethoxyethane; DPPA for diphenylphosphoryl azide; NEt$_3$ for triethylamine; EtOAc for ethyl acetate; Et$_2$O for diethyl ether; IPA for isopropanol; MeOH for methanol; Me-THF for 2-methyl tetrahydrofuran; MTBE for methyl tert-butyl ether; PPh$_3$ for triphenyl phosphine; Ph for phenyl; Ra—Ni for Raney nickel; SFC for supercritical fluid chromatography; TEA for triethylamine; THF for tetrahydrofuran; and HPLC for high performance liquid chromatography.

Ureas of general formula (I) can be prepared as described in Scheme 1. Amines of formula (1) can be reacted with disuccinyl carbonate in the presence of a base such as, but not limited to, pyridine, and in a solvent such as dichloromethane to provide activated carbamates of general formula (2). Treatment of succinyl carbamates (2) with nucleophiles of formula (3) in the presence of an amine base such as, but not limited to, diisopropylethylamine, provides ureas of general formula (I).

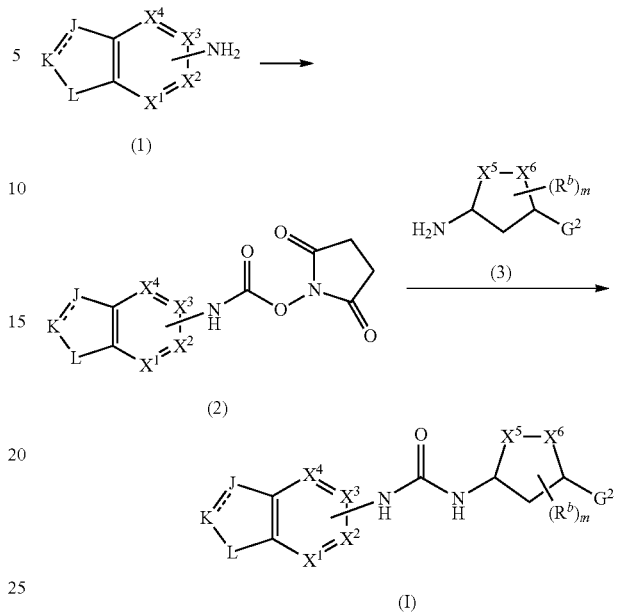

Scheme 1

Ureas of general formula (I) can also be prepared utilizing general procedures as described in Scheme 2. Amines of formula (1) can be treated with trichloroacetic anhydride and a base such as, but not limited to, pyridine in a solvent such as acetonitrile to provide trichloroacetamides of general formula (4). Trichloroacetamides of general formula (4) can be treated with amines of general formula (3), and a non-nucleophilic base such as, but not limited to, DBU or potassium carbonate, in a solvent such as, but not limited to, dimethylformamide to provide ureas of general formula (I).

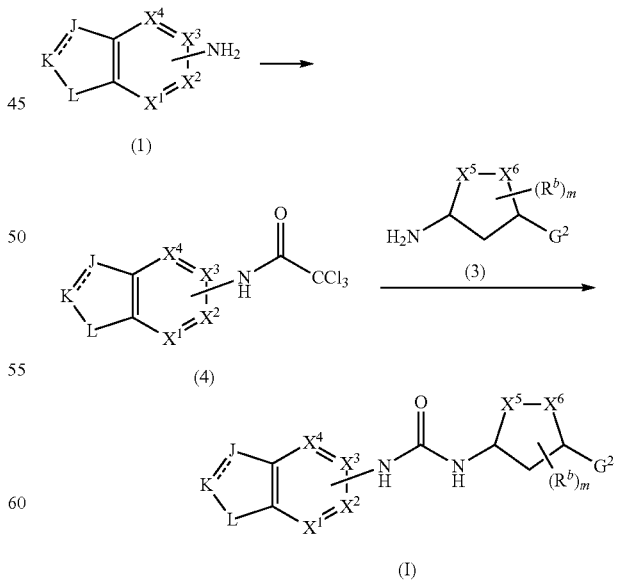

Scheme 2

Diastereomeric mixtures of amines of general formula (3) wherein $X^5$-$X^6$ is C(R$^3$R$^4$)C(R$^5$R$^6$) or C(R$^9$R$^{10}$)C(R$^{11}$R$^{12}$)C (R$^{13}$R$^{14}$) can be prepared from the corresponding cycloalkanones (5) as shown in Scheme 3. Cycloalkanones (5) (prepared according to Lukin, et al. *J. Org. Chem.* 2009, 74, 929) can be treated with amines of formula (5a) wherein $R^{101}$ is hydrogen or alkyl to provide oximes of general formula (6). The oxime group of (6) can be reduced using methodologies known by one skilled in the art, for example, by hydrogenolysis in the presence of a catalyst such as palladium on carbon, to provide the amines of general formula (7).

Amines of general formula (3) where $G^2$ is cyclohexyl and $X^5$-$X^6$ is $C(R^3R^4)C(R^5R^6)$ or $C(R^9R^{10})C(R^{11}R^{12})C(R^{13}R^{14})$ can be prepared from 3-phenylcyclopentanamines (12) as shown in Scheme 5. 3-Phenylcycloalkylamines (12) wherein $X^5$-$X^6$ is $C(R^3R^4)C(R^5R^6)$ or $C(R^9R^{10})C(R^{11}R^{12})C(R^{13}R^{14})$ can be hydrogenated over a catalyst such as rhodium on alumina in a solvent such as trifluoroethanol to provide amines (13).

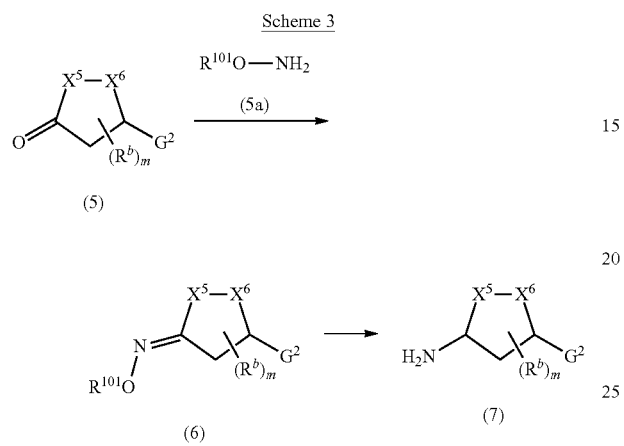

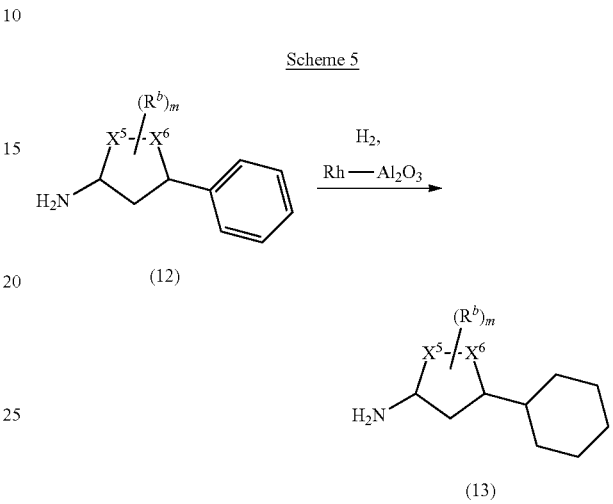

Amines of general formula (3) where $X^5$-$X^6$ is $CR^7$=$CR^8$ and $G^2$ is aryl or heteroaryl can be prepared from 4-acetoxy-2-cyclopenten-1-ol (8) as shown in Scheme 4. According to the procedure of Ainai, T.; Ito, M.; Kobayashi, Y. *Tetrahedron Lett.* 2003, 44, 3983, 4-acetoxy-2-cyclopenten-1-ol (8) can be treated with a Grignard reagent of formula $Ar^1MgX$ wherein $Ar^1$ is aryl or heteroaryl and X is Cl or Br, in the presence of a copper salt such as, but not limited to, copper(I) cyanide, in a solvent such as THF, to provide cyclopentenes of general formula (9) with inversion of configuration. Cyclopentenes (9) can be treated with diphenylphosphoryl azide and a base such as, but not limited to, DBU, in a solvent such as toluene to provide azides of general formula (10) with inversion of configuration. Azides (10) can be reduced with a phosphine such as, but not limited to, triphenylphosphine, in the presence of water, in a solvent such as 2-methyltetrahydrofuran to provide amines of general formula (11).

Scheme 6 describes a general approach to the preparation of amines of general formula (I) wherein ===== is a single bond, $X^1$, $X^2$, and $X^3$ are $C(R^a)$, $X^4$ is C, J is $CH_2$, K is C(H)(OH), and L is $CH_2$. Acylated indanols of general formula (14) can be prepared according to the procedure outlined in US2003/109700. Treatment of (14) with potassium carbonate in the presence of a solvent such as but not limited to methanol provides racemic indanols of general formula (15). Single enantiomers (16) and (17) can be separated from racemic alcohol (15) by chiral HPLC using a chiral column such as, but not limited to, a Chiralpak IC or Chiralcel AD-H column (Chiral Technologies Inc., West Chester, Pa.) and solvent mixtures containing, for example, methanol, hexane, and isopropanol.

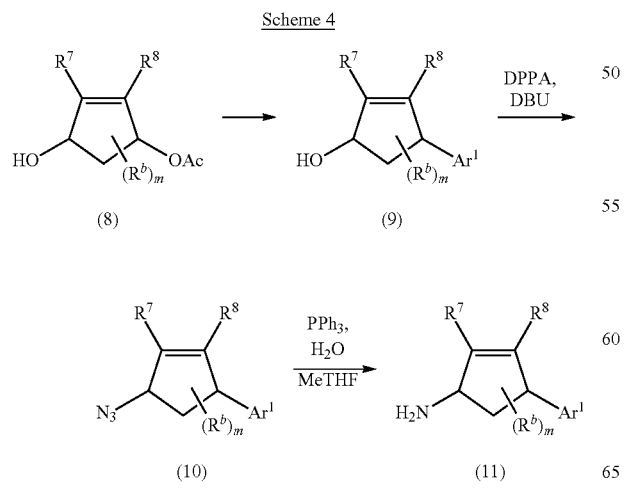

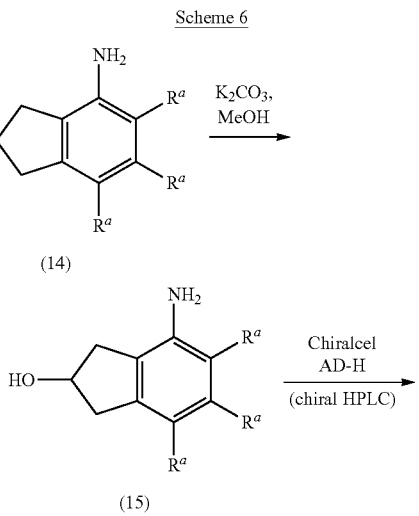

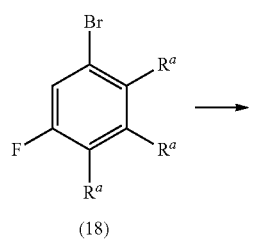

(16)     (17)

Amines of general formula (I) wherein ===== is a double bond, $X^1$, $X^2$, and $X^3$ are $C(R^a)$, $X^4$ is C, J is CH, K is N, and L is $NR^{3L}$, can be prepared via the methods described in Scheme 7. 1-Bromo-3-fluorobenzene (18) can be deprotonated with a base such as lithium diisopropylamide in a solvent such as THF, then reacted with dimethylformamide to provide aldehydes (19). Aldehydes (19) can be treated with hydrazines of formula (19a) in a solvent such as DMSO, to give bromoindazoles of general formula (20). Bromoindazoles (20) can react with benzophenone imine with a catalyst such as palladium(II) acetate, a ligand such as Xantphos, and a base such as sodium tert-butoxide, to give, after imine hydrolysis with an acid such as aqueous 6N HCl, indazoles of general formula (21).

Scheme 7

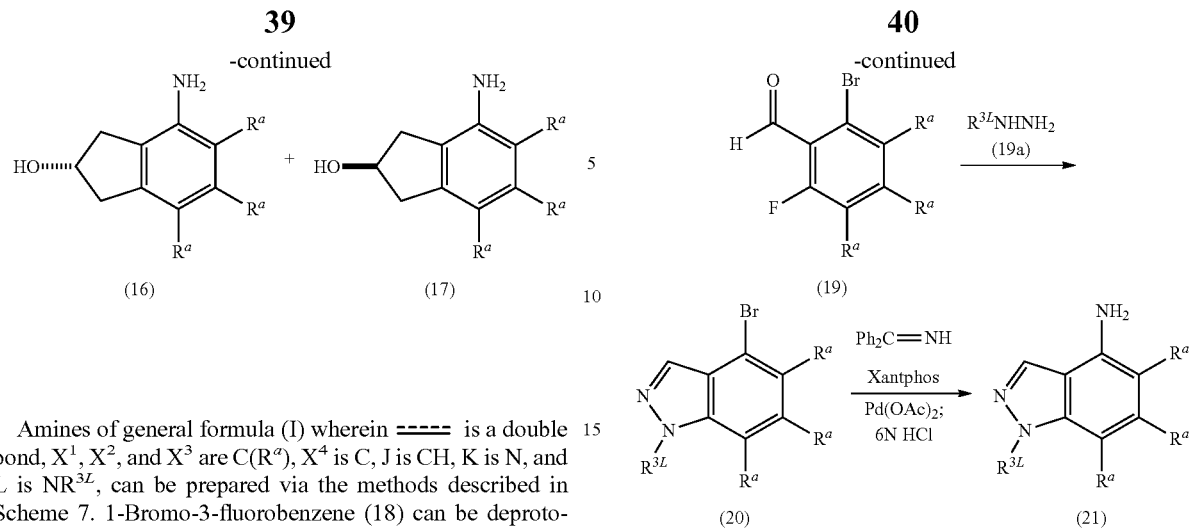

(18)   (19)   (20)   (21)

Construction of substituted isoquinolines can be accomplished using the method of Blurton, P. et al. WO2004/046133 as described in Scheme 8. Benzylamines of general formula (22) can be reacted with aldehyde dimethyl acetal of formula (22a) and a reducing agent such as, but not limited to, sodium tricacetoxyborohydride in a halogenated solvent such as dichloroethane to provide acetal derivatives of general formula (23). Subsequent treatment of acetals of general formula (23) with an acid such as, but not limited to, chlorosulfonic acid provides substituted isoquinolines of general formula (24). In another approach to the synthesis of isoqinolines, 2-bromo benzaldehydes of general formula (25) can be reacted with alkynes of formula (25a) and copper(I) iodide in the presence of a catalyst such as $Cl_2Pd(PPh_3)_2$ and a base such as, but not limited to, triethylamine in a solvent such as dimethylformamide to provide alkynyl aldehydes of general formula (26). Reaction of (26) with ammonia in a solvent such as, but not limited to, methanol also provides isoquinolines of general formula (24). Isoquinolines (24) can be nitrated with a reagent such as nitronium tetrafluoroborate in a solvent such as sulfolane, followed by nitro hydrogenation over a catalyst such as Raney Nickel in a solvent such as methanol, to provide substituted isoquinolines of general formula (27).

Scheme 8

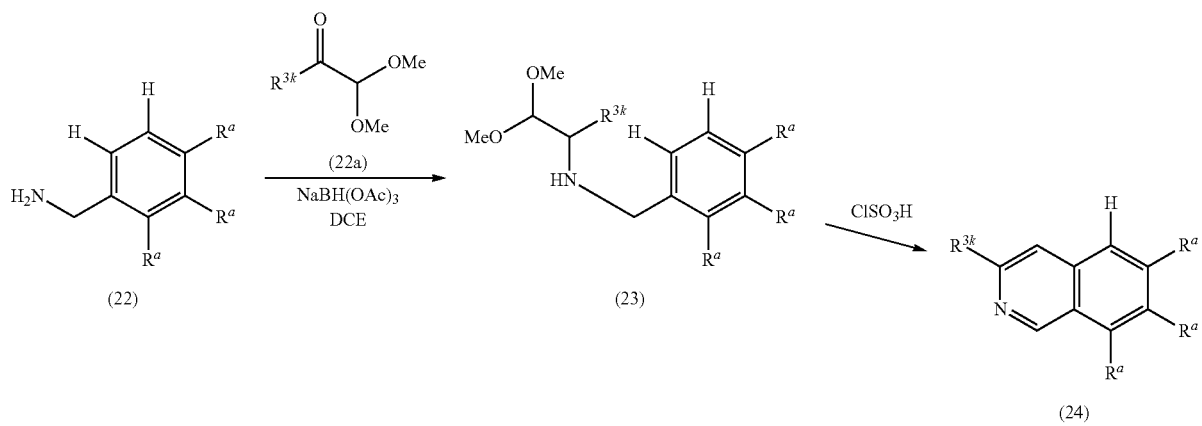

(22)   (23)   (24)

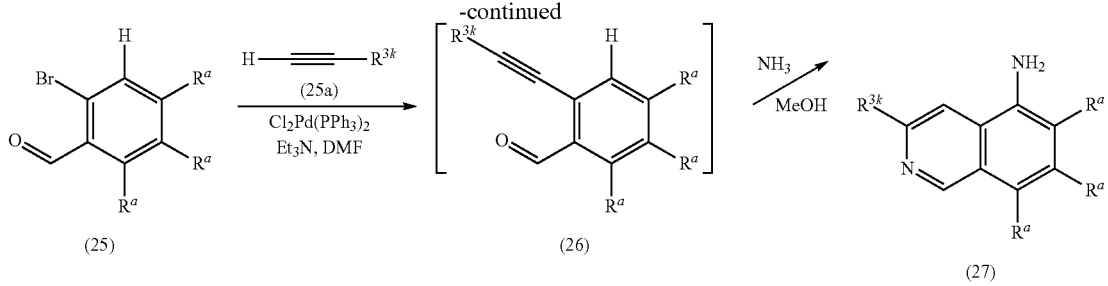

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

D) BIOLOGICAL DATA

In Vitro Evaluations:

(i) Capsaicin Activation Assay

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methyl phenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human TRPV1 receptor (hTRPV1) were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine®. Forty-eight hours after transfection, the neomycin-resistant cells were selected with growth medium containing 800 µg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the TRPV1 receptor was determined by measurement of intracellular $Ca^{2+}$ levels ($[Ca^{2+}]_i$) using the Fluorescence Imaging Plate Reader (FLIPR)$^{TETRA}$®. All compounds were tested over a 12-point one-third-log concentration range. Compound stocks, 10 mM, were prepared in DMSO, and diluted serially across a 384-well plate using a Bravo BenchCel workstation (Agilent Technologies, Santa Clara, Calif.). A stock concentration of capsaicin (10 mM) was made in DMSO, and diluted in D-PBS to a final concentration of 200 nM (4×). On the day prior to the experiment, recombinant HEK293 cells that stably express human TRPV1 were removed from tissue culture flasks and plated in growth medium into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment, growth medium was removed, and the no-wash FLIPR® Calcium-4 dye ($\lambda_{EX}$=470-495 nm, $\lambda_{EM}$=515-575 nm; Molecular Devices, Sunnyvale, Calif.) was added to each well using the Multidrop® dispenser. Cells were incubated for 90-120 minutes in the dark at room temperature. Test compounds were added to the cells 3 minutes prior to the addition of 200 nM capsaicin (4×), and the final assay volume was 80 µL. Fluorescence readings were made at 1 to 5 second intervals over the course of the experimental run. The peak increase in relative fluorescence units (minus baseline) was calculated, and expressed as a percentage of the 50 nM capsaicin (control) response. Curve-fits of the data were solved using a four-parameter logistic Hill equation in GraphPad Prism® (GraphPad Software, Inc., San Diego, Calif.), and IC$_{50}$ values (concentration of the test compounds that inhibits 50% of the intracellular Ca$^{2+}$ concentration increase induced by capasin) (hTRPV1 cap IC$_{50}$) were calculated.

(ii) Acid Activation Assay

Dulbecco's modified Eagle's medium (DMEM) with 4.5 mg/mL D-glucose, fetal bovine serum, L-glutamine, and 2-morpholinoethanesulfonic acid (MES) were purchased from Sigma-Aldrich Co. (St. Louis, Mo.). Dulbecco's phosphate-buffered saline (DPBS) with Ca$^{2+}$, Mg$^{2+}$, and 1 mg/mL D-glucose (pH 7.4), Geneticin®, 0.25% trypsin-1 mM EDTA, and penicillin-streptomycin were purchased from Invitrogen Corp. (Carlsbad, Calif.). The FLIPR® Calcium 4 assay kit was purchased from Molecular Devices (Sunnyvale, Calif.).

The cDNAs for the human TRPV1 receptor (hTRPV1) were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine. Forty-eight hours after transfection, the neomycin-resistant cells were selected with growth medium containing 800 µg/mL Geneticin (Gibco BRL). Surviving individual colonies were isolated and screened for TRPV1 receptor activity. Cells expressing recombinant homomeric TRPV1 receptors were maintained at 37° C. in DMEM containing 4 mM L-glutamine, 300 µg/mL G418 (Cal-biochem) and 10% fetal bovine serum under a humidified 5% CO$_2$ atmosphere.

The functional activity of compounds at the TRPV1 receptor was determined by measurement of intracellular Ca$^{2+}$ levels ([Ca$^{2+}$]$_i$) using the Fluorescence Imaging Plate Reader (FLIPR)$^{TETRA}$®. All compounds were tested over a 12-point one-half-log concentration range. Compound stocks, 10 mM, were prepared in DMSO, and diluted serially across a 384-well plate using a Bravo BenchCel workstation (Agilent Technologies, Santa Clara, Calif.).

On the day of the experiment growth medium was removed, and the no-wash FLIPR® Calcium-4 dye ($\lambda_{EX}$=470-495 nm, $\lambda_{EM}$=515-575 nm) was added to each well using the Multidrop® dispenser. Cells were incubated for 90-120 minutes in the dark at 25° C. Test compounds were dissolved in DMSO, and plates were prepared using an Agilent Bravo workstation (Agilent Technologies Inc., Santa Clara, Calif.). Compounds were added to the cells 3 minutes prior to the addition of a pH 5.0 solution. Reagents were delivered at a rate of 40 µL/sec, and the final assay volume was 80 µL. Acidic pH solutions were prepared by titration of DPBS/MES with 1 N HCl. The intensity of the fluorescence was captured and digitally transferred to an interfaced PC. Using a 37.5 µM concentration of the TRPV1 antagonist, the peak increase in fluorescence over baseline (relative fluorescence units) was calculated and expressed as the percentage (max % remain) of the maximal pH 5.0-induced response.

TABLE 1

| Example | hTRPV1 cap IC$_{50}$ (nM) | hTRPV1 H$^+$ (max % remain) |
|---|---|---|
| 1 | 106 | 93 |
| 2 | 29 | 40 |
| 3 | 55 | 2 |
| 4 | 18 | 37 |
| 5 | 70 | 81 |
| 6 | 4 | 62 |
| 7 | 9 | 32 |
| 8 | 123 | 78 |
| 9 | 205 | 14 |
| 10 | 84 | 3 |
| 11 | 84 | 49 |
| 12 | 207 | 65 |
| 13 | 13 | 60 |
| 14 | 30 | 36 |
| 15 | 179 | 20 |
| 16 | 80 | 87 |
| 17 | 373 | 25 |
| 18 | 70 | 18 |
| 19 | >37500 | 81 |
| 20 | 5 | 32 |
| 21 | 20 | 8 |
| 22 | 286 | 41 |
| 23 | 138 | 88 |
| 24 | 85 | 1 |
| 25 | 628 | 46 |
| 26 | 544 | 65 |
| 27 | 7 | 60 |
| 28 | 64 | 41 |
| 29 | 1730 | 68 |
| 30 | 1050 | 26 |
| 31 | 1840 | 35 |
| 32 | 795 | 32 |
| 33 | 8640 | 68 |
| 35 | 292 | 11 |
| 36 | 56 | 8 |
| 37 | 427 | 6 |
| 38 | 499 | 53 |
| 39 | 862 | 33 |
| 40 | 78 | 1 |
| 41 | 311 | 1 |
| 42 | 17 | 3 |
| 43 | 221 | 55 |
| 44 | 169 | 13 |
| 45 | 26 | 9 |
| 46 | 87 | 7 |
| 47 | 290 | 3 |
| 48 | 42 | 49 |
| 49 | 66 | 68 |

TABLE 1-continued

| Example | hTRPV1 cap IC$_{50}$ (nM) | hTRPV1 H$^+$ (max % remain) |
|---|---|---|
| 50 | 78 | 59 |
| 51 | 13 | 56 |
| 52 | 22388 | 67 |
| 53 | >37500 | 84 |
| 54 | 1342 | 69 |
| 55 | 37 | 11 |
| 56 | 14 | 10 |
| 57 | 64 | 4 |
| 58 | 8645 | 53 |
| 59 | 435 | 79 |
| 60 | 331 | 72 |
| 61 | 32 | 44 |
| 62 | 10 | 5 |
| 63 | 122 | 38 |
| 64 | 29 | 25 |
| 65 | 8 | 12 |
| 66 | 8.2 | 29 |
| 67 | 11 | 18 |
| 68 | 48 | 41 |
| 69 | 12 | 2 |
| 70 | 5.6 | 22 |
| 71 | 8.6 | 15 |
| 72 | 80 | 22 |
| 73 | 164 | 11 |
| 74 | 3.5 | 44 |
| 75 | 21 | 16 |
| 76 | 2.0 | 9 |
| 77 | >37500 | 56 |
| 78 | 6.5 | 78 |
| 79 | 11 | 75 |
| 80 | 10 | 55 |
| 81 | 2.3 | 66 |
| 82 | 3.3 | 12 |
| 83 | 5.3 | 48 |
| 84 | 5.4 | 13 |
| 85 | 8.9 | 21 |
| 86 | 80 | 0 |
| 87 | 248 | 17 |
| 88 | 20 | 16 |
| 89 | 88 | 15 |
| 90 | 109 | 54 |
| 91 | 338 | 63 |
| 92 | 79 | 66 |
| 93 | 93 | 55 |
| 94 | 14 | 46 |
| 95 | 58 | 34 |
| 96 | 63 | 66 |
| 97 | 69 | 46 |
| 98 | 54 | 32 |
| 99 | 16 | 46 |
| 100 | 25 | 43 |
| 101 | 25 | 4 |
| 102 | 218 | 34 |
| 103 | 14 | 19 |
| 104 | 97 | 42 |
| 105 | 956 | 91 |
| 106 | >37500 | 75 |
| 107 | >37500 | 77 |
| 108 | 804 | 88 |
| 109 | >37500 | 76 |
| 110 | >37500 | 72 |
| 111 | 362 | 32 |
| 112 | 1369 | 35 |
| 113 | 7705 | 50 |
| 114 | 830 | 62 |
| 115 | 653 | 47 |
| 116 | 930 | 48 |
| 117 | 804 | 47 |
| 118 | >37500 | 50 |
| 119 | 720 | 18 |
| 120 | 1912 | 54 |
| 121 | 75 | 10 |
| 122 | 20529 | 68 |
| 123 | 1114 | 29 |
| 124 | 6484 | 50 |
| 125 | 1464 | 41 |
| 126 | 997 | 23 |
| 127 | 5755 | 54 |
| 128 | 8642 | 54 |
| 129 | 404 | 6 |
| 130 | 721 | 5 |
| 131 | 133 | 1 |
| 132 | 324 | 40 |
| 133 | 507 | 16 |
| 134 | 156 | 36 |
| 135 | 1789 | 57 |
| 136 | >37500 | 46 |
| 137 | 100 | 42 |
| 138 | 156 | 0 |
| 139 | >37500 | 89 |
| 140 | 9599 | 90 |
| 141 | >37500 | 82 |
| 142 | 116 | 66 |
| 143 | 145 | 24 |
| 144 | >37500 | 62 |
| 145 | 614 | 91 |
| 146 | >37500 | 39 |
| A | 4 | 2 |
| B | 6 | 1 |
| C | 5 | 2 |
| D | 13 | 2 |
| E | 5 | 1 |
| F | 5 | 6 |
| G | 4 | 2 |

Compound A: 1-[(7R)-7-hydroxy-5,6,7,8-tetrahydronaphthalen-1-yl]-3-[(1S,3S)-3-phenylcyclopentyl]urea;
Compound B: 1-[(7S)-7-hydroxy-5,6,7,8-tetrahydronaphthalen-1-yl]-3-[(1S,3R)-3-phenylcyclopentyl]urea;
Compound C: 1-[(7S)-7-hydroxy-5,6,7,8-tetrahydronaphthalen-1-yl]-3-[(1R,3S)-3-phenylcyclopentyl]urea;
Compound D: 1-[(7S)-7-hydroxy-5,6,7,8-tetrahydronaphthalen-1-yl]-3-[(1S,3S)-3-phenylcyclopentyl]urea;
Compound E: 1-[(7R)-7-hydroxy-5,6,7,8-tetrahydronaphthalen-1-yl]-3-[(1R,3R)-3-phenylcyclopentyl]urea;
Compound F: 1-[(7S)-7-hydroxy-5,6,7,8-tetrahydronaphthalen-1-yl]-3-[(1R,3R)-3-phenylcyclopentyl]urea;
Compound G: 1-[(7R)-7-hydroxy-5,6,7,8-tetrahydronaphthalen-1-yl]-3-[(1R,3S)-3-phenylcyclopentyl]urea.

In Vivo Evaluations:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

(i) Rat Tail Immersion Protocol:

Compounds were tested for their effects on noxious thermosensation using the tail immersion assay. Testing was performed one hour following oral administration of 100 μmol/kg of the compound in 10% ethanol/20% Tween-80/70% PEG-400 (2 mL/kg). Morphine (6 mg/kg) was administered interperitoneally (i.p.) using saline (2 mL/kg) as the vehicle. For testing, a circulating water bath was heated to 55° C. Thirty to sixty minutes post dosing, the rats were handled for a few seconds to calm them down and then cupped with their back against the tester's hand at a slight angle with head facing away from the tester. With rat in one hand and a 0.01 second stopwatch in the other hand, the tail was quickly immersed 6-8 cm in the water bath or to a distance leaving 2-3 cm of tail out of water. The timer was started simultaneously.

When the rat flinched or attempted withdrawal, timer was immediately stopped and the rat's tail was quickly removed from water bath. This response latency (in seconds) was recorded. Process was repeated 3 times with 3-4 minutes between readings and the average response latency was calculated.

Table 2 shows the effect of reference compounds (Compounds H-L and morphine) as well as Examples 2, 4, 6, 7, 14, 20, 21, 27, 28, 48, 51, 66, 78, and 96 in the rat tail immersion assay at one hour post dosing (100 µmol/kg), relative to vehicle. For a given example, a percent increase in the average response latency (in seconds) for tail withdrawal relative to a vehicle control was determined.

% increase=$[(t_c-t_v)/t_v] \times 100\%$ $t_c$=response latency (in seconds) with oral dosing of compounds $t_v$=response latency (in seconds) with oral dosing of vehicle The % increases in tail withdrawal latency relative to vehicle control are divided into the following categories:

+++ is greater than or equal to 25% increase

++ is greater than or equal to 10% but less than 25% increase

+ is less than 10% increase

− is no statistically significant increase relative to vehicle control

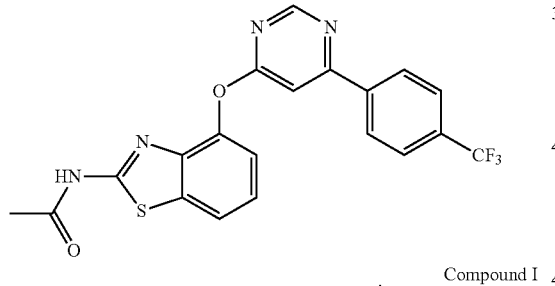

Compound H

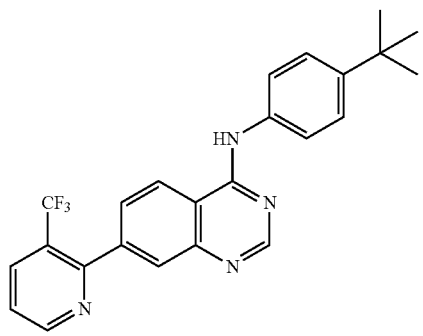

Compound I

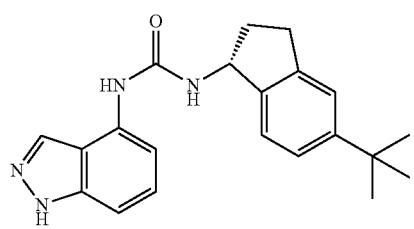

Compound J

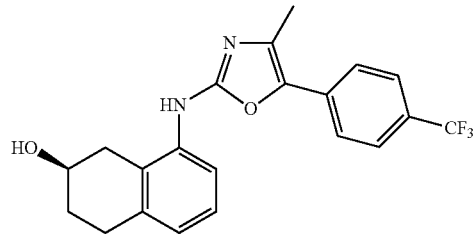

Compound K

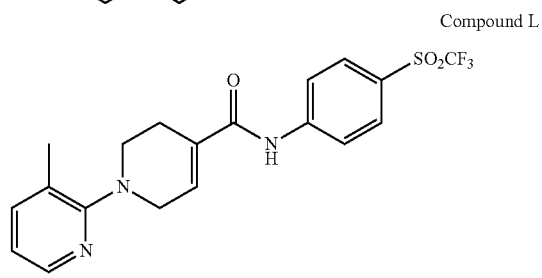

Compound L

TABLE 2

| Example | hTRPV1 cap $IC_{50}$ (nM) | hTRPV1 $H^+$ (max % remain) | % Increase in tail withdrawal latency |
|---|---|---|---|
| H | 20 | 10 | +++ |
| I | 55 | 1 | +++ |
| J | 35 | 1 | +++ |
| K | 180 | 3 | +++ |
| L | 100 | 2 | +++ |
| Morphine | | | +++ |
| 2 | 29 | 40 | − |
| 4 | 22 | 21 | − |
| 6 | 4 | 62 | − |
| 7 | 9 | 32 | − |
| 14 | 30 | 36 | − |
| 20 | 5 | 32 | − |
| 21 | 20 | 8 | ++ |
| 27 | 6 | 60 | − |
| 28 | 64 | 41 | − |
| 48 | 42 | 49 | − |
| 51 | 13 | 56 | − |
| 66 | 8 | 29 | +++ |
| 78 | 7 | 78 | ++ |
| 96 | 63 | 66 | ++ |

(ii) Rat Acute Capsaicin-Induced Flinching Behavior:

Rats were placed in individual observation cages. Following an acclimation period of 30 minutes, representative compounds of the invention were administered at a dose of 100 µmol/kg orally in 10% ethanol/20% Tween 80/70% polyethylene glycol-400 vehicle at a volume of 2 mL/kg. One hour after administration of the test compound, 2.5 µg of capsaicin in a 10 µL solution of 10% ethanol/90% hydroxypropyl-β-cyclodextrin was injected subcutaneously into the dorsal aspect of the right hind paw. The observation cage was then suspended above mirrors in order to facilitate observation. Rats were observed for a continuous period of five minutes. The number of flinching behaviors of the injured paw was recorded during the five minute observation period (Gilchrist, H. D.; Allard, B. L.; Simone, D. A.; Enhanced withdrawal responses to heat and mechanical stimuli following intraplantar injection of capsaicin in rats. *Pain,* 1996, 67, 179-188). The percent reduction in the number of flinching behaviors produced with oral administration of representative compounds of the present invention relative to control-treated animals (% effect) is reported in Table 3.

(iii) Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 minutes following the administration of capsaicin (Joshi et al 2006, Neuroscience 143, 587-596). Compounds were administered orally (p.o.) one hour before testing (90 minutes post-capsaicin).

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, Quantitative assessment of tactile allodynia in the rat paw, J. Neurosci. Methods, 1994, 53, 55. Rats were placed into inverted individual plastic containers (20×12.5×20 cm) on top of a suspended wire mesh grid, and acclimated to the test chambers for 20 minutes. The von Frey filaments with different bending forces (starting with the lowest first and then progressively increasing) were presented perpendicularly to the plantar surface of the selected hind paw, and then hold in this position for approximately 8 sec with enough force to cause a slight bend in the filament. Positive responses included an abrupt withdrawal of the hind paw from the stimulus, or flinching behavior immediately following removal of the stimulus. Table 3 illustrates that representative compounds tested showed a statistically significant change in paw withdrawal latency versus a vehicle-dosed control after administration of a single acute oral dose.

(iv) Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26 G needle. The dose of the sodium iodoacetate (3 mg/i.a.injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio), to elicit paw withdrawal. The grip force data was converted to a maximum hindlimb cumulative compressive force (CFmax) (gram force)/kg body weight for each animal. The analgesic effects of test compounds were determined 20 days following the i.a. injection of sodium iodoacetate. The vehicle control group for each compound being tested was assigned 0% whereas the age matched naïve group was assigned as being 100% (normal). The % effect for each dose group was then expressed as % return to normalcy compared to the naïve group. Test compounds were administered orally in 10% ethanol/20% Tween 80/70% polyethylene glycol-400 vehicle at a volume of 2 mL/kg. The assessment of the analgesic effects of test compounds was made 1 hour following oral administration. The assessment of the analgesic effects of test compounds can be made following a single dose or following repeated administration wherein the frequency of dosing is 1 to 2 times daily. The duration of such repeated daily dosing may last for any time greater than one day. A typical duration of repeated daily dosing is about 5 days to about 12 days. Table 3 illustrates that representative compounds tested showed a statistically significant change in hind limb grip force strength versus a vehicle-dosed control after administration of a single acute oral dose.

(v) Chronic Constriction Injury Model of Neuropathic Pain

A model of chronic constriction injury-induced (CCI) neuropathic pain was produced in rats by following the method of Bennett and Xie (Pain, 1988, 33:87). Following sterilization and anesthetic procedures, a 1.5 cm incision was made dorsal to the pelvis, and the biceps femoris and gluteous superficialis (right side) were separated. The right common sciatic nerve was exposed/isolated, and loosely ligated by 4 ligatures of chromic gut (5-0) with <1 mm spacing using hemostats and forceps. The wound was sutured (layer of muscle closed with 6.0 absorbable sutures, and the skin closed with wound clips or tissue glue. The animals were allowed to recover on a warming plate and were returned to their home cages (soft bedding) when able to walk on their own. Loose ligation of the sciatic nerve in rats would lead to the development of neuropathic pain within two weeks. Compounds were tested in the animals two or three weeks post-surgery.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, Quantitative assessment of tactile allodynia in the rat paw, J. Neurosci. Methods, 1994, 53, 55. Rats were placed into inverted individual plastic containers (20×12.5×20 cm) on top of a suspended wire mesh grid, and acclimated to the test chambers for 20 min. The von Frey filaments with different bending forces (starting with the lowest first and then progressively increasing) were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus.

Table 3 demonstrates that representative compounds tested showed a statistically significant change in paw withdrawal latency versus a vehicle-dosed control after administration of a single acute oral dose. The assessment of the analgesic effects of test compounds was made 1 hour following oral administration.

(vi) Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test the compounds of the present application. The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds was also assessed in several control groups, including naive, sham-operated, and saline infused animals as well as in the contralateral paws of nerve-injured rats. The assessment of the analgesic effects of test compounds was made 1 hour following oral administration.

TABLE 3

| Example | In vivo model | Dose (p.o.) | % effect |
|---|---|---|---|
| 4 | Iodoacetate-induced knee joint pain | 10 mg/kg | 50 |
| 6 | Acute Capsaicin-Induced Flinching | 100 μmol/kg | 88 |
| 6 | Capsaicin-induced secondary mechanical hypersensitivity | 10 μmol/kg | 59 |
| 14 | Acute Capsaicin-Induced Flinching | 10 μmol/kg | 76 |
| 14 | Capsaicin-induced secondary mechanical hypersensitivity | 100 μmol/kg | 48 |
| 14 | Chronic constriction injury | 100 μmol/kg | 53 |
| 21 | Iodoacetate-induced knee joint pain | 10 mg/kg | 37 |
| 28 | Acute Capsaicin-Induced Flinching | 10 μmol/kg | 60 |
| 28 | Capsaicin-induced secondary mechanical hypersensitivity | 100 μmol/kg | 81 |
| 28 | Iodoacetate-induced knee joint pain | 100 μmol/kg | 78 |
| 28 | Chronic constriction injury | 100 μmol/kg | 54 |
| 51 | Acute Capsaicin-Induced Flinching | 100 μmol/kg | 30 |
| 61 | Iodoacetate-induced knee joint pain | 10 mg/kg | 34 |
| 64 | Iodoacetate-induced knee joint pain | 10 mg/kg | 48 |

Most compounds disclosed and tested as shown in Table 1 partially inhibit calcium flux following activation by the pH 5.0 solution, for example, compounds tested exhibit an about 25% or more of the calcium flux response remaining (i.e., block of about 75% or less) upon acid (pH 5.0) activation of TRPV1.

As shown in Tables 1 compounds tested are potent TRPV1 antagonists that inhibit the increase in cellular calcium in response to the capsaicin (10 nM) addition; for example, compounds tested exhibit $IC_{50}$ (cap) of less than about 1000 nM, for example, in the range of about 500 nM to about 1000 nM, or in the range of about 100 to about 500 nM, or in the range of about less than 100 nM.

Furthermore, most compounds impart little or no impairment of the subject's ability to sense noxious temperature. For example, most of the compounds tested showed no statistically significant increase in tail withdrawal latency in rats when administered orally, relative to those that were dosed with vehicle.

Compounds described herein are TRPV1 antagonists. It is expected that the compounds have promising effect of treating or preventing various diseases and conditions described herein.

One embodiment provides a method for treating a disorder that can be ameliorated by suppressing activation of the vanilloid receptor subtype 1 (TRPV1) receptor in a host mammal in need of such treatment. The method comprises administering therapeutically effective amounts of a compound described herein or a pharmaceutically acceptable salt, solvate, salt of a solvate, or solvate of a salt thereof, with or without a pharmaceutically acceptable carrier, and alone, or in combination with an analgesic (e.g. acetaminophen, opioids such as morphine), or an NSAID, or combinations thereof.

Another embodiment provides a method for treating pain in a mammal in need of such treatment. The method comprises administering a therapeutically effective amount of a compound described herein or a pharmaceutically acceptable salt, solvate, salt of a solvate, or solvate of a salt thereof, with or without a pharmaceutically acceptable carrier, and alone, or in combination with an analgesic (e.g. acetaminophen, opioids), or with an NSAID, or combinations thereof.

Yet another embodiment provides a method for treating pain including, but not limited to, chronic pain, neuropathic pain, nociceptive pain, allodynia, inflammatory pain, inflammatory hyperalgesia, post herpetic neuralgia, post operative pain, post stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchoconstriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia, acute cerebral ischemia; emesis such as cancer chemotherapy-induced emesis, and obesity, in mammals, especially humans. For example, the present compounds are useful for the treatment of pain, particularly nociceptive and inflammatory pain. The method comprises administering a therapeutically effective amount of a compound described herein or a pharmaceutically acceptable salt, solvate, salt of a solvate, or solvate of a salt thereof, with or without a pharmaceutically acceptable carrier, and alone, or in combination with an analgesic (e.g. acetaminophen, opioids), or with an NSAID, or combinations thereof.

The present compounds can be used to treat pain as demonstrated by Nolano, M. et al. Pain 1999, 81, 135-145; Caterina, M. J. and Julius, D. Annu. Rev. Neurosci. 2001, 24, 487-517; Caterina, M. J. et al. Science 2000, 288, 306-313; Caterina, M. J. et al. Nature 1997, 389, 816-824.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan in Prog. Neurobiol. 1999, 57, 1-164 for a review). These sensory fibers are known as nociceptors and are characteristically small-diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain can generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors that can better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter *Science* 2000, 288, 1765-1768).

Clinical pain is present when discomfort and abnormal sensitivity feature among the patient's symptoms. Patients tend to be quite heterogeneous and can present with various pain symptoms. Such symptoms include: 1) spontaneous pain which can be dull, burning, or stabbing; 2) exaggerated pain responses to noxious stimuli (hyperalgesia); and 3) pain produced by normally innocuous stimuli (allodynia: Meyer et al. Textbook of Pain, 13-44 (1994)). Although patients suffering from various forms of acute and chronic pain can have similar symptoms, the underlying mechanisms can be different and can, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury.

Pain afferents are activated by transduction of stimuli by nociceptors at the site of injury and activate neurons in the spinal cord at the level of their termination. This is then relayed up the spinal tracts to the brain where pain is perceived (Meyer et al. Textbook of Pain, 13-44 (1994). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e.g. bone pain, headache, facial pain or visceral pain) or pain associated with cancer therapy (e.g. post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament. Back pain can resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological, as it has no protective role. It is often present well after the original cause has dissipated, commonly lasting for years, significantly decreasing a patient's quality of life (Woolf and Mannion *Lancet* 1999, 353, 1959-1964). The symptoms of neuropathic pain are difficult to treat, as they are often heterogeneous even between patients with the same disease (Woolf and Decosterd *Pain Supp.* 1999, 6, S141-S147; Woolf and Mannion *Lancet* 1999, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, Textbook of Pain, 45-56 (1994)). Arthritic pain is the most common inflammatory pain.

Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors can be important (Grennan & Jayson, Textbook of Pain, 397-407 (1994)). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder *Ann. Pharmacother.* 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs. Fernihough, J. et al. describe in *Neurosci. Lett.* 2005, 75-80 a potential role for TRPV1 in the manifestation of pain behavior accompanied by osteoarthritis changes in the knee.

Compounds described herein are TRPV1 antagonists and thus are useful in ameliorating acute and chronic inflammatory pain and postoperative pain as demonstrated in Honore, P. et al. *J. Pharmacol. Exp. Ther.* 2005, 410-421.

Another type of inflammatory pain is visceral pain, which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain.

Commonly encountered gastrointestinal (GI) disorders that cause pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Elevated TRPV1 immunoreactivity has been observed in colonic sensory nerve fibers in patients with IBD (Szallasi, A. et al. *Nature Rev.* 2007, 6, 357-373).

Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain. It has been shown that CGRP-receptor antagonists block the vasodilation effects of CGRP and exhibits efficacy in patients with migraine and cluster headaches. CGRP is strongly co-expressed in many TRPV1 expressing nerve fibers, it is plausible that activation of TRPV1 could partially underlie a neurogenic-mediated component of headache.

Another type of pain is ocular pain (eye pain), which includes pain associated with dry eye syndrome, increased intraocular pressure, glaucoma, accidental trauma, and surgical procedures. intraocular pressure. Activation of TRPV1 induces inflammatory cytokine release in corneal epithelium in the eye (Zhang, F. et al. *J. Cell. Physiol* 2007, 213, 730; Murata, Y. et al. *Brain Res.* 2006, 1085, 87). Retinal ganglion cell apoptosis induced by elevated hydrostatic pressure arises substantially through TRPV1, likely through the influx of extracellular $Ca^{2+}$ (Sappington, R. M. et al. Invest. Ophth. Vis. Sci. 2009, 50, 717). TRPV1 antagonists can effectively reduce symptoms of dry eye without causing anesthesia effects on the ocular surface (US2009/0131449). Silencing of TRPV1 by administration of siRNA can be a useful therapy in the treatment of ocular pain associated with dry eye syndrome and could reduce side effects associated with medications currently used to treat patients suffering from this pathology. Investigators at Sylentis have reported data indicating that an siRNA targeting TRPV1 could be used to decrease the behavioral response of guinea pigs to ocular surface irritation (Association for Research in Vision and Ophthalmology Meeting, 2008). Administration of the TRPV1 agonist capsaicin resulted in a significant increase in irritation parameters compared with saline and that topical administration of TRPV1 siRNA twice a day for three days resulted in reduced scratching and wiping movements for up to nine days in the treated eyes. The reported analgesic effect was greater than that observed using the reference standard capsazepine.

It is known that capsaicin, a TRPV1 agonist, induces cough and reduced airway conductance in human clinical trials. TRPV1 antagonists such as capsazepine have been shown to block capsaicin and citric acid-induced cough responses in guinea pigs as demonstrated by Geppetti, P. et al. *Eur. J. Pharmacol.* 2006, 533, 207-214. Thus, TRPV1 antagonists demonstrate potential in the treatment of asthma, cough, chronic obstructive pulmonary disease (COPD) and bronchoconstriction as demonstrated by Watanabe, N. et al. *Pulmonary Pharmacol. Ther.* 2005, 18, 187-197 and Jia, Y. et al. *Br. J. Pharmacol.* 2002, 137, 831-836.

Present compounds can be used to treat bladder overactivity and/or urinary incontinence as demonstrated by Fowler, C. *Urology* 2005, 65, 400-405.

Present compounds can be used to treat inflammatory thermal hyperalgesia as demonstrated by Davis, J. et al. *Nature* 2000, 405, 183-187.

Present compounds can be used for the treatment of anxiety-related disorders as demonstrated by Marsch, R. et al. *J. Neurosci.* 2007, 27, 832-839.

Present compounds can be used for the treatment of disorders associated with hyperdopaminergia such as psychosis, attention deficit hyperactivity disorder and schizophrenia as demonstrated by Tzavara, E. et al. *Biol. Psych.* 2006, 59, 508-515.

Present compounds can be used for the treatment of diabetes and obesity as demonstrated by Suni, A. and Sallazi, A. *Trends Pharmacol. Sci.* 2008, 29, 29-36.

Ischemia (e.g. cerebral ischemia) is the shortage or inadequate of oxygenated blood flow to body parts and organs, and often results in dysfunction or damage of tissue. The neuroprotective efficacy of induced hypothermia following or during cerebral ischemia is evident in experimental anima models of stroke (Barone, F. C. et al. *Neurosci. Biobehav. Rev.* 1997; 2(1), 31-44; Onesti, S. T. et al. *Neurosurgery* 1991, 29, 369; Coimbra, C. et al. *Acta Neuropathol. (Berl)* 1994; 87, 325; Zhang, Y. et al. *Acta Anaesthesiol. Sin.* 2001, 39, 65; Yamashita, K. et al. Stroke 1991, 22, 1574; Ooboshi, H. et al. *Brain Res.* 2000, 884, 23; Colbourne, F. et al. *J. Cereb. Blood Flow Metab.* 2000, 20(1-2), 1702; Kawai, N. et al. *Stroke* 2000, 3, 1982; Maier, C. M. et al. *J. Neurosurg.* 2001, 94, 90; Maier, C. M. et al. *Stroke* 1998, 29, 2171). Two trials conducted in cardiac arrest patients have demonstrated improved neurological outcome of inducing hypothermia (Mild therapeutic hypothermia to improve the neurologic outcome after cardiac arrest: Bernard, S. A. et al. *N. Engl. J. Med.* 2002, 346, 549 and *N. Engl. J. Med.* 2002, 346, 557). Induction of hypothermia by lowering of the core temperature has been attempted by mechanical devices such as surface cooling using catheters placed in a large vessel. However, such mechanical devices have been shown to have considerable side effects, including shivering, serious infections, and lung puncture. Regulation of the core body temperature by pharmaceutical compositions comprising TRPV1 agonists as a safer and less expensive alternative to the mechanical method was discussed in WO2008/040360 and WO2008/040361. Such treatments can have unintended side effects such as the sensation of burning pain, known to be elicited by TRPV1 agonists. TRPV1 antagonists that are capable of inducing hypothermia can be used for the treatment of ischemia without the pungent effects.

Present compounds can be administered alone, or in combination with one or more other compounds described herein, or in combination (i.e. co-administered) with one or more additional pharmaceutical agents. For example, a compound of formula (I), or a pharmaceutically acceptable salt or solvate thereof, can be administered in combination with one or more analgesics (e.g. acetaminophen, or an opioid such as morphine), or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of one or more analgesic (e.g. acetaminophen, opioids) and one or more NSAID. In certain embodiments, the nonsteroidal anti-inflammatory drug (NSAID) is ibuprofen. In certain embodiments, the analgesic is acetaminophen. Combination therapy includes administration of a single pharmaceutical dosage formulation containing one or more of the compounds described herein and one or more additional pharmaceutical agents, as well as administration of the compounds of the invention and each additional pharmaceutical agent, in its own separate pharmaceutical dosage formulation. For example, a compound of formula (I) and one or more additional pharmaceutical agent(s) can be administered to the patient together, in a single oral dosage composition having a fixed ratio of each active ingredient, such as a tablet or capsule; or each agent can be administered in separate oral dosage formulations.

Where separate dosage formulations are used, the present compounds and one or more additional pharmaceutical agents can be administered at essentially the same time (e.g., concurrently) or at separately staggered times (e.g., sequentially).

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salts thereof. The present compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or lower animal range from about 0.10 µg/kg body weight to about 25 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions can contain such amounts or submultiples thereof to make up the daily dose.

E) PHARMACEUTICAL COMPOSITIONS

Described herein are also pharmaceutical compositions comprising of compounds described herein, or pharmaceutically acceptable salts or solvates thereof, formulated together with one or more pharmaceutically acceptable carriers. The pharmaceutical compositions can be formulated for oral administration in solid or liquid form, for parenteral injection or for rectal administration.

The compounds identified by the methods described herein can be administered as the sole pharmaceutical agent or in combination with one or more other pharmaceutical agents. For example, the compounds or salts or solvate thereof can be combined with one or more analgesics, or with one or more nonsteroidal anti-inflammatory drug (NSAID, or with a combination of one or more analgesic and one or more NSAID. Thus, the present invention also includes pharmaceutical compositions which are comprised of therapeutically effective amount of compounds identified by the methods described herein, or pharmaceutically acceptable salts or solvates thereof, one or more pharmaceutical agents as disclosed hereinabove, and one or more pharmaceutically acceptable carriers.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition can be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, can depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They can be sterilized, for example, by filtration through a bacteria-retaining filter or by incorporation of sterilizing agents in the form of sterile solid compositions, which can be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration includes ointments, pastes, creams, lotions, gels, powders, solutions, sprays, inhalants or patches. A desired compound of the invention is admixed under sterile conditions with a pharmaceutically acceptable carrier and any needed preservatives or buffers as can be required. Ophthalmic formulation, eardrops, eye ointments, powders and solutions are also contemplated as being within the scope of this invention.

The ointments, pastes, creams and gels can contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of interest, lactose, talc, silicic acid, aluminum hydroxide, calcium silicates and polyamide powder, or mixtures of these substances. Sprays can additionally contain customary propellants such as chlorofluorohydrocarbons.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of interest, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., p 33 et seq (1976).

Dosage forms for topical administration include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds can be used in the form of pharmaceutically acceptable salts derived from inorganic or organic acids. The term "pharmaceutically acceptable salts" as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by mixing together solutions of the compounds of invention and a suitable acid or base. The salt can precipitate from the solution and be collected by filtration or can be recovered by evaporation of the solvent. The degree of ionization in the salt can vary from completely ionized to almost non-ionized.

Suitable acid addition salts are formed from acids which form non-toxic salts. Representative acid addition salts include, but are not limited to acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, gluconate, glucuronate, glutamate, hydrochloride, hydrobromide, hydroiodide, 2-hydroxyethansulfonate (isethionate), lactate, maleate, malate, malonate, methanesulfonate, nicotinate, 2-naphthalenesulfonate, nicotinate, nitrate, orotate, oxalate, palmitate, pamoate, pectinate, persulfate, 3-phenylpropionate, picrate, pivalate, propionate, saccharate, stearate, succinate, sulfate, tartrate, thiocyanate, phosphate, hydrogen-phosphate, dihydrogen phosphate, p-toluenesulfonate, trifluoroacetate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, zinc, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrug" or "prodrug" as used herein, represents those prodrugs of the compounds of the invention which are, within the scope of sound medical judgment, suitable for use in contact with the tissues of humans and animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof can be converted through in vivo biotransformation into compounds of the invention.

The compounds of the invention can exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

F) EXAMPLES

Following Examples can be used for illustrative purposes and should not be deemed to narrow the scope of the invention.

Example 1

1-[(2R)-2-hydroxy-2,3-dihydro-1H-inden-4-yl]-3-[(1R,3S)-3-phenylcyclopentyl]urea Example 1A 4-amino-2,3-dihydro-1H-inden-2-ol A slurry of 4-amino-2,3-dihydro-1H-inden-2-yl acetate (12.6 g, 65.9 mmol; prepared according to US2003109700), MeOH (63 mL), and potassium carbonate (13.7 g, 99.0 mmol) was stirred at ambient temperature for 15 minutes. The reaction mixture was diluted with IPA (630 mL), passed through a plug of silica gel, washed with IPA (100 mL), and concentrated to give the title compound (9.70 g, 65.0 mmol, 99%). MS (DCI) m/z 267 $(M+NH_4)^+$.

Example 1B (R)-4-amino-2,3-dihydro-1H-inden-2-ol

Example 1A (9.70 g, 65.0 mmol) was dissolved in MeOH (120 mL), then IPA (120 mL) and hexanes (240 mL) were added. This solution was passed through a Chiralpak AD-H semi-prep column (2 cm×25 cm), 15% IPA/hexanes isochratic mobile phase, 10 mL/min, 5 mL/injection, to provide the title compound (first eluting enantiomer, 4.89 g, 50%), and (S)-4-amino-2,3-dihydro-1H-inden-2-ol (second eluting enantiomer, 4.56 g, 47%). Analytical chiral HPLC showed >99.9% ee. MS (DCI) m/z 267 $(M+NH_4)^+$.

Example 1C (S)-3-(4-bromophenyl)cyclopentanone oxime

A slurry of (S)-3-(4-bromophenyl)cyclopentanone (prepared according to *J. Org. Chem.*, 2009, 74, 929; 10.9 g, 45.5 mmol), MeOH (110 mL), sodium acetate (5.59 g, 68.2 mmol), and hydroxylamine hydrochloride (4.74 g, 68.2 mmol) was stirred at room temperature. After 10 minutes, LCMS showed complete reaction. Diluted with MTBE (300 mL) and washed with water (100 mL) and brine (50 mL). The organic layer was dried ($Na_2SO_4$), filtered, and concentrated. The residue was purified by silica gel chromatography (gradient elution, 25-50% EtOAc/hexanes) to afford the title compound (11.0 g, 43.3 mmol, 95%). MS (DCI) m/z 254 $(M+H)^+$.

Example 1D (3S)-3-phenylcyclopentanamine

A solution of Example 1C (10 g, 39.4 mmol) and 7M $NH_3$/MeOH (100 mL) was added to Ra—Ni 2800, water slurry (40.0 g, 682 mmol) in a 50 mL pressure bottle. The mixture was stirred at room temperature for 32 hours at 30 psi. HPLC indicated complete reaction. The mixture was filtered through a nylon membrane, concentrated, and diluted with MTBE (300 mL) and 2N NaOH (150 mL). The layers were separated and the organic layer was washed with water (100 mL) and brine (50 mL), dried ($Na_2SO_4$), filtered, and concentrated to afford the title compound (5.86 g, 36.3 mmol, 92%). MS (LCMS) m/z 162 $(M+H)^+$.

Example 1E (1R,3S)-3-phenylcyclopentanamine

Example 1D (4.00 g, 24.8 mmol) was purified by preparatory HPLC on a Luna CN 2×25 cm column (5 µm) in 5% EtOH/hexane (containing 1% n-propylamine). The combined pure fractions of the main peak were concentrated to produce 2.43 g of the mixture of diastereomers. This mixture was separated on a chiral OD-H column (3×25 cm, 5 µm particles) in 5% IPA/hexane (containing 0.5% n-propylamine) at 40 mL/min (detection at 254 nm). The sample was dissolved in about 25 mL of the mobile phase and 1.5 mL (about 150 mg) was injected per run, about 20 injections total were made. The combined fractions corresponding to peaks 1 and 2 (order of elution) were concentrated to produce the title compound (first eluting diastereomer, 1.15 g) and (1S,3S)-3-phenylcyclopentanamine (second eluting diastereomer, 0.94 g) as colorless oils with chiral purities ~99.9%. MS (LCMS) m/z 162 $(M+H)^+$.

Example 1F

1-[(2R)-2-hydroxy-2,3-dihydro-1H-inden-4-yl]-3-[(1R,3S)-3-phenylcyclopentyl]urea In a 20 mL vial was added a solution of Example 1B (33 mg, 0.22 mmol) in 1 mL of acetonitrile, followed by N,N-disuccinimidyl carbonate (57 mg, 0.22 mmol) and pyridine (15 µL, 0.18 mmol). The mixture was allowed to stir at room temperature for 30 minutes, then di-isopropyl ethyl amine (97 µL, 0.54 mmol) and a solution of Example 1E (30 mg, 0.18 mmol) in 2 mL of 1:1 N,N-dimethylacetamide:pyridine solution was added. The vial was capped and stirred at room temperature overnight. The crude mixture was concentrated to dryness. The residue was dissolved in 1.4 mL of DMSO: MeOH (1:1) and purified through reverse phase HPLC [Phenomenex Luna C8(2) 5 µm 100 Å AXIA column (30 mm×75 mm). A gradient of 10-100% methanol (A) and 10 mM ammonium acetate in water (B) was used, at a flow rate of 2.0 mL/min (0-0.1 min 10% A, 0.1-2.6 min 10-100% A, 2.6-2.9 min 100% A, 2.9-3.0 min 100-10% A. 0.5 min post-run delay] to afford the title compound. $^1$H NMR (500 MHz, DMSO-$d_6$/Deuterium Oxide) δ 7.69 (d, J=8.1 Hz, 1H), 7.26-7.33 (m, 4H), 7.18-7.22 (m, 1H), 7.04 (dd, J=8.1, 7.5 Hz, 1H), 6.82 (d, J=7.4 Hz, 1H), 4.47-4.58 (m, 1H), 4.05-4.14 (m, 1H), 3.02-3.11 (m, 2H), 2.95 (dd, J=16.0, 6.2 Hz, 1H), 2.74 (dd, J=16.2, 3.5 Hz, 1H), 2.65 (dd, J=16.0, 3.5 Hz, 1H), 2.38-2.44 (m, 1H), 2.00-2.08 (m, 2H), 1.65-1.75 (m, 1H), 1.56-1.64 (m, 1H), 1.39-1.47 (m, 1H); MS ($ESI^+$) M/Z 337 $[M+H]^+$.

Example 2

1-[(2S)-2-hydroxy-2,3-dihydro-1H-inden-4-yl]-3-[(1R,3S)-3-phenylcyclopentyl]urea The title compound was prepared according to Example 1F, substituting (S)-4-amino-2,3-dihydro-1H-inden-2-ol (second eluting enantiomer from Example 1B) for Example 1B. $^1$H NMR (500 MHz, DMSO-$d_6$/Deuterium Oxide) δ 7.69 (d, J=8.1 Hz, 1H), 7.27-7.33 (m, 4H), 7.18-7.22 (m, 1H), 7.04 (dd, J=7.9, 7.6 Hz, 1H), 6.82 (d, J=7.3 Hz, 1H), 4.50-4.54 (m, 1H), 4.04-4.14 (m, 1H), 3.03-3.10 (m, 2H), 2.96 (dd, J=16.1, 6.2 Hz, 1H), 2.74 (dd, J=16.0, 3.7 Hz, 1H), 2.65 (dd, J=16.0, 3.5 Hz, 1H), 2.39-2.44 (m, 1H), 2.00-2.08 (m, 2H), 1.64-1.75 (m, 1H), 1.55-1.64 (m, 1H), 1.40-1.46 (m, 1H); MS ($ESI^+$) M/Z 337 $[M+H]^+$.

Example 3

1-[(2R)-2-methyl-3-oxo-3,4-dihydro-2H-1,4-benzoxazin-8-yl]-3-[(1R,3S)-3-phenylcyclopentyl]urea The title compound was prepared according to Example 1F, substituting (R)-8-amino-2-methyl-2H-benzo[b][1,4]oxazin-3(4H)-one for Example 1B. $^1$H NMR (500 MHz, DMSO-$d_6$/Deuterium Oxide) δ 7.74 (dd, J=8.4, 1.4 Hz, 1H), 7.26-7.34 (m, 4H), 7.17-7.22 (m, 1H), 6.85 (dd, J=8.3, 8.0 Hz, 1H), 6.51 (dd, J=7.9, 1.5 Hz, 1H), 4.67 (q, J=6.8 Hz, 1H), 4.06-4.13 (m, 1H), 2.99-3.13 (m, 1H), 2.36-2.48 (m, 1H), 1.97-2.10 (m, 2H), 1.65-1.75 (m, 1H), 1.56-1.65 (m, 1H), 1.47 (d, J=6.9 Hz, 3H), 1.39-1.44 (m, 1H); MS (ESI+) M/Z 366 [M+H]+.

Example 4

1-(1-methyl-1H-indazol-4-yl)-3-[(1R,3S)-3-phenyl-cyclopentyl]urea

Example 4A 2-bromo-6-fluorobenzaldehyde

1-Bromo-3-fluorobenzene (17.3 g, 100 mmol) was added over 5 minutes to a solution of lithium diisopropylamide (prepared from the addition of 40 mL of 2.5 N-butyllithium in hexanes to 11.5 g of 0.1 M diisopropylamine at 0° C.) in THF at −70° C. The mixture was stirred cold for 1 hour, after which DMF (8 mL) was added over 10 minutes. The mixture was stirred at −70° C. for an additional 40 minutes, followed by treatment with acetic acid (26 g). The mixture was allowed to warm to ambient temperature and transferred into a mixture of MTBE (200 mL), water (200 mL), and hydrochloric acid (4 N, 150 mL). The layers were partitioned and the organic portion was concentrated under reduced pressure to provide the title compound. MS (DCI/NH$_3$) m/z 202 (M+H)+.

Example 4B 4-bromo-1-methyl-1H-indazole

A solution of Example 4A (2.00 g, 9.95 mmol) in DMSO (3.5 mL) was added to methylhydrazine (98%, 3.20 g of 98% reagent, 69.6 mmol). The mixture was heated at 85° C. for 24 hours, then cooled to ambient temperature and diluted with water (50 mL). The solution was extracted with CH$_2$Cl$_2$ (2×50 mL) and the combined organic layers were dried (MgSO$_4$), filtered, and concentrated under reduced pressure to provide the title compound which was used without further purification. MS (DCI/NH$_3$) m/z 202 (M+H)+.

Example 4C 1-methyl-1H-indazol-3-amine

A mixture of palladium(II) acetate (82 mg, 2 mol %) and Xantphos (287 mg, 3 mol %) in toluene (10 mL) was stirred for 5 minutes at ambient temperature. To the solution was added a solution of Example 4B (3.68 g, 17.4 mmol) and benzophenone imine (3.00 g, 17.4 mmol) in toluene (30 mL). The mixture was evacuated and purged with nitrogen two times, then stirred at ambient temperature for 15 minutes. Sodium tert-butoxide (1.90 g, 24.4 mmol) was added and the mixture was evacuated and purged with nitrogen. The mixture was heated at between 80 and 85° C. for 2 hours, cooled to ambient temperature, and diluted with water (30 mL). The layers were partitioned and the aqueous layer was extracted with additional toluene (20 mL). The combined organic layers were stirred with 6 N HCl (10 mL) for 1 hour, then 40 mL of water was added to dissolve the solids. The toluene layer was discarded and the aqueous layer filtered to remove insoluble material. The aqueous layer was adjusted to pH 14 with the addition of 50% NaOH and the resulting solid was filtered and dried to provide the title compound. MS (DCI/NH$_3$) m/z 202 (M+H)+.

Example 4D 1-(1-methyl-1H-indazol-4-yl)-3-[(1R,3S)-3-phenyl-cyclopentyl]urea The title compound was prepared according to Example 1F, substituting Example 4C for Example 1B. $^1$H NMR (500 MHz, DMSO-d$_6$/Deuterium Oxide) δ 8.06 (d, J=0.9 Hz, 1H), 7.62 (dd, J=7.6, 0.7 Hz, 1H), 7.27-7.34 (m, 5H), 7.18-7.22 (m, 1H), 7.14-7.16 (m, 1H), 4.11-4.18 (m, 1H), 4.00 (s, 3H), 3.05-3.12 (m, 1H), 2.39-2.47 (m, 1H), 2.01-2.13 (m, 2H), 1.59-1.77 (m, 2H), 1.45-1.51 (m, 1H); MS (ESI+) M/Z 335 [M+H]+.

Example 5

1-(2-oxo-1,2,3,4-tetrahydroquinolin-7-yl)-3-[(1R,3S)-3-phenylcyclopentyl]urea

The title compound was prepared according to Example 1F, substituting 7-amino-3,4-dihydroquinolin-2(1H)-one for Example 1B. $^1$H NMR (500 MHz, DMSO-d$_6$/Deuterium Oxide) δ ppm 7.25-7.35 (m, 4H), 7.17-7.22 (m, 1H), 7.00-7.05 (m, 2H), 6.89 (dd, J=8.1, 2.1 Hz, 1H), 4.05-4.12 (m, 1H), 3.00-3.12 (m, 1H), 2.78 (t, J=7.6 Hz, 2H), 2.33-2.47 (m, 3H), 1.97-2.08 (m, 2H), 1.54-1.75 (m, 2H), 1.39-1.49 (m, 1H); MS (ESI+) M/Z 350 [M+H]+.

Example 6

1-(6-fluoro-3-methylisoquinolin-5-yl)-3-[(1R,3S)-3-phenylcyclopentyl]urea

Example 6A 6-fluoro-3-methylisoquinoline

DMF (50 mL) and NEt$_3$ (10.30 mL, 73.9 mmol) were added to 2-bromo-4-fluorobenzaldehyde (10 g, 49.3 mmol) under argon in a 300 mL stainless steel reactor. The vessel was sparged with propyne and chilled in dry ice, then propyne (18.22 mL, 296 mmol) was distilled in. Bis(triphenylphosphine)palladium(II) chloride (0.173 g, 0.246 mmol) and copper(I) iodide (0.047 g, 0.246 mmol) were added, and the reactor was sealed and stirred for 4 hours at room temperature. The mixture was chilled and sampled. HPLC analysis indicated 90% conversion. 2 M NH$_3$/MeOH (150 mL) was added to the chilled (and solidified) mixture, and the resulting solution was stirred 1.5 hours at 85° C. HPLC indicated complete conversion of alkyne to isoquinoline. The mixture was cooled and concentrated. Water (200 mL) and EtOAc (200 mL) were added, the layers were separated, and the organic layer was washed with brine (2×50 mL). The organic portion was extracted with 2N HCl (100 mL) and water (100 mL), then the aqueous layer was basified with 2N NaOH (120 mL). The mixture was extracted with EtOAc (2×100 mL) and the organic layer was washed with brine (50 mL), dried (Na$_2$SO$_4$), and concentrated, giving the title compound (6.87 g, 42.6 mmol, 87% yield). MS (DCI/NH$_3$) m/z 162 (M+H)+.

Example 6B 6-fluoro-3-methyl-5-nitroisoquinoline

In a 1-L round-bottom under nitrogen with a glass/teflon overhead stirrer, sulfolane (270 g) was melted in a 50° C. water bath. At 35° C., nitronium tetrafluoroborate (44.0 g, 322 mmol) was added. Example 6A (25.5 g, 158 mmol) was added carefully over 8 minutes, causing an exotherm to 71° C. After the addition, HPLC showed complete reaction. The mixture was cooled to 30° C. and 1.5 M aqueous NaOH (330 mL) was added over 20 minutes keeping the temperature below 40° C. The resulting slurry was filtered and washed with water (40 mL×4). The solid was dried in a vacuum oven at 50° C., to provide the title compound (26.7 g, 82%). MS (DCI/NH$_3$) m/z 207 (M+H)$^+$.

Example 6C 6-fluoro-3-methylisoquinolin-5-amine

A 1.8 L Parr shaker was charged with MeOH (750 mL) and Example 6B (25.0 g). Raney nickel (Grace 2800, 50 wt % dry basis, 12.5 g) was weighed out quantitatively and the water was decanted off. The Raney nickel was transferred to the reactor with the aid of MeOH and the reactor was sealed, purged with nitrogen, then purged with hydrogen. The reactor was pressurized to 30 psi with hydrogen and stirred for 1 hour at room temperature. HPLC showed complete conversion. The mixture was filtered and the filtrate was concentrated to afford a tannish solid. The solid was dissolved in dichloromethane (500 mL) and washed with brine (150 mL). The organic layer was separated, dried (MgSO$_4$), filtered, and concentrated to afford a light tanish solid (20 g). The solid was dissolved in EtOAc (100 mL) at 65° C., then hexanes (100 mL) was added dropwise. The resulting slurry was cooled to <5° C., filtered, and washed with 1:1 EtOAc/hexanes. The solid was dried in a vacuum oven at 45° C., to provide the title compound (16.6 g, 63%); MS (DCI/NH$_3$) m/z 177 (M+H)$^+$.

Example 6D 2,2,2-trichloro-N-(6-fluoro-3-methylisoquinolin-5-yl)acetamide

A cold (−10° C.) slurry of Example 6C (16.4 g, 93.3 mmol) and pyridine (18.8 mL, 233 mmol) in acetonitrile (164 mL) was treated dropwise with trichloroacetic anhydride (22.1 mL, 121 mmol). The reaction temperature was maintained at <−10° C. After 10 minutes, HPLC indicated complete reaction. After 35 minutes, water (320 mL) was added dropwise at <−10° C. After 10 minutes, the slurry was filtered and washed with cold 1:2 acetonitrile/water (100 mL). The product was dried in a vacuum oven at 48° C., to provide the title compound (29.1 g, 97%). MS (DCI/NH$_3$) m/z 321 (M+H)$^+$.

Example 6E 1-(6-fluoro-3-methylisoquinolin-5-yl)-3-[(1R,3S)-3-phenylcyclopentyl]urea In a 4 mL microwave vial was added a solution of Example 6D (20 mg, 0.06 mmol) dissolved in DMF (1 mL), followed by a solution of Example 1E (15 mg, 0.09 mmol) in DMF (1 mL) and potassium carbonate (42 mg, 0.31 mmol). The mixture was allowed to stir at 150° C. for 30 minutes in a parallel Anton Parr microwave. The crude mixture was concentrated to dryness. The residue was dissolved in 1:1 DMSO:MeOH (1.4 mL) and purified through reverse phase HPLC (Ammonium acetate method in Example 1F) to afford the title compound. $^1$H NMR (500 MHz, DMSO-d$_6$/Deuterium Oxide) δ 9.21 (s, 1H), 8.06 (dd, J=9.0, 5.0 Hz, 1H), 7.60 (d, J=1.0 Hz, 1H), 7.53 (dd, J=9.5 Hz, 1H), 7.29-7.33 (m, 4H), 7.18-7.22 (m, 1H), 4.08-4.16 (m, 1H), 3.02-3.10 (m, 1H), 2.62 (s, 3H), 2.37-2.43 (m, 1H), 2.01-2.08 (m, 2H), 1.64-1.78 (m, 2H), 1.51-1.61 (m, 1H); MS (ESI$^+$) M/Z 364 [M+H]$^+$.

Example 7

1-(1H-indazol-4-yl)-3-[(1R,3S)-3-phenylcyclopentyl]urea

A yellow solution of Example 1E (150 mg, 0.930 mmol), DMF (3.1 mL), N,N-diisopropyl ethylamine (0.341 mL, 1.95 mmol), and methyl 4-((2,5-dioxopyrrolidin-1-yloxy)carbonylamino)-1H-indazole-1-carboxylate (prepared as in *Org. Proc. Res. Dev.*, 2007, 11, 578; 309 mg, 0.930 mmol) was stirred at room temperature. After 20 minutes, LCMS showed nearly complete conversion to methyl carbamate intermediate. After 40 minutes, MeOH (6.20 mL), water (1.24 mL), and triethylamine (0.271 mL, 1.95 mmol) were added and the solution was heated to 50° C. After 15 hours, LCMS showed complete reaction. Water (9 mL) was added dropwise, and the white slurry was aged for 10 minutes and filtered. The precipitate was collected and washed with cold 2:3 MeOH/water (5 mL) and dried in a vacuum oven at 50° C., to provide the title compound (197 mg, 0.615 mmol, 66%). $^1$H NMR (300 MHz, DMSO-d$_6$) δ ppm 12.97-13.01 (bs, 1H), 8.53 (s, 1H), 8.08 (d, J=1.0 Hz, 1H), 7.63 (dd, J=7.6, 0.7 Hz, 1H), 7.16-7.31 (m, 6H), 7.04 (d, J=8.2 Hz, 1H), 6.58 (d, J=7.0 Hz, 1H), 4.18-4.30 (m, 1H), 3.24 (p, J=8.7 Hz, 1H), 2.08-2.29 (m, 2H), 1.90-1.98 (m, 2H), 1.50-1.68 (m, 2H); MS (ESI$^+$) M/Z 321 (M+H)$^+$.

Example 8

1-[(2R)-2-hydroxy-2,3-dihydro-1H-inden-4-yl]-3-[(1S,3S)-3-phenylcyclopentyl]urea The title compound was prepared according to Example 1F, substituting (1S,3S)-3-phenylcyclopentanamine (second eluting diastereomer from Example 1E) for Example 1E. $^1$H NMR (500 MHz, DMSO-d$_6$/Deuterium Oxide) δ 7.71 (d, J=8.1 Hz, 1H), 7.24-7.36 (m, 4H), 7.17-7.21 (m, 1H), 7.04 (dd, J=7.8 Hz, 1H), 6.82 (d, J=7.4 Hz, 1H), 4.50-4.55 (m, 1H), 4.14-4.22 (m, 1H), 3.16-3.27 (m, 1H), 3.06 (dd, J=16.1, 6.2 Hz, 1H), 2.96 (dd, J=16.1, 6.2 Hz, 1H), 2.75 (dd, J=16.1, 3.6 Hz, 1H), 2.65 (dd, J=16.0, 3.5 Hz, 1H), 2.02-2.23 (m, 2H), 1.90 (dd, J=8.9, 5.7 Hz, 2H), 1.49-1.63 (m, 2H); MS (ESI$^+$) M/Z 337 [M+H]$^+$.

Example 9

1-[(2S)-2-hydroxy-2,3-dihydro-1H-inden-4-yl]-3-[(1S,3S)-3-phenylcyclopentyl]urea The title compound was prepared according to Example 1F, substituting (S)-4-amino-2,3-dihydro-1H-inden-2-ol (second eluting enantiomer from Example 1B) for Example 1B, and substituting (1S,3S)-3-phenylcyclopentanamine (second eluting diastereomer from Example 1E) for Example 1E. $^1$H NMR (500 MHz, DMSO-d$_6$/Deuterium Oxide) δ 7.71 (d, J=8.1 Hz, 1H), 7.26-7.34 (m, 4H), 7.17-7.21 (m, 1H), 7.04 (dd, J=7.8 Hz, 1H), 6.82 (d, J=7.4 Hz, 1H), 4.50-4.57 (m, 1H), 4.14-4.23 (m, 1H), 3.15-3.27 (m, 1H), 3.06 (dd, J=16.2, 6.1 Hz, 1H), 2.96 (dd, J=16.1, 6.2 Hz, 1H), 2.75 (dd, J=16.2, 3.4 Hz, 1H), 2.65 (dd, J=16.1, 3.4 Hz, 1H), 2.09-2.25 (m, 2H), 1.87-1.92 (m, 2H), 1.47-1.67 (m, 2H); MS (ESI$^+$) M/Z 337 [M+H]$^+$.

Example 10

1-[(2R)-2-methyl-3-oxo-3,4-dihydro-2H-1,4-benzoxazin-8-yl]-3-[(1S,3S)-3-phenylcyclopentyl]urea The title compound was prepared according to Example 1F, substituting (R)-8-amino-2-methyl-2H-benzo[b][1,4]oxazin-3(4H)-one for Example 1B; and substituting (1S,3S)-3-phenylcyclopentanamine (second eluting diastereomer from Example 1E) for Example 1E. $^1$H NMR (500 MHz, DMSO-d$_6$/Deuterium Oxide) δ 7.74 (dd, J=8.3, 1.4 Hz, 1H), 7.26-7.33 (m, 4H), 7.17-7.21 (m, 1H), 6.85 (dd, J=8.2 Hz, 1H), 6.51 (dd, J=7.9, 1.4 Hz, 1H), 4.68 (q, J=6.8 Hz, 1H), 4.14-4.23 (m, 1H), 3.16-3.26 (m, 1H), 2.02-2.22 (m, 2H), 1.90 (dd, J=8.9, 5.6 Hz, 2H), 1.49-1.67 (m, 2H), 1.47 (d, J=6.8 Hz, 3H); MS (ESI$^+$) M/Z 366 [M+H]$^+$.

Example 11

1-(1-methyl-1H-indazol-4-yl)-3-[(1S,3S)-3-phenylcyclopentyl]urea

The title compound was prepared according to Example 1F, substituting Example 4C for Example 1B, and substituting (1S,3S)-3-phenylcyclopentanamine (second eluting diastereomer from Example 1E) for Example 1E. $^1$H NMR (500 MHz, DMSO-d$_6$/Deuterium Oxide) δ 8.07 (d, J=1.0 Hz, 1H), 7.63 (dd, J=7.6, 0.7 Hz, 1H), 7.27-7.33 (m, 5H), 7.17-7.23 (m, 1H), 7.15 (ddd, J=8.4, 0.8 Hz, 1H), 4.24 (p, J=5.9 Hz, 1H), 4.00 (s, 3H), 3.20-3.27 (m, 1H), 2.06-2.27 (m, 2H), 1.92-1.96 (m, 2H), 1.53-1.68 (m, 2H); MS (ESI$^+$) M/Z 335 [M+H]$^+$.

Example 12

1-(2-oxo-1,2,3,4-tetrahydroquinolin-7-yl)-3-[(1S,3S)-3-phenylcyclopentyl]urea

The title compound was prepared according to Example 1F, substituting 7-amino-3,4-dihydroquinolin-2(1H)-one for Example 1B, and substituting (1S,3S)-3-phenylcyclopentanamine (second eluting diastereomer from Example 1E) for Example 1E. $^1$H NMR (500 MHz, DMSO-d$_6$/Deuterium Oxide) δ 7.25-7.32 (m, 4H), 7.17-7.21 (m, 1H), 7.01-7.03 (m, 2H), 6.89 (dd, J=8.1, 2.1 Hz, 1H), 4.17 (p, J=6.0 Hz, 1H), 3.16-3.23 (m, 1H), 2.78 (t, J=7.5 Hz, 2H), 2.40-2.44 (m, 2H), 2.02-2.20 (m, 2H), 1.90 (d, J=6.0 Hz, 1H), 1.88 (d, J=5.8 Hz, 1H), 1.45-1.62 (m, 2H); MS (ESI$^+$) M/Z 350 [M+H]$^+$.

Example 13

1-(6-fluoro-3-methylisoquinolin-5-yl)-3-[(1S,3S)-3-phenylcyclopentyl]urea

A slurry of Example 6D (199 mg, 0.620 mmol), (1S,3S)-3-phenylcyclopentanamine (100 mg, 0.620 mmol) (second eluting diastereomer from Example 1E), DMF (3 mL), and K$_2$CO$_3$ (21.4 mg, 0.155 mmol) was heated to 85° C. After 10 hours, the slurry was cooled, diluted with EtOAc (50 mL), and washed with 10% aqueous KH$_2$PO$_4$ (30 mL×2), brine (30 mL×2), 2N NaOH (50 mL), and brine (30 mL). The organic layer was dried (Na$_2$SO$_4$), filtered, and concentrated. The residue was purified by flash column chromatography (0-10% MeOH/EtOAc gradient elution), to provide the title compound (153 mg, 0.421 mmol, 68%). $^1$H NMR (300 MHz, DMSO-d$_6$) δ ppm 9.21 (s, 1H), 8.02 (dd, J=9.2, 5.3 Hz, 1H), 7.99 (s, 1H), 7.60 (d, J=1.1 Hz, 1H), 7.52 (dd, J=9.9, 9.1 Hz, 1H), 7.24-7.34 (m, 4H), 7.14-7.22 (m, 1H), 6.61 (d, J=7.2 Hz, 1H), 4.10-4.26 (m, 1H), 3.20-3.30 (m, 1H), 2.62 (s, 3H), 2.08-2.28 (m, 2H), 1.85-2.06 (m, 2H), 1.50-1.68 (m, 2H); MS (ESI$^-$) M/Z 362 (M−H)$^-$.

Example 14

1-(1H-indazol-4-yl)-3-[(1S,3S)-3-phenylcyclopentyl]urea

The title compound was prepared according to Example 7, substituting (1S,3S)-3-phenylcyclopentanamine (second eluting diastereomer from Example 1E) for Example 1E. $^1$H NMR (300 MHz, DMSO-d$_6$) δ ppm 12.92-13.03 (bs, 1H), 8.54 (s, 1H), 8.07 (d, J=1.0 Hz, 1H), 7.62 (dd, J=7.6, 0.7 Hz, 1H), 7.26-7.36 (m, 4H), 7.14-7.24 (m, 2H), 7.05 (dt, J=8.3, 0.9 Hz, 1H), 6.54 (d, J=7.2 Hz, 1H), 4.08-4.21 (m, 1H), 3.05-3.11 (m, 1H), 2.38-2.47 (m, 1H), 1.95-2.16 (m, 2H), 1.59-1.82 (m, 2H), 1.48 (ddd, J=12.4, 11.1, 8.6 Hz, 1H); MS (ESI$^+$) M/Z 321 (M+H)$^+$.

Example 15

1-[(2R)-2-hydroxy-2,3-dihydro-1H-inden-4-yl]-3-[(1R,3R)-3-phenylcyclopentyl]urea

Example 15A (3R)-3-phenylcyclopentanamine

The title compound was prepared according to Example 1C and 1D, substituting (R)-3-(4-bromophenyl)cyclopentanone for (S)-3-(4-bromophenyl)cyclopentanone. MS (DCI) m/z 162 (M+H)$^+$.

Example 15B (1R,3R)-3-phenylcyclopentanamine

A solution of Example 15A (1.82 g, 11.3 mmol) was dissolved in 90/10 hexanes/isopropyl alcohol (20 mL, containing 0.1% diethylamine), and the solution was passed through a Chiralcel OD-H 3×25 cm chiral HPLC column, eluting with 90/10 hexanes/isopropyl alcohol at 40 mL/min, 2 mL (180 mg) per injection. The pure fractions were combined and concentrated, to provide the title compound (first eluting diastereomer, 805 mg, 4.99 mmol, 44%) and (1S,3R)-3-phenylcyclopentanamine (second eluting diastereomer, 865 mg, 5.36 mmol, 48%). MS (DCI) m/z 162 (M+H)$^+$.

Example 15C

1-[(2R)-2-hydroxy-2,3-dihydro-1H-inden-4-yl]-3-[(1R,3R)-3-phenylcyclopentyl]urea The title compound was prepared according to Example 1F, substituting Example 15B for Example 1E. $^1$H NMR (400 MHz, DMSO-d$_6$/Deuterium Oxide) δ 7.71 (dd, J=8.2, 0.7 Hz, 1H), 7.24-7.35 (m, 4H), 7.16-7.23 (m, 1H), 7.04 (dd, J=8.0, 7.5 Hz, 1H), 6.82 (dd, J=7.3, 0.6 Hz, 1H), 4.50-4.55 (m, 1H), 4.13-4.24 (m, 1H), 3.16-3.26 (m, 1H), 3.06 (dd, J=16.1, 6.2 Hz, 1H), 2.96 (dd, J=16.2, 6.3 Hz, 1H), 2.75 (dd, J=16.1, 3.6

Hz, 1H), 2.66 (dd, J=16.0, 3.4 Hz, 1H), 2.08-2.25 (m, 2H), 1.90 (dd, J=8.9, 5.7 Hz, 2H), 1.47-1.64 (m, 2H); MS (ESI$^+$) M/Z 337 [M+H]$^+$.

Example 16

1-[(2S)-2-hydroxy-2,3-dihydro-1H-inden-4-yl]-3-[(1R,3R)-3-phenylcyclopentyl]urea The title compound was prepared according to Example 15C, substituting (S)-4-amino-2,3-dihydro-1H-inden-2-ol (second eluting enantiomer from Example 1B) for Example 1B. $^1$H NMR (400 MHz, DMSO-d$_6$/Deuterium Oxide) δ 7.70 (d, J=8.1 Hz, 1H), 7.25-7.34 (m, 4H), 7.16-7.22 (m, 1H), 7.04 (dd, J=7.8 Hz, 1H), 6.82 (d, J=7.3 Hz, 1H), 4.50-4.55 (m, 1H), 4.15-4.22 (m, 1H), 3.15-3.27 (m, 1H), 3.06 (dd, J=16.1, 6.2 Hz, 1H), 2.96 (dd, J=16.1, 6.2 Hz, 1H), 2.75 (dd, J=16.2, 3.7 Hz, 1H), 2.65 (dd, J=16.0, 3.5 Hz, 1H), 2.10-2.24 (m, 2H), 1.90 (dd, J=8.9, 5.7 Hz, 2H), 1.48-1.64 (m, 2H); MS (ESI$^+$) M/Z 337 [M+H]$^+$.

Example 17

1-[(2R)-2-methyl-3-oxo-3,4-dihydro-2H-1,4-benzoxazin-8-yl]-3-[(1R,3R)-3-phenylcyclopentyl]urea The title compound was prepared according to Example 1F, substituting (R)-8-amino-2-methyl-2H-benzo[b][1,4]oxazin-3(4H)-one for Example 1B, and substituting Example 15B for Example 1E. $^1$H NMR (400 MHz, DMSO-d$_6$/Deuterium Oxide) δ 7.74 (dd, J=8.3, 1.4 Hz, 1H), 7.24-7.35 (m, 4H), 7.16-7.22 (m, 1H), 6.85 (dd, J=8.2 Hz, 1H), 6.51 (dd, J=7.9, 1.4 Hz, 1H), 4.67 (q, J=6.7 Hz, 1H), 4.14-4.22 (m, 1H), 3.14-3.27 (m, 1H), 2.08-2.23 (m, 2H), 1.90 (dd, J=8.9, 5.6 Hz, 2H), 1.49-1.64 (m, 2H), 1.47 (d, J=6.8 Hz, 3H); MS (ESI$^+$) M/Z 366 [M+H]$^+$.

Example 18

1-(1-methyl-1H-indazol-4-yl)-3-[(1R,3R)-3-phenylcyclopentyl]urea

The title compound was prepared according to Example 1F, substituting Example 4C for Example 1B, and substituting Example 15B for Example 1E. $^1$H NMR (400 MHz, DMSO-d$_6$/Deuterium Oxide) δ ppm 8.07 (d, J=0.9 Hz, 1H), 7.63 (d, J=7.6 Hz, 1H), 7.26-7.34 (m, 5H), 7.17-7.22 (m, 1H), 7.15 (dt, J=8.4, 0.8 Hz, 1H), 4.20-4.27 (m, 1H), 4.00 (s, 3H), 3.23 (p, J=8.6 Hz, 1H), 2.10-2.28 (m, 2H), 1.91-1.97 (m, 2H), 1.52-1.66 (m, 2H); MS (ESI$^+$) M/Z 335 [M+H]$^+$.

Example 19

1-(2-oxo-1,2,3,4-tetrahydroquinolin-7-yl)-3-[(1R,3R)-3-phenylcyclopentyl]urea

The title compound was prepared according to Example 1F, substituting 7-amino-3,4-dihydroquinolin-2(1H)-one for Example 1B, and substituting Example 15B for Example 1E. $^1$H NMR (400 MHz, DMSO-d$_6$/Deuterium Oxide) δ 7.25-7.33 (m, 4H), 7.16-7.21 (m, 1H), 7.02 (dd, J=5.2, 3.0 Hz, 2H), 6.89 (dd, J=8.1, 2.1 Hz, 1H), 4.17 (p, J=6.0 Hz, 1H), 3.15-3.24 (m, 1H), 2.78 (t, J=7.5 Hz, 2H), 2.42 (dd, J=8.0, 6.2 Hz, 2H), 2.06-2.23 (m, 2H), 1.89 (dd, J=8.9, 5.8 Hz, 2H), 1.47-1.63 (m, 2H); MS (ESI$^+$) M/Z 350 [M+H]$^+$.

Example 20

1-(6-fluoro-3-methylisoquinolin-5-yl)-3-[(1R,3R)-3-phenylcyclopentyl]urea

The title compound was prepared according to Example 6E, substituting Example 15B for Example 1E. $^1$H NMR (500 MHz, DMSO-d$_6$/Deuterium Oxide) δ 9.21 (s, 1H), 8.06 (dd, J=9.0, 5.0 Hz, 1H), 7.61 (d, J=1.1 Hz, 1H), 7.53 (t, J=9.4 Hz, 1H), 7.27-7.33 (m, 4H), 7.14-7.21 (m, 1H), 4.15-4.24 (m, 1H), 3.21-3.29 (m, 1H), 2.63 (s, 3H), 2.18-2.26 (m, 1H), 2.09-2.18 (m, 1H), 1.87-2.02 (m, 2H), 1.54-1.64 (m, 2H); MS (ESI$^+$) M/Z 364 [M+H]$^+$.

Example 21

1-(1H-indazol-4-yl)-3-[(1R,3R)-3-phenylcyclopentyl]urea

The title compound was prepared according to Example 7, substituting Example 15B for Example 1E. $^1$H NMR (300 MHz, DMSO-d$_6$) δ ppm 12.97-13.00 (bs, 1H), 8.52 (s, 1H), 8.07 (s, 1H), 7.63 (d, J=7.5 Hz, 1H), 7.25-7.36 (m, 4H), 7.14-7.24 (m, 2H), 7.04 (d, J=8.2 Hz, 1H), 6.57 (d, J=7.0 Hz, 1H), 4.18-4.30 (m, 1H), 3.24 (dt, J=16.6, 8.3 Hz, 1H), 2.11-2.29 (m, 2H), 1.90-1.98 (m, 2H), 1.52-1.68 (m, 2H); MS (ESI$^+$) M/Z 321 (M+H)$^+$.

Example 22

1-[(2R)-2-hydroxy-2,3-dihydro-1H-inden-4-yl]-3-[(1S,3R)-3-phenylcyclopentyl]urea The title compound was prepared according to Example 1F, substituting (1S,3R)-3-phenylcyclopentanamine (second eluting diastereomer from Example 15B) for Example 1E. $^1$H NMR (500 MHz, DMSO-d$_6$/Deuterium Oxide) δ 7.70 (d, J=8.1 Hz, 1H), 7.28-7.33 (m, 4H), 7.18-7.22 (m, 1H), 7.04 (dd, J=7.8 Hz, 1H), 6.82 (d, J=7.4 Hz, 1H), 4.50-4.54 (m, 1H), 4.08-4.12 (m, 1H), 3.02-3.11 (m, 2H), 2.95 (dd, J=16.1, 6.2 Hz, 1H), 2.75 (dd, J=16.0, 3.6 Hz, 1H), 2.65 (dd, J=16.0, 3.5 Hz, 1H), 2.38-2.44 (m, 1H), 2.00-2.08 (m, 2H), 1.64-1.76 (m, 1H), 1.54-1.64 (m, 1H), 1.39-1.46 (m, 1H); MS (ESI$^+$) M/Z 337 [M+H]$^+$.

Example 23

1-[(2S)-2-hydroxy-2,3-dihydro-1H-inden-4-yl]-3-[(1S,3R)-3-phenylcyclopentyl]urea The title compound was prepared according to Example 1F, substituting (S)-4-amino-2,3-dihydro-1H-inden-2-ol (second eluting enantiomer from Example 1B) for Example 1B, and substituting (1S,3R)-3-phenylcyclopentanamine (second eluting diastereomer from Example 15B) for Example 1E. $^1$H NMR (500 MHz, DMSO-d$_6$/Deuterium Oxide) δ 7.70 (d, J=8.2 Hz, 1H), 7.25-7.33 (m, 4H), 7.18-7.22 (m, 1H), 7.04 (dd, J=8.0, 7.4 Hz, 1H), 6.82 (d, J=7.4 Hz, 1H), 4.50-4.54 (m, 1H), 4.06-4.12 (m, 1H), 3.03-3.10 (m, 2H), 2.96 (dd, J=16.1, 6.2 Hz, 1H), 2.75 (dd, J=16.0, 3.6 Hz, 1H), 2.65 (dd, J=16.1, 3.5 Hz, 1H), 2.39-2.44 (m, 1H), 2.00-2.08 (m, 2H), 1.64-1.75 (m, 1H), 1.55-1.64 (m, 1H), 1.40-1.46 (m, 1H); MS (ESI$^+$) M/Z 337 [M+H]$^+$.

Example 24

1-[(2R)-2-methyl-3-oxo-3,4-dihydro-2H-1,4-benzoxazin-8-yl]-3-[(1S,3R)-3-phenylcyclopentyl]urea The title compound was prepared according to Example 1F, substituting (R)-8-amino-2-methyl-2H-benzo[b][1,4]oxazin-3(4H)-one for Example 1B, and substituting (1S,3R)-3-phenylcyclopentanamine (second eluting diastereomer from Example 15B) for Example 1E. $^1$H NMR (500 MHz, DMSO-$d_6$/Deuterium Oxide) δ 7.74 (dd, J=8.3, 1.4 Hz, 1H), 7.27-7.33 (m, 4H), 7.18-7.22 (m, 1H), 6.85 (dd, J=8.1 Hz, 1H), 6.51 (dd, J=7.9, 1.4 Hz, 1H), 4.67 (q, J=6.8 Hz, 1H), 4.09-4.10 (m, 1H), 3.01-3.10 (m, 1H), 2.39-2.44 (m, 1H), 1.99-2.07 (m, 2H), 1.64-1.75 (m, 1H), 1.54-1.64 (m, 1H), 1.46 (d, J=6.9 Hz, 3H), 1.39-1.45 (m, 1H); MS (ESI$^+$) M/Z 366 [M+H]$^+$.

Example 25

1-(1-methyl-1H-indazol-4-yl)-3-[(1S,3R)-3-phenylcyclopentyl]urea

The title compound was prepared according to Example 1F, substituting Example 4C for Example 1B, and substituting (1S,3R)-3-phenylcyclopentanamine (second eluting diastereomer from Example 15B) for Example 1E. $^1$H NMR (500 MHz, DMSO-$d_6$/Deuterium Oxide) δ 8.07 (d, J=1.0 Hz, 1H), 7.63 (d, J=7.6 Hz, 1H), 7.27-7.34 (m, 5H), 7.17-7.23 (m, 1H), 7.16 (dt, J=8.4, 0.8 Hz, 1H), 4.11-4.18 (m, 1H), 4.00 (s, 3H), 3.05-3.12 (m, 1H), 2.41-2.47 (m, 1H), 2.00-2.13 (m, 2H), 1.59-1.77 (m, 2H), 1.45-1.51 (m, 1H); MS (ESI$^+$) M/Z 335 [M+H]$^+$.

Example 26

1-(2-oxo-1,2,3,4-tetrahydroquinolin-7-yl)-3-[(1S,3R)-3-phenylcyclopentyl]urea The title compound was prepared according to Example 1F, substituting 7-amino-3,4-dihydroquinolin-2(1H)-one for Example 1B, and substituting (1S,3R)-3-phenylcyclopentanamine (second eluting diastereomer from Example 15B) for Example 1E. $^1$H NMR (500 MHz, DMSO-$d_6$/Deuterium Oxide) δ 7.27-7.33 (m, 4H), 7.17-7.21 (m, 1H), 7.00-7.04 (m, 2H), 6.89 (dd, J=8.1, 2.1 Hz, 1H), 4.06-4.12 (m, 1H), 3.01-3.09 (m, 1H), 2.78 (t, J=7.5 Hz, 2H), 2.42 (dd, J=8.3, 6.8 Hz, 2H), 2.35-2.40 (m, 1H), 1.99-2.07 (m, 2H), 1.56-1.72 (m, 2H), 1.41-1.48 (m, 1H); MS (ESI$^+$) M/Z 350 [M+H]$^+$.

Example 27

1-(6-fluoro-3-methylisoquinolin-5-yl)-3-[(1S,3R)-3-phenylcyclopentyl]urea

The title compound was prepared according to Example 6E, substituting (1S,3R)-3-phenylcyclopentanamine (second eluting diastereomer from Example 15B) for Example 1E. $^1$H NMR (500 MHz, DMSO-$d_6$/Deuterium Oxide) δ 9.21 (s, 1H), 8.06 (dd, J=9.0, 5.0 Hz, 1H), 7.60 (d, J=1.1 Hz, 1H), 7.53 (dd, J=9.8, 9.2 Hz, 1H), 7.25-7.36 (m, 4H), 7.17-7.22 (m, 1H), 4.07-4.17 (m, 1H), 3.01-3.11 (m, 1H), 2.62 (s, 3H), 2.34-2.45 (m, 1H), 2.01-2.10 (m, 2H), 1.63-1.79 (m, 2H), 1.49-1.60 (m, 1H); MS (ESI$^+$) M/Z 364 [M+H]$^+$.

Example 28

1-(1H-indazol-4-yl)-3-[(1S,3R)-3-phenylcyclopentyl]urea

The title compound was prepared according to Example 7, substituting (1S,3R)-3-phenylcyclopentanamine (second eluting diastereomer from Example 15B) for Example 1E. $^1$H NMR (300 MHz, DMSO-$d_6$) δ ppm 12.68-13.25 (bs, 1H), 8.60 (s, 1H), 8.09 (d, J=1.0 Hz, 1H), 7.62 (dd, J=7.6, 0.8 Hz, 1H), 7.21-7.32 (m, 4H), 7.15-7.23 (m, 2H), 7.05 (d, J=8.2 Hz, 1H), 6.60 (d, J=7.2 Hz, 1H), 4.11-4.22 (m, 1H), 3.00-3.17 (m, 1H), 2.44 (dt, J=13.0, 6.7 Hz, 1H), 1.96-2.15 (m, 2H), 1.58-1.83 (m, 2H), 1.49 (ddd, J=12.2, 11.1, 8.7 Hz, 1H); MS (ESI$^+$) M/Z 321 (M+H)$^+$.

Example 29

1-[3-(4-tert-butylphenyl)cyclohexyl]-3-(1H-indazol-4-yl)urea

Example 29A

3-(4-tert-butylphenyl)cyclohexanone

To a 40 mL microwave flask containing 10/1 dioxane/H$_2$O (22 mL) was added cyclohex-1-en-1-one (1.35 g, 14.0 mmol), acetylacetonatobis(ethylene)rhodium(I) (0.36 g, 1.40 mmol), racemic 2,2'-bis(diphenylphosphino)-1,1'-binaphthyl (0.88 g, 1.40 mmol) and 4-tert-butylphenylboronic acid (5.0 g, 28.0 mmol). The reaction mixture was heated in the microwave at 100° C. for 20 minutes. The material was poured into a separatory funnel and extracted with ethyl acetate (150 mL), washed with saturated aqueous NaHCO$_3$ (75 mL), dried (Na$_2$SO$_4$), filtered, and concentrated. The residue was purified by silica gel chromatography (20% EtOAc/hexanes) to afford the title compound (1.97 g, 61%) as a yellow oil. $^1$H NMR (CD$_3$OD, 300 MHz) δ 1.30 (s, 9H), 1.68-2.17 (m, 4H), 2.32-2.38 (m, 3H), 2.64 (dt, J=1.01, 12.0 Hz, 1H), 2.91-3.01 (m, 1H), 7.11-7.20 (m, 2H), 7.31-7.36 (m, 2H); MS (DCI) m/z 248 (M+H)$^+$.

Example 29B

3-(4-tert-butylphenyl)cyclohexanone O-methyl oxime

To a flask containing Example 29A (1.97 g, 8.60 mmol) was added pyridine (10 mL) followed by methoxyamine hydrochloride (0.81 g, 9.60 mmol), and the reaction mixture was stirred at room temperature overnight. The mixture was concentrated and the residue diluted with ethyl acetate (150 mL), washed with saturated aqueous NaHCO$_3$ (75 mL), dried (Na$_2$SO$_4$), filtered, and concentrated. The residue was purified by silica gel chromatography (20% EtOAc/hexanes) to afford the title compound (1.80 g, 81%) as a yellow solid. $^1$H NMR (CD$_3$OD, 300 MHz) δ 1.26 (s, 9H), 1.37-1.56 (m, 1H), 1.60-1.74 (m, 1H), 1.77-2.02 (m, 3H), 2.10-2.32 (m, 2H), 2.51-2.66 (m, 1H), 3.09-3.15 (m, 1H), 3.72 (d, J=4.75 Hz, 3H), 7.17 (dd, J=2.03, 6.44 Hz, 2H), 7.32 (dd, J=1.02, 6.42, 2H); MS (DCI) m/z 260 (M+H)$^+$.

Example 29C

3-(4-tert-butylphenyl)cyclohexanamine

To a flask containing Example 29B (1.80 g, 6.90 mmol) was added saturated NH$_3$/CH$_3$OH (50 mL), RaNi (20%) (5.0 eq by weight), and a H₂ atm (60 psi) was applied. The reaction was stirred at room temperature for 3 hours. The reaction mixture was filtered, washed with methanol (50 mL), and concentrated. The residue was purified by silica gel chromatography (50% EtOAc/hexanes) to afford the title compound (1.36 g, 85%) as a yellow oil. $^1$H NMR (CD$_3$OD, 300 MHz) δ 1.29 (s, 9H), 1.40-1.72 (m, 2H), 1.78-2.10 (m, 2H), 2.15-2.38 (m, 2H), 2.54-2.66 (m, 1H), 3.12-3.19 (m, 1H), 3.23-3.40 (m, 2H), 7.12 (d, J=7.46 Hz, 2H), 7.29 (dd, J=7.12, 2H); MS (DCI) m/z 232 (M+H)$^+$.

Example 29D methyl 4-(3-(3-(4-tert-butylphenyl)cyclohexyl)ureido)-1H-indazole-1-carboxylate To a flask containing Example 29C (1.25 g, 5.40 mmol) was added DMF (10 mL) diisopropylethylamine (5.0 mL) and methyl 4-((2,5-dioxopyrrolidin-1-yloxy)carbonylamino)-1H-indazole-1-carboxylate (prepared as in *Org. Proc. Res. Dev.*, 2007, 11, 578; 1.66 g, 5.0 mmol), and the reaction mixture was stirred at room temperature for 2 hours. The mixture was concentrated and the residue was diluted with ethyl acetate (100 mL) and washed with saturated aqueous NaHCO$_3$ (50 mL), dried (Na$_2$SO$_4$), filtered, and concentrated. The residue was purified by silica gel chromatography (50% EtOAc/hexanes) to afford the title compound (1.89 g, 84%). $^1$H NMR (DMSO-d$_6$, 300 MHz) δ 1.26 (s, 9H), 1.31-1.86 (m, 6H), 1.96-2.07 (m, 1H), 2.58-2.62 (m, 1H), 2.66-2.79 (m, 1H), 3.59-3.70 (m, 1H), 4.02-4.04 (m, 3H), 6.33 (d, J=7.80 Hz, 1H), 7.19 (dd, J=2.38, 8.48 Hz, 2H), 7.30 (dd, J=2.03, 6.78 Hz, 2H), 7.44-7.50 (m, 1H), 7.65-7.69 (m, 1H), 7.78-7.87 (m, 1H), 8.43 (d, J=8.47 Hz, 1H), 8.84 (d, J=6.79 Hz, 1H); MS (DCI) m/z 449 (M+H)$^+$.

Example 29E

1-[3-(4-tert-butylphenyl)cyclohexyl]-3-(1H-indazol-4-yl)urea

To a flask containing Example 29D (1.89 g, 4.20 mmol) was added methanol (10 mL) and 5 N NaOH in methanol (0.84 mL) and the reaction mixture was stirred at room temperature for 2 hours. The mixture was concentrated and the residue was purified by silica gel chromatography (gradient elution, 50-70% EtOAc/hexanes) to afford the title compound (1.32 g, 81%) as a white solid. $^1$H NMR (DMSO-d$_6$, 300 MHz) δ 1.26 (s, 9H), 1.32-1.86 (m, 5H), 1.97-2.07 (m, 2H), 2.58-2.62 (m, 1H), 2.66-2.76 (m, 1H), 3.58-3.69 (m, 1H), 4.01-4.04 (m, 1H), 6.95-7.16 (m, 1H), 7.22-7.29 (m, 3H), 7.30-7.33 (m, 2H), 7.60-7.68 (m, 1H), 8.08 (d, J=10.9 Hz, 1H), 8.58 (d, J=16.6 Hz, 1H), 12.99 (d, J=10.5 Hz, 1H); MS (DCI) m/z 391 (M+H)$^+$.

Example 30

1-(1H-indazol-4-yl)-3-{3-[4-(trifluoromethyl)phenyl]cyclohexyl}urea

The title compound was prepared according to the procedures as described in Examples 29A, 29B, 29C, 29D, and 29E, substituting 4-(trifluoromethyl)-phenylboronic acid for 4-tert-butylphenyl boronic acid (in Example 29A). $^1$H NMR (CD$_3$OD, 300 MHz) δ 1.21-2.39 (m, 8H), 2.74-2.93 (m, 1H), 3.73-3.83 (m, 1H), 7.14 (d, J=8.48 Hz, 1H), 7.25-7.32 (m, 1H), 7.42-7.45 (m, 2H), 7.51 (d, J=7.46 Hz, 1H), 7.56-7.61 (m, 2H), 8.10 (d, J=12.55 Hz, 1H); MS (DCI) m/z 403 (M+H)$^+$.

Example 31

1-(1H-indazol-4-yl)-3-{(1R,3R)-3-[4-(trifluoromethyl)phenyl]cyclohexyl}urea

The title compound was obtained from the separation of Example 30 using a Chiralpak AD HPLC column eluted with hexane/(10%) ethanol-methanol (1/1) at a flow rate of 10 mL/min over a 35 minute run time. [α]$_D$=−49.2 c=1.0 (CH$_3$OH); $^1$H NMR (CD$_3$OD, 300 MHz) δ 1.57-1.88 (m, 7H), 1.95-2.13 (m, 1H), 2.91-2.96 (m, 1H), 4.11-4.20 (m, 1H), 7.15 (d, J=8.31 Hz, 1H), 7.29 (t, J=8.0, 16.0 Hz, 1H), 7.45 (d, J=8.0 Hz, 2H), 7.57-7.60 (m, 3H), 8.12 (s, 1H); MS (DCI) m/z 403 (M+H)$^+$. Calc for C$_{21}$H$_{21}$N$_4$OF$_3$: C, 62.68; H, 5.26; N, 13.92. Found: C, 62.56; H, 5.42; N, 13.87.

Example 32

1-(1H-indazol-4-yl)-3-{(1S,3S)-3-[4-(trifluoromethyl)phenyl]cyclohexyl}urea

The title compound was obtained from the separation of Example 30 using a Chiralpak AD HPLC column eluted with hexane/(10%) ethanol-methanol (1/1) at a flow rate of 10 mL/min over a 35 minute run time. [α]$_D$=+62.2 c=1.0 (CH$_3$OH); $^1$H NMR (CD$_3$OD, 300 MHz) δ 1.52-1.64 (m, 1H), 1.67-1.95 (m, 6H), 2.01-2.13 (m, 1H), 2.90-2.96 (m, 1H), 4.10-4.21 (m, 1H), 7.15 (d, J=8.31 Hz, 1H), 7.29 (t, J=7.69, 16.0 Hz, 1H), 7.45 (d, J=8.31 Hz, 2H), 7.57-7.60 (m, 3H), 8.12 (s, 1H); MS (DCI) m/z 403 (M+H)$^+$. Calc for C$_{21}$H$_{21}$N$_4$OF$_3$: C, 62.68; H, 5.26; N, 13.92. Found: C, 62.71; H, 5.48; N, 13.81.

Example 33

1-(1H-indazol-4-yl)-3-{(1S,3R)-3-[4-(trifluoromethyl)phenyl]cyclohexyl}urea

The title compound was obtained from the separation of Example 30 using a Chiralpak AD HPLC column eluted with hexane/(10%) ethanol-methanol (1/1) at a flow rate of 10 mL/min over a 35 minute run time. [α]$_D$=−23.0 c=1.0 (CH$_3$OH); $^1$H NMR (CD$_3$OD, 300 MHz) δ 1.23-1.39 (m, 1H), 1.42-1.54 (m, 2H), 1.57-1.63 (m, 1H), 1.86-1.89 (m, 1H), 1.95-1.99 (m, 1H), 2.09-2.13 (m, 1H), 2.19-2.22 (m, 1H), 2.76-2.82 (m, 1H), 3.75-3.81 (m, 1H), 7.15 (d, J=7.39, 1H), 7.28 (t, J=7.38, 15.69 Hz, 1H), 7.43 (d, J=8.31 Hz, 2H), 7.51 (d, J=7.08 Hz, 1H), 7.57 (d, J=8.0 Hz, 2H), 8.08 (s, 1H); MS (DCI) m/z 403 (M+H)$^+$. Calc for C$_{21}$H$_{21}$N$_4$OF$_3$: C, 62.68; H, 5.26; N, 13.92. Found: C, 62.46; H, 5.01; N, 13.71.

Example 34

1-(1H-indazol-4-yl)-3-{(1R,3S)-3-[4-(trifluoromethyl)phenyl]cyclohexyl}urea

The title compound was obtained from the separation of Example 30 using a Chiralpak AD HPLC column eluted with hexane/(10%) ethanol-methanol (1/1) at a flow rate of 10 mL/min over a 35 minute run time. [α]$_D$=+ 21.6 c=1.0 (CH$_3$OH); $^1$H NMR (CD$_3$OD, 300 MHz) δ 1.23-1.27 (m, 1H), 1.29-1.39 (m, 2H), 1.41-1.64 (m, 1H), 1.85-1.90 (m, 1H), 1.94-1.98 (m, 1H), 2.09-2.13 (m, 1H), 2.19-2.21 (m, 1H), 2.75-2.81 (m, 1H), 3.75-3.81 (m, 1H), 7.15 (d, J=8.62 Hz, 1H), 7.27 (t, J=7.69, 15.99 Hz, 1H), 7.43 (d, J=8.31 Hz, 2H), 7.51 (d, J=7.69 Hz, 1H), 7.59 (d, J=18.30 Hz, 2H), 8.09 (s, 1H); MS (DCI) m/z 403 (M+H)$^+$. Calc for $C_{21}H_{21}N_4OF_3$: C, 62.68; H, 5.26; N, 13.92. Found: C, 62.51; H, 5.04; N, 13.91.

Example 35

1-(1H-indazol-4-yl)-3-[(1S,3S)-3-phenylcyclohexyl] urea

Example 35A (3S)-3-phenylcyclohexanamine

The title compound was prepared using the procedures described in Examples 29A, 29B, and 29C, substituting phenylboronic acid for 4-tert-butylphenyl boronic acid and substituting S-BINAP for racemic BINAP (in Example 29A). $^1$H NMR (CD$_3$OD, 300 MHz) δ 1.08-1.67 (m, 4H), 1.73-2.20 (m, 4H), 2.53-2.63 (m, 1H), 2.71-2.81 (m, 1H), 6.74-6.80 (m, 1H), 7.11-7.28 (m, 4H); MS (DCI) m/z 176 (M+H)$^+$.

Example 35B methyl 4-{3-[(3S)-3-phenylcyclohexyl]ureido}-1H-indazole-1-carboxylate The title compound was prepared using the procedure as described in Example 29D, substituting Example 35A for Example 29C. $^1$H NMR (CD$_3$OD, 300 MHz) δ 1.23-2.01 (m, 7H), 2.07-2.20 (m, 1H), 2.64-2.86 (m, 1H), 3.72-3.80 (m, 1H), 4.11 (d, J=2.72 Hz, 3H), 7.20-7.35 (m, 5H), 7.45-7.52 (m, 1H), 7.67 (d, J=7.79 Hz, 1H), 7.78 (t, J=8.14 Hz, 1H), 8.07-8.09 (m, 1H); MS (DCI) m/z 393 (M+H)$^+$.

Example 35C methyl 4-{3-[(1S,3S)-3-phenylcyclohexyl]ureido}-1H-indazole-1-carboxylate The title compound was obtained from the separation of Example 35B using a Chiralpak AD HPLC column eluted with hexane/(10%) ethanol-methanol (1/1) at a flow rate of 15 mL/min. $^1$H NMR (CD$_3$OD, 300 MHz) δ 1.21-1.65 (m, 4H), 1.84-2.01 (m, 2H), 2.08-2.20 (m, 2H), 2.64-2.74 (m, 1H), 3.71-3.81 (m, 1H), 4.10 (s, 3H), 7.13-7.18 (m, 1H), 7.21-7.30 (m, 5H), 7.51 (dd, J=0.68, 5.77 Hz, 1H), 7.67 (d, J=7.47 Hz, 1H), 8.07 (d, J=1.02 Hz, 1H); MS (DCI) m/z 393 (M+H)$^+$.

Example 35D 1-(1H-indazol-4-yl)-3-[(1S,3S)-3-phenylcyclohexyl] urea

The title compound was prepared according to the procedure in Example 29E, substituting Example 35C for Example 29D. $[α]_D^{20}$=+30.3 (c=1.0, CH$_3$OH); $^1$H NMR (DMSO-d$_6$, 300 MHz) δ 1.52-1.61 (m 1H), 1.63-1.91 (m, 6H), 1.96-2.01 (m, 1H), 2.79-2.85 (m, 1H), 4.19-4.20 (m, 1H), 7.13-7.16 (m, 2H), 7.22-7.30 (m, 5H), 7.61 (d, J=7.39 Hz, 1H), 8.12 (s, 1H); MS (DCI) m/z 335 (M+H)$^+$.

Example 36

1-(1H-indazol-4-yl)-3-[(1R,3S)-3-phenylcyclohexyl] urea

Example 36A methyl 4-{3-[(1R,3S)-3-phenylcyclohexyl]ureido}-1H-indazole-1-carboxylate The title compound was obtained from the separation of Example 35B using a Chiralpak AD HPLC column eluted with hexane/(10%) ethanol-methanol (1/1) at a flow rate of 15 mL/min. $^1$H NMR (CD$_3$OD, 300 MHz) δ 1.24-1.67 (m, 4H), 1.87-2.04 (m, 2H), 2.08-2.23 (m, 2H), 2.62-2.74 (m, 1H), 3.72-3.80 (m, 1H), 4.11 (s, 3H), 7.14-7.18 (m, 1H), 7.20-7.31 (m, 5H), 7.49-7.51 (m, 1H), 7.65-7.67 (m, 1H), 8.09-8.10 (m, 1H); MS (DCI) m/z 393 (M+H)$^+$.

Example 36B 1-(1H-indazol-4-yl)-3-[(1R,3S)-3-phenylcyclohexyl] urea

The title compound was prepared according to the procedure in Example 29E, substituting Example 36A for Example 29D. $[α]_D^{20}$=+22.0 (c=1.0, CH$_3$OH); $^1$H NMR (DMSO-d$_6$, 300 MHz) δ 1.21-1.45 (m, 1H), 1.52-1.59 (m, 2H), 1.60-1.64 (m, 1H), 1.82-1.85 (m, 1H), 1.90-1.96 (m, 1H), 2.01-2.09 (m, 1H), 2.12-2.19 (m, 1H), 2.63-2.69 (m, 1H), 3.73-3.79 (m, 1H), 7.13-7.16 (m, 2H), 7.20-7.30 (m, 5H), 7.52 (d, J=7.52 Hz, 1H), 8.08 (s, 1H); MS (DCI) m/z 335 (M+H)$^+$.

Example 37

1-[3-(4-tert-butylphenyl)cyclopentyl]-3-(1H-indazol-4-yl)urea

The title compound was prepared according to the procedures described in Examples 29A, 29B, 29C, 29D, and 29E, substituting 2-cyclopenten-1-one for cyclohexen-1-one (in Example 29A). $^1$H NMR (DMSO-d$_6$, 300 MHz) δ 1.27 (s, 9H), 1.42-1.74 (m, 2H), 1.89-2.25 (m, 4H), 2.98-3.33 (m, 1H), 4.11-4.26 (m, 1H), 6.56 (t, J=8.47 Hz, 1H), 7.05 (d, J=8.48 Hz, 1H), 7.17-7.22 (m, 3H), 7.29-7.34 (m, 2H), 7.63 (d, J=7.81 Hz, 1H), 8.08 (s, 1H), 8.55 (d, J=9.50 Hz, 1H), 12.99 (s, 1H); MS (DCI) m/z 377 (M+H)$^+$.

Example 38

1-(1H-indazol-4-yl)-3-[cis-3-(pyridin-2-yl)cyclopentyl]urea

Example 38A 3-(pyridin-2-yl)cyclopentanone

A solution of thiophene (0.50 g, 6.0 mmol), diethyl ether (50 mL), and n-BuLi (2.5 M, 2.20 mL, 5.50 mmol) was stirred at room temperature for 1 hour. The reaction mixture was cooled to <5° C. and copper iodide (1.05 g, 5.50 mmol) was added. The reaction mixture was warmed to room temperature and stirred for 1 hour. In a separate flask, a solution of 2-bromopyridine (0.87 g, 5.50 mmol) in diethyl ether (50 mL) was cooled to <–70° C. and n-BuLi (2.5 M, 2.20 mL, 5.50 mmol) was added. The reaction mixture was warmed to room temperature and stirred for 10 minutes. The 2-lithiopyridine reagent was added to the first reaction mixture via cannula and stirred at room temperature for 1 hour. To the reaction mixture was added 2-cyclopenten-1-one (0.45 g, 5.50 mmol) in diethyl ether (10 mL) and the reaction mixture was stirred for 1 hour. The reaction was poured into EtOAc (150 mL) and washed with brine (100 mL), dried ($Na_2SO_4$), filtered, and concentrated. The material was purified by flash column chromatography (20% EtOAc/hexanes), to provide the title compound (0.38 g, 43%). $^1$H NMR ($CD_3OD$, 300 MHz) δ 2.10-2.19 (m, 1H), 2.13-2.66 (m, 5H), 3.56-3.68 (m, 1H), 7.27 (ddd, J=1.0, 5.1, 7.5 Hz, 1H), 7.38 (dd, J=1.02, 7.80 Hz, 1H), 7.76 (ddd, J=2.0, 7.80, 7.80 Hz, 1H), 8.47-8.50 (m, 1H); MS (DCI) m/z 162 (M+H)$^+$.

Example 38B 1-(1H-indazol-4-yl)-3-[cis-3-(pyridin-2-yl)cyclopentyl]urea

The title compound was prepared according to the procedures described in Examples 29B, 29C, 29D, and 29E, substituting Example 38A for Example 29A (in Example 29B). The product diastereomers were separated by flash column chromatography (gradient elution, 20-80% EtOAc/hexanes), to provide title compound. $^1$H NMR ($CD_3OD$, 300 MHz) δ 1.69-1.80 (m, 2H), 1.84-1.97 (m, 1H), 2.06-2.19 (m, 2H), 2.46-2.51 (m, 1H), 3.27-3.35 (m, 1H), 4.28-4.34 (m, 1H), 7.13-7.22 (m, 2H), 7.24-7.33 (m, 2H), 7.50 (d, J=7.69 Hz, 1H), 7.73 (ddd, J=1.85, 7.70, 7.70 Hz, 1H), 8.07 (s, 1H), 8.40 (d, J=4.61 Hz, 1H); MS (DCI) m/z 322 (M+H)$^+$.

Example 39

1-(1H-indazol-4-yl)-3-[trans-3-(pyridin-2-yl)cyclopentyl]urea

The racemic title compound was isolated from the diastereomer separation in Example 38B. $^1$H NMR ($CD_3OD$, 300 MHz) δ 1.65-1.70 (m, 1H), 1.77-1.85 (m, 1H), 2.04-2.10 (m, 1H), 2.12-2.20 (m, 2H), 2.22-2.37 (m, 1H), 3.42-3.49 (m, 1H), 4.38-4.41 (m, 1H), 7.20 (d, J=5.54 Hz, 1H), 7.30-7.33 (m, 1H), 7.35 (t, J=7.36, 7.36 Hz, 1H), 7.39 (d, J=7.50 Hz, 1H), 7.53 (d, J=7.39 Hz, 1H), 7.73-7.76 (m, 1H), 8.10 (s, 1H), 8.44-8.45 (d, J=3.38 Hz, 1H); MS (DCI) m/z 322 (M+H)$^+$.

Example 40

1-(1H-indazol-4-yl)-3-[3-(4-methoxyphenyl)cyclopentyl]urea

The title compound was prepared according to the procedures described in Examples 29A, 29B, 29C, 29D, and 29E, substituting 2-cyclopenten-1-one for cyclohexen-1-one and 4-methoxyphenylboronic acid for 4-tert-butylphenyl boronic acid (in Example 29A). $^1$H NMR ($CD_3OD$, 300 MHz) δ 1.47-1.89 (m, 2H), 1.98-2.54 (m, 4H), 3.04-3.26 (m, 1H), 3.76 (s, 3H), 4.22-4.35 (m, 1H), 6.81-6.87 (m, 2H), 7.14-7.21 (m, 3H), 7.29 (t, J=7.46 Hz, 1H), 7.54 (dd, J=2.38, 6.79 Hz, 1H), 8.07-8.10 (m, 1H); MS (DCI) m/z 351 (M+H)$^+$.

Example 41

1-(1H-indazol-4-yl)-3-{(1S,3S)-3-[4-(trifluoromethyl)phenyl]cyclopentyl}urea

Example 41A methyl 4-(3-{(1S,3S)-3-[4-(trifluoromethyl)phenyl]cyclopentyl}ureido)-1H-indazole-1-carboxylate The title compound was prepared according to the procedures described in Examples 29A, 29B, 29C, and 29D, substituting 2-cyclopenten-1-one for cyclohexen-1-one, 4-(trifluoromethyl)-phenylboronic acid for 4-tert-butylphenyl boronic acid, and S-BINAP for racemic BINAP (in Example 29A). The mixture of diastereomers was separated on a Chiralpak AD HPLC column and eluted with hexane/(10%) ethanol-methanol (1/1) at a flow rate of 15 mL/min to afford the title compound. $^1$H NMR ($CD_3OD$, 300 MHz) δ 1.69-1.78 (m, 2H), 2.07-2.11 (m, 2H), 2.23-2.42 (m, 2H), 3.35-3.41 (m, 1H), 4.11 (s, 3H), 4.35-4.42 (m, 1H), 7.15 (d, J=8.48 Hz, 1H), 7.29 (t, J=7.46, 7.46 Hz, 1H), 7.45-7.50 (m, 2H), 7.58 (d, J=8.14 Hz, 2H), 7.57 (d, J=7.80 Hz, 1H), 7.82 (d, J=8.48 Hz, 1H); MS (DCI) m/z 435 (M+H)$^+$.

Example 41B 1-(1H-indazol-4-yl)-3-{(1S,3S)-3-[4-(trifluoromethyl)phenyl]cyclopentyl}urea The title compound was prepared according to the procedure described in Example 29E, substituting Example 41A for Example 29D. [α]$_D^{20}$=+21.2 (c=1.0, $CH_3OH$); $^1$H NMR ($CD_3OD$, 300 MHz) δ 1.63-1.80 (m, 2H), 2.06-2.11 (m, 2H), 2.20-2.42 (m, 2H), 3.35-3.44 (m, 1H), 4.33-4.41 (m, 1H), 7.15 (d, J=8.14 Hz, 1H), 7.29 (t, J=7.80, 8.14 Hz, 1H), 7.47 (d, J=8.14 Hz, 2H), 7.52-7.60 (m, 3H), 8.09 (s, 1H); MS (DCI) m/z 389 (M+H)$^+$.

Example 42

1-(1H-indazol-4-yl)-3-{(1R,3S)-3-[4-(trifluoromethyl)phenyl]cyclopentyl}urea

Example 42A methyl 4-(3-{(1R,3S)-3-[4-(trifluoromethyl)phenyl]cyclopentyl}ureido)-1H-indazole-1-carboxylate The mixture of diastereomers from Example 41A was separated on a Chiralpak AD HPLC column and eluted with hexanes/ethanol-methanol (1/1) (10%) at a flow rate of 15 mL/min to afford the title compound. $^1$H NMR ($CD_3OD$, 300 MHz) δ 1.67-1.70 (m, 2H), 2.05-2.14 (m, 2H), 2.23-2.45 (m, 2H), 3.36-3.46, 1H), 4.11 (s, 3H), 4.37-4.42 (m, 1H), 7.14 (d, J=8.40 Hz, 1H), 7.31 (t, J=7.40, 7.40 Hz, 1H), 7.45-7.51 (m, 2H), 7.5 (d, J=8.20 Hz, 2H), 7.57 (d, J=7.80 Hz, 1H), 7.82 (d, J=8.50 Hz, 1H); MS (DCI) m/z 435 (M+H)$^+$.

Example 42B 1-(1H-indazol-4-yl)-3-{(1R,3S)-3-[4-(trifluoromethyl)phenyl]cyclopentyl}urea The title compound was prepared according to the procedure described in Example 29E, substituting Example 42A for Example 29D. $^1$H NMR ($CD_3OD$, 300 MHz) δ 1.54-1.65 (m, 1H), 1.72-1.89 (m, 2H), 2.06-2.25 (m, 2H), 2.54-2.63 (m, 1H), 3.26-3.36 (m, 1H), 4.11-4.34 (m, 1H), 7.15 (d, J=8.48 Hz, 1H), 7.28 (t, J=7.80, 8.14 Hz, 1H), 7.47-7.54 (m, 3H), 7.59 (d, J=8.24 Hz, 2H), 8.09 (d, J=0.68 Hz, 1H); MS (DCI) m/z 389 (M+H)$^+$.

Example 43

1-(1H-indazol-4-yl)-3-{(1S,3R)-3-[4-(trifluoromethyl)phenyl]cyclopentyl}urea

Example 43A methyl 4-(3-{(1S,3R)-3-[4-(trifluoromethyl)phenyl]cyclopentyl}ureido)-1H-indazole-1-carboxylate The title compound was prepared according to the procedures described in Examples 29A, 29B, 29C, and 29D, substituting 2-cyclopenten-1-one for cyclohexen-1-one, 4-(trifluoromethyl)-phenylboronic acid for 4-tert-butylphenyl boronic acid, and R-BINAP for racemic BINAP (in Example 29A). The mixture of diastereomers was separated on a Chiralpak AD HPLC column and eluted with hexane/ethanol-methanol (1/1) (10%) at a flow rate of 15 mL/min to afford the title compound. $^1$H NMR (CD$_3$OD, 300 MHz) δ 1.69-1.78 (m, 2H), 2.07-2.11 (m, 2H), 2.23-2.42 (m, 2H), 3.35-3.41 (m, 1H), 4.11 (s, 3H), 4.35-4.42 (m, 1H), 7.15 (d, J=8.48 Hz, 1H), 7.29 (t, J=7.46, 7.46 Hz, 1H), 7.45-7.50 (m, 2H), 7.58 (d, J=8.14 Hz, 2H), 7.57 (d, J=7.80 Hz, 1H), 7.82 (d, J=8.48 Hz, 1H); MS (DCI) m/z 435 (M+H)$^+$.

Example 43B 1-(1H-indazol-4-yl)-3-{(1S,3R)-3-[4-(trifluoromethyl)phenyl]cyclopentyl}urea The title compound was prepared according to the procedure described in Example 29E, substituting Example 43A for Example 29D. $[α]_D^{20}$=+7.46 (c=1.0, CH$_3$OH); $^1$H NMR (DMSO-d$_6$, 300 MHz) δ 1.49-1.56 (m, 1H), 1.61-1.80 (m, 2H), 2.06-2.13 (m, 2H), 2.46-2.53 (m, 1H), 3.16-3.23 (m, 1H), 4.15-4.29 (m, 1H), 6.56 (d, J=7.38 Hz, 1H), 7.06 (d, J=8.30 Hz, 1H), 7.19 (t, J=5.00 Hz, 1H), 7.51-7.53 (m, 2H), 7.63-7.67 (m, 3H), 8.10 (s, 1H), 8.58 (s, 1H), 12.99 (s, 1H); MS (DCI) m/z 389 (M+H)$^+$.

Example 44

1-(1H-indazol-4-yl)-3-{(1R,3R)-3-[4-(trifluoromethyl)phenyl]cyclopentyl}urea

Example 44A methyl 4-(3-{(1R,3R)-3-[4-(trifluoromethyl)phenyl]cyclopentyl}ureido)-1H-indazole-1-carboxylate The mixture of diastereomers from Example 43A was separated on a Chiralpak AD HPLC column and eluted with hexanes/ethanol-methanol (1/1) (10%) at a flow rate of 15 mL/min to afford the title compound. $^1$H NMR (CD$_3$OD, 300 MHz) δ 1.67-1.70 (m, 2H), 2.05-2.14 (m, 2H), 2.23-2.45 (m, 2H), 3.36-3.46, 1H), 4.11 (s, 3H), 4.37-4.42 (m, 1H), 7.14 (d, J=8.40 Hz, 1H), 7.31 (t, J=7.40, 7.40 Hz, 1H), 7.45-7.51 (m, 2H), 7.5 (d, J=8.20 Hz, 2H), 7.57 (d, J=7.80 Hz, 1H), 7.82 (d, J=8.50 Hz, 1H); MS (DCI) m/z 435 (M+H)$^+$.

Example 44B 1-(1H-indazol-4-yl)-3-{(1R,3R)-3-[4-(trifluoromethyl)phenyl]cyclopentyl}urea The title compound was prepared according to the procedure described in Example 29E, substituting Example 44A for Example 29D. $[α]_D^{20}$=−17.80 (c=1.0, CH$_3$OH); $^1$H NMR (DMSO-d$_6$, 300 MHz) δ 1.47-1.76 (m, 2H), 1.94-2.03 (m, 2H), 2.17-2.33 (m, 2H), 3.30-3.38 (m, 1H), 4.23-4.30 (m, 1H), 6.58 (d, J=7.07 Hz, 1H), 7.05 (d, J=8.31 Hz, 1H), 7.20 (t, J=8.0 Hz, 1H), 7.51-7.53 (m, 2H), 7.63-7.66 (m, 3H), 8.09 (s, 1H), 8.55 (s, 1H), 12.98 (s, 1H); MS (DCI) m/z 389 (M+H)$^+$.

Example 45

1-[(3S)-3-(4-fluorophenyl)cyclopentyl]-3-(1H-indazol-4-yl)urea

The title compound was prepared according to the procedures described in Examples 29A, 29B, 29C, 29D, and 29E, substituting 2-cyclopenten-1-one for cyclohexen-1-one, 4-fluorophenylboronic acid for 4-tert-butylphenyl boronic acid, and S-BINAP for racemic BINAP (in Example 29A). $^1$H NMR (CD$_3$OD, 300 MHz) δ 1.47-1.81 (m, 3H), 1.91-2.57 (m, 3H), 3.08-3.32 (m, 1H), 4.11-4.36 (m, 1H), 6.96-7.17 (m, 2H), 7.16 (d, J=8.48 Hz, 1H), 7.23-7.31 (m, 3H), 7.52-7.55 (m, 1H), 8.08-8.10 (m, 1H); MS (DCI) m/z 339 (M+H)$^+$.

Example 46

1-(1H-indazol-4-yl)-3-{(3S)-3-[4-(methylsulfanyl)phenyl]cyclopentyl}urea

The title compound was prepared according to the procedures described in Examples 29A, 29B, 29C, 29D, and 29E, substituting 2-cyclopenten-1-one for cyclohexen-1-one, 4-(thiomethyl)-phenylboronic acid for 4-tert-butylphenyl boronic acid, and S-BINAP for racemic BINAP (in Example 29A). $^1$H NMR (CD$_3$OD, 300 MHz) δ 1.48-1.85 (m, 2H), 2.01-2.56 (m, 7H), 3.06-3.35 (m, 1H), 4.08-4.37 (m, 1H), 7.10-7.31 (m, 6H), 7.52-7.55 (m, 1H), 8.07-8.09 (m, 1H); MS (DCI) m/z 367 (M+H)$^+$.

Example 47

1-{(3S)-3-[4-(dimethylamino)phenyl]cyclopentyl}-3-(1H-indazol-4-yl)urea

The title compound was prepared according to the procedures described in Examples 29A, 29B, 29C, 29D, and 29E, substituting 2-cyclopenten-1-one for cyclohexen-1-one, 4-(dimethylamino)-phenylboronic acid for 4-tert-butylphenyl boronic acid, and S-BINAP for racemic BINAP (in Example 29A). $^1$H NMR (DMSO-d$_6$, 300 MHz) δ 1.38-1.69 (m, 3H), 1.85-1.88 (m, 1H), 1.96-2.11 (m, 2H), 2.16-2.22 (m, 0.5H), 2.35-2.40 (m, 0.5H), 2.84 (s, 6H), 2.92-2.99 (m, 0.5H), 3.09-3.14 (m, 0.5H), 4.10-4.14 (m, 0.5H), 4.10-4.23 (m, 0.5H), 6.51-6.55 (m, 1H), 6.66-6.70 (m, 1H), 7.03-7.11 (m, 3H), 7.18 (t, J=8.31 Hz, 1H), 7.62-7.74 (m, 1H), 8.07 (s, 1H), 8.51 (d, J=14.77 Hz, 1H), 12.97 (s, 1H); MS (DCI) m/z 364 (M+H)$^+$.

Example 48

1-(1H-indazol-4-yl)-3-[(1S,4R)-4-phenylcyclopent-2-en-1-yl]urea

Example 48A (1R,4R)-4-phenylcyclopent-2-enol

A solution of (1R,4S)-4-acetoxy-2-cyclopenten-1-ol (491 mg, 3.45 mmol), THF (10 mL), and copper(I) cyanide (93 mg, 1.04 mmol) was cooled to <−20° C. and phenylmagnesium chloride (2.0 M in THF, 5.18 mL, 10.4 mmol) was added at the same temperature. After 10 minutes, TLC (50% EtOAc/hexanes) showed complete conversion. Saturated aqueous NH$_4$Cl (50 mL) was added, extracted with EtOAc (3×50 mL), and dried (Na$_2$SO$_4$) the combined organic layers. Concentrated and purified the residue by flash column chromatography (10-50% EtOAc/hexanes, gradient elution), to provide the title compound (463 mg, 2.89 mmol, 84%). MS (DCI) m/z 143 (M−OH)$^+$.

Example 48B ((1R,4S)-4-azidocyclopent-2-enyl)benzene

A solution of Example 48A (458 mg, 2.86 mmol) and toluene (4.6 mL) was cooled to <5° C. and diphenylphosphoryl azide (0.740 mL, 3.43 mmol) and DBU (0.603 mL, 4.00 mmol) were added. After 5 hours at room temperature, LCMS showed complete reaction. Water (20 mL) and toluene (50 mL) were added and organic layer was washed with water (20 mL), 2N HCl (20 mL), and brine (10 mL) sequentially. The organic layer was dried (Na$_2$SO$_4$), filtered, and concentrated, and crude title compound was used in the next step. MS (DCI) m/z 203 (M+NH$_4$)$^+$.

Example 48C (1S,4R)-4-phenylcyclopent-2-enamine

A solution of Example 48B (530 mg, 2.86 mmol), 2-methyl tetrahydrofuran (9.5 mL), water (1.056 mL), and triphenylphosphine (900 mg, 3.43 mmol) was heated to 70° C. After 50 minutes, LCMS showed complete reaction. The mixture was diluted with MTBE (50 mL) and extracted with 2N HCl (25 mL) and water (25 mL). Aqueous 2N NaOH (30 mL) was added to the aqueous layer, followed by extraction with MTBE (50 mL×3). The final organic layers were dried (Na$_2$SO$_4$), filtered, and concentrated to provide the title compound, which was used crude in the next step. MS (DCI) m/z 160 (M+H)$^+$.

Example 48D 1-(1H-indazol-4-yl)-3-[(1S,4R)-4-phenylcyclopent-2-en-1-yl]urea

A solution of Example 48C (455 mg, 2.86 mmol), DMF (8 mL), diisopropylethylamine (1.05 mL, 6.01 mmol), and methyl 4-((2,5-dioxopyrrolidin-1-yloxy)carbonylamino)-1H-indazole-1-carboxylate (prepared as in Org. Proc. Res. Dev., 2007, 950 mg, 2.86 mmol) was stirred at room temperature. After 15 minutes, LCMS showed complete conversion to methyl carbamate. Methanol (16 mL) and 50% aqueous sodium hydroxide (0.50 mL, 8.6 mmol) were added to the reaction mixture. After 10 minutes, LCMS showed complete conversion to product. Water (24 mL) was added dropwise, and the resulting white slurry was stirred at room temperature for 15 minutes. The slurry was filtered and washed with 1:1 MeOH/water (10 mL). The white solid was dried in a vacuum oven at 50° C. to provide the title compound (646 mg, 2.03 mmol, 71% over three steps). $^1$H NMR (300 MHz, DMSO-d$_6$) δ 13.11-12.64 (m, 1H), 8.56 (s, 1H), 8.06 (d, J=0.9 Hz, 1H), 7.63 (d, J=7.4 Hz, 1H), 7.52-7.30 (m, 2H), 7.21 (m, 4H), 7.05 (d, J=8.3 Hz, 1H), 6.59 (d, J=8.1 Hz, 1H), 5.93 (s, 2H), 4.86 (q, J=7.8 Hz, 1H), 3.86 (t, J=7.3 Hz, 1H), 2.90 (dt, J=13.1, 8.2 Hz, 1H), 1.47-1.28 (m, 1H); MS (DCI) m/z 319 (M+H)$^+$.

Example 49

1-((1S,3R)-3-cyclohexylcyclopentyl)-3-(1H-indazol-4-yl)urea

Example 49A (1S,3R)-3-cyclohexylcyclopentanamine

A solution of (1S,3R)-3-phenylcyclopentanamine (second eluting diastereomer from Example 15B, 106 mg, 0.657 mmol) and 1,1,1-trifluoroethanol (20 mL) was added to 5% Rh/Al$_2$O$_3$ (42.4 mg) in a 50 mL pressure bottle. The reaction was heated for 16 hours under 30 psi hydrogen pressure and at 50° C. The mixture was filtered through a nylon membrane, washing with EtOH (50 mL). The solution was concentrated to provide the title compound (77 mg, 70%). MS (DCI) m/z 168 (M+H)$^+$.

Example 49B 1-((1S,3R)-3-cyclohexylcyclopentyl)-3-(1H-indazol-4-yl)urea

The title compound was prepared according to the procedure in Example 48D, substituting Example 49A for Example 48C. $^1$H NMR (300 MHz, DMSO-d$_6$) δ 12.96 (bs, 1H), 8.49 (s, 1H), 8.06 (d, J=1.0 Hz, 1H), 7.61 (d, J=7.5 Hz, 1H), 7.18 (t, J=7.9 Hz, 1H), 7.03 (d, J=8.2 Hz, 1H), 6.38 (d, J=7.2 Hz, 1H), 4.04-3.86 (m, 1H), 2.19-2.06 (m, 1H), 1.90-0.86 (m, 17H); MS (DCI) m/z 327 (M+H)$^+$.

Example 50

1-(1-methyl-2-oxo-1,2-dihydroquinolin-5-yl)-3-((1S,3R)-3-phenylcyclopentyl)urea

Example 50A 1-methyl-5-nitroquinolin-2(1H)-one

To a solution of 5-nitroquinoline (10.0 g, 57.4 mmol) in dichloromethane (250 mL) was added methyl trifluoromethanesulfonate (6.50 mL, 57.4 mmol), keeping the temperature at less than about 35° C. After 15 minutes of stirring at room temperature, the reaction mixture was warmed to 30° C. After 45 minutes, the slurry was concentrated, giving crude triflate salt intermediate. DMSO (30 mL) and potassium ferricyanide (47.3 g, 144 mmol) were added, followed by slow addition of aqueous sodium hydroxide (2 N, 201 mL, 402 mmol), keeping the temperature at less than about 35° C. After 10 minutes, water (200 mL) was added and the mixture was stirred vigorously, and the yellow slurry was filtered, washing with water (200 mL). EtOAc (200 mL) was added to the yellow slurry and was sonicated for 5 minutes and filtered, washing with EtOAc (50 mL). The yellow solid was dried in a vacuum oven at 60° C., to provide the title compound (6.85 g). The mother liquors were concentrated and sonicated with 50 mL EtOAc, filtered, and dried, to provide more title compound (2.18 g). MS (DCI) m/z 222 (M+NH$_4$)$^+$.

Example 50B 5-amino-1-methylquinolin-2(1H)-one

A solution of Example 50A (2.16 g, 10.6 mmol) in tetrahydrofuran (50 mL) was added to 5% Pd—C, wet (0.432 g, 4.06 mmol) in a 250 mL stainless steel pressure bottle. After 3 hours at about room temperature under 30 psi of hydrogen pressure, the mixture was filtered through a nylon membrane and concentrated. EtOH (22 mL) was added, and the yellow slurry was sonicated for 5 minutes and filtered, washing with EtOH (10 mL). The yellow solid was dried in a vacuum oven at 50° C. to provide the title compound (1.40 g, 8.04 mmol, 75% yield). MS (DCI) m/z 175 (M+N)$^+$.

Example 50C 1-(1-methyl-2-oxo-1,2-dihydroquinolin-5-yl)-3-((1S,3R)-3-phenylcyclopentyl)urea The title compound was prepared according to Example 1F, substituting Example 50B for Example 1B, and substituting (1S,3R)-3-phenylcyclopentanamine (second eluting diastereomer from Example 15B) for Example 1E. $^1$H NMR (500 MHz, DMSO-d$_6$/Deuterium Oxide) δ 8.02 (d, J=9.8 Hz, 1H), 7.65 (d, J=8.0 Hz, 1H), 7.55 (t, J=8.3 Hz, 1H), 7.36-7.25 (m, 5H), 7.25-7.14 (m, 2H), 6.64 (d, J=9.8 Hz, 1H), 4.25-4.01 (m, 1H), 3.62 (s, 3H), 3.17-2.97 (m, 1H), 2.48-2.36 (m, 1H), 2.13-1.97 (m, 2H), 1.81-1.58 (m, 2H), 1.56-1.37 (m, 1H); MS (ESI$^+$) M/Z 362 [M+H]$^+$.

Example 51

1-(1-methyl-2-oxo-1,2-dihydroquinolin-5-yl)-3-((1R,3S)-3-phenylcyclopentyl)urea

The title compound was prepared according to Example 1F, substituting Example 50B for Example 1B. $^1$H NMR (500 MHz, DMSO-d$_6$/Deuterium Oxide) δ 8.02 (d, J=9.8 Hz, 1H), 7.65 (d, J=7.9 Hz, 1H), 7.55 (t, J=8.3 Hz, 1H), 7.36-7.26 (m, 5H), 7.26-7.13 (m, 2H), 6.64 (d, J=9.9 Hz, 1H), 4.23-4.01 (m, 1H), 3.62 (s, 3H), 3.14-2.96 (m, 1H), 2.42 (dt, J=18.2, 5.8 Hz, 1H), 2.12-1.98 (m, 2H), 1.82-1.58 (m, 2H), 1.56-1.40 (m, 1H); MS (ESI$^+$) M/Z 362 [M+H]$^+$.

Example 52

1-((1S,2S,3R,4S)-2,3-dihydroxy-4-phenylcyclopentyl)-3-(1H-indazol-4-yl)urea

A slurry of Example 48D (50.0 mg, 0.157 mmol), acetonitrile (0.3 mL), THF (0.150 mL), water (0.075 mL), 4-methylmorpholine N-oxide (22.1 mg, 0.188 mmol), and osmium tetroxide (4 wt % in water, 0.037 mL, 4.71 μmol) was stirred at ambient temperature. The mixture was too viscous to stir efficiently, so more solvents were added (equal volumes to the first additions). After 5 hours, citric acid (60.3 mg, 0.314 mmol) and osmium tetroxide (4 wt % in water, 0.037 mL, 4.71 μmol) were added. After stirring for 3 days at ambient temperature, the mixture was diluted with 1:1 DMSO/MeOH (1.5 mL) and purified by reverse phase HPLC. The pure fractions were combined, rinsing with MeOH, and concentrated to provide the title compound (first eluting isomer, 11 mg, 0.031 mmol, 20% yield) and Example 53 (second eluting isomer, 22 mg, 0.062 mmol, 40% yield). $^1$H NMR (501 MHz, CD$_3$OD) δ 8.13 (s, 1H), 7.55 (d, J=7.6 Hz, 1H), 7.36-7.23 (m, 5H), 7.23-7.10 (m, 2H), 4.13-4.00 (m, 2H), 3.96 (t, J=5.6 Hz, 1H), 3.14 (dt, J=10.7, 7.9 Hz, 1H), 2.59-2.52 (m, 1H), 1.57 (dd, J=21.9, 10.7 Hz, 1H). MS (LCMS) M/Z 353 [M+H]$^+$.

Example 53

1-((1S,2R,3S,4S)-2,3-dihydroxy-4-phenylcyclopentyl)-3-(1H-indazol-4-yl)urea

The title compound was obtained as the second major eluting peak from Example 52. $^1$H NMR (501 MHz, CD$_3$OD) δ 8.13 (s, 1H), 7.51 (d, J=7.5 Hz, 1H), 7.27 (dt, J=14.4, 7.5 Hz, 5H), 7.13 (dt, J=14.0, 7.8 Hz, 2H), 4.30 (q, J=7.4 Hz, 1H), 4.17 (dd, J=7.3, 4.0 Hz, 1H), 4.13 (t, J=4.3 Hz, 1H), 3.08 (ddd, J=21.1, 17.2, 12.2 Hz, 1H), 2.45 (dt, J=13.1, 7.8 Hz, 1H), 2.02 (td, J=12.5, 7.2 Hz, 1H). MS (LCMS) M/Z 353 [M+H]$^+$.

Example 54

1-((1R,2R,4S,5R)-6,6-difluoro-4-phenylbicyclo[3.1.0]hex-2-yl)-3-(1H-indazol-4-yl)urea Example 54A 2-((1R,4S)-4-phenylcyclopent-2-enyl)isoindoline-1,3-dione A solution of Example 63A (309 mg, 1.94 mmol), toluene (3.1 mL), and phthalic anhydride (316 mg, 2.14 mmol) was heated to 100° C. After 15 hours, the mixture was concentrated and the residue was purified by flash column chromatography (0-25% EtOAc/hexanes, gradient elution), giving the title compound (423 mg, 1.46 mmol, 75% yield). MS (DCI) M/Z 307 [M+NH$_4$]$^+$.

Example 54B 2-((1R,2R,4S,5R)-6,6-difluoro-4-phenylbicyclo[3.1.0]hexan-2-yl)isoindoline-1,3-dione A mixture of Example 54A (419 mg, 1.45 mmol), toluene (0.2 mL), and sodium fluoride (21.3 mg, 0.507 mmol) was heated in a 120° C. oil bath and trimethylsilyl 2,2-difluoro-2-(fluorosulfonyl)acetate (1.43 mL, 7.24 mmol) was added via syringe pump over 2 hours. After 2 hours, the mixture was diluted with EtOAc (50 mL) and washed with saturated aqueous NaHCO$_3$ (25 mL) and brine (10 mL), dried (Na$_2$SO$_4$), and concentrated. The residue was purified by flash column chromatography (0-25% EtOAc/hexanes, gradient elution) to provide the title compound (145 mg, 0.427 mmol, 30% yield). MS (DCI) M/Z 357 [M+NH$_4$]$^+$.

Example 54C (1R,2R,4S,5R)-6,6-difluoro-4-phenylbicyclo[3.1.0]hexan-2-amine

Example 54B (144 mg, 0.424 mmol), MeOH (7 mL), and hydrazine monohydrate (0.517 mL, 10.6 mmol) heated to 50° C. After 90 minutes, the mixture was cooled to ambient temperature, diluted with MTBE (50 mL) and water (25 mL). The layers were separated, and the organic layer was washed with water (10 mL) and brine (10 mL), dried (Na$_2$SO$_4$), and concentrated to provide the title compound (79 mg, 0.378 mmol, 89% yield). MS (DCI) M/Z 210 [M+H]+.

Example 54D 1-((1R,2R,4S,5R)-6,6-difluoro-4-phenylbicyclo[3.1.0]hexan-2-yl)-3-(1H-indazol-4-yl)urea An orange solution of Example 54C (77 mg, 0.368 mmol), DMF (0.8 mL), i-Pr$_2$NEt (0.135 mL, 0.773 mmol), and methyl 4-((2,5-dioxopyrrolidin-1-yloxy)carbonylamino)-1H-indazole-1-carboxylate (128 mg, 0.386 mmol) was stirred at ambient temperature. After 15 minutes, MeOH (1.60 mL) and sodium hydroxide (50 wt % in water, 0.058 mL, 1.1 mmol) were added. After 20 minutes of stirring, the mixture was diluted with EtOAc (30 mL) and washed with water (10 mL) and brine (10 mL), dried (Na$_2$SO$_4$), and concentrated. The residue was purified by flash column chromatography (75-100% EtOAc/hexanes, gradient elution) to provide the title compound (117 mg, 0.318 mmol, 86% yield). $^1$H NMR (400 MHz, DMSO-d$_6$) δ 13.01 (s, 1H), 8.72 (s, 1H), 8.03 (s, 1H), 7.58 (d, J=7.3 Hz, 1H), 7.47-7.30 (m, 4H), 7.30-7.14 (m, 2H), 7.07 (d, J=8.3 Hz, 1H), 6.48 (d, J=6.1 Hz, 1H), 4.30 (s, 1H), 3.54 (d, J=6.6 Hz, 1H), 2.64-2.50 (m, 3H), 1.81 (d, J=13.8 Hz, 1H). MS (DCI) M/Z 369 [M+H]+.

Example 55

1-(1H-indazol-4-yl)-3-((1S,2R,4S,5S)-4-phenylbicyclo[3.1.0]hex-2-yl)urea

Example 55A

N-((1R,4S)-4-phenylcyclopent-2-enyl)acetamide

A solution of Example 63A (500 mg, 3.14 mmol) in CH$_2$Cl$_2$ (5 mL) and pyridine (0.381 mL, 4.71 mmol) was cooled to <0° C. and acetyl chloride (0.268 mL, 3.77 mmol) was added dropwise at <0° C. After 15 minutes, water (10 mL) and MTBE (30 mL) were added and the layers were separated. The organic layer was washed with brine (10 mL), dried (Na$_2$SO$_4$), and concentrated. The residue was purified by flash column chromatography (50-100% EtOAc/hexanes, gradient elution) to provide the title compound (455 mg, 2.26 mmol, 72.0% yield) as a white solid. MS (DCI) M/Z 202 [M+H]+.

Example 55B

N-((1S,2R,4S,5S)-4-phenylbicyclo[3.1.0]hexan-2-yl)acetamide

A solution of Example 55A (100 mg, 0.497 mmol) and CH$_2$Cl$_2$ (5 mL) was cooled to −10° C. and diethylzinc (1M solution, 4.97 mL, 4.97 mmol) was added at <0° C. After 5 minutes, diiodomethane (0.441 mL, 5.47 mmol) was added at <0° C. The mixture was slowly warmed to ambient temperature and the reaction was complete after 3 hours. The mixture was cooled to <0° C., brine (5 mL) and 2N HCl (5 mL) were added, then diluted with MTBE (50 mL) and added saturated aqueous Na$_2$S$_2$O$_3$ (10 mL). The organic layer was washed with brine (10 mL), dried (Na$_2$SO$_4$), and concentrated. The residue was purified by flash column chromatography (50-100% EtOAc/hexanes, gradient elution) to provide the title compound (82 mg, 0.381 mmol, 77% yield). MS (DCI) M/Z 216 [M+H]+.

Example 55C (1S,2R,4S,5S)-4-phenylbicyclo[3.1.0]hexan-2-amine

A slurry of Example 55B (79 mg, 0.367 mmol) and barium hydroxide (0.25 M in water, 4.4 mL, 1.1 mmol) was heated to 95° C. After 4 hours, DMSO (1 mL) was added. After heating overnight, conversion to the product was still very slow. More barium hydroxide (0.25 M slurry, 4 mL) and DMSO (1 mL) were added. After 6 hours, the mixture was cooled to ambient temperature, diluted with MTBE (50 mL), and washed with water (20 mL×2) and brine (10 mL). The organic phase was washed with 2N HCl (40 mL) and water sequentially, and the layers separated. The resulting aqueous phase was basified with 2N NaOH (50 mL) and extracted with MTBE (20 mL×3), dried (Na$_2$SO$_4$), and concentrated to provide the title compound (20 mg, 0.115 mmol, 31.5% yield). MS (LCMS) M/Z 157 (M+NH$_2$)+.

Example 55D 1-(1H-indazol-4-yl)-3-((1S,2R,4S,5S)-4-phenylbicyclo[3.1.0]hex-2-yl)urea An orange solution of Example 55C (20 mg, 0.115 mmol), DMF (1 mL), DIPEA (0.042 mL, 0.242 mmol), and methyl 4-((2,5-dioxopyrrolidin-1-yloxy)carbonylamino)-1H-indazole-1-carboxylate (40.3 mg, 0.121 mmol) was stirred at ambient temperature. After 15 minutes, MeOH (2.00 mL) and sodium hydroxide (50 wt % in water, 0.018 mL, 0.346 mmol) were added. After 20 minutes of stirring, the mixture was diluted with EtOAc (30 mL) and washed with water (10 mL) and brine (10 mL), dried (Na$_2$SO$_4$), and concentrated. The residue was purified by flash column chromatography (75-100% EtOAc/hexanes, gradient elution) to provide the title compound (27.5 mg, 0.083 mmol, 71.7% yield). $^1$H NMR (400 MHz, DMSO-d$_6$) δ 13.0 (brs, 1H), 8.63 (s, 1H), 8.09 (d, J=1.0 Hz, 1H), 7.65 (d, J=7.6 Hz, 1H), 7.39-7.33 (m, 2H), 7.30 (t, J=7.5 Hz, 2H), 7.24-7.16 (m, 2H), 7.05 (d, J=8.2 Hz, 1H), 6.52 (d, J=7.6 Hz, 1H), 4.49-4.38 (m, 1H), 3.50-3.41 (m, 1H), 2.24 (dt, J=12.7, 7.6 Hz, 1H), 1.66-1.58 (m, 2H), 1.29-0.90 (m, 1H), 0.69 (q, J=4.2 Hz, 1H), 0.48 (td, J=7.7, 5.2 Hz, 1H). MS (DCI) M/Z 350 [M+NH$_4$]+.

Example 56

1-(1H-indazol-4-yl)-3-(cis-3-phenylcyclobutyl)urea

Example 56A 3-phenylcyclobutanone oxime

A yellow slurry of 3-phenylcyclobutanone (1.09 g, 7.44 mmol), MeOH (33.8 mL), water (3.38 mL), potassium carbonate (2.26 g, 16.4 mmol), and hydroxylamine hydrochloride (1.14 g, 16.4 mmol) was heated at 50° C. for 14 hours. The mixture was diluted with EtOAc (50 mL), washed with water (10 mL) and brine (10 mL), dried (Na$_2$SO$_4$), and concentrated. The residue was purified by flash column chromatography (0-50% EtOAc/hexanes, gradient elution) to provide the title compound (947 mg, 5.87 mmol, 79% yield). MS (DCI) M/Z 162 [M+H]+.

Example 56B 3-phenylcyclobutanamine

Example 56A (933 mg, 5.79 mmol), NH$_3$-MeOH (7M, 10 mL), and Ra—Ni 2800, water slurry (1866 mg, 31.8 mmol) in a 50 mL pressure bottle was stirred for 2 hours at 30 psi and ambient temperature. The mixture was filtered through a nylon membrane. The catalyst was washed with THF, and the filtrate concentrated to provide the title compound (737 mg, 5.01 mmol, 86% yield). MS (DCI) M/Z 143 [M+H]$^+$.

Example 56C 1-(1H-indazol-4-yl)-3-(cis-3-phenylcyclobutyl)urea

An orange solution of Example 56B (98 mg, 0.666 mmol), DMF (1 mL), i-Pr$_2$NEt (0.244 mL, 1.40 mmol), and methyl 4-((2,5-dioxopyrrolidin-1-yloxy)carbonylamino)-1H-indazole-1-carboxylate (232 mg, 0.699 mmol) was stirred at ambient temperature 15 minutes, followed by the addition of MeOH (2.00 mL) and sodium hydroxide (50% in water, 0.105 mL, 2.00 mmol). After 10 minutes, water (3 mL) was added dropwise and a sticky gum was observed. The mixture was heated to reflux and a slurry persisted. The mixture was cooled slowly to ambient temperature and filtered, washing with 1:1 MeOH/water (6 mL). The white solid was dried in a vacuum oven at 50° C. to provide (1H-indazol-4-yl)-3-(3-phenylcyclobutyl)urea (144 mg, 0.470 mmol, 70.6% yield). Analytical chiral HPLC (20% IPA/hexanes isochratic method, 0.7 mL/min, AD-H column) showed two peaks (Retention times: major: 10.1 min; minor: 12.1 min) in a 2:1 ratio. The mixture was dissolved in 1:1 IPA/MeOH (20 mL) and separated on a 30×250 mm AD-H semi-prep column (10 mL/min, 2 mL/injection, 15% IPA/hexanes isochratic, 28 min runs, stack injection) to provide the title compound (55 mg, 0.18 mmol, 38% yield) and Example 57 (23 mg, 0.074 mmol, 16% yield). $^1$H NMR (500 MHz, DMSO-d$_6$) 13.15 (s, 1H), 8.75 (s, 1H), 8.24 (s, 1H), 7.74 (d, J=7.6 Hz, 1H), 7.62-7.25 (m, 6H), 7.21 (d, J=8.3 Hz, 1H), 6.84 (d, J=8.0 Hz, 1H), 4.33 (dq, J=16.5, 8.2 Hz, 1H), 3.35-3.24 (m, 1H), 2.84 (ddd, J=15.6, 7.7, 2.8 Hz, 2H), 2.13 (td, J=10.4, 2.6 Hz, 2H). MS (DCI) M/Z 324 [M+NH$_4$]$^+$.

Example 57

1-(1H-indazol-4-yl)-3-(trans-3-phenylcyclobutyl)urea

The title compound was isolated as the second major eluting peak from Example 56C. $^1$H NMR (500 MHz, DMSO-d$_6$) δ 12.99 (s, 1H), 8.64 (s, 1H), 8.09 (s, 1H), 7.58 (d, J=7.6 Hz, 1H), 7.34-7.30 (m, 4H), 7.19 (ddd, J=12.3, 6.9, 3.5 Hz, 2H), 7.05 (d, J=8.3 Hz, 1H), 6.84 (d, J=7.1 Hz, 1H), 4.29 (h, J=6.7 Hz, 1H), 3.62-3.49 (m, 1H), 2.46-2.35 (m, 4H). MS (DCI) M/Z 324 [M+NH$_4$]$^+$.

Example 58

1-[(trans)-3-hydroxy-3-phenylcyclopentyl]-3-(1H-indazol-4-yl)urea

Example 58A 2-(3-oxocyclopentyl)isoindoline-1,3-dione

A slurry of methanol (88 mL), 2-cyclopenten-1-one (10.2 mL, 122 mmol), and phthalimide (17.9 g, 122 mmol) was stirred at ambient temperature and sodium carbonate (2M in water, 7.92 mL, 15.8 mmol) was added. After 22 hours, the thick white slurry was filtered and washed with MeOH (100 mL). Water (100 mL) was added to the wet cake, stirred for 1 hour, and filtered. The solid was washed with water (50 mL) and dried in a vacuum oven at 50° C. for 14 hours to provide the title compound (17.8 g, 78.0 mmol, 64% yield). MS (DCI) M/Z 247 [M+NH$_4$]$^+$.

Example 58B 2-(3-hydroxy-3-phenylcyclopentyl)isoindoline-1,3-dione

A solution of Example 58A (1.00 g, 4.36 mmol) and THF (20 mL) was cooled to <–70° C. and phenylmagnesium chloride (2.40 mL, 4.80 mmol) was added at <–70° C. After 2 hours, saturated aqueous NH$_4$Cl (20 mL) was added and the mixture was extracted with MTBE (50 mL). The organic layer was dried (Na$_2$SO$_4$) and concentrated. The residue was puridifed by flash column chromatography (0-20% EtOAc/hexanes, gradient elution), to provide the title compound (370 mg, 1.20 mmol, 27.6% yield).

Example 58C 3-amino-1-phenylcyclopentanol

A solution of Example 58B (107 mg, 0.348 mmol), MeOH (5.5 mL), and hydrazine monohydrate (0.424 mL, 8.70 mmol) was heated at 50° C. for 1 hour, cooled to ambient temperature, and diluted with MTBE (50 mL) and water (25 mL). The layers were separated. The organic layer was washed with water (10 mL) and brine (10 mL), dried (Na$_2$SO$_4$), and concentrated to provide the title compound (34 mg, 0.19 mmol, 55% yield).

Example 58D

1-[(trans)-3-hydroxy-3-phenylcyclopentyl]-3-(1H-indazol-4-yl)urea

An orange solution of Example 58C (33 mg, 0.186 mmol), DMF (0.65 mL), i-Pr$_2$NEt (0.068 mL, 0.391 mmol), and methyl 4-((2,5-dioxopyrrolidin-1-yloxy)carbonylamino)-1H-indazole-1-carboxylate (65.0 mg, 0.195 mmol) was stirred at ambient temperature for 15 minutes, followed by the addition of MeOH (1.30 mL) and sodium hydroxide (50 wt % in water, 0.029 mL, 0.559 mmol). After 20 minutes, water (2 mL) was added dropwise (solution) and cooled to <5° C. (white slurry). The slurry was stirred for 30 minutes and filtered, washing the solid with cold 1:1 MeOH/water (2 mL). The solide was dried in a vacuum oven at 50° C. to provide the title compound (44.4 mg, 0.132 mmol, 71% yield). $^1$H NMR (300 MHz, DMSO-d$_6$) δ 12.94 (s, 1H), 8.80 (s, 1H), 8.13 (s, 1H), 7.67 (d, J=7.6 Hz, 1H), 7.50 (d, J=7.4 Hz, 2H), 7.41-7.10 (m, 4H), 7.02 (d, J=8.2 Hz, 1H), 6.70 (d, J=8.6 Hz, 1H), 5.21 (s, 1H), 4.45-4.33 (m, 1H), 2.26 (s, 2H), 2.03-1.75 (m, 4H). MS (DCI) M/Z 337 [M+H]$^+$.

Example 59

1-[(2R)-2-hydroxy-2,3-dihydro-1H-inden-4-yl]-3-(trans-3-phenylcyclobutyl)urea

N,N'-Disuccinimidyl carbonate (193 mg, 0.754 mmol), acetonitrile (1 mL), Example 1B (112 mg, 0.754 mmol), and pyridine (0.061 mL, 0.754 mmol) were combined at ambient temperature for 10 minutes, followed by addition of i-Pr$_2$NEt (0.261 mL, 1.51 mmol) and Example 56B (74 mg, 0.503 mmol) and the mixture was stirred for another 10 minutes. MeOH (1 mL) was added, followed by dropwise addition of water (2 mL). The resulting white slurry was stirred for 10 minutes and filtered. The solid collected was washed with 1:1 MeOH/water (4 mL), and dried in a vacuum oven, giving a mix of cis- and trans-products (125 mg, 77%). Analytical chiral HPLC (AD-3, 20% IPA/hexanes isochratic, 0.7 mL/min) showed two peaks at 14.1 min (63.5%) and 16.6 min (36.5%). The solid was dissolved in 5 mL 10% MeOH/IPA, added 5 mL hexanes, and separated on a 30×250 mm AD-H semi-prep column (20% IPA/hexanes isochratic, 2 mL/injection, 50 min runs) to provide the title compound (first major peak, 24.4 mg, 0.076 mmol, 15.1% yield) and Example 60 (second major peak, 47.8 mg, 0.148 mmol, 29.5% yield). Data for Example 59: $^1$H NMR (300 MHz, DMSO-$d_6$) δ 7.79-7.54 (m, 2H), 7.44-7.12 (m, 5H), 7.11-6.87 (m, 2H), 6.77 (t, J=6.1 Hz, 1H), 4.85 (d, J=4.1 Hz, 1H), 4.61-4.42 (m, 1H), 4.35-4.13 (m, 1H), 3.65-3.44 (m, 1H), 3.13-2.86 (m, 2H), 2.81-2.61 (m, 2H), 2.47-2.26 (m, 4H). MS (DCI) M/Z 340 [M+NH$_4$]$^+$.

Example 60

1-[(2R)-2-hydroxy-2,3-dihydro-1H-inden-4-yl]-3-(cis-3-phenylcyclobutyl)urea

The title compound was isolated as the second major eluting peak from Example 59C. $^1$H NMR (300 MHz, DMSO-$d_6$) δ 7.70 (d, J=8.0 Hz, 1H), 7.60 (s, 1H), 7.40-7.08 (m, 5H), 7.01 (t, J=7.8 Hz, 1H), 6.78 (d, J=7.3 Hz, 2H), 4.85 (d, J=4.1 Hz, 1H), 4.50 (s, 1H), 4.13 (d, J=7.9 Hz, 1H), 3.24-2.90 (m, 4H), 2.65 (dd, J=15.3, 12.6 Hz, 4H), 1.91 (s, 1H). MS (DCI) M/Z 340 [M+NH$_4$]$^+$.

Example 61

1-[(1R,3S)-3-(2-fluorophenyl)cyclopentyl]-3-(1H-indazol-4-yl)urea

Example 61A (S)-3-(2-fluorophenyl)cyclopentanone

According to the method described in *J. Org. Chem.*, 2009, 74, 929, bis(norbornadiene)rhodium tetrafluoroborate (0.22 g, 0.59 mmol) and (S)-(−)-2,2'-bis(diphenylphosphino)-1,1'-binaphthyl (0.39 g, 0.62 mmol) were added to a mixture of 2-fluorophenylboronic acid (5.37 g, 38.4 mmol) in nitrogen sparged dioxane (30 mL) under nitrogen atmosphere. After 2 hours of agitation at ambient temperature, water was added (4.6 mL) followed by 2-cyclopenten-1-one (3.06 mL, 36.5 mmol) and triethylamine (5.09 g, 36.5 mmol). The agitation was continued for 24 h at 30° C. then the mixture was diluted with heptane (30 mL), MTBE (10 mL), and water (30 mL). The organic layer was separated and washed with water (50 mL). The aqueous layers were combined and extracted with MTBE/heptane (1:2, 50 mL). Combined organic extracts were dried (Na$_2$SO$_4$) and concentrated. Purification by chromatography (SiO$_2$, hexane/20% ethyl acetate) afforded the title compound (3.94 g, 22.1 mmol, 61%). $^1$H NMR (300 MHZ, DMSO-$d_6$) δ 7.46-7.27 (M, 1H), 7.25-7.05 (M, 3H), 3.56-3.26 (M, 1H), 2.22-1.41 (M, 6H). MS (ESI) m/z 177 (M−H)$^+$.

Example 61B (3S)-3-(2-fluorophenyl)cyclopentanamine

The title compound was prepared according to Example 1C and 1D, substituting Example 61A for (S)-3-(4-bromophenyl)cyclopentanone. MS (ESI$^+$) M/Z 180 (M+H)$^+$.

Example 61C

1-[(1R,3S)-3-(2-fluorophenyl)cyclopentyl]-3-(1H-indazol-4-yl)urea

A solution of Example 61B (0.35 g, 1.95 mmol), DMF (10 mL), N,N-diisopropyl ethylamine (0.72 mL, 4.1 mmol) and methyl 4-((2,5-dioxopyrrolidin-1-yloxy)carbonylamino)-1H-indazole-1-carboxylate (prepared as in *Org. Proc. Res. Dev.*, 2007, 11, 578; 0.65 g, 1.95 mmol) was stirred at ambient temperature. After 5 minutes, LCMS showed complete conversion to the methyl carbamate intermediate. Methanol (20 mL) and 2N sodium hydroxide (5.86 mmol) were added resulting in a white slurry. The mixture was diluted with water and extracted with ethyl acetate (100 mL). The organic extract was washed with brine (50 mL), dried (Na$_2$SO$_4$), filtered and concentrated. The mixture was separated using a Chiralpak AD-H column and eluting with 5-50% MeOH:CO$_2$ 10 min at 3 mL/min to provide the title compound (303 mg, 31%) and Example 62 (181 mg, 27%). Data for Example 61C: $^1$H NMR (300 MHz, DMSO-$d_6$) δ 12.98 (bs, 1H), 8.56 (s, 1H), 8.07 (d, J=1.0 Hz, 1H), 7.62 (d, J=7.9 Hz, 1H), 7.46-7.36 (m, 1H), 7.32-7.01 (m, 5H), 6.55 (d, J=7.2 Hz, 1H), 4.23-3.99 (m, 3H), 2.16-1.97 (m, 2H), 1.82-1.46 (m, 3H). MS (ESI$^+$) M/Z 339 (M+H)$^+$.

Example 62

1-[(1S,3S)-3-(2-fluorophenyl)cyclopentyl]-3-(1H-indazol-4-yl)urea

The title compound was isolated from the separation of Example 61C. $^1$H NMR (300 MHz, DMSO-$d_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 1H), 3.47 (p, J=8.6 Hz, 1H), 2.28-1.90 (m, 4H), 1.74-1.51 (m, 3H). MS (ESI+) M/Z 339 (M+H)+.

Example 63

1-(1H-indazol-4-yl)-3-[(1R,4S)-4-phenylcyclopent-2-en-1-yl]urea

Example 63A (1R,4S)-4-phenylcyclopent-2-enamine

The title compound was prepared according to Example 48A-C, substituting (1S,4R)-4-acetoxy-2-cyclopenten-1-ol for (1R,4S)-4-acetoxy-2-cyclopenten-1-ol. MS (DCI$^+$) M/Z 160 (M+H)$^+$.

Example 63B 1-(1H-indazol-4-yl)-3-[(1R,4S)-4-phenylcyclopent-2-en-1-yl]urea

The title compound was prepared according to Example 48D, substituting Example 63A for Example 48C. $^1$H NMR (300 MHz, DMSO-d$_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 1H), 3.47 (p, J=8.6 Hz, 1H), 2.28-1.90 (m, 4H), 1.74-1.51 (m, 2H). MS (DCI$^+$) M/Z 336 (M+NH4)$^+$.

Example 64

1-[(1S,3S)-3-(3-fluorophenyl)cyclopentyl]-3-(1H-indazol-4-yl)urea

Example 64A

(S)-3-(3-fluorophenyl)cyclopentanone

The title compound was prepared according to Example 61A, substituting 3-fluorophenylboronic acid for 2-fluorophenylboronic acid. $^1$H NMR (300 MHz, DMSO-d$_6$) δ 7.46-7.27 (m, 1H), 7.25-7.05 (m, 3H), 3.56-3.26 (m, 2H), 2.22-1.41 (m, 4H). MS (ESI–) M/Z 177 (M–H)+.

Example 64B

(3S)-3-(3-fluorophenyl)cyclopentanamine

The title compound was prepared according to Examples 1C and 1D, substituting Example 64A for (S)-3-(4-bromophenyl)cyclopentanone. (ESI$^+$) M/Z 180 (M+H)$^+$.

Example 64C

1-[(1S,3S)-3-(3-fluorophenyl)cyclopentyl]-3-(1H-indazol-4-yl)urea

The title compounds were prepared according to Example 61C, substituting Example 64B for Example 61B. The mixture of isomers was separated using a Chiralpak OD-H column and eluting with 5-50% MeOH:CO$_2$ 10 min at 3 mL/min to provide the title compound (82 mg, 15%) and Example 65 (74 mg, 13%). Data for Example 64C: $^1$H NMR (300 MHz, DMSO-d$_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 2H), 3.47 (p, J=8.6 Hz, 1H), 2.28-1.90 (m, 4H), 1.74-1.51 (m, 2H). MS (DCI$^+$) M/Z 339 (M+H)$^+$.

Example 65

1-[(1R,3S)-3-(3-fluorophenyl)cyclopentyl]-3-(1H-indazol-4-yl)urea

The title compound was isolated from the separation of Example 64C. $^1$H NMR (300 MHz, DMSO-d$_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 5H), 7.04 (d, J=8.2 Hz, 1H), 6.62 (d, J=7.0 Hz, 1H), 4.30-4.02 (m, 1H), 3.47 (p, J=8.6 Hz, 1H), 2.28-1.90 (m, 4H), 1.74-1.51 (m, 2H). MS (DCI$^+$) M/Z 339 (M+H)$^+$.

Example 66

1-[(1R,3R)-3-(2-fluorophenyl)cyclopentyl]-3-(1H-indazol-4-yl)urea

Example 66A

(R)-3-(2-fluorophenyl)cyclopentanone

The title compound was prepared according to Example 61A, substituting (R)-(+)-2,2'-bis(diphenylphosphino)-1,1'-binaphthyl for (S)-(–)-2,2'-bis(diphenylphosphino)-1,1'-binaphthyl. $^1$H NMR (300 MHz, DMSO-d$_6$) δ 7.46-7.27 (m, 1H), 7.25-7.05 (m, 3H), 3.56-3.26 (m, 2H), 2.22-1.41 (m, 4H). MS (ESI–) M/Z 177 (M–H)$^+$.

Example 66B

(3R)-3-(2-fluorophenyl)cyclopentanamine

The title compound was prepared according to Example 1C and 1D, substituting Example 66A for (S)-3-(4-bromophenyl)cyclopentanone. MS (ESI$^+$) M/Z 180 (M+H)$^+$.

Example 66C

1-[(1R,3R)-3-(2-fluorophenyl)cyclopentyl]-3-(1H-indazol-4-yl)urea

The title compound was prepared according to Example 61C, substituting Example 66B for Example 61B. The mixture of isomers was separated using a Chiralpak OJ-H column and eluting with 5-50% MeOH:CO$_2$ 10 min at 3 mL/min to afford the title compound (141 mg, 0.417 mmol, 21% yield) and Example 67 (160 mg, 0.473 mmol, 24% yield). Data for Example 66C: $^1$H NMR (300 MHz, DMSO-d$_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 2H), 3.47 (p, J=8.6 Hz, 1H), 2.28-1.90 (m, 4H), 1.74-1.51 (m, 2H). MS (DCI$^+$) M/Z 339 (M+H)$^+$.

Example 67

1-[(1S,3R)-3-(2-fluorophenyl)cyclopentyl]-3-(1H-indazol-4-yl)urea

The title compound was isolated from Example 66C. $^1$H NMR (300 MHz, DMSO-d$_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 2H), 3.47 (p, J=8.6 Hz, 1H), 2.28-1.90 (m, 4H), 1.74-1.51 (m, 2H). MS (DCI+) M/Z 339 (M+H)$^+$.

Example 68

1-[(1R,3R)-3-(3-fluorophenyl)cyclopentyl]-3-(1H-indazol-4-yl)urea

Example 68A

(R)-3-(3-fluorophenyl)cyclopentanone

The title compound was prepared according to Example 61A, substituting 3-fluorophenylboronic acid for 2-fluorophenylboronic acid and substituting (R)-(+)-2,2'-bis(diphenylphosphino)-1,1'-binaphthyl for (S)-(–)-2,2'-bis(diphenylphosphino)-1,1'-binaphthyl. $^1$H NMR (300 MHz, DMSO-d$_6$) δ 7.46-7.27 (m, 1H), 7.25-7.05 (m, 3H), 3.56-3.26 (m, 2H), 2.22-1.41 (m, 4H). MS (ESI–) M/Z 177 (M–H)$^+$.

Example 68B

(3R)-3-(3-fluorophenyl)cyclopentanamine

The title compound was prepared according to Example 1C and 1D, substituting Example 68A for (S)-3-(4-bromophenyl)cyclopentanone. (ESI$^+$) M/Z 180 (M+H)$^+$.

Example 68C

1-[(1R,3R)-3-(3-fluorophenyl)cyclopentyl]-3-(1H-indazol-4-yl)urea

The title compounds were prepared according to Example 61C, substituting Example 68B for Example 61B. The mixture of isomers was separated using a Chiralpak OJ-H column and eluting with 5-50% MeOH:$CO_2$ 10 min at 3 mL/min to afford the title compound (111 mg. 17%) and Example 69 (89 mg, 14%). Data for Example 68C: $^1$H NMR (300 MHz, DMSO-$d_6$) δ 8.55 (s, 1H), 8.08 (d, J=0.9 Hz, 1H), 7.63 (d, J=7.6 Hz, 1H), 7.44-7.34 (m, 1H), 7.31-7.09 (m, 4H), 7.04 (d, J=8.2 Hz, 1H), 6.62 (d, J=7.0 Hz, 1H), 4.30-4.02 (m, 2H), 3.47 (p, J=8.6 Hz, 1H), 2.28-1.90 (m, 4H), 1.74-1.51 (m, 2H). MS (DCI+) M/Z 339 (M+H)$^+$.

Example 69

1-[(1S,3R)-3-(3-fluorophenyl)cyclopentyl]-3-(1H-indazol-4-yl)urea

The title compound was isolated from Example 68C. $^1$H NMR (300 MHz, DMSO-$d_6$) δ 8.54 (s, 1H), 8.08 (d, J=0.9 Hz, 1H), 7.62 (d, J=7.6 Hz, 1H), 7.44-7.34 (m, 1H), 7.31-7.07 (m, 4H), 7.05 (d, J=8.2 Hz, 1H), 6.62 (d, J=7.0 Hz, 1H), 4.31-4.03 (m, 2H), 3.48 (p, J=8.6 Hz, 1H), 2.28-1.90 (m, 4H), 1.75-1.52 (m, 2H). MS (DCI+) M/Z 339 (M+H)$^+$.

Example 70

1-(6-fluoro-3-methylisoquinolin-5-yl)-3-[(1R,3S)-3-(2-fluorophenyl)cyclopentyl]urea A mixture of Example 6D (511 mg, 1.59 mmol), Example 61B (285 mg, 1.59 mmol), DMF (3 mL), and $K_2CO_3$ (54.9 mg, 0.398 mmol) was heated at 85° C. for 10 hours. After cooling to ambient temperature, the mixture was diluted with EtOAc, and washed with 10% aqueous $KH_2PO_4$ (2×) and brine (2×), 2N aqueous NaOH, and brine, dried ($Na_2SO_4$), and concentrated. Purification by chromatography ($SiO_2$, ethyl acetate/methanol 0-10% gradient over 20 minutes with a 90 minute hold) afforded the mixture of isomers (272 mg). The isomers were separated using chiral SFC chromatography (Chiralpak AD-H column and eluting with 5-50% MeOH:$CO_2$ 10 min at 3 mL/min) to afford the title compound (123 mg, 20%) and Example 71 (147 mg, 24%). Data for Example 70: $^1$H NMR (500 MHz, DMSO-$d_6$) δ 9.21 (s, 1H), 8.23-7.91 (m, 8H), 7.67-5.86 (m, 2H), 4.30-3.94 (m, 4H), 3.57-3.37 (m, 2H), 3.35 (s, 1H), 2.56 (d, J=55.8 Hz, 1H), 2.48-0.73 (m, 2H). MS (DCI$^+$) M/Z 382 (M+H)$^+$.

Example 71

1-(6-fluoro-3-methylisoquinolin-5-yl)-3-[(1S,3S)-3-(2-fluorophenyl)cyclopentyl]urea The title compound was isolated from Example 70. $^1$H NMR (500 MHz, DMSO-$d_6$) δ 9.21 (s, 1H), 8.08-8.00 (m, 2H), 7.60 (s, 1H), 7.56-6.70 (m, 5H), 6.66 (d, J=7.2 Hz, 1H), 4.30-4.03 (m, 2H), 3.35 (s, 2H), 2.62 (s, 3H), 2.55-1.85 (m, 2H), 1.85-1.53 (m, 2H). MS (DCI$^+$) M/Z 382 (M+H)$^+$.

Example 72

1-(1H-indazol-4-yl)-3-[(1S,3R)-3-methyl-3-phenylcyclopentyl]urea

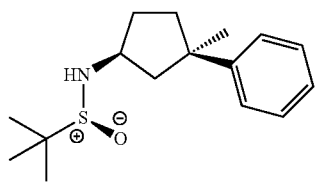 [SMILES: CC(C)(C)[S@+]([O-])N[C@H]1CC[C@@](C)(c2ccccc2)C1]

Example 72A

(S)-2-methyl-N-((S,3R)-3-methyl-3-phenylcyclopentyl)propane-2-sulfinamide

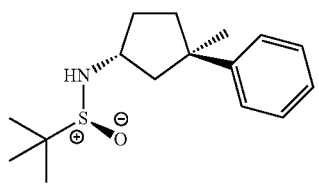 [SMILES: CC(C)(C)[S@+]([O-])N[C@@H]1CC[C@@](C)(c2ccccc2)C1]

Example 72B

(S)-2-methyl-N-((1R,3R)-3-methyl-3-phenylcyclopentyl)propane-2-sulfinamide

A solution of (R)-3-methyl-3-phenylcyclopentanone (prepared according to J. Am. Chem. Soc., 2011, 133, 6902; 900 mg, 5.17 mmol), (s)-(–)-2-methyl-2-propanesulfinamide (939 mg, 7.75 mmol), THF (20 mL), and titanium(IV) ethoxide (3.47 mL, 16.53 mmol) was heated at 50° C. for 30 minutes. The mixture was cooled to <–30° C., sodium borohydride (391 mg, 10.3 mmol) was added. After 20 minutes, 15% aqueous glycolic acid with 0.8 equivalents NaOH (relative to glycolic acid) was added and the mixture was stirred vigorously for 10 minutes. The mixture was extracted with MTBE, and the organic layer was washed with brine, dried ($Na_2SO_4$), and concentrated. Purification by chromatography ($SiO_2$, 50-100% EtOAc/hexanes gradient) afforded Example 72A (126 mg, 0.45 mmol, 9% yield) and Example 72B (374 mg, 1.34 mmol, 26% yield). MS (ESI$^+$) M/Z 280 (M+H)$^+$.

Example 72C

(1S,3R)-3-methyl-3-phenylcyclopentanaminium chloride

Methanol (0.098 mL, 2.42 mmol) was cooled to 0-5° C. and acetyl chloride (0.038 mL, 0.54 mmol) was added. In a separate flask, Example 72A (75 mg, 0.27 mmol) was dissolved in MTBE (7 mL) and the HCl/methanol solution was added dropwise. A white slurry was observed immediately and LCMS showed complete reaction after 5 minutes. The solid was collected by filtrations (MTBE wash) and dried in a vacuum oven at 50° C., to give the title compound (51 mg, 0.24 mmol, 90% yield). $^1$H NMR (500 MHz, CD$_3$OD) δ 7.37-7.26 (m, 4H), 7.21-7.14 (m, 1H), 3.93-3.83 (m, 1H), 2.47 (ddd, J=12.7, 7.4, 1.6 Hz, 1H), 2.41 (dq, J=14.1, 8.9 Hz, 1H), 2.18 (dt, J=12.7, 9.6 Hz, 1H), 2.08-1.99 (m, 1H), 1.90 (dd, J=12.7, 9.0 Hz, 1H), 1.86-1.76 (m, 1H), 1.28 (s, 3H). MS (ESI$^+$) M/Z 177 (M+H)$^+$.

Example 72D 1-(1H-indazol-4-yl)-3-[(1S,3R)-3-methyl-3-phenyl-cyclopentyl]urea

The title compound was prepared according to Example 7, substituting Example 72C for Example 1E. $^1$H NMR (500 MHz, DMSO-d$_6$) δ 13.00 (bs, 1H), 8.55 (s, 1H), 8.07 (s, 1H), 7.63 (d, J=7.6 Hz, 1H), 7.38-7.28 (m, 4H), 7.24-7.15 (m, 2H), 7.06 (d, J=8.2 Hz, 1H), 6.47 (d, J=7.4 Hz, 1H), 4.32 (h, J=7.5 Hz, 1H), 2.33 (dd, J=12.6, 7.3 Hz, 1H), 2.24 (dq, J=13.2, 8.2 Hz, 1H), 2.03 (dt, J=12.6, 8.9 Hz, 1H), 1.93-1.85 (m, 1H), 1.75 (dd, J=12.6, 8.5 Hz, 1H), 1.63-1.53 (m, 1H), 1.25 (s, 3H). MS (ESI$^+$) M/Z 335 (M+H)$^+$.

Example 73

1-(1H-indazol-4-yl)-3-[(1R,3R)-3-methyl-3-phenyl-cyclopentyl]urea

Example 73A (1R,3R)-3-methyl-3-phenylcyclopentanaminium chloride

The title compound was prepared according to Example 72C, substituting Example 72B for Example 72A. $^1$H NMR (500 MHz, CD$_3$OD) δ 7.36 (dd, J=8.1, 1.5 Hz, 2H), 7.35-7.28 (m, 2H), 7.22-7.15 (m, 1H), 3.60-3.49 (m, 1H), 2.70 (ddd, J=13.4, 8.1, 1.4 Hz, 1H), 2.29-2.20 (m, 1H), 2.17-2.06 (m, 1H), 1.98 (dt, J=12.8, 7.8 Hz, 1H), 1.84-1.70 (m, 2H), 1.42 (s, 3H). MS (ESI$^+$) M/Z 177 (M+H)$^+$.

Example 73B 1-(1H-indazol-4-yl)-3-[(1R,3R)-3-methyl-3-phenyl-cyclopentyl]urea

The title compound was prepared according to Example 7, substituting Example 73A for Example 1E. $^1$H NMR (500 MHz, DMSO-d$_6$) δ 12.99 (s, 1H), 8.54 (d, J=13.5 Hz, 1H), 8.08 (s, 1H), 7.70-7.09 (m, 7H), 7.04 (d, J=8.2 Hz, 1H), 6.56 (t, J=9.7 Hz, 1H), 4.19-3.90 (m, 1H), 3.36 (s, 3H), 2.68-1.43 (m, 6H). MS (ESI$^+$) M/Z 335 (M+H)$^+$.

Example 74

1-(6-fluoro-3-methylisoquinolin-5-yl)-3-[(1S,3S)-3-(3-fluorophenyl)cyclopentyl]urea Example 74A benzyl((1S,3S)-3-(3-fluorophenyl)cyclopentyl)carbamate Example 74B benzyl((1R,3S)-3-(3-fluorophenyl)cyclopentyl)carbamate To a solution of Example 64B (3.93 g, 21.9 mmol) in acetonitrile (100 mL) and TEA (3.7 mL, 26.3 mmol) was added benzyl chloroformate (4.5 mL, 31.5 mmol). The mixture was stirred for 4 hours, diluted with MTBE (300 mL), and washed with saturated aqueous NH$_4$Cl (300 mL) and water (300 mL) sequentially. The organic layer was dried over Na$_2$SO$_4$ and concentrated. Purification by chromatography (30 g SiO$_2$, 5/1 heptane/isopropyl acetate) afforded 3.13 g (46%) of the mixture of benzyl carbamates. The diastereomeric mixture was dissolved in 1:1 hexane-EtOH (31 mL) and injected (1 mL) on a Chiralpak AD-H column (3×25 cm, 5 μm particles, hexane 85%/MeOH-EtOH (8:2), flow rate 20 mL/min, detection at 254 nm) to give Example 74A (847 mg, first peak) and Example 74B (956 mg, second peak).

Example 74C (1S,3S)-3-(3-fluorophenyl)cyclopentanamine

A solution of Example 74A (847 mg, 2.70 mmol) in THF (10 mL) were added to 20% Pd(OH)$_2$/C, wet (169 mg, 1.21 mmol) in a 50 mL pressure bottle and stirred under 30 psi of H$_2$ at room temperature for 1 hour. The mixture was filtered and concentrated to afford the title compound (385 mg, 74%). $^1$H NMR (300 MHz, DMSO-d$_6$) δ 7.30 (td, J=7.6, 6.6 Hz, 1H), 7.14-7.06 (m, 2H), 7.04-6.92 (m, 1H), 3.10-2.94 (m, 1H), 2.28-1.43 (m, 5H), 1.38-1.22 (m, 2H). MS (ESI$^+$) M/Z 180 (M+H)$^+$.

Example 74D 1-(6-fluoro-3-methylisoquinolin-5-yl)-3-[(1S,3S)-3-(3-fluorophenyl)cyclopentyl]urea The title compound was prepared according to Example 13, substituting Example 74C for (1S,3S)-3-phenylcyclopentanamine (second eluting diastereomer from Example 1E). $^1$H NMR (300 MHz, DMSO-d$_6$) δ 9.21 (s, 1H), 8.07-7.97 (m, 2H), 7.60 (d, J=1.1 Hz, 1H), 7.57-7.46 (m, 1H), 7.34 (td, J=8.0, 6.3 Hz, 1H), 7.15-7.06 (m, 2H), 7.05-6.95 (m, 1H), 6.60 (d, J=7.2 Hz, 1H), 4.25-4.00 (m, 2H), 3.42 (s, 3H), 2.24-1.84 (m, 4H), 1.67-1.49 (m, 2H). MS (ESI$^+$) M/Z 382 (M+H)$^+$.

Example 75

1-(6-fluoro-3-methylisoquinolin-5-yl)-3-[(1R,3R)-3-methyl-3-phenylcyclopentyl]urea A mixture of Example 6D (61 mg, 0.19 mmol), Example 73A (40 mg, 0.19 mmol) and potassium carbonate (33 mg, 0.24 mmol) in DMF was heated at 85° C. for 6 hours. After cooling to ambient temperature, the mixture was diluted with EtOAc, and washed with water (2×50 mL) and brine (50 mL) sequentially. The organic layer was dried (Na$_2$SO4) and concentrated. Purification by chromatography (SiO$_2$, 0-100% ethyl acetate/hexane gradient) provided the title compound (18 mg, 25% yield). $^1$H NMR (300 MHz, DMSO-d$_6$) δ 9.21 (s, 1H), 8.06-7.98 (m, 3H), 7.58 (d, J=1.1 Hz, 1H), 7.51 (t, J=9.5 Hz, 1H), 7.39-7.26 (m, 3H), 7.25-7.06 (m, 1H), 6.59 (d, J=7.4 Hz, 1H), 4.09-3.98 (m, 2H), 2.18-1.99 (m, 2H), 2.01-1.82 (m, 3H), 1.65 (d, J=12.6 Hz, 2H), 1.36 (s, 3H), 1.32-1.13 (m, 1H). MS (ESI$^+$) M/Z 378 (M+H)$^+$.

Example 76

1-(6-fluoro-3-methylisoquinolin-5-yl)-3-[(1R,3S)-3-(3-fluorophenyl)cyclopentyl]urea

Example 76A

(1R,3S)-3-(3-fluorophenyl)cyclopentanamine

The title compound was prepared according to Example 74C, substituting Example 74B for Example 74A. MS (ESI$^+$) M/Z 180 (M+H)$^+$.

Example 76B

1-(6-fluoro-3-methylisoquinolin-5-yl)-3-[(1R,3S)-3-(3-fluorophenyl)cyclopentyl]urea The title compound was prepared according to Example 75, substituting Example 76A for Example 73A. $^1$H NMR (300 MHz, DMSO-d$_6$) δ 9.21 (s, 1H), 8.07-7.98 (m, 2H), 7.59 (d, J=1.1 Hz, 1H), 7.52 (t, J=9.5 Hz, 1H), 7.40-7.29 (m, 1H), 7.17-7.09 (m, 2H), 7.07-6.96 (m, 1H), 6.56 (d, J=7.4 Hz, 1H), 4.17-3.99 (m, 1H), 3.20-3.04 (m, 2H), 2.50 (s, 3H), 2.12-1.89 (m, 2H), 1.86-1.61 (m, 2H), 1.61-1.47 (m, 1H). MS (ESI$^+$) M/Z 382 (M+H)$^+$.

Example 77

1-(1-methyl-2-oxo-1,2,3,4-tetrahydroquinolin-7-yl)-3-[(1R,3S)-3-phenylcyclopentyl]urea The title compound was prepared according to Example 1F, substituting 7-amino-1-methyl-3,4-dihydroquinolin-2(1H)-one for Example 1B. $^1$H NMR (400 MHz, DMSO-d$_6$/Deuterium oxide) δ 7.35-7.30 (m, 1H), 7.30-7.25 (m, 4H), 7.22-7.16 (m, 1H), 7.07 (d, J=8.1 Hz, 1H), 6.94 (dd, J=8.0, 2.0 Hz, 1H), 4.18-4.03 (m, 1H), 3.22 (s, 3H), 3.14-2.97 (m, 1H), 2.82-2.69 (m, 2H), 2.52-2.46 (m, 2H), 2.44-2.30 (m, 1H), 2.10-1.93 (m, 2H), 1.74-1.54 (m, 2H), 1.52-1.41 (m, 1H). MS (ESI$^+$) M/Z 364 [M+H]$^+$.

Example 78

1-[(1R,3R)-3-(3-fluorophenyl)cyclopentyl]-3-(1-methyl-2-oxo-1,2-dihydroquinolin-5-yl)urea

Example 78A

(1R,3R)-3-(3-fluorophenyl)cyclopentanamine

Example 78B

(1S,3R)-3-(3-fluorophenyl)cyclopentanamine

Example 68B (3.4 g, 19 mmol) was dissolved in 1:1 hexane-EtOH (68 mL, 1 mL injections) and subjected to chiral preparative HPLC (3×25 cm AD-H column, 5 μm particles, 10% of 8:2 MeOH-EtOH in hexane containing 0.1% of n-propylamine, 45 mL/min, UV detection at 254 nm, recycling, automated fraction collection) to provide Example 78A (first peak, 1.43 g) and Example 78B (second peak, 1.67 g). MS (ESI$^+$) M/Z 180 (M+H)$^+$.

Example 78C

1-[(1R,3R)-3-(3-fluorophenyl)cyclopentyl]-3-(1-methyl-2-oxo-1,2-dihydroquinolin-5-yl)urea The title compound was prepared according to Example 1F, substituting 5-amino-1-methylquinolin-2(1H)-one (WO2005/016915) for Example 1B, and substituting Example 78A for Example 1E. $^1$H NMR (500 MHz, DMSO-d$_6$/Deuterium oxide) δ 8.03 (d, J=9.8 Hz, 1H), 7.66 (d, J=8.0 Hz, 1H), 7.55 (t, J=8.3 Hz, 1H), 7.45-7.26 (m, 1H), 7.22 (d, J=8.5 Hz, 1H), 7.16-7.06 (m, 2H), 7.04-6.92 (m, 1H), 6.65 (d, J=9.8 Hz, 1H), 4.20 (tt, J=13.6, 6.8 Hz, 1H), 3.63 (s, 3H), 3.36-3.12 (m, 1H), 2.33-2.00 (m, 2H), 2.04-1.84 (m, 2H), 1.80-1.37 (m, 2H). MS (ESI$^+$) M/Z 380 [M+H]$^+$.

Example 79

1-[(1S,3R)-3-(3-fluorophenyl)cyclopentyl]-3-(1-methyl-2-oxo-1,2-dihydroquinolin-5-yl)urea The title compound was prepared according to Example 1F, substituting 5-amino-1-methylquinolin-2(1H)-one (WO2005/016915) for Example 1B, and substituting Example 78A for Example 1E. $^1$H NMR (500 MHz, DMSO-d$_6$) δ 8.43 (s, 2H), 7.91 (t, J=59.3 Hz, 2H), 7.66 (d, J=8.0 Hz, 1H), 7.47 (t, J=8.3 Hz, 1H), 7.41-7.22 (m, 1H), 7.17-7.04 (m, 3H), 6.97 (td, J=8.6, 2.3 Hz, 1H), 6.70-6.41 (m, 2H), 4.25-3.96 (m, 2H), 3.57 (s, 3H), 3.07 (dt, J=10.4, 8.6 Hz, 1H), 2.40-2.27 (m, 1H), 2.12-1.87 (m, 2H), 1.81-1.53 (m, 2H), 1.52-1.26 (m, 2H). MS (ESI$^+$) M/Z 380 [M+H]$^+$.

Example 80

1-[(1S,3R)-3-(2-fluorophenyl)cyclopentyl]-3-(1-methyl-2-oxo-1,2-dihydroquinolin-5-yl)urea

Example 80A

(1R,3R)-3-(2-fluorophenyl)cyclopentanamine

Example 80B

(1S,3R)-3-(2-fluorophenyl)cyclopentanamine

Example 66B (3.1 g, 17 mmol) was dissolved in 1:1 hexane-EtOH (60 mL, 1 mL injections) and subjected to chiral preparative HPLC (3×25 cm AD-H column, 5 μm particles, 5% of 8:2 MeOH-EtOH in hexane containing 0.1% of n-propylamine, 45 mL/min, UV detection at 254 nm, recycling, automated fraction collection) to provide Example 80A (first eluting diastereomer, 1.07 g) and Example 80B (second eluting diastereomer, 1.21 g). MS (ESI$^+$) M/Z 180 (M+H)$^+$.

Example 80C

1-[(1S,3R)-3-(2-fluorophenyl)cyclopentyl]-3-(1-methyl-2-oxo-1,2-dihydroquinolin-5-yl)urea The title compound was prepared according to Example 1F, substituting 5-amino-1-methylquinolin-2(1H)-one (WO2005/016915) for Example 1B, and substituting Example 80B for Example 1E. $^1$H NMR (500 MHz, DMSO-d₆/Deuterium oxide) δ 8.11-7.95 (m, 1H), 7.67 (d, J=8.0 Hz, 1H), 7.55 (t, J=8.3 Hz, 1H), 7.38 (td, J=7.8, 1.6 Hz, 1H), 7.33-7.08 (m, 4H), 6.65 (d, J=9.8 Hz, 1H), 4.39-4.15 (m, 1H), 3.63 (s, 3H), 3.56-3.31 (m, 1H), 2.30-2.09 (m, 2H), 2.05-1.84 (m, 2H), 1.78-1.43 (m, 2H). MS (ESI⁺) M/Z 380 [M+H]⁺.

Example 81

1-[(1R,3R)-3-(2-fluorophenyl)cyclopentyl]-3-(1-methyl-2-oxo-1,2-dihydroquinolin-5-yl)urea The title compound was prepared according to Example 1F, substituting 5-amino-1-methylquinolin-2(1H)-one (WO2005/016915) for Example 1B, and substituting Example 80A for Example 1E. ¹H NMR (500 MHz, DMSO-d₆/Deuterium oxide) δ 8.02 (d, J=9.8 Hz, 1H), 7.65 (d, J=7.9 Hz, 1H), 7.55 (t, J=8.3 Hz, 1H), 7.41 (td, J=7.7, 1.6 Hz, 1H), 7.30-7.04 (m, 4H), 6.64 (d, J=9.8 Hz, 1H), 4.23-4.04 (m, 1H), 3.63 (s, 3H), 3.33-3.10 (m, 1H), 2.45-2.29 (m, 1H), 2.25-1.96 (m, 2H), 1.82-1.61 (m, 2H), 1.53 (tt, J=27.7, 13.8 Hz, 1H). MS (ESI⁺) M/Z 380 [M+H]⁺.

Example 82

1-(6-fluoro-3-methylisoquinolin-5-yl)-3-[(1R,3R)-3-(2-fluorophenyl)cyclopentyl]urea The title compound was prepared according to Example 6E, substituting Example 80A for Example 1E. ¹H NMR (500 MHz, DMSO-d₆/Deuterium oxide) δ 9.27 (s, 1H), 8.23-8.06 (m, 1H), 7.66 (s, 1H), 7.57 (t, J=9.4 Hz, 1H), 7.48-7.36 (m, 1H), 7.35-7.23 (m, 1H), 7.23-7.07 (m, 2H), 4.24-3.97 (m, 1H), 3.38-3.18 (m, 1H), 2.64 (s, 3H), 2.45-2.29 (m, 1H), 2.21-1.98 (m, 2H), 1.85-1.65 (m, 2H), 1.65-1.49 (m, 1H). MS (ESI⁺) M/Z 382 [M+H]⁺.

Example 83

1-(6-fluoro-3-methylisoquinolin-5-yl)-3-[(1S,3R)-3-(2-fluorophenyl)cyclopentyl]urea The title compound was prepared according to Example 6E, substituting Example 80B for Example 1E. ¹H NMR (500 MHz, DMSO-d₆/Deuterium oxide) δ 9.21 (s, 1H), 8.13-7.95 (m, 1H), 7.61 (s, 1H), 7.58-7.49 (m, 1H), 7.46-7.32 (m, 1H), 7.30-7.22 (m, 1H), 7.22-7.00 (m, 2H), 4.36-4.13 (m, 1H), 3.62-3.38 (m, 1H), 2.63 (s, 3H), 2.26-2.08 (m, 2H), 2.03-1.79 (m, 2H), 1.66-1.49 (m, 2H). MS (ESI⁺) M/Z 382 [M+H]⁺.

Example 84

1-(6-fluoro-3-methylisoquinolin-5-yl)-3-[(1R,3R)-3-(3-fluorophenyl)cyclopentyl]urea The title compound was prepared according to Example 6E, substituting Example 78A for Example 1E. ¹H NMR (500 MHz, DMSO-d₆) δ 9.21 (s, 1H), 8.03 (t, J=6.9 Hz, 2H), 7.60 (s, 1H), 7.52 (t, J=9.4 Hz, 1H), 7.34 (dd, J=14.5, 7.9 Hz, 1H), 7.11 (t, J=8.2 Hz, 2H), 7.06-6.91 (m, 1H), 6.62 (t, J=11.8 Hz, 1H), 4.31-4.16 (m, 1H), 3.33-3.20 (m, 1H), 2.51 (s, 3H), 2.28-2.05 (m, 2H), 2.05-1.82 (m, 2H), 1.70-1.48 (m, 2H). MS (DCI⁺) M/Z 382 [M+H]⁺.

Example 85

1-(6-fluoro-3-methylisoquinolin-5-yl)-3-[(1S,3R)-3-(3-fluorophenyl)cyclopentyl]urea The title compound was prepared according to Example 6E, substituting Example 78B for Example 1E. ¹H NMR (500 MHz, DMSO-d₆) δ 9.21 (s, 1H), 8.12-7.94 (m, 2H), 7.59 (s, 1H), 7.52 (t, J=9.4 Hz, 1H), 7.38-7.28 (m, 1H), 7.20-7.07 (m, 2H), 7.02 (td, J=8.5, 2.0 Hz, 1H), 6.61 (dd, J=16.8, 7.3 Hz, 1H), 4.18-4.03 (m, 1H), 3.15-2.99 (m, 1H), 2.62 (s, 3H), 2.45-2.30 (m, 1H), 2.13-1.95 (m, 2H), 1.84-1.62 (m, 2H), 1.62-1.45 (m, 1H). MS (DCI⁺) M/Z 382 [M+H]⁺.

Example 86

1-[(1R,3R)-3-(3-fluorophenyl)cyclopentyl]-3-[(2S)-2-hydroxy-2,3-dihydro-1H-inden-4-yl]urea The title compound was prepared according to Example 1F, substituting (S)-4-amino-2,3-dihydro-1H-inden-2-ol (second eluting enantiomer from Example 1B) for Example 1B, and substituting Example 78A for Example 1E. ¹H NMR (500 MHz, DMSO-d₆/Deuterium oxide) δ 7.69 (t, J=18.1 Hz, 1H), 7.35 (dd, J=14.3, 7.9 Hz, 1H), 7.18-7.05 (m, 2H), 7.05-6.96 (m, 2H), 6.81 (d, J=7.3 Hz, 1H), 4.61-4.44 (m, 1H), 4.34-4.03 (m, 1H), 3.33-3.15 (m, 1H), 3.15-3.00 (m, 1H), 2.96 (dd, J=16.1, 6.2 Hz, 1H), 2.75 (dd, J=16.1, 3.6 Hz, 1H), 2.72-2.60 (m, 1H), 2.27-2.00 (m, 2H), 2.00-1.77 (m, 2H), 1.63-1.27 (m, 2H). MS (ESI⁺) M/Z 355 [M+H]⁺.

Example 87

1-[(1S,3R)-3-(3-fluorophenyl)cyclopentyl]-3-[(2S)-2-hydroxy-2,3-dihydro-1H-inden-4-yl]urea The title compound was prepared according to Example 1F, substituting (S)-4-amino-2,3-dihydro-1H-inden-2-ol (second eluting enantiomer from Example 1B) for Example 1B, and substituting Example 78B for Example 1E. ¹H NMR (500 MHz, DMSO-d₆/Deuterium oxide) δ 7.69 (d, J=8.1 Hz, 1H), 7.35 (dd, J=14.4, 7.8 Hz, 1H), 7.15-7.06 (m, 2H), 7.06-6.92 (m, 2H), 6.82 (d, J=7.3 Hz, 1H), 4.63-4.40 (m, 1H), 4.23-3.96 (m, 1H), 3.13-3.03 (m, 2H), 2.96 (dd, J=16.1, 6.2 Hz, 1H), 2.75 (dd, J=16.1, 3.5 Hz, 1H), 2.65 (dd, J=16.1, 3.4 Hz, 1H), 2.49-2.33 (m, 1H), 2.12-1.93 (m, 2H), 1.76-1.53 (m, 2H), 1.50-1.32 (m, 1H). MS (ESI⁺) M/Z 355 [M+H]⁺.

Example 88

1-[(1R,3R)-3-(2-fluorophenyl)cyclopentyl]-3-[(2S)-2-hydroxy-2,3-dihydro-1H-inden-4-yl]urea The title compound was prepared according to Example 1F, substituting (S)-4-amino-2,3-dihydro-1H-inden-2-ol (second eluting enantiomer from Example 1B) for Example 1B, and substituting Example 80A for Example 1E. ¹H NMR (500 MHz, DMSO-d₆/Deuterium oxide) δ 7.70 (d, J=8.1 Hz, 1H), 7.39 (dd, J=10.9, 4.6 Hz, 1H), 7.32-7.21 (m, 1H), 7.21-7.10 (m, 2H), 7.04 (t, J=7.7 Hz, 1H), 6.82 (d, J=7.4 Hz, 1H), 4.61-4.39 (m, 1H), 4.20-4.00 (m, 1H), 3.38-3.22 (m, 1H), 3.06 (dd, J=16.1, 6.2 Hz, 1H), 2.96 (dd, J=16.1, 6.2 Hz, 1H), 2.74 (dd, J=16.1, 3.6 Hz, 1H), 2.70-2.55 (m, 1H), 2.48-2.26 (m, 1H), 2.14-1.92 (m, 2H), 1.84-1.67 (m, 1H), 1.67-1.55 (m, 1H), 1.49 (td, J=11.6, 8.7 Hz, 1H). MS (ESI⁺) M/Z 355 [M+H]⁺.

Example 89

1-[(1S,3R)-3-(2-fluorophenyl)cyclopentyl]-3-[(2S)-2-hydroxy-2,3-dihydro-1H-inden-4-yl]urea The title compound was prepared according to Example 1F, substituting (S)-4-amino-2,3-dihydro-1H-inden-2-ol (second eluting enantiomer from Example 1B) for Example 1B, and substituting Example 80B for Example 1E. $^1$H NMR (500 MHz, DMSO-$d_6$/Deuterium oxide) δ 7.71 (t, J=8.3 Hz, 1H), 7.37 (t, J=7.7 Hz, 1H), 7.26 (dd, J=13.3, 6.0 Hz, 1H), 7.21-7.11 (m, 2H), 7.04 (t, J=7.7 Hz, 1H), 6.82 (d, J=7.3 Hz, 1H), 4.59-4.45 (m, 1H), 4.33-4.12 (m, 1H), 3.51-3.37 (m, 1H), 3.06 (dd, J=16.1, 6.2 Hz, 1H), 2.96 (dd, J=16.1, 6.2 Hz, 1H), 2.75 (dd, J=16.1, 3.5 Hz, 1H), 2.65 (dd, J=16.1, 3.4 Hz, 1H), 2.29-2.05 (m, 2H), 2.05-1.83 (m, 2H), 1.66-1.42 (m, 2H). MS (ESI$^+$) M/Z 355 [M+H]$^+$.

Example 90

1-[(1R,3R)-3-(3-fluorophenyl)cyclopentyl]-3-[(2R)-2-hydroxy-2,3-dihydro-1H-inden-4-yl]urea The title compound was prepared according to Example 1F, substituting Example 78A for Example 1E. $^1$H NMR (500 MHz, DMSO-$d_6$/Deuterium oxide) δ 7.70 (dd, J=8.1, 3.9 Hz, 1H), 7.42-7.25 (m, 1H), 7.17-7.07 (m, 2H), 7.07-6.94 (m, 2H), 6.82 (d, J=7.3 Hz, 1H), 4.64-4.41 (m, 1H), 4.27-4.07 (m, 1H), 3.33-3.15 (m, 1H), 3.06 (dd, J=16.1, 6.2 Hz, 1H), 2.96 (dd, J=16.1, 6.2 Hz, 1H), 2.74 (dd, J=16.1, 3.5 Hz, 1H), 2.70-2.57 (m, 1H), 2.31-2.05 (m, 2H), 1.95-1.81 (m, 2H), 1.72-1.45 (m, 2H). MS (ESI$^+$) M/Z 355 [M+H]$^+$.

Example 91

1-[(1S,3R)-3-(3-fluorophenyl)cyclopentyl]-3-[(2R)-2-hydroxy-2,3-dihydro-1H-inden-4-yl]urea The title compound was prepared according to Example 1F, substituting Example 78B for Example 1E. $^1$H NMR (500 MHz, DMSO-$d_6$/Deuterium oxide) δ 7.69 (d, J=8.1 Hz, 1H), 7.35 (dd, J=14.3, 7.9 Hz, 1H), 7.13 (ddd, J=16.0, 12.7, 4.8 Hz, 2H), 7.02 (ddd, J=11.2, 10.6, 5.2 Hz, 2H), 6.82 (d, J=7.3 Hz, 1H), 4.67-4.31 (m, 1H), 4.21-3.94 (m, 1H), 3.16-3.02 (m, 2H), 2.96 (dd, J=16.1, 6.2 Hz, 1H), 2.74 (dd, J=16.1, 3.6 Hz, 1H), 2.71-2.60 (m, 1H), 2.51-2.34 (m, 1H), 2.19-1.91 (m, 2H), 1.81-1.51 (m, 2H), 1.51-1.25 (m, 1H). MS (ESI$^+$) M/Z 355 [M+H]$^+$.

Example 92

1-[(1R,3R)-3-(2-fluorophenyl)cyclopentyl]-3-[(2R)-2-hydroxy-2,3-dihydro-1H-inden-4-yl]urea The title compound was prepared according to Example 1F, substituting Example 80A for Example 1E. $^1$H NMR (500 MHz, DMSO-$d_6$/Deuterium oxide) δ 7.77-7.66 (m, 1H), 7.39 (dd, J=10.9, 4.6 Hz, 1H), 7.27-7.21 (m, 1H), 7.21-7.09 (m, 2H), 7.04 (t, J=7.7 Hz, 1H), 6.82 (d, J=7.4 Hz, 1H), 4.59-4.37 (m, 1H), 4.20-3.94 (m, 1H), 3.40-3.18 (m, 1H), 3.06 (dd, J=16.1, 6.2 Hz, 1H), 2.95 (dd, J=16.1, 6.2 Hz, 1H), 2.74 (dd, J=16.1, 3.6 Hz, 1H), 2.70-2.58 (m, 1H), 2.50-2.27 (m, 1H), 2.13-1.95 (m, 2H), 1.83-1.66 (m, 1H), 1.66-1.55 (m, 1H), 1.55-1.36 (m, 1H). MS (ESI$^+$) M/Z 355 [M+H]$^+$.

Example 93

1-[(1S,3R)-3-(2-fluorophenyl)cyclopentyl]-3-[(2R)-2-hydroxy-2,3-dihydro-1H-inden-4-yl]urea The title compound was prepared according to Example 1F, substituting Example 80B for Example 1E. $^1$H NMR (500 MHz, DMSO-$d_6$/Deuterium oxide) δ 7.70 (t, J=8.5 Hz, 1H), 7.43-7.32 (m, 1H), 7.32-7.20 (m, 1H), 7.17 (ddd, J=18.9, 18.3, 4.9 Hz, 2H), 7.04 (t, J=7.8 Hz, 1H), 6.81 (d, J=7.3 Hz, 1H), 4.60-4.45 (m, 1H), 4.28-3.95 (m, 1H), 3.55-3.36 (m, 1H), 3.06 (dd, J=16.1, 6.2 Hz, 1H), 2.96 (dd, J=16.1, 6.2 Hz, 1H), 2.74 (dd, J=16.1, 3.5 Hz, 1H), 2.64 (dt, J=16.0, 8.0 Hz, 1H), 2.28-2.06 (m, 2H), 1.95-1.79 (m, 2H), 1.73-1.46 (m, 2H). MS (ESI$^+$) M/Z 355 [M+H]$^+$.

Example 94

1-(1-methyl-2-oxo-1,2,3,4-tetrahydroquinolin-5-yl)-3-[(1R,3S)-3-phenylcyclopentyl]urea The title compound was prepared according to Example 1F, substituting 5-amino-1-methyl-3,4-dihydroquinolin-2(1H)-one (WO2004/046133) for Example 1B. $^1$H NMR (500 MHz, DMSO-$d_6$/Deuterium oxide) δ 7.41 (dd, J=12.8, 8.2 Hz, 1H), 7.38-7.25 (m, 4H), 7.27-7.13 (m, 2H), 6.83 (d, J=8.1 Hz, 1H), 4.20-4.03 (m, 1H), 3.25 (s, 3H), 3.06 (ddd, J=18.1, 10.4, 7.5 Hz, 1H), 2.80-2.65 (m, 2H), 2.49-2.30 (m, 1H), 2.12-1.97 (m, 2H), 1.75-1.54 (m, 2H), 1.54-1.33 (m, 1H). MS (ESI$^+$) M/Z 364 [M+H]$^+$.

Example 95

1-(1-methyl-2-oxo-1,2,3,4-tetrahydroquinolin-5-yl)-3-[(1S,3R)-3-phenylcyclopentyl]urea The title compound was prepared according to Example 1F, substituting 5-amino-1-methyl-3,4-dihydroquinolin-2(1H)-one (WO2004/046133) for Example 1B, and substituting (1S,3R)-3-phenylcyclopentanamine (second eluting diastereomer from Example 15B) for Example 1E. $^1$H NMR (500 MHz, DMSO-$d_6$/Deuterium oxide) δ 7.43-7.37 (m, 1H), 7.36-7.24 (m, 4H), 7.23-7.16 (m, 2H), 6.83 (d, J=8.1 Hz, 1H), 4.19-3.98 (m, 1H), 3.25 (s, 3H), 3.13-3.00 (m, 1H), 2.86-2.67 (m, 2H), 2.50 (dd, J=8.6, 6.4 Hz, 2H), 2.44-2.34 (m, 1H), 2.14-1.95 (m, 2H), 1.82-1.57 (m, 2H), 1.57-1.34 (m, 1H). MS (ESI$^+$) M/Z 364 [M+H]$^+$.

Example 96

1-(1-methyl-2-oxo-1,2,3,4-tetrahydroquinolin-5-yl)-3-[(1S,3S)-3-phenylcyclopentyl]urea The title compound was prepared according to Example 1F, substituting 5-amino-1-methyl-3,4-dihydroquinolin-2(1H)-one (WO2004/046133) for Example 1B; and substituting (1S,3S)-3-phenylcyclopentanamine (second eluting diastereomer from Example 1E) for Example 1E. $^1$H NMR (500 MHz, DMSO-$d_6$/Deuterium oxide) δ 7.41 (t, J=10.4 Hz, 1H), 7.36-7.25 (m, 4H), 7.25-7.12 (m, 2H), 6.82 (d, J=8.0 Hz, 1H), 4.27-4.11 (m, 1H), 3.24 (d, J=10.9 Hz, 3H), 3.22-3.16 (m, 1H), 2.85-2.63 (m, 2H), 2.50 (t, J=4.5 Hz, 2H), 2.30-2.06 (m, 2H), 1.89 (dt, J=19.1, 9.5 Hz, 2H), 1.68-1.36 (m, 2H). MS (ESI$^+$) M/Z 364 [M+H]$^+$.

Example 97

1-[(1R,3R)-3-(3-fluorophenyl)cyclopentyl]-3-(1-methyl-2-oxo-1,2,3,4-tetrahydroquinolin-5-yl)urea The title compound was prepared according to Example 1F, substituting 5-amino-1-methyl-3,4-dihydroquinolin-2(1H)-one (WO2004/046133) for Example 1B; and substituting Example 78A for Example 1E. $^1$H NMR (500 MHz, DMSO-$d_6$/Deuterium oxide) δ 7.42 (d, J=8.0 Hz, 1H), 7.40-7.32 (m, 1H), 7.19 (t, J=8.2 Hz, 1H), 7.16-7.08 (m, 2H), 7.00

(td, J=8.6, 2.5 Hz, 1H), 6.82 (d, J=7.9 Hz, 1H), 4.31-4.08 (m, 1H), 3.23 (d, J=13.5 Hz, 4H), 2.80-2.65 (m, 2H), 2.51-2.45 (m, 2H), 2.31-2.06 (m, 2H), 1.94-1.65 (m, 2H), 1.65-1.37 (m, 2H). MS (ESI$^+$) M/Z 382 [M+H]$^+$.

Example 98

1-[(1S,3R)-3-(3-fluorophenyl)cyclopentyl]-3-(1-methyl-2-oxo-1,2,3,4-tetrahydroquinolin-5-yl)urea The title compound was prepared according to Example 1F, substituting 5-amino-1-methyl-3,4-dihydroquinolin-2(1H)-one (WO2004/046133) for Example 1B; and substituting Example 78B for Example 1E. $^1$H NMR (500 MHz, DMSO-d$_6$/Deuterium oxide) δ 7.42-7.30 (m, 2H), 7.22-7.16 (m, 1H), 7.16-7.09 (m, 2H), 7.09-6.94 (m, 1H), 6.84-6.73 (m, 1H), 4.27-4.00 (m, 1H), 3.25 (s, 3H), 3.18-3.02 (m, 1H), 2.80-2.65 (m, 2H), 2.51-2.46 (m, 2H), 2.44-2.31 (m, 1H), 2.14-1.91 (m, 2H), 1.78-1.53 (m, 2H), 1.53-1.31 (m, 1H). MS (ESI$^+$) M/Z 382 [M+H]$^+$.

Example 99

1-[(1R,3R)-3-(2-fluorophenyl)cyclopentyl]-3-(1-methyl-2-oxo-1,2,3,4-tetrahydroquinolin-5-yl)urea The title compound was prepared according to Example 1F, substituting 5-amino-1-methyl-3,4-dihydroquinolin-2(1H)-one (WO2004/046133) for Example 1B; and substituting Example 80A for Example 1E. $^1$H NMR (500 MHz, DMSO-d$_6$/Deuterium oxide) δ 7.44-7.30 (m, 2H), 7.28-7.16 (m, 1H), 7.16-7.07 (m, 2H), 7.07-6.91 (m, 1H), 6.90-6.66 (m, 1H), 4.14-4.00 (m, 1H), 3.25 (s, 3H), 3.18-2.96 (m, 1H), 2.86-2.67 (m, 2H), 2.51-2.48 (m, 2H), 2.45-2.29 (m, 1H), 2.12-1.91 (m, 2H), 1.75-1.53 (m, 2H), 1.53-1.35 (m, 1H). MS (ESI$^+$) M/Z 382 [M+H]$^+$.

Example 100

1-[(1S,3R)-3-(2-fluorophenyl)cyclopentyl]-3-(1-methyl-2-oxo-1,2,3,4-tetrahydroquinolin-5-yl)urea The title compound was prepared according to Example 1F, substituting 5-amino-1-methyl-3,4-dihydroquinolin-2(1H)-one (WO2004/046133) for Example 1B; and substituting Example 80B for Example 1E. $^1$H NMR (500 MHz, DMSO-d$_6$/Deuterium oxide) δ 7.50-7.34 (m, 2H), 7.32-7.23 (m, 1H), 7.24-7.08 (m, 4H), 6.94-6.67 (m, 1H), 4.29-4.13 (m, 1H), 3.47-3.37 (m, 1H), 3.25 (s, 4H), 2.79-2.66 (m, 3H), 2.51-2.49 (m, 2H), 2.24-2.07 (m, 2H), 1.99-1.77 (m, 2H), 1.67-1.44 (m, 3H). MS (ESI$^+$) M/Z 382 [M+H]$^+$.

Example 101

1-[(1R,3R)-3-(3-fluorophenyl)cyclopentyl]-3-(1-methyl-420-1-21H-indazol-4-yl)urea The title compound was prepared according to Example 1F, substituting Example 4C for Example 1B, and substituting Example 78A for Example 1E. $^1$H NMR (500 MHz, DMSO-d$_6$/Deuterium oxide) δ 8.07 (d, J=0.5 Hz, 1H), 7.69-7.55 (m, 1H), 7.39-7.32 (m, 1H), 7.32-7.22 (m, 1H), 7.22-7.05 (m, 3H), 7.01 (td, J=8.6, 2.6 Hz, 1H), 4.33-4.18 (m, 1H), 4.00 (s, 3H), 3.43-3.18 (m, 1H), 2.33-2.09 (m, 2H), 2.04-1.84 (m, 2H), 1.70-1.45 (m, 2H). MS (ESI$^+$) M/Z 353 [M+H]$^+$.

Example 102

1-[(1S,3R)-3-(3-fluorophenyl)cyclopentyl]-3-(1-methyl-1H-indazol-4-yl)urea

The title compound was prepared according to Example 1F, substituting Example 4C for Example 1B, and substituting Example 78B for Example 1E. $^1$H NMR (500 MHz, DMSO-d$_6$/Deuterium oxide) δ 8.07 (s, 1H), 7.63 (d, J=7.6 Hz, 1H), 7.45-7.33 (m, 1H), 7.29 (dd, J=14.7, 6.6 Hz, 1H), 7.27-7.11 (m, 3H), 7.07-6.86 (m, 1H), 4.25-4.09 (m, 1H), 4.00 (s, 3H), 3.28-3.00 (m, 1H), 2.49-2.37 (m, 1H), 2.18-1.94 (m, 2H), 1.79-1.57 (m, 2H), 1.57-1.28 (m, 1H). MS (ESI$^+$) M/Z 353 [M+H]$^+$.

Example 103

1-[(1R,3R)-3-(2-fluorophenyl)cyclopentyl]-3-(1-methyl-1H-indazol-4-yl)urea

The title compound was prepared according to Example 1F, substituting Example 4C for Example 1B, and substituting Example 80A for Example 1E. $^1$H NMR (500 MHz, DMSO-d$_6$/Deuterium oxide) δ 8.07 (s, 1H), 7.61 (dd, J=18.8, 7.7 Hz, 1H), 7.41 (td, J=7.7, 1.6 Hz, 1H), 7.36-7.21 (m, 2H), 7.21-7.02 (m, 3H), 4.25-4.11 (m, 1H), 4.00 (s, 3H), 3.41-3.25 (m, 1H), 2.46-2.35 (m, 1H), 2.22-1.93 (m, 2H), 1.85-1.72 (m, 1H), 1.72-1.60 (m, 1H), 1.60-1.39 (m, 1H). MS (ESI$^+$) M/Z 353 [M+H]$^+$.

Example 104

1-[(1S,3R)-3-(2-fluorophenyl)cyclopentyl]-3-(1-methyl-1H-indazol-4-yl)urea

The title compound was prepared according to Example 1F, substituting Example 4C for Example 1B, and substituting Example 80B for Example 1E. $^1$H NMR (500 MHz, DMSO-d$_6$/Deuterium oxide) δ 8.07 (s, 1H), 7.72-7.59 (m, 1H), 7.44-7.33 (m, 1H), 7.33-7.23 (m, 2H), 7.23-7.08 (m, 3H), 4.41-4.12 (m, 1H), 4.00 (s, 3H), 3.62-3.38 (m, 1H), 2.30-2.06 (m, 2H), 2.06-1.86 (m, 2H), 1.78-1.49 (m, 2H). MS (ESI$^+$) M/Z 353 [M+H]$^+$.

Example 105

1-(1-methyl-2-oxo-1,2,3,4-tetrahydroquinolin-7-yl)-3-[(1S,3R)-3-phenylcyclopentyl]urea The title compound was prepared according to Example 1F, substituting 7-amino-1-methyl-3,4-dihydroquinolin-2(1H)-one for Example 1B, and substituting (1S,3R)-3-phenylcyclopentanamine (second eluting diastereomer from Example 15B) for Example 1E. $^1$H NMR (400 MHz, DMSO-d$_6$/Deuterium oxide) δ 7.38-7.24 (m, 5H), 7.24-7.14 (m, 1H), 7.07 (d, J=8.1 Hz, 1H), 6.94 (dd, J=8.0, 2.0 Hz, 1H), 4.19-4.03 (m, 1H), 3.22 (s, 3H), 3.16-2.99 (m, 1H), 2.82-2.65 (m, 2H), 2.50 (d, J=6.7 Hz, 1H), 2.37 (dd, J=12.9, 6.6 Hz, 1H), 2.07-1.98 (m, 2H), 1.76-1.52 (m, 2H), 1.52-1.33 (m, 1H). MS (ESI$^+$) M/Z 364 [M+H]$^+$.

Example 106

1-(1-methyl-2-oxo-1,2,3,4-tetrahydroquinolin-7-yl)-3-[(1S,3S)-3-phenylcyclopentyl]urea The title compound was prepared according to Example 1F, substituting 7-amino-1-methyl-3,4-dihydroquinolin-2

(1H)-one for Example 1B, and substituting (1S,3S)-3-phenylcyclopentanamine (second eluting diastereomer from Example 1E) for Example 1E. ¹H NMR (400 MHz, DMSO-d₆/Deuterium oxide) δ 7.35-7.26 (m, 5H), 7.25-7.15 (m, 1H), 7.07 (d, J=8.1 Hz, 1H), 6.93 (dt, J=4.7, 3.3 Hz, 1H), 4.19 (p, J=6.0 Hz, 1H), 3.27-3.14 (m, 4H), 2.82-2.71 (m, 2H), 2.52-2.47 (m, 2H), 2.21-2.03 (m, 2H), 1.97-1.78 (m, 2H), 1.69-1.35 (m, 2H). MS (ESI⁺) M/Z 364 [M+H]⁺.

Example 107

1-[(1R,3R)-3-(3-fluorophenyl)cyclopentyl]-3-(1-methyl-2-oxo-1,2,3,4-tetrahydroquinolin-7-yl)urea The title compound was prepared according to Example 1F, substituting 7-amino-1-methyl-3,4-dihydroquinolin-2(1H)-one for Example 1B, and Example 78A for Example 1E. ¹H NMR (400 MHz, DMSO-d₆/Deuterium oxide) δ 7.34 (td, J=7.9, 6.5 Hz, 1H), 7.28 (d, J=1.9 Hz, 1H), 7.14-7.04 (m, 3H), 7.00 (ddd, J=8.3, 2.6, 1.3 Hz, 1H), 6.93 (dd, J=8.0, 2.0 Hz, 1H), 4.18 (p, J=6.0 Hz, 1H), 3.28-3.17 (m, 4H), 2.90-2.71 (m, 2H), 2.50 (t, J=4.5 Hz, 2H), 2.29-1.99 (m, 2H), 2.00-1.75 (m, 2H), 1.64-1.40 (m, 2H). MS (ESI⁺) M/Z 382 [M+H]⁺.

Example 108

1-[(1S,3R)-3-(3-fluorophenyl)cyclopentyl]-3-(1-methyl-2-oxo-1,2,3,4-tetrahydroquinolin-7-yl)urea The title compound was prepared according to Example 1F, substituting 7-amino-1-methyl-3,4-dihydroquinolin-2(1H)-one for Example 1B, and substituting Example 78B for Example 1E. ¹H NMR (400 MHz, DMSO-d₆/Deuterium oxide) δ 7.46-7.30 (m, 1H), 7.27 (d, J=2.0 Hz, 1H), 7.19-7.04 (m, 3H), 7.03-6.97 (m, 1H), 6.94 (dd, J=8.1, 2.0 Hz, 1H), 4.18-4.01 (m, 1H), 3.22 (s, 3H), 3.18-2.96 (m, 1H), 2.87-2.63 (m, 2H), 2.50 (d, J=6.8 Hz, 1H), 2.44-2.27 (m, 1H), 2.23-1.91 (m, 2H), 1.84-1.54 (m, 2H), 1.53-1.27 (m, 1H). MS (ESI⁺) M/Z 382 [M+H]⁺.

Example 109

1-[(1R,3R)-3-(2-fluorophenyl)cyclopentyl]-3-(1-methyl-2-oxo-1,2,3,4-tetrahydroquinolin-7-yl)urea The title compound was prepared according to Example 1F, substituting 7-amino-1-methyl-3,4-dihydroquinolin-2(1H)-one for Example 1B, and substituting Example 80A for Example 1E. ¹H NMR (400 MHz, DMSO-d₆/Deuterium oxide) δ 7.40 (dt, J=10.6, 3.7 Hz, 1H), 7.33-7.22 (m, 2H), 7.22-7.10 (m, 2H), 7.10-7.01 (m, 1H), 7.00-6.82 (m, 1H), 4.22-4.02 (m, 1H), 3.39-3.25 (m, 1H), 3.26-3.18 (m, 3H), 2.81-2.67 (m, 2H), 2.52-2.48 (m, 2H), 2.42-2.24 (m, 1H), 2.14-1.95 (m, 2H), 1.80-1.60 (m, 2H), 1.59-1.34 (m, 1H). MS (ESI⁺) M/Z 382 [M+H]⁺.

Example 110

1-[(1S,3R)-3-(2-fluorophenyl)cyclopentyl]-3-(1-methyl-2-oxo-1,2,3,4-tetrahydroquinolin-7-yl)urea The title compound was prepared according to Example 1F, substituting 7-amino-1-methyl-3,4-dihydroquinolin-2(1H)-one for Example 1B, and substituting Example 80B for Example 1E. ¹H NMR (400 MHz, DMSO-d₆/Deuterium oxide) δ 7.43-7.34 (m, 1H), 7.34-7.24 (m, 2H), 7.19-7.10 (m, 2H), 7.08 (dd, J=8.6, 4.4 Hz, 1H), 7.00-6.78 (m, 1H), 4.30-4.11 (m, 1H), 3.54-3.35 (m, 1H), 3.22 (s, 3H), 2.83-2.70 (m, 2H), 2.52-2.34 (m, 2H), 2.27-2.04 (m, 2H), 1.99-1.79 (m, 2H), 1.72-1.44 (m, 2H). MS (ESI⁺) M/Z 382 [M+H]⁺.

Example 111

1-(2,3-dihydro-1H-inden-4-yl)-3-[(1R,3S)-3-phenylcyclopentyl]urea

The title compound was prepared according to Example 1F, substituting 2,3-dihydro-1H-inden-4-amine for Example 1B. ¹H NMR (500 MHz, DMSO-d₆/Deuterium oxide) δ 7.79-7.60 (m, 1H), 7.38-7.24 (m, 4H), 7.23-7.14 (m, 1H), 7.05 (dt, J=28.8, 7.7 Hz, 1H), 6.87 (dd, J=37.4, 7.2 Hz, 1H), 4.22-4.01 (m, 1H), 3.13-3.00 (m, 1H), 2.90-2.79 (m, 2H), 2.74 (t, J=7.4 Hz, 2H), 2.47-2.32 (m, 1H), 2.13-1.89 (m, 4H), 1.73-1.57 (m, 2H), 1.46-1.27 (m, 1H). MS (ESI⁺) M/Z 321 [M+H]⁺.

Example 112

1-(2,3-dihydro-1H-inden-4-yl)-3-[(1S,3S)-3-phenylcyclopentyl]urea

The title compound was prepared according to Example 1F, substituting 2,3-dihydro-1H-inden-4-amine and substituting (1S,3S)-3-phenylcyclopentanamine (second eluting diastereomer from Example 1E) for Example 1B. ¹H NMR (500 MHz, DMSO-d₆/Deuterium oxide) δ 7.84-7.60 (m, 1H), 7.36-7.14 (m, 4H), 7.10-6.99 (m, 2H), 6.87 (dd, J=39.4, 7.3 Hz, 1H), 4.26-4.10 (m, 1H), 3.30-3.14 (m, 1H), 2.93-2.81 (m, 2H), 2.79-2.66 (m, 2H), 2.16 (m, J=10.2, 6.6, 2.4 Hz, 2H), 2.08-1.97 (m, 2H), 1.96-1.81 (m, 2H), 1.68-1.41 (m, 2H). MS (ESI⁺) M/Z 321 [M+H]⁺.

Example 113

1-[3-(2-hydroxyethyl)-2-oxo-1,2,3,4-tetrahydroquinazolin-7-yl]-3-[(1S,3R)-3-phenylcyclopentyl]urea The title compound was prepared according to Example 1F, substituting 7-amino-3-(2-((tert-butyldimethylsilyl)oxy)ethyl)-3,4-dihydroquinazolin-2(1H)-one (WO2008/091021) for Example 1B, and substituting (1S,3R)-3-phenylcyclopentanamine (second eluting diastereomer from Example 15B) for Example 1E, except that 1.5 equivalents of solid tetra-n-butyl ammonium fluoride hydrate were added and the mixture shaken at room temperature overnight to remove the silyl group prior to HPLC purification. ¹H NMR (500 MHz, DMSO-d₆/Deuterium oxide) δ 7.37-7.24 (m, 4H), 7.24-7.11 (m, 1H), 6.93 (dd, J=5.1, 3.0 Hz, 2H), 6.85 (dd, J=8.2, 2.0 Hz, 1H), 4.42 (s, 2H), 4.14-3.94 (m, 1H), 3.57 (t, J=6.0 Hz, 2H), 3.36 (t, J=5.9 Hz, 2H), 3.13-2.94 (m, 1H), 2.42-2.29 (m, 1H), 2.12-1.92 (m, 2H), 1.76-1.50 (m, 2H), 1.50-1.32 (m, 1H). MS (ESI⁺) M/Z 395 [M+H]⁺.

Example 114

1-[3-(2-hydroxyethyl)-2-oxo-1,2,3,4-tetrahydroquinazolin-7-yl]-3-[(1S,3S)-3-phenylcyclopentyl]urea The title compound was prepared according to Example 1F, substituting 7-amino-3-(2-((tert-butyldimethylsilyl)oxy)ethyl)-3,4-dihydroquinazolin-2(1H)-one (WO2008/091021) for Example 1B, and substituting (1S,3S)-3-phenylcyclopentanamine (second eluting diastereomer from Example 1E) for Example 1E, except that 1.5 equivalents of solid tetra-n-butyl ammonium fluoride hydrate were added and the mixture shaken at room temperature overnight to remove the silyl group prior to HPLC purification. $^1$H NMR (500 MHz, DMSO-$d_6$/Deuterium oxide) δ 7.39-7.22 (m, 4H), 7.18 (dd, J=9.9, 4.3 Hz, 1H), 6.96-6.90 (m, 2H), 6.84 (d, J=2.0 Hz, 1H), 4.42 (s, 2H), 4.26-4.02 (m, 1H), 3.56 (t, J=5.9 Hz, 2H), 3.36 (t, J=5.9 Hz, 2H), 3.27-3.08 (m, 1H), 2.26-2.04 (m, 2H), 1.94-1.83 (m, 2H), 1.63-1.44 (m, 2H). MS (ESI$^+$) M/Z 395 [M+H]$^+$.

Example 115

1-[(1R,3R)-3-(3-fluorophenyl)cyclopentyl]-3-[3-(2-hydroxyethyl)-2-oxo-1,2,3,4-tetrahydroquinazolin-7-yl]urea The title compound was prepared according to Example 1F, substituting 7-amino-3-(2-((tert-butyldimethylsilyl)oxy)ethyl)-3,4-dihydroquinazolin-2(1H)-one (WO2008/091021) for Example 1B, and substituting Example 78A for Example 1E, except that 1.5 equivalents of solid tetra-n-butyl ammonium fluoride hydrate were added and the mixture shaken at room temperature overnight to remove the silyl group prior to HPLC purification. $^1$H NMR (500 MHz, DMSO-$d_6$/Deuterium oxide) δ 7.41-7.26 (m, 1H), 7.18-7.06 (m, 2H), 7.03-6.97 (m, 1H), 6.92 (dd, J=5.2, 3.0 Hz, 2H), 6.85 (dd, J=8.2, 2.0 Hz, 1H), 4.42 (s, 2H), 4.25-4.06 (m, 1H), 3.59-3.48 (m, 2H), 3.36 (t, J=5.9 Hz, 2H), 3.30-3.11 (m, 1H), 2.23-2.02 (m, 2H), 1.94-1.84 (m, 2H), 1.63-1.39 (m, 2H). MS (ESI$^+$) M/Z 413 [M+H]$^+$.

Example 116

1-[(1S,3R)-3-(3-fluorophenyl)cyclopentyl]-3-[3-(2-hydroxyethyl)-2-oxo-1,2,3,4-tetrahydroquinazolin-7-yl]urea The title compound was prepared according to Example 1F, substituting 7-amino-3-(2-((tert-butyldimethylsilyl)oxy)ethyl)-3,4-dihydroquinazolin-2(1H)-one (WO2008/091021) for Example 1B, and substituting Example 78B for Example 1E, except that 1.5 equivalents of solid tetra-n-butyl ammonium fluoride hydrate were added and the mixture shaken at room temperature overnight to remove the silyl group prior to HPLC purification. $^1$H NMR (500 MHz, DMSO-$d_6$/Deuterium oxide) δ 7.34 (dd, J=14.3, 7.9 Hz, 1H), 7.16-7.06 (m, 2H), 7.06-6.95 (m, 1H), 6.96-6.90 (m, 2H), 6.85 (dd, J=8.2, 2.0 Hz, 1H), 4.42 (s, 2H), 4.21-3.95 (m, 1H), 3.61-3.48 (m, 2H), 3.36 (t, J=5.9 Hz, 2H), 3.23-3.00 (m, 1H), 2.47-2.26 (m, 1H), 2.18-1.90 (m, 2H), 1.77-1.51 (m, 2H), 1.50-1.22 (m, 1H). MS (ESI$^+$) M/Z 413 [M+H]$^+$.

Example 117

1-[(1S,3R)-3-(2-fluorophenyl)cyclopentyl]-3-[3-(2-hydroxyethyl)-2-oxo-1,2,3,4-tetrahydroquinazolin-7-yl]urea The title compound was prepared according to Example 1F, substituting 7-amino-3-(2-((tert-butyldimethylsilyl)oxy)ethyl)-3,4-dihydroquinazolin-2(1H)-one (WO2008/091021) for Example 1B, and substituting Example 80B for Example 1E, except that 1.5 equivalents of solid tetra-n-butyl ammonium fluoride hydrate were added and the mixture shaken at room temperature overnight to remove the silyl group prior to HPLC purification. $^1$H NMR (500 MHz, DMSO-$d_6$/Deuterium oxide) δ 7.40-7.31 (m, 1H), 7.31-7.22 (m, 1H), 7.22-7.09 (m, 2H), 6.99-6.88 (m, 2H), 6.85 (dd, J=8.2, 2.1 Hz, 1H), 4.42 (s, 2H), 4.29-4.05 (m, 1H), 3.62-3.48 (m, 2H), 3.44-3.27 (m, 3H), 2.26-2.02 (m, 2H), 1.98-1.83 (m, 2H), 1.71-1.47 (m, 2H). MS (ESI$^+$) M/Z 413 [M+H]$^+$.

Example 118

1-(1-methyl-2-oxo-1,2-dihydroquinolin-5-yl)-3-[(1S,3S)-3-phenylcyclopentyl]urea

The title compound was prepared according to Example 1F, substituting Example 50B for Example 1B, and substituting (1S,3S)-3-phenylcyclopentanamine (second eluting diastereomer from Example 1E) for Example 1E. $^1$H NMR (500 MHz, DMSO-$d_6$/D$_2$O) δ ppm 1.58 (s, 2H) 1.92 (s, 2H) 2.14 (s, 1H) 2.21 (s, 1H) 3.23 (s, 1H) 3.63 (s, 3H) 4.22 (s, 1H) 6.65 (d, J=9.76 Hz, 1H) 7.21 (s, 2H) 7.30 (s, 4H) 7.55 (s, 1H) 7.67 (d, J=7.63 Hz, 1H) 8.03 (d, J=9.76 Hz, 1H); MS (ESI$^+$) M/Z 362 [M+H]$^+$.

Example 119

1-(1H-indazol-4-yl)-3-[(trans)-3-(4-methyl-1,3-thiazol-2-yl)cyclopentyl]urea

The title compound was obtained from the chromatographic separation of the residue obtained in Example 120D. $^1$H NMR (300 MHz, DMSO-$d_6$) δ ppm 1.50-1.65 (m, 1H) 1.77-1.89 (m, 1H) 1.94-2.05 (m, 1H) 2.08-2.30 (m, 3H) 2.33 (s, 3H) 3.55-3.71 (m, 1H) 4.13-4.26 (m, J=5.43 Hz, 1H) 6.55 (d, J=7.12 Hz, 1H) 7.01-7.11 (m, 2H) 7.19 (t, J=7.97 Hz, 1H) 7.61 (d, J=7.46 Hz, 1H) 8.06 (s, 1H) 8.52 (s, 1H) 12.97 (s, 1H)); MS (ESI$^+$) M/Z 342 [M+H]$^+$.

Example 120

1-(1H-indazol-4-yl)-3-[(1S*,3R*)-3-(4-methyl-1,3-thiazol-2-yl)cyclopentyl]urea

Example 120A tert-butyl(cis)-3-carbamoylcyclopentylcarbamate

To a solution of racemic (1R,3S)-3-(tert-butoxycarbonylamino)cyclopentane-carboxylic acid (AMRI, 3.9 g, 17.0 mmol) in dichloromethane (100 mL) was added 1-hydroxybenzotriazole monohydrate (3.1 g, 20.4 mmol), N-(3-Dimethylaminopropyl)-N'-ethylcarbodiimide hydrochloride (4.7 g, 24.7 mmol) and ammonium hydroxide (19.9 g, 170 mmol). The reaction mixture was stirred at room temperature for 16 h and then diluted with water (20 mL). The aqueous layer was extracted with dichloromethane (3×20 mL). The combined organic extracts were dried over Na$_2$SO$_4$, filtered, and concentrated under reduced pressure. The residue was triturated in 50 mL of 1:1 ethyl acetate/hexanes and collected by filtration to obtain 1.7 g of the title compound. MS (ESI$^+$) M/Z 228 [M+H]$^+$.

Example 120B tert-butyl(cis)-3-carbamothioylcyclopentylcarbamate

A solution of Example 120A (0.5 g, 2.2 mmol) in tetrahydrofuran (10 mL) was added Lawesson's reagent (0.53 g, 1.3 mmol). After stirring at room temperature for 5 hours, the reaction mixture was poured into ethyl acetate (50 mL). The organic layer was washed with saturated NaHCO₃ aqueous solution and brine, dried over Na₂SO₄, filtered and concentrated under reduced pressure. The residue was purified by column chromatography (Analogix® Intelliflash280™, SiO₂, 0-100% of ethyl acetate in hexanes) to obtain 0.33 g of the title compound. MS (ESI⁺) M/Z 245 [M+H]⁺.

Example 120C (cis)-3-(4-methylthiazol-2-yl)cyclopentanamine hydrochloride

To a solution of Example 120B (100 mg, 0.41 mmol) in ethyl alcohol (3 mL) was added chloroacetone (0.036 mL, 0.45 mmol). The reaction mixture was stirred at reflux overnight, then 2 mL of 2N aqueous HCl was and the mixture was stirred at reflux for 4 h. The mixture was concentrated and the residue triturated in diethyl ether to provide the title compound as a 2:1 cis/trans mixture of diastereomers. MS (ESI⁺) M/Z 145 [M+H]⁺.

Example 120D 1-(1H-indazol-4-yl)-3-[(cis)-3-(4-methyl-1,3-thiazol-2-yl)cyclopentyl]urea A solution of Example 120C (89 mg, 0.41 mmol), N,N-dimethylformamide (3 mL), diisopropylethylamine (0.15 mL, 0.85 mmol) and methyl 4-((2,5-dioxopyrrolidin-1-yloxy)carbonylamino)-1H-indazole-1-carboxylate (prepared as in *Org. Proc. Res. Dev.,* 2007, 11, 578; 135 mg, 0.41 mmol) was stirred at room temperature for 10 minutes. Methanol (6 mL) and 5N aqueous NaOH (0.24 mL, 1.2 mmol) were added and stirring continued for 2 hours at room temperature. The reaction mixture was diluted with water (10 mL), concentrated to half the volume, and extracted with ethyl acetate (2×20 mL). The combined organic extracts were washed with brine, dried over Na₂SO₄, filtered, and concentrated under reduced pressure. The residue was purified by column chromatography using an Analogix® Intelliflash280™ (SiO₂, 0-100% of methanol/ethyl acetate (1:10) in hexanes) to obtain the title compound (60 mg, 43%) and Example 119 (28 mg, 20%). MS (ESI⁺) M/Z 342 [M+H]⁺.

Example 120E 1-(1H-indazol-4-yl)-3-[(1S*,3R*)-3-(4-methyl-1,3-thiazol-2-yl)cyclopentyl]urea Example 120D (60 mg) was dissolved in 4 mL of 1:1 mixture of IPA and hexanes This solution was passed through a Chiralpak AD-H semi-prep column, 20% IPA/hexanes isocratic mobile phase, 10 mL/min, 2 mL/injection, to provide the title compound (first eluting enantiomer, 23 mg) and Example 121 (second eluting enantiomer, 20 mg). ¹H NMR (300 MHz, DMSO-d₆) δ ppm 1.53-1.79 (m, 2H) 1.83-2.23 (m, 4H) 2.33 (s, 3H) 3.39-3.58 (m, 1H) 4.07-4.27 (m, 1H) 6.55 (d, J=7.46 Hz, 1H) 6.98-7.13 (m, 2H) 7.14-7.29 (m, 1H) 7.61 (d, J=7.46 Hz, 1H) 8.06 (s, 1H) 8.54 (s, 1H) 12.97 (s, 1H). MS (ESI⁺) M/Z 342 [M+H]⁺.

Example 121

1-(1H-indazol-4-yl)-3-[(1R*,3S*)-3-(4-methyl-1,3-thiazol-2-yl)cyclopentyl]urea

The title compound was the second eluted enantiomer from the chiral separation described in Example 120E. ¹H NMR (300 MHz, DMSO-d₆) δ ppm 1.53-1.79 (m, 2H) 1.83-2.23 (m, 4H) 2.33 (s, 3H) 3.39-3.58 (m, 1H) 4.07-4.27 (m, 1H) 6.55 (d, J=7.46 Hz, 1H) 6.98-7.13 (m, 2H) 7.14-7.29 (m, 1H) 7.61 (d, J=7.46 Hz, 1H) 8.06 (s, 1H) 8.54 (s, 1H) 12.97 (s, 1H). MS (ESI⁺) M/Z 342 [M+H]⁺.

Example 122

1-(1H-indazol-4-yl)-3-[(1S*,3R*)-3-(4-methyl-1,3-oxazol-2-yl)cyclopentyl]urea

Example 122A (cis)-3-(4-methyloxazol-2-yl)cyclopentanamine hydrochloride

To a solution of Example 120A (300 mg, 1.3 mmol) in EtOH (2 mL) was added chloroacetone (0.3 mL, 3.9 mmol). The reaction mixture was stirred at reflux for 64 hours, cooled to ambient temperature, and concentrated. Trituration of the residue in diethyl ether afforded the title compound. LC/MS (ESI⁺) M/Z 167 [M+H]⁺.

Example 122B 1-(1H-indazol-4-yl)-3-[(cis)-3-(4-methyl-1,3-oxazol-2-yl)cyclopentyl]urea The title compound was prepared according to Example 120D, substituting Example 122A for Example 120C. MS (ESI⁺) M/Z 326 [M+H]⁺.

Example 122C 1-(1H-indazol-4-yl)-3-[(1S*,3R*)-3-(4-methyl-1,3-oxazol-2-yl)cyclopentyl]urea Example 122B (100 mg) was dissolved in 4 mL of 1:1 mixture of IPA and hexanes. This solution was passed through a Chiralpak AD-H semi-prep column, 20% IPA/hexanes isocratic mobile phase, 10 mL/min, 2 mL/injection, to provide the title compound (first eluting enantiomer, 35 mg) and Example 123 (second eluting enantiomer, 40 mg) ¹H NMR (300 MHz, DMSO-d₆) δ ppm 1.49-1.77 (m, 2H) 1.84-2.03 (m, 3H) 2.05 (d, J=1.36 Hz, 3H) 2.38-2.46 (m, 1H) 3.18-3.27 (m, 1H) 4.05-4.21 (m, 1H) 6.51 (d, J=7.12 Hz, 1H) 7.04 (d, J=8.48 Hz, 1H) 7.19 (t, J=7.97 Hz, 1H) 7.55-7.72 (m, 2H) 8.05 (s, 1H) 8.54 (s, 1H) 12.97 (s, 1H). MS (ESI⁺) M/Z 326 [M+H]⁺.

Example 123

1-(1H-indazol-4-yl)-3-[(1R*,3S*)-3-(4-methyl-1,3-oxazol-2-yl)cyclopentyl]urea

The title compound was isolated as the second eluting enantiomer from the chiral separation described in Example 122C. ¹H NMR (300 MHz, DMSO-d₆) δ ppm 1.49-1.77 (m, 2H) 1.84-2.03 (m, 3H) 2.05 (d, J=1.36 Hz, 3H) 2.38-2.46 (m, 1H) 3.18-3.27 (m, 1H) 4.05-4.21 (m, 1H) 6.51 (d, J=7.12 Hz, 1H) 7.04 (d, J=8.48 Hz, 1H) 7.19 (t, J=7.97 Hz, 1H) 7.55-7.72 (m, 2H) 8.05 (s, 1H) 8.54 (s, 1H) 12.97 (s, 1H). MS (ESI⁺) M/Z 326 [M+H]⁺.

Example 124

1-(2,3-dihydro-1H-inden-4-yl)-3-[(1S,3R)-3-phenyl-cyclopentyl]urea

The title compound was prepared according to Example 1F, substituting 2,3-dihydro-1H-inden-4-amine for Example 1B and substituting (1S,3R)-3-phenylcyclopentanamine (second eluting diastereomer from Example 15B) for Example 1E. $^1$H NMR (500 MHz, DMSO-d$_6$/Deuterium oxide) δ 7.79-7.60 (m, 1H), 7.38-7.24 (m, 4H), 7.23-7.14 (m, 1H), 7.05 (dt, J=28.8, 7.7 Hz, 1H), 6.87 (dd, J=37.4, 7.2 Hz, 1H), 4.22-4.01 (m, 1H), 3.13-3.00 (m, 1H), 2.90-2.79 (m, 2H), 2.74 (t, J=7.4 Hz, 2H), 2.47-2.32 (m, 1H), 2.13-1.89 (m, 4H), 1.73-1.57 (m, 2H), 1.46-1.27 (m, 1H). MS (ESI$^+$) M/Z 321 [M+H]$^+$.

Example 125

1-(6-fluoro-3-methylisoquinolin-5-yl)-3-[(1S*,3R*)-3-(5-methyl-1,3-oxazol-2-yl)cyclopentyl]urea

Example 125A tert-butyl(cis)-3-(prop-2-ynylcarbamoyl)cyclopentyl-carbamate

The title compound was prepared according to Example 120A, substituting propargylamine for ammonium hydroxide. MS (ESI$^+$) M/Z 267 [M+H]$^+$.

Example 125B tert-butyl(cis)-3-(5-methyloxazol-2-yl)cyclopentyl-carbamate

To a solution of Example 125A (500 mg, 1.88 mmol) in acetonitrile (8 mL) was added a solution of gold (III) chloride (56.9 mg, 0.188 mmol) in acetonitrile (2 mL). The reaction mixture was stirred at 50° C. for 16 hours and then concentrated. The residue was purified by column chromatography using an Analogix® Intelliflash280™ (SiO$_2$, 0-50% of MeOH/EtOAc (1:10) in hexanes) to obtain 400 mg (80%) the title compound. MS (ESI$^+$) M/Z 267 [M+H]$^+$.

Example 125C tert-butyl (1S*,3R*)-3-(5-methyloxazol-2-yl)cyclo-pentylcarbamate

Example 125D tert-butyl (1R*,3S*)-3-(5-methyloxazol-2-yl)cyclo-pentylcarbamate

Example 125B (700 mg) was dissolved in 9 mL of 1:1 mixture of IPA and hexanes. This solution was passed through a Chiralpak AD-H semi-prep column, 8% IPA/hexanes isocratic mobile phase, 10 mL/min, 1.5 mL/injection, to provide Example 125C (first eluting enantiomer, 250 mg) and Example 125D (second eluting enantiomer, 200 mg). MS (ESI$^+$) M/Z 267 [M+H]$^+$.

Example 125E

(1S*,3R*)-3-(5-methyloxazol-2-yl)cyclopentanamine hydrochloride

Methanol (0.34 mL, 8.45 mmol) was cooled to <5° C. and acetyl chloride (0.13 mL, 1.88 mmol) was added. To a solution of Example 125C (250 mg, 0.94 mmol) in MTBE (5 mL), the above prepared HCl/methanol solution was added dropwise. White slurry was observed immediately, which was filtered, washed with MTBE and dried in a vacuum oven at 50° C. to afford 185 mg (97%) of the title compound. MS (ESI$^+$) M/Z 167 [M+H]$^+$.

Example 125F

1-(6-fluoro-3-methylisoquinolin-5-yl)-3-[(1S*,3R*)-3-(5-methyl-1,3-oxazol-2-yl)cyclopentyl]urea A mixture of Example 6D (60 mg, 0.18 mmol), Example 125E (38 mg, 0.18 mmol) and potassium carbonate (32 mg, 0.23 mmol) in DMF (2 mL) was stirred at 85° C. overnight. The reaction mixture was cooled to ambient temperature, diluted with 1M aqueous NaHCO$_3$ (10 mL). The aqueous layer was extracted with EtOAc (2×20 mL). The combined organic layers were dried over Na$_2$SO$_4$, filtered and concentrated under reduced pressure. The residue was purified by column chromatography using an Analogix® Intelliflash280™ (SiO$_2$, 0-80% of 1/10 MeOH/EtOAc in hexanes) to obtain the title compound. $^1$H NMR (300 MHz, DMSO-d$_6$) δ ppm 1.52-1.64 (m, 1H) 1.69-1.82 (m, 1H) 1.85-2.05 (m, 3H) 2.25 (s, 3H) 2.29-2.42 (m, 1H) 2.62 (s, 3H) 3.17-3.27 (m, 1H) 4.02-4.18 (m, 1H) 6.52 (d, J=7.46 Hz, 1H) 6.66 (d, J=1.02 Hz, 1H) 7.46-7.57 (m, 1H) 7.59 (s, 1H) 7.97-8.10 (m, 2H) 9.22 (s, 1H). MS (ESI$^+$) M/Z 369 [M+H]$^+$.

Example 126

1-(1H-indazol-4-yl)-3-[(1S*,3R*)-3-(5-methyl-1,3-oxazol-2-yl)cyclopentyl]urea The title compound was prepared according to Example 120D, substituting Example 125E for Example 120C. $^1$H NMR (300 MHz, DMSO-d$_6$) δ ppm 1.50-1.63 (m, 1H) 1.65-1.82 (m, 1H) 1.84-2.08 (m, 3H) 2.26 (s, 3H) 2.33-2.46 (m, 1H) 3.19-3.31 (m, 1H) 4.03-4.22 (m, 1H) 6.53 (d, J=7.46 Hz, 1H) 6.70 (s, 1H) 7.04 (d, J=8.14 Hz, 1H) 7.21 (s, 1H) 7.61 (d, J=7.46 Hz, 1H) 8.06 (s, 1H) 8.58 (s, 1H) 12.97 (s, 1H) MS (ESI$^+$) M/Z 326 [M+H]$^+$.

Example 127

1-(6-fluoro-3-methylisoquinolin-5-yl)-3-[(1R*,3S*)-3-(5-methyl-1,3-oxazol-2-yl)cyclopentyl]urea

Example 127A

(1R*,3S*)-3-(5-methyloxazol-2-yl)cyclopentanamine hydrochloride

The title compound was prepared according to Example 125E, substituting Example 125D for Example 125C. MS (ESI$^+$) M/Z 167 [M+H]$^+$.

Example 127B

1-(6-fluoro-3-methylisoquinolin-5-yl)-3-[(1R*,3S*)-3-(5-methyl-1,3-oxazol-2-yl)cyclopentyl]urea The title compound was prepared according to Example 125F, substituting Example 127A for Example 125E. $^1$H NMR (300 MHz, DMSO-d$_6$) δ ppm 1.52-1.64 (m, 1H) 1.69-1.82 (m, 1H) 1.85-2.05 (m, 3H) 2.25 (s, 3H) 2.29-2.42 (m, 1H) 2.62 (s, 3H) 3.17-3.27 (m, 1H) 4.02-4.18 (m, 1H) 6.52 (d, J=7.46 Hz, 1H) 6.66 (d, J=1.02 Hz, 1H) 7.46-7.57 (m, 1H) 7.59 (s, 1H) 7.97-8.10 (m, 2H) 9.22 (s, 1H). MS (ESI$^+$) M/Z 369 [M+H]$^+$.

Example 128

1-(1H-indazol-4-yl)-3-[(1R*,3S*)-3-(5-methyl-1,3-oxazol-2-yl)cyclopentyl]urea

The title compound was prepared according to Example 120D, substituting Example 127A for Example 120C. $^1$H NMR (300 MHz, DMSO-d$_6$) δ ppm 1.50-1.63 (m, 1H) 1.65-1.82 (m, 1H) 1.84-2.08 (m, 3H) 2.26 (s, 3H) 2.33-2.46 (m, 1H) 3.19-3.31 (m, 1H) 4.03-4.22 (m, 1H) 6.53 (d, J=7.46 Hz, 1H) 6.70 (s, 1H) 7.04 (d, J=8.14 Hz, 1H) 7.21 (s, 1H) 7.61 (d, J=7.46 Hz, 1H) 8.06 (s, 1H) 8.58 (s, 1H) 12.97 (s, 1H) MS (ESI$^+$) M/Z 326 [M+H]$^+$.

Example 129

1-(1H-indazol-4-yl)-3-{(1R*,3R*)-3-[4-(trifluoromethyl)-1,3-thiazol-2-yl]cyclopentyl}urea Example 129A 3-(4-(trifluoromethyl)thiazol-2-yl)cyclopentanamine hydrochloride The title compound was prepared according to Example 120C, substituting 3-chloro-1,1,1-trifluoroacetone (Synquest) for chloroacetone. MS (ESI$^+$) M/Z 273 [M+H]$^+$.

Example 129B 1-(1H-indazol-4-yl)-3-(3-(4-(trifluoromethyl)thiazol-2-yl)cyclopentyl)urea The title compound was prepared according to Example 120D, substituting Example 129A for Example 120C. MS (ESI$^+$) M/Z 396 [M+H]$^+$.

Example 129C 1-(1H-indazol-4-yl)-3-{(1R*,3R*)-3-[4-(trifluoromethyl)-1,3-thiazol-2-yl]cyclopentyl}urea Example 129B was dissolved in 6 mL of 1:1 mixture of IPA and hexanes. This solution was passed through a Chiralpak AD-H semi-prep column, 10% IPA/hexanes isocratic mobile phase, 10 mL/min, 1 mL/injection, to provide the title compound (first eluting isomer), Example 130 (second eluting isomer), and Example 131 (third eluting peak) Data for Example 129C: $^1$H NMR (300 MHz, DMSO-d$_6$) δ ppm 1.53-1.69 (m, 1H) 1.79-1.93 (m, 1H) 2.04-2.23 (m, 3H) 2.26-2.39 (m, 1H) 3.68-3.82 (m, 1H) 4.20 (s, 1H) 6.73 (d, J=7.12 Hz, 1H) 7.04 (d, J=8.48 Hz, 1H) 7.13-7.23 (m, 1H) 7.61 (d, J=7.46 Hz, 1H) 8.10 (s, 1H) 8.38 (s, 1H) 8.68 (s, 1H) 12.97 (s, 1H). MS (ESI$^+$) M/Z 396 [M+H]$^+$.

Example 130

1-(1H-indazol-4-yl)-3-{(1R*,3S*)-3-[4-(trifluoromethyl)-1,3-thiazol-2-yl]cyclopentyl}urea Example 130 was the second compound eluted from the chiral separation described in Example 129C. $^1$H NMR (300 MHz, DMSO-d$_6$) δ ppm 1.61-1.79 (m, 1H) 1.86-2.11 (m, 2H) 2.13-2.25 (m, 1H) 2.55-2.64 (m, 2H) 3.65 (s, 1H) 4.17 (s, 1H) 6.64 (d, J=7.12 Hz, 1H) 7.04 (d, J=8.14 Hz, 1H) 7.14-7.22 (m, 1H) 7.61 (d, J=7.80 Hz, 1H) 8.07 (s, 1H) 8.38 (s, 1H) 8.61 (s, 1H) 12.97 (s, 1H). MS (ESI$^+$) M/Z 396 [M+H]$^+$.

Example 131

1-(1H-indazol-4-yl)-3-{(1R)-3-[4-(trifluoromethyl)-1,3-thiazol-2-yl]cyclopentyl}urea The title compound was the third major component eluted from the chiral separation described in Example 129C. $^1$H NMR (300 MHz, DMSO-d$_6$) δ ppm 1.57-1.73 (m, 1H) 1.74-2.01 (m, 2H) 2.05-2.34 (m, 2H) 2.54-2.67 (m, 1H) 3.53-3.83 (m, 1H) 4.10-4.27 (m, 1H) 6.60-6.71 (m, J=12.38, 6.95 Hz, 1H) 7.04 (d, J=8.48 Hz, 1H) 7.18 (t, J=7.97 Hz, 1H) 7.61 (d, J=7.80 Hz, 1H) 8.04-8.11 (m, 1H) 8.38 (s, 1H) 8.57-8.66 (m, J=8.48 Hz, 1H) 12.97 (s, 1H). MS (ESI$^+$) M/Z 396 [M+H]$^+$.

Example 132

1-(6-fluoro-3-methylisoquinolin-5-yl)-3-[(1R,3S)-3-(4-methyl-1,3-thiazol-2-yl)cyclopentyl]urea Example 132A tert-butyl (1R,3S)-3-carbamoylcyclopentylcarbamate The title compound was prepared according to Example 120A, substituting (1S,3R)-3-(tert-butoxycarbonylamino)cyclopentanecarboxylic acid (Acros) for racemic (1R,3S)-3-(tert-butoxycarbonylamino)cyclopentanecarboxylic acid. MS (ESI$^+$) M/Z 228 [M+H]$^+$.

Example 132B tert-butyl (1R,3S)-3-carbamothioylcyclopentylcarbamate

The title compound was prepared according to Example 120B, substituting Example 132A for Example 120A. MS (ESI$^+$) M/Z 245 [M+H]$^+$.

Example 132C (1R,3S)-3-(4-methylthiazol-2-yl)cyclopentanamine hydrochloride

The title compound was prepared according to Example 120C, substituting Example 132B for Example 120B. MS (ESI$^+$) M/Z 183 [M+H]$^+$.

Example 132D 1-(6-fluoro-3-methylisoquinolin-5-yl)-3-[(1R,3S)-3-(4-methyl-1,3-thiazol-2-yl)cyclopentyl]urea The title compound was prepared according to Example 125F, substituting Example 132C for Example 125E. $^1$H NMR (300 MHz, DMSO-d$_6$) δ ppm 1.58-1.89 (m, 3H) 1.89-2.18 (m, 3H) 2.32 (s, 3H) 2.61 (s, 3H) 3.46 (s, 1H) 4.05-4.20

(m, 1H) 6.59 (d, J=7.54 Hz, 1H) 7.10 (s, 1H) 7.45-7.56 (m, 1H) 7.58 (s, 1H) 7.98-8.04 (m, 1H) 8.05 (s, 1H) 9.21 (s, 1H). MS (ESI⁺) M/Z 385 [M+H]⁺.

Example 133

1-(6-fluoro-3-methylisoquinolin-5-yl)-3-[(1R,3R)-3-(4-methyl-1,3-thiazol-2-yl)cyclopentyl]urea Example 133A tert-butyl (1R,3R)-3-(4-methylthiazol-2-yl)cyclopentylcarbamate The title compound was obtained as a byproduct from the procedure described in Example 132C. MS (ESI⁺) M/Z 283 [M+H]⁺.

Example 133B (1R,3R)-3-(4-methylthiazol-2-yl)cyclopentanamine hydrochloride

The title compound was prepared according to Example 125E, substituting Example 133A for Example 125C. MS (ESI⁺) M/Z 183 [M+H]⁺.

Example 133C 1-(6-fluoro-3-methylisoquinolin-5-yl)-3-[(1R,3R)-3-(4-methyl-1,3-thiazol-2-yl)cyclopentyl]urea The title compound was prepared according to Example 125F, substituting Example 133B for Example 125E. ¹H NMR (300 MHz, DMSO-d₆) δ ppm 1.52-1.67 (m, 1H) 1.71-1.86 (m, 1H) 1.97-2.29 (m, 4H) 2.32 (s, 3H) 2.62 (s, 3H) 3.63 (s, 1H) 4.10-4.24 (m, 1H) 6.63 (d, J=7.54 Hz, 1H) 7.09 (d, J=1.19 Hz, 1H) 7.47-7.56 (m, 1H) 7.59 (s, 1H) 7.98-8.09 (m, 2H) 9.21 (s, 1H). MS (ESI⁺) M/Z 385 [M+H]⁺.

Example 134

1-(6-fluoro-3-methylisoquinolin-5-yl)-3-[(1S,3S)-3-(4-methyl-1,3-thiazol-2-yl)cyclopentyl]urea Example 134A tert-butyl (1S,3S)-3-(4-methylthiazol-2-yl)cyclopentylcarbamate The title compound was obtained as a by-product from the procedure described for Example 135C. MS (ESI⁺) M/Z 283 [M+H]⁺.

Example 134B (1S,3S)-3-(4-methylthiazol-2-yl)cyclopentanamine hydrochloride

The title compound was prepared according to Example 125E, substituting Example 134A for Example 125C. MS (ESI⁺) M/Z 183 [M+H]⁺.

Example 134C 1-(6-fluoro-3-methylisoquinolin-5-yl)-3-[(1S,3S)-3-(4-methyl-1,3-thiazol-2-yl)cyclopentyl]urea The title compound was prepared according to Example 125F, substituting Example 134B for Example 125E. ¹H NMR (300 MHz, DMSO-d₆) δ ppm 1.52-1.67 (m, 1H) 1.71-1.86 (m, 1H) 1.97-2.29 (m, 4H) 2.32 (s, 3H) 2.62 (s, 3H) 3.63 (s, 1H) 4.10-4.24 (m, 1H) 6.63 (d, J=7.54 Hz, 1H) 7.09 (d, J=1.19 Hz, 1H) 7.47-7.56 (m, 1H) 7.59 (s, 1H) 7.98-8.09 (m, 2H) 9.21 (s, 1H). MS (ESI⁺) M/Z 385 [M+H]⁺.

Example 135

1-(6-fluoro-3-methylisoquinolin-5-yl)-3-[(1S,3R)-3-(4-methyl-1,3-thiazol-2-yl)cyclopentyl]urea Example 135A tert-butyl (1S,3R)-3-carbamoylcyclopentylcarbamate The title compound was prepared according to Example 120A, substituting (1R,3S)-3-(tert-butoxycarbonylamino)cyclopentanecarboxylic acid (Chempex cat 15221) for racemic (1R,3S)-3-(tert-butoxycarbonylamino)cyclopentanecarboxylic acid. MS (ESI⁺) M/Z 228 [M+H]⁺.

Example 135B tert-butyl (1S,3R)-3-carbamothioylcyclopentylcarbamate

The title compound was prepared according to Example 120B, substituting Example 135A for Example 120A. MS (ESI⁺) M/Z 245 [M+H]⁺.

Example 135C tert-butyl (1S,3R)-3-(4-methylthiazol-2-yl)cyclopentylcarbamate (1R,3S)-3-(4-methylthiazol-2-yl)cyclopentanamine hydrochloride was obtained according to the procedure of Example 120C, substituting Example 135B for Example 120B. The crude amine product was treated with di-tert-butyl dicarbonate. The residue was purified by column chromatography using an Analogix® Intelliflash280™ (SiO₂, 0-30% of EtOAc in hexanes) to provide the title compound (first eluting product) and Example 134A (second eluting product) (diasteriomeric ratio was 2.5:1). MS (ESI⁺) M/Z 283 [M+H]⁺.

Example 135D (1S,3R)-3-(4-methylthiazol-2-yl)cyclopentanamine hydrochloride

The title compound was prepared according to 125E, substituting Example 135C for Example 125C. MS (ESI⁺) M/Z 183 [M+H]⁺.

Example 135E 1-(6-fluoro-3-methylisoquinolin-5-yl)-3-[(1S,3R)-3-(4-methyl-1,3-thiazol-2-yl)cyclopentyl]urea The title compound was prepared according to Example 125F, substituting Example 135D for Example 125E. ¹H NMR (300 MHz, DMSO-d₆) δ ppm 1.58-1.89 (m, 3H) 1.89-2.18 (m, 3H) 2.32 (s, 3H) 2.61 (s, 3H) 3.46 (s, 1H) 4.05-4.20 (m, 1H) 6.59 (d, J=7.54 Hz, 1H) 7.10 (s, 1H) 7.45-7.56 (m, 1H) 7.58 (s, 1H) 7.98-8.04 (m, 1H) 8.05 (s, 1H) 9.21 (s, 1H). MS (ESI⁺) M/Z 385 [M+H]⁺.

Example 136

1-(1-chloroisoquinolin-5-yl)-3-[(1R,3S)-3-phenylcyclopentyl]urea

To a solution of 5-amino-1-chloroisoquinoline (1.00 g, 5.60 mmol) in acetonitrile (25 mL) at room temperature was added pyridine (0.14 mL, 1.7 mmol) followed by phenyl chloroformate (0.70 mL, 5.6 mmol). After 15 minutes, Example 1E (0.903 g, 5.60 mmol) and N,N-diisopropylethylamine (3.9 mL, 22.4 mmol) were added and stirring continued for 15 minutes, followed by the addition of water. The solid was collected by filtration, washed with water then ether, and dried in a vacuum oven at 50° C. to provide the title compound (1.53 g, 75%). $^1$H NMR (300 MHz, DMSO-$d_6$) δ 8.66 (s, 1H), 8.46-8.28 (m, 2H), 8.03-7.86 (m, 2H), 7.73 (t, J=8.1 Hz, 1H), 7.38-7.09 (m, 5H), 6.82 (d, J=7.2 Hz, 1H), 4.16 (dd, J=13.7, 6.8 Hz, 1H), 3.20-2.98 (m, 1H), 2.44 (dd, J=12.9, 6.6 Hz, 1H), 2.19-1.93 (m, 2H), 1.86-1.59 (m, 2H), 1.59-1.39 (m, 1H). MS (DCI/NH$_3$) m/z 366 [M+H]$^+$.

Example 137

1-(1H-indol-4-yl)-3-[(1R,3S)-3-phenylcyclopentyl]urea

The title compound was prepared according to Example 136, substituting 4-aminoindole for 5-amino-1-chloroisoquinoline to provide the title compound (508 mg 53%). $^1$H NMR (300 MHz, DMSO-$d_6$) δ 11.02 (s, 1H), 8.09 (s, 1H), 7.63 (dd, J=6.7, 2.0 Hz, 1H), 7.41-7.11 (m, 6H), 7.02-6.85 (m, 2H), 6.67-6.41 (m, 2H), 4.27-3.98 (m, 1H), 3.18-2.95 (m, 1H), 2.48-2.32 (m, 1H), 2.18-1.91 (m, 2H), 1.82-1.54 (m, 2H), 1.45 (ddd, J=12.2, 11.2, 8.6 Hz, 1H). MS (DCI/NH$_3$) m/z 320 [M+H]$^+$.

Example 138

1-[(1R,3S)-3-phenylcyclopentyl]-3-(5,6,7,8-tetrahydronaphthalen-1-yl)urea

The title compound was prepared according to Example 136, substituting 5,6,7,8-tetrahydro-1-naphthylamine for 5-amino-1-chloroisoquinoline to provide the title compound (701 mg, 84%). $^1$H NMR (300 MHz, DMSO-$d_6$) δ 7.65 (d, J=8.0 Hz, 1H), 7.37 (s, 1H), 7.34-7.13 (m, 5H), 6.96 (t, J=7.8 Hz, 1H), 6.69 (t, J=7.9 Hz, 2H), 4.19-3.96 (m, 1H), 3.16-2.95 (m, 1H), 2.69 (t, J=6.1 Hz, 2H), 2.46-2.32 (m, 1H), 2.13-1.92 (m, 2H), 1.84-1.51 (m, 7H), 1.43 (ddd, J=12.3, 11.1, 8.4 Hz, 1H). MS (DCI/NH$_3$) m/z 335 [M+H]$^+$.

Example 139

1-[6-fluoro-3-(2-methylpropyl)isoquinolin-5-yl]-3-[(1R,3S)-3-phenylcyclopentyl]urea

Example 139A 6-fluoro-3-isobutylisoquinoline

The title compound was prepared according to Example 6A, substituting 4-methylpent-1-yne for propyne. MS (ESI) m/z 204 (M+H)$^+$.

Example 139B 6-fluoro-3-isobutyl-5-nitroisoquinoline

To melted sulfolane (17 mL) was added nitronium tetrafluororborate (3.22 g, 24.3 mmol) followed by neat Example 139A (2.35 g, 11.6 mmol), dropwise, to maintain internal temperature under 55° C. Upon completeion of the addition, LCMS showed near complete consumption of starting material. The reation vessel was placed and an ince bath and the mixture was cooled to 12° C. and 1N aqueous sodium hydroxide (28.9 mL, 28.9 mmol) was added while mainintaining the internal temperature below 40° C. The mixture was stirred until the internal temperature reached 15° C. The solid was collected by filtration (water wash), and dried at 50° C. in a vacuum to afford the title compound (2.39 g, 83%). MS (ESI) m/z 249 (M+H)$^+$.

Example 139C 6-fluoro-3-isobutylisoquinolin-5-amine

A solution of Example 139B (2.39 g, 9.63 mmol) in THF (50 mL) was added to a Ra—Ni 2800, water slurry (2.390 g, 40.7 mmol) in a 250 mL pressure bottle and stirred for 100 min at 30 psi and ambient temperature. The mixture was filtered through a nylon membrane and then concentrated under reduced pressure to provide the title compound (2.15 g, 100% yield), which was used without further purification. (ESI) m/z 219.2 (M+H)$^+$.

Example 139D

1-[6-fluoro-3-(2-methylpropyl)isoquinolin-5-yl]-3-[(1R,3S)-3-phenylcyclopentyl]urea The title compound was prepared according to Example 6D and Example 6E, substituting Example 139C for Example 6C. $^1$H NMR (300 MHz, DMSO-$d_6$) δ 9.24 (d, J=0.9 Hz, 1H), 8.07-7.98 (m, 2H), 7.53 (t, J=9.5 Hz, 2H), 7.33-7.28 (m, 4H), 7.25-7.14 (m, 1H), 6.58 (d, J=7.3 Hz, 1H), 4.17-4.03 (m, 1H), 3.14-2.97 (m, 1H), 2.72 (d, J=7.1 Hz, 2H), 2.44-2.33 (m, 1H), 2.21-1.93 (m, 3H), 1.81-1.47 (m, 3H), 0.90 (dd, J=6.6, 1.1 Hz, 6H). MS (ESI) m/z 406 (M+H)$^+$.

Example 140

1-(3-ethyl-6-fluoroisoquinolin-5-yl)-3-[(1R,3S)-3-phenylcyclopentyl]urea

The title compound was prepared according to Examples 6A-E, substituting 1-butyne for propyne. $^1$H NMR (300 MHz, DMSO-$d_6$) δ 9.24 (d, J=0.9 Hz, 1H), 8.07-7.99 (m, 2H), 7.58 (s, 1H), 7.52 (dd, J=9.9, 9.1 Hz, 1H), 7.33-7.24 (m, 4H), 7.23-7.10 (m, 1H), 6.57 (d, J=7.4 Hz, 1H), 4.20-4.05 (m, 1H), 3.11-2.97 (m, 1H), 2.89 (q, J=7.5 Hz, 2H), 2.41-2.25 (m, 1H), 2.10-1.92 (m, 2H), 1.81-1.43 (m, 3H), 1.30 (t, J=7.5 Hz, 3H). MS (ESI) m/z 378 (M+H)$^+$.

Example 141

1-(3-amino-1-methylisoquinolin-5-yl)-3-[(1R,3S)-3-phenylcyclopentyl]urea

Example 141A 1-methylisoquinolin-3-amine

To a dry flask under N$_2$ containing methyllithium (13 mL, 21 mmol) in THF (40 mL) at 0° C. was added a solution of 2-(cyanomethyl)benzonitrile (1.00 g, 7.03 mmol) in THF (20 mL) dropwise. After 10 minutes the ice bath was removed and the mixture was allowed to warm to ambient temperature. The mixture was quenched with saturated aqueous NH$_4$Cl and then concentrated. The mixture was extracted twice with CH$_2$Cl$_2$, and the combined organic extracts were washed with brine and dried (Na$_2$SO$_4$). Purification by chromatography (SiO$_2$, 10% acetone/hexanes) afforded the title compound 0.71 g (79% yield). MS (ESI) m/z 159 (M+H)$^+$.

Example 141B

N-(1-methylisoquinolin-3-yl)acetamide

Acetic anhydride (1.4 mL, 15 mmol) was added to a suspension of Example 141A (0.79 g, 5.0 mmol) and triethylamine (0.76 ml, 5.5 mmol) in CH$_2$Cl$_2$ (20 mL) at ambient temperature. The mixture was stirred for 3.5 hours, then the volatiles were removed under reduced pressure. The residue was chased with toluene (3×25 mL) and then concentrated under reduced pressure to provide the title compound. MS (ESI) m/z 201 (M+H)$^+$.

Example 141C 1-methyl-5-nitroisoquinolin-3-amine

A flask was charged with concentrated H$_2$SO$_4$ (9.1 mL) and Example 141B (5 mmol) at 0° C., was stirred until most of the starting material dissolve. Solid potassium nitrate (0.61 g, 6.0 mmol) was then added in four approximately equal portions over 10 minutes. The mixture was stirred for 4 hours, and then poured over ice (30 g) in a beaker that was cooled in an ice bath. The pH of the mixture was adjusted to about 8 by dropwise addition of concentrated aqueous NH$_4$OH (21 mL), during which time additional ice (~20 g) was added to maintain the temperature <25° C. The precipitate was then collected by filtration (water wash) and dried at 50° C. uner vacuum to afford the title compound. MS (ESI) m/z 204 (M+H)$^+$.

Example 141D

N-(1-methyl-5-nitroisoquinolin-3-yl)acetamide

Acetic anhydride (1.4 mL, 15 mmol) was added to a suspension of Example 141C (5 mmol) and triethylamine (0.76 mL, 5.5 mmol) in CH$_2$Cl$_2$ (20 mL) at ambient temperature. The mixture was stirred for 3.5 hours, then the volatiles were removed under reduced pressure. The residue was chased with toluene (3×25 mL) and concentrated under reduced pressure to afford the title compound (0.40 g, 33% yield over three steps). MS (ESI) m/z 246 (M+H)$^+$.

Example 141E

N-(5-amino-1-methylisoquinolin-3-yl)acetamide

Example 141D (0.33 g, 1.35 mmol) in 1:1 MeOH/THF (20 mL) was added to 10% palladium/carbon (0.066 g, 0.620 mmol) in a 250 mL pressure bottle and stirred for 4 hours at ambient temperature. The mixture was filtered through a nylon membrane and concentrated under reduced pressure. Purification of the residue by chromatography (silica gel, 40-100% EtOAc/Hexanes gradient) afforded the title compound 0.25 g (87% yield). MS (ESI) m/z 216 (M+H)$^+$.

Example 141F

N-(1-methyl-5-(3-((1R,3S)-3-phenylcyclopentyl)ureido)isoquinolin-3-yl)acetamide

The title compound was prepared according to Example 1F, substituting Example 141E for Example 1E. MS (ESI) m/z 403 (M+H)$^+$.

Example 141G 1-(3-amino-1-methylisoquinolin-5-yl)-3-[(1R,3S)-3-phenylcyclopentyl]urea Example 141F (0.12 g, 0.30 mmol) was taken up in MeOH (3 mL), followed by addition of 3N aqueous sodium hydroxide (1 mL, 3.0 mmol). The reaction mixture was heated at 85° C. for 1.5 hours, then cooled to ambient temperature and diluted with water (1 mL). The solid was collected by filtration, washed with 1:1 MeOH/H$_2$O and H$_2$O, then dried in a vacuum oven at 50° C. for 30 minutes. Purification by chromatography (silica gel, 40-80% EtOAc/Hexanes gradient) afforded the title compound (50 mg, 46% yield). $^1$H NMR (300 MHz, DMSO-d$_6$) δ 8.06 (s, 1H), 7.83 (d, J=6.9 Hz, 1H), 7.58 (d, J=8.4 Hz, 1H), 7.34-7.24 (m, 4H), 7.23-7.14 (m, 1H), 7.11-7.01 (m, 1H), 6.69 (d, J=7.2 Hz, 1H), 6.57 (s, 1H), 5.80 (s, 2H), 4.22-4.06 (m, 1H), 3.16-2.96 (m, 1H), 2.70 (s, 3H), 2.47-2.36 (m, 1H), 2.14-1.91 (m, 2H), 1.78-1.57 (m, 2H), 1.53-1.37 (m, 1H). MS (ESI) m/z 361 (M+H)$^+$.

Example 142

1-[3-(morpholin-4-yl)-2-oxo-1,2,3,4-tetrahydroquinolin-7-yl]-3-[(1R,3S)-3-phenylcyclopentyl]urea The title compound was prepared according to Example 1F, substituting 7-amino-3-morpholino-3,4-dihydroquinolin-2(1H)-one (US 2010/0016285) for Example 1E. Characterization of the hydrochloride salt: $^1$H NMR (300 MHz, DMSO-d$_6$) δ 10.87 (s, 1H), 10.59-10.40 (m, 1H), 8.48 (s, 1H), 7.34-7.24 (m, 4H), 7.22-7.14 (m, 2H), 7.09 (d, J=8.0 Hz, 1H), 6.97 (dd, J=8.0, 1.4 Hz, 1H), 6.33 (d, J=7.3 Hz, 1H), 4.55 (s, 1H), 4.14-4.03 (m, 1H), 4.03-3.67 (m, 4H), 3.27-2.98 (m, 4H), 2.45-2.32 (m, 2H), 2.02 (t, J=7.7 Hz, 2H), 1.77-1.53 (m, 2H), 1.51-1.37 (m, 1H). MS (ESI) m/z 435 (M+H)$^+$.

Example 143

1-[3-(1,4-oxazepan-4-yl)-2-oxo-1,2,3,4-tetrahydroquinolin-7-yl]-3-[(1R,3S)-3-phenylcyclopentyl]urea The title compound was prepared according to Example 1F, substituting 7-amino-3-(1,4-oxazepan-4-yl)-3,4-dihydroquinolin-2(1H)-one (US 2010/0016285) for Example 1E. Characterization of the hydrochloride salt: $^1$H NMR (300 MHz, DMSO-d$_6$) δ 10.89-10.82 (m, 1H), 10.22-10.05 (m, 1H), 8.50 (bs, 1H), 7.34-7.24 (m, 4H), 7.22-7.16 (m, 2H), 7.10 (d, J=8.1 Hz, 1H), 6.98 (dd, J=8.3, 1.1 Hz, 1H), 6.34 (d, J=7.6 Hz, 1H), 4.69-4.56 (m, 1H), 4.16-4.00 (m, 1H), 3.97-3.82 (m, 2H), 3.79-3.68 (m, 1H), 3.64-3.40 (m, 4H), 3.32-3.16 (m Hz, 4H), 3.12-2.97 (m, 1H), 2.43-2.31 (m, 1H), 2.07-1.93 (m, 3H), 1.76-1.58 (m, 2H), 1.44 (td, J=11.7, 8.7 Hz, 1H). MS (ESI) m/z 449 (M+H)$^+$.

Example 144

1-{3-[(2-methoxyethyl)(methyl)amino]-2-oxo-1,2,3, 4-tetrahydroquinolin-7-yl}-3-[(1R,3S)-3-phenylcyclopentyl]urea The title compound was prepared according to Example 1F, substituting 7-amino-3-((2-methoxyethyl)(methyl) amino)-3,4-dihydroquinolin-2(1H)-one (US 2010/0016285) for Example 1E. Characterization of the hydrochloride salt: $^1$H NMR (300 MHz, DMSO-d$_6$) δ 11.01-10.48 (m, 1H), 10.00 (s, 1H), 8.51 (s, 1H), 7.34-7.24 (m, 4H), 7.24-7.10 (m, 2H), 7.06 (d, J=8.0 Hz, 1H), 6.95 (d, J=7.9, 1H), 6.37 (d, J=6.2 Hz, 1H), 4.50 (s, 1H), 4.17-4.00 (m, 1H), 3.64 (s, 2H), 3.27 (s, 3H), 3.21-2.77 (m, 5H), 2.44-2.31 (m, 2H), 2.11-1.92 (m, 2H), 1.77-1.07 (m, 5H). MS (ESI) m/z 437 (M+H)$^+$.

Example 145

1-(4-methyl-3,4-dihydro-2H-1,4-benzoxazin-6-yl)-3-[(1R,3S)-3-phenylcyclopentyl]urea The title compound was prepared according to Example 1F, substituting 4-methyl-3,4-dihydro-2H-benzo[b][1,4]oxazin-6-amine for Example 1E. $^1$H NMR (300 MHz, DMSO-d$_6$) δ 7.94 (s, 1H), 7.35-7.23 (m, 4H), 7.23-7.12 (m, 1H), 6.82 (s, 1H), 6.49 (d, J=1.1 Hz, 2H), 6.10 (d, J=7.4 Hz, 1H), 4.19-4.12 (m, 2H), 4.12-4.01 (m, 1H), 3.24-3.15 (m, 2H), 3.12-2.95 (m, 1H), 2.78 (s, 3H), 2.43-2.30 (m, 1H), 2.10-1.89 (m, 2H), 1.77-1.49 (m, 2H), 1.42 (ddd, J=12.2, 11.2, 8.6 Hz, 1H). MS (DCI$^+$) m/z 352 (M+H)$^+$.

Example 146

1-(3,4-dihydro-2H-1,4-benzoxazin-6-yl)-3-[(1R,3S)-3-phenylcyclopentyl]urea

The title compound was prepared according to Example 1F, substituting 3,4-dihydro-2H-benzo[b][1,4]oxazin-6-amine for Example 1E. $^1$H NMR (300 MHz, DMSO-d$_6$) δ 7.89 (s, 1H), 7.34-7.23 (m, 4H), 7.23-7.12 (m, 1H), 6.78 (d, J=2.3 Hz, 1H), 6.49 (d, J=8.5 Hz, 1H), 6.41 (dd, J=8.5, 2.4 Hz, 1H), 6.08 (s, 1H), 4.12-3.97 (m, 4H), 3.31-3.17 (m, 2H), 3.11-2.96 (m, 1H), 2.42-2.29 (m, 1H), 2.09-1.90 (m, 2H), 1.75-1.49 (m, 2H), 1.48-1.34 (m, 1H). MS (DCI$^+$) m/z 338 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:

1. A compound having formula (I) or pharmaceutically acceptable salt, solvate, or a combination thereof

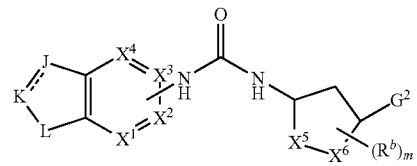

(I)

wherein
one of $X^1$, $X^2$, $X^3$, and $X^4$ is C, and the others are $C(R^a)$; wherein each $R^a$ is the same or different, and is independently hydrogen, —CN, NO$_2$, alkyl, halogen, haloalkyl, OR$^x$, or N(R$^x$)$_2$;
J is $CR^{3J}$;
K is N;
L is $NR^{3L}$;
===== is a double bond;
$R^{3L}$ is hydrogen, alkyl, or haloalkyl;
$R^{3J}$ is hydrogen, alkyl, halogen, haloalkyl, OR$^x$, or N(R$^x$)$_2$;
$X^5$-$X^6$ is $CR^{3a}R^{3b}$, $C(R^3R^4)C(R^5R^6)$, $CR^7$=$CR^8$, or $C(R^9R^{10})C(R^{11}R^{12})C(R^{13}R^{14})$;
$R^4$, $R^6$, $R^7$, $R^8$, $R^{10}$, $R^{12}$, and $R^{14}$, are the same or different, and are each independently hydrogen, alkyl, or haloalkyl;
$R^{3a}$ and $R^{3b}$ are each independently hydrogen, alkyl, halogen, or haloalkyl;
$R^3$, $R^5$, $R^9$, $R^{11}$, and $R^{13}$, are the same or different, and are each independently hydrogen, —CN, alkyl, halogen, haloalkyl, OR$^x$, or N(R$^x$)$_2$;
$R^3$ and $R^5$, together with the carbon atoms to which they are attached, optionally form a $C_3$-$C_6$ cycloalkyl that is optionally substituted with 1, 2, 3, or 4 substituents independently selected from the group consisting of alkyl, halogen, and haloalkyl;
m is 0, 1, 2, 3, or 4;
each $R^b$ is an optional substituent and at each occurrence, is independently —CN, alkyl, halogen, haloalkyl, OR$^x$, or N(R$^x$)$_2$;
each $R^x$ is independently hydrogen, alkyl, or haloalkyl;
ring $G^2$ is aryl, heteroaryl, cycloalkyl, cycloalkenyl, or heterocycle, each of which is independently unsubstituted or substituted with 1, 2, 3, 4, or 5 substituents independently selected from the group consisting of alkyl, alkenyl, alkynyl, halogen, oxo, haloalkyl, CN, NO$_2$, —OR$^f$, —OC(O)R$^e$, —OC(O)N(R$^f$)(R$^g$), —SR$^f$, —S(O)$_2$R$^e$, —S(O)$_2$N(R$^f$)(R$^g$), —C(O)R$^f$, —C(O)OR$^f$, —C(O)N(R$^f$)(R$^g$), —N(R$^f$)(R$^g$), —N(R$^g$)C(O)R$^e$, —N(R$^g$)S(O)$_2$R$^e$, —N(R$^g$)C(O)O(R$^e$), —N(R$^g$)C(O)N (R$^f$)(R$^g$), G$^a$, —(C$_1$-C$_6$ alkylenyl)-OR$^f$, —(C$_1$-C$_6$ alkylenyl)-OC(O)R$^e$, —(C$_1$-C$_6$ alkylenyl)-OC(O)N(R$^f$) (R$^g$), —(C$_1$-C$_6$ alkylenyl)-S(O)$_2$R$^e$, —(C$_1$-C$_6$ alkylenyl)-S(O)$_2$N(R$^f$)(R$^g$), —(C$_1$-C$_6$ alkylenyl)-C(O) R$^f$, —(C$_1$-C$_6$ alkylenyl)-C(O)OR$^f$, —(C$_1$-C$_6$ alkylenyl)-C(O)N(R$^f$)(R$^g$), —(C$_1$-C$_6$ alkylenyl)-N(R$^f$)(R$^g$), —(C$_1$-C$_6$ alkylenyl)-N(R$^g$)C(O)R$^e$, —(C$_1$-C$_6$ alkylenyl)-N (R$^g$)S(O)$_2$R$^e$, —(C$_1$-C$_6$ alkylenyl)-N(R$^g$)C(O)O(R$^e$), —(C$_1$-C$_6$ alkylenyl)-N(R$^g$)C(O)N(R$^f$)(R$^g$), —(C$_1$-C$_6$ alkylenyl)-CN, and —(C$_1$-C$_6$ alkylenyl)-G$^a$;
R$^e$, at each occurrence, is independently alkyl, alkenyl, alkynyl, haloalkyl, hydroxyalkyl, alkoxyalkyl, haloalkoxyalkyl, G$^a$, or —(C$_1$-C$_6$ alkylenyl)-G$^a$;
R$^f$, at each occurrence, is independently hydrogen, alkyl, alkenyl, alkynyl, haloalkyl, hydroxyalkyl, alkoxyalkyl, haloalkoxyalkyl, G$^a$, or —(C$_1$-C$_6$ alkylenyl)-G$^a$;

R$^g$, at each occurrence, is independently hydrogen, alkyl, alkenyl, alkynyl, haloalkyl, benzyl, or monocyclic cycloalkyl;

G$^a$, at each occurrence, is independently aryl, heteroaryl, cycloalkyl, cycloalkenyl, or heterocycle, each of which is optionally substituted with 1, 2, 3, 4, or 5 substituents independently selected from the group consisting of alkyl, alkenyl, alkynyl, halogen, haloalkyl, —CN, oxo, —OR$^h$, —OC(O)R$^i$, —OC(O)N(R$^h$)$_2$, —SR$^h$, —S(O)$_2$R$^i$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, —(C$_1$-C$_6$ alkylenyl)-OR$^i$, —(C$_1$-C$_6$ alkylenyl)-OC(O)R$^i$, —(C$_1$-C$_6$ alkylenyl)-OC(O)N(R$^h$)$_2$, —(C$_1$-C$_6$ alkylenyl)-S(O)$_2$R$^i$, —(C$_1$-C$_6$ alkylenyl)-S(O)$_2$N(R$^h$)$_2$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)N(R$^h$)$_2$, —(C$_1$-C$_6$ alkylenyl)-N(R$^h$)$_2$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)N(R$^h$)$_2$, and —(C$_1$-C$_6$ alkylenyl)-CN;

R$^h$, at each occurrence, is independently hydrogen, alkyl, or haloalkyl; and

R$^i$, at each occurrence, is independently alkyl or haloalkyl.

2. The compound of claim 1 of formula (I) or a pharmaceutically acceptable salt, solvate, or a combination thereof wherein one of X$^1$, X$^2$, X$^3$, and X$^4$ is C, and the others are C(R$^a$); and each R$^a$ is the same or different, and are each independently hydrogen or halogen.

3. The compound of claim 2 of formula (I) or a pharmaceutically acceptable salt, solvate, or a combination thereof wherein X$^5$-X$^6$ is C(R$^3$R$^4$)C(R$^5$R$^6$); and G$^2$ is optionally substituted aryl.

4. The compound of claim 1 of formula (I-i) or a pharmaceutically acceptable salt, solvate, or a combination thereof

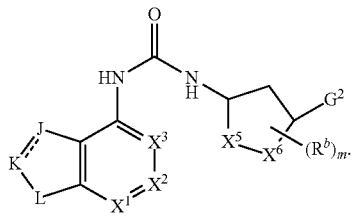

(I-i)

5. The compound of claim 4 or a pharmaceutically acceptable salt, solvate, or a combination thereof, wherein X$^5$-X$^6$ is CR$^{3a}$R$^{3b}$, C(R$^3$R$^4$)C(R$^5$R$^6$), or C(R$^9$R$^{10}$)C(R$^{11}$R$^{12}$)C(R$^{13}$R$^{14}$).

6. The compound of claim 4 or a pharmaceutically acceptable salt, solvate, or a combination thereof, wherein X$^5$-X$^6$ is C(R$^3$R$^4$)C(R$^5$R$^6$); and G$^2$ is aryl, heteroaryl, or cycloalkyl, each of which is optionally substituted.

7. The compound of claim 6 or a pharmaceutically acceptable salt, solvate, or a combination thereof, wherein G$^2$ is optionally substituted phenyl.

8. The compound of claim 1 of formula (I-iii) or a pharmaceutically acceptable salt, solvate, or a combination thereof

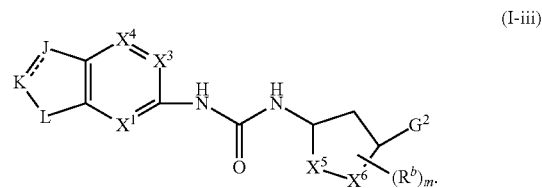

(I-iii)

9. The compound according to claim 1, or a pharmaceutically acceptable salt, solvate, or a combination thereof, wherein the compound is selected from the group consisting of 1-(1-methyl-1H-indazol-4-yl)-3-[(1R,3S)-3-phenylcyclopentyl]urea;

1-(1H-indazol-4-yl)-3-[(1R,3S)-3-phenylcyclopentyl]urea;

1-(1-methyl-1H-indazol-4-yl)-3-[(1S,3S)-3-phenylcyclopentyl]urea;

1-(1H-indazol-4-yl)-3-[(1S,3S)-3-phenylcyclopentyl]urea;

1-(1-methyl-1H-indazol-4-yl)-3-[(1R,3R)-3-phenylcyclopentyl]urea;

1-(1H-indazol-4-yl)-3-[(1R,3R)-3-phenylcyclopentyl]urea;

1-(1-methyl-1H-indazol-4-yl)-3-[(1S,3R)-3-phenylcyclopentyl]urea;

1-(1H-indazol-4-yl)-3-[(1S,3R)-3-phenylcyclopentyl]urea;

1-[3-(4-tert-butylphenyl)cyclohexyl]-3-(1H-indazol-4-yl)urea;

1-(1H-indazol-4-yl)-3-{3-[4-(trifluoromethyl)phenyl]cyclohexyl}urea;

1-(1H-indazol-4-yl)-3-{(1R,3R)-3-[4-(trifluoromethyl)phenyl]cyclohexyl}urea;

1-(1H-indazol-4-yl)-3-{(1S,3S)-3-[4-(trifluoromethyl)phenyl]cyclohexyl}urea;

1-(1H-indazol-4-yl)-3-{(1S,3R)-3-[4-(trifluoromethyl)phenyl]cyclohexyl}urea;

1-(1H-indazol-4-yl)-3-{(1R,3S)-3-[4-(trifluoromethyl)phenyl]cyclohexyl}urea;

1-(1H-indazol-4-yl)-3-[(1S,3S)-3-phenylcyclohexyl]urea;

1-(1H-indazol-4-yl)-3-[(1R,3S)-3-phenylcyclohexyl]urea;

1-[3-(4-tert-butylphenyl)cyclopentyl]-3-(1H-indazol-4-yl)urea;

1-(1H-indazol-4-yl)-3-[cis-3-(pyridin-2-yl)cyclopentyl]urea;

1-(1H-indazol-4-yl)-3-[trans-3-(pyridin-2-yl)cyclopentyl]urea;

1-(1H-indazol-4-yl)-3-[3-(4-methoxyphenyl)cyclopentyl]urea;

1-(1H-indazol-4-yl)-3-{(1S,3S)-3-[4-(trifluoromethyl)phenyl]cyclopentyl}urea;

1-(1H-indazol-4-yl)-3-{(1R,3S)-3-[4-(trifluoromethyl)phenyl]cyclopentyl}urea;

1-(1H-indazol-4-yl)-3-{(1S,3R)-3-[4-(trifluoromethyl)phenyl]cyclopentyl}urea;

1-(1H-indazol-4-yl)-3-{(1R,3R)-3-[4-(trifluoromethyl)phenyl]cyclopentyl}urea;

1-[(3S)-3-(4-fluorophenyl)cyclopentyl]-3-(1H-indazol-4-yl)urea;

1-(1H-indazol-4-yl)-3-{(3S)-3-[4-(methylsulfanyl)phenyl]cyclopentyl}urea;

1-{(3S)-3-[4-(dimethylamino)phenyl]cyclopentyl}-3-(1H-indazol-4-yl)urea;
1-(1H-indazol-4-yl)-3-[(1S,4R)-4-phenylcyclopent-2-en-1-yl]urea;
1-((1S,3R)-3-cyclohexylcyclopentyl)-3-(1H-indazol-4-yl)urea;
1-[(1S,2S,3R,4S)-2,3-dihydroxy-4-phenylcyclopentyl]-3-(1H-indazol-4-yl)urea;
1-[(1S,2R,3S,4S)-2,3-dihydroxy-4-phenylcyclopentyl]-3-(1H-indazol-4-yl)urea;
1-[(1R,2R,4S,5R)-6,6-difluoro-4-phenylbicyclo[3.1.0]hex-2-yl]-3-(1H-indazol-4-yl)urea;
1-(1H-indazol-4-yl)-3-[(1S,2R,4S,5S)-4-phenylbicyclo[3.1.0]hex-2-yl]urea;
1-(1H-indazol-4-yl)-3-(cis-3-phenylcyclobutyl)urea;
1-(1H-indazol-4-yl)-3-(trans-3-phenylcyclobutyl)urea;
1-[(trans)-3-hydroxy-3-phenylcyclopentyl]-3-(1H-indazol-4-yl)urea;
1-[(1R,3S)-3-(2-fluorophenyl)cyclopentyl]-3-(1H-indazol-4-yl)urea;
1-[(1S,3S)-3-(2-fluorophenyl)cyclopentyl]-3-(1H-indazol-4-yl)urea;
1-(1H-indazol-4-yl)-3-[(1R,4S)-4-phenylcyclopent-2-en-1-yl]urea;
1-[(1S,3S)-3-(3-fluorophenyl)cyclopentyl]-3-(1H-indazol-4-yl)urea;
1-[(1R,3S)-3-(3-fluorophenyl)cyclopentyl]-3-(1H-indazol-4-yl)urea;
1-[(1R,3R)-3-(2-fluorophenyl)cyclopentyl]-3-(1H-indazol-4-yl)urea;
1-[(1S,3R)-3-(2-fluorophenyl)cyclopentyl]-3-(1H-indazol-4-yl)urea;
1-[(1R,3R)-3-(3-fluorophenyl)cyclopentyl]-3-(1H-indazol-4-yl)urea;
1-[(1S,3R)-3-(3-fluorophenyl)cyclopentyl]-3-(1H-indazol-4-yl)urea;
1-(1H-indazol-4-yl)-3-[(1S,3R)-3-methyl-3-phenylcyclopentyl]urea;
1-(1H-indazol-4-yl)-3-[(1R,3R)-3-methyl-3-phenylcyclopentyl]urea;
1-[(1R,3R)-3-(3-fluorophenyl)cyclopentyl]-3-(1-methyl-1H-indazol-4-yl)urea;
1-[(1S,3R)-3-(3-fluorophenyl)cyclopentyl]-3-(1-methyl-1H-indazol-4-yl)urea;
1-[(1R,3R)-3-(2-fluorophenyl)cyclopentyl]-3-(1-methyl-1H-indazol-4-yl)urea;
1-[(1S,3R)-3-(2-fluorophenyl)cyclopentyl]-3-(1-methyl-1H-indazol-4-yl)urea;
1-(1H-indazol-4-yl)-3-[(trans)-3-(4-methyl-1,3-thiazol-2-yl)cyclopentyl]urea;
1-(1H-indazol-4-yl)-3-[(1S,3R)-3-(4-methyl-1,3-thiazol-2-yl)cyclopentyl]urea;
1-(1H-indazol-4-yl)-3-[(1R,3S)-3-(4-methyl-1,3-thiazol-2-yl)cyclopentyl]urea;
1-(1H-indazol-4-yl)-3-[(1S,3R)-3-(4-methyl-1,3-oxazol-2-yl)cyclopentyl]urea;
1-(1H-indazol-4-yl)-3-[(1R,3S)-3-(4-methyl-1,3-oxazol-2-yl)cyclopentyl]urea;
1-(1H-indazol-4-yl)-3-[(1S,3R)-3-(5-methyl-1,3-oxazol-2-yl)cyclopentyl]urea;
1-(1H-indazol-4-yl)-3-[(1R,3S)-3-(5-methyl-1,3-oxazol-2-yl)cyclopentyl]urea;
1-(1H-indazol-4-yl)-3-{(1R*,3R*)-3-[4-(trifluoromethyl)-1,3-thiazol-2-yl]cyclopentyl}urea;
1-(1H-indazol-4-yl)-3-{(1R*,3S*)-3-[4-(trifluoromethyl)-1,3-thiazol-2-yl]cyclopentyl}urea; and
1-(1H-indazol-4-yl)-3-{(1R)-3-[4-(trifluoromethyl)-1,3-thiazol-2-yl]cyclopentyl}urea.

10. A pharmaceutical composition comprising a therapeutically effective amount of a compound of formula (I) according to claim 1, or a pharmaceutically acceptable salt, solvate, or a combination thereof, in combination with a pharmaceutically acceptable carrier.

11. The pharmaceutical composition according to claim 10 further comprising an analgesic or a nonsteroidal anti-inflammatory drug, or a combination thereof.

12. A method for treating pain comprising administering a therapeutically effective amount of a compound of formula (I) according to claim 1 or a pharmaceutically acceptable salt, solvate, or a combination thereof, to a subject in need thereof, with or without a pharmaceutically acceptable carrier.

13. The method according to claim 12 further comprising the step of co-administering with an analgesic or a nonsteroidal anti-inflammatory drug, or a combination thereof.

14. The method according to claim 13 wherein the nonsteroidal anti-inflammatory drug is ibuprofen.

15. The compound of formula 1 according to claim 1 or pharmaceutical acceptable salt or solvate thereof wherein said compound exhibits less than about a 25% increase in response latency of noxious thermosensation in a tail immersion model relative to vehicle control.

16. The compound according to claim 15 or pharmaceutical acceptable salt or solvate thereof, wherein the compound is selected from the group consisting of
1-(1-methyl-1H-indazol-4-yl)-3-[(1R,3S)-3-phenylcyclopentyl]urea;
1-(1H-indazol-4-yl)-3-[(1R,3S)-3-phenylcyclopentyl]urea;
1-(1H-indazol-4-yl)-3-[(1S,3S)-3-phenylcyclopentyl]urea;
1-(1H-indazol-4-yl)-3-[(1R,3R)-3-phenylcyclopentyl]urea;
1-(1H-indazol-4-yl)-3-[(1S,3R)-3-phenylcyclopentyl]urea; and
1-(1H-indazol-4-yl)-3-[(1S,4R)-4-phenylcyclopent-2-en-1-yl]urea.

17. The compound of formula 1 according to claim 1, or pharmaceutical acceptable salt or solvate thereof wherein said compound exhibits less than about a 10% increase in response latency of noxious thermosensation in a tail immersion model relative to vehicle control.

18. The compound according to claim 17 or pharmaceutical acceptable salt or solvate thereof, wherein the compound is selected from the group consisting of
1-(1-methyl-1H-indazol-4-yl)-3-[(1R,3S)-3-phenylcyclopentyl]urea;
1-(1H-indazol-4-yl)-3-[(1R,3S)-3-phenylcyclopentyl]urea;
1-(1H-indazol-4-yl)-3-[(1S,3S)-3-phenylcyclopentyl]urea;
1-(1H-indazol-4-yl)-3-[(1S,3R)-3-phenylcyclopentyl]urea; and
1-(1H-indazol-4-yl)-3-[(1S,4R)-4-phenylcyclopent-2-en-1-yl]urea.

19. The compound of formula 1, according to claim 1, or pharmaceutical acceptable salt or solvate thereof wherein said compound blocks about 75% or less calcium flux caused by activation of human TRPV1 at about a pH of 5.0, and exhibits less than about a 25% increase in response latency of noxious thermosensation in a tail immersion model relative to vehicle control.

20. The compound according to claim 19 or pharmaceutical acceptable salt or solvate thereof, wherein the compound is selected from the group consisting of
- 1-(1H-indazol-4-yl)-3-[(1R,3S)-3-phenylcyclopentyl] urea;
- 1-(1H-indazol-4-yl)-3-[(1S,3S)-3-phenylcyclopentyl] urea;
- 1-(1H-indazol-4-yl)-3-[(1S,3R)-3-phenylcyclopentyl] urea; and
- 1-(1H-indazol-4-yl)-3-[(1S,4R)-4-phenylcyclopent-2-en-1-yl]urea.

21. The compound of formula 1 according to claim 1, or pharmaceutical acceptable salt or solvate thereof wherein said compound blocks about 75% or less calcium flux caused by activation of human TRPV1 at about a pH of 5.0, and exhibits less than about a 10% increase in response latency of noxious thermosensation in a tail immersion model relative to vehicle control.

22. The compound according to claim 21 or pharmaceutical acceptable salt or solvate thereof, wherein the compound is selected from the group consisting of
- 1-(1H-indazol-4-yl)-3-[(1R,3S)-3-phenylcyclopentyl] urea;
- 1-(1H-indazol-4-yl)-3-[(1S,3S)-3-phenylcyclopentyl] urea;
- 1-(1H-indazol-4-yl)-3-[(1S,3R)-3-phenylcyclopentyl] urea; and
- 1-(1H-indazol-4-yl)-3-[(1S,4R)-4-phenylcyclopent-2-en-1-yl]urea.

23. The compound or salt according to claim 1 that is 1-(1H-indazol-4-yl)-3-[(1S,3R)-3-phenylcyclopentyl]urea, or a pharmaceutically acceptable salt thereof.

24. The pharmaceutical composition according to claim 10, wherein the composition comprises 1-(1H-indazol-4-yl)-3-[(1S,3R)-3-phenylcyclopentyl]urea, or a pharmaceutically acceptable salt thereof.

25. The method for treating pain according to claim 12, wherein the method comprises administering a therapeutically effective amount of 1-(1H-indazol-4-yl)-3-[(1S,3R)-3-phenylcyclopentyl]urea, or a pharmaceutically acceptable salt thereof, to the subject in need thereof.

* * * * *